United States Patent
Kanai et al.

(10) Patent No.: US 6,806,266 B1
(45) Date of Patent: Oct. 19, 2004

(54) STAUROSPORIN DERIVATIVES

(75) Inventors: Fumihiko Kanai, Chiyoda-ku (JP); Nobuyoshi Amishiro, Sunto-gun (JP); Yushi Kitamura, Sunto-gun (JP); Chikara Murakata, Sunto-gun (JP); Tadakazu Akiyama, Sunto-gun (JP); Shiro Akinaga, Chiyoda-ku (JP); Eiichi Fuse, Sunto-gun (JP); Takashi Kuwabara, Sunto-gun (JP); Kenichi Yasoshima, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/030,618

(22) PCT Filed: Jul. 13, 2000

(86) PCT No.: PCT/JP00/04702

§ 371 (c)(1), (2), (4) Date: Jan. 11, 2002

(87) PCT Pub. No.: WO01/04125

PCT Pub. Date: Jan. 18, 2001

(30) Foreign Application Priority Data

Jul. 13, 1999 (JP) .............................. 11-198393

(51) Int. Cl.[7] .................... C07D 498/22; A61K 31/553; A61P 35/00
(52) U.S. Cl. ................... 514/211.08; 540/545
(58) Field of Search ....................... 514/211.08; 540/545

(56) References Cited

U.S. PATENT DOCUMENTS

| | | | |
|---|---|---|---|
| 4,935,415 A | 6/1990 | Nakano et al. | 514/211 |
| 5,382,675 A | 1/1995 | Wacker | 549/420 |
| 5,604,219 A | 2/1997 | Murakata et al. | 514/211 |
| 5,674,867 A | 10/1997 | Tamaoki et al. | 514/219 |
| 5,736,542 A | 4/1998 | Henry et al. | 514/211 |
| 5,827,846 A | 10/1998 | Regenass et al. | 514/211 |

FOREIGN PATENT DOCUMENTS

| | | |
|---|---|---|
| EP | 383 919 | 8/1990 |
| EP | 643 966 | 3/1995 |
| JP | 3-72485 | 3/1991 |
| JP | 03072485 | 3/1991 |
| JP | 03-220194 | 9/1991 |
| JP | 03220194 | 9/1991 |
| JP | 4-364186 | 12/1992 |
| JP | 04364186 | 12/1992 |
| JP | 05140168 | 6/1993 |
| WO | WO 95/32975 | 12/1995 |
| WO | WO 95/32976 | 12/1995 |
| WO | WO 97/05141 | 2/1997 |
| WO | WO 99/02532 | 1/1999 |

OTHER PUBLICATIONS

Cantrell et al. (Natural Product Letters (1999). Abstract.*
Schupp et al. (Journal of Natural Products (1999), 62(7), 959–962). Abstract.*
Yamada et al. (Journal of Antibiotics (1996), 49(10), 1070–1072). Abstract.*
Funato et al. (Tetrahedron Letters (1994), 35(8), 1251–4). Abstract.*
JP 05140168 (1993). Abstract.*
Kinnet et al. (Journal of Organic Chemistry (1992), 57(23), 6327–9). Abstract.*
Tsubotani et al. (Tetrahedron (1991), 47(22), 3565–74. Abstract.*
Schupp, et al., "Staurosporine Derivatives from the Ascidian *Eudistoma toealensis* and . . . ", J. Nat. Prod. (1999), vol. 62, pp. 959–962.
Yamada, et al., "Synthesis and Anti–platelet Aggregation Activity of Water–soluable . . . ", The Journal of Antibiotics, vol. 49, No. 10 (1996), pp. 1070–1072.

* cited by examiner

*Primary Examiner*—Bruck Kifle
(74) *Attorney, Agent, or Firm*—Fitzpatrick, Cella, Harper & Scinto

(57) ABSTRACT

The present invention provides an antitumor agent comprising a staurosporin derivative or a pharmaceutically acceptable salt thereof, as an active ingredient, which is represented by the general formula (I):

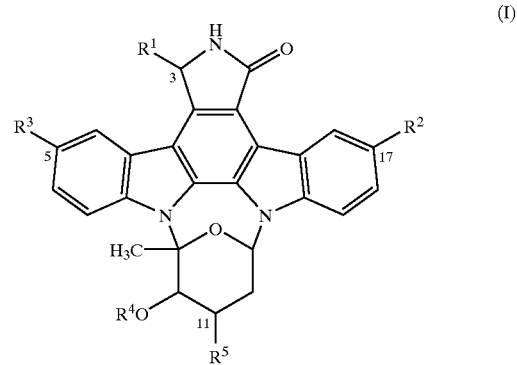

wherein $R^1$ represents hydrogen, hydroxy or lower alkoxy, $R^2$ and $R^3$ are the same or different and represent hydrogen, substituted or unsubstituted alkyl, substituted or unsubstituted lower alkenyl, substituted or unsubstituted lower alkynyl, substituted or unsubstituted aryl, a substituted or unsubstituted heterocyclic group, halogen, nitro, formyl, etc., $R^4$ represents hydrogen, etc., $R^5$ represents $NR^{11A}R^{12A}$ (wherein $R^{11A}$ and $R^{12A}$ represent hydrogen, substituted or unsubstituted lower alkyl, etc.), provided that $R^2$ and $R^3$ are not simultaneously hydrogen.

14 Claims, No Drawings

STAUROSPORIN DERIVATIVES

TECHNICAL FIELD

The present invention relates to staurosporin derivatives or pharmaceutically acceptable salts thereof, which are useful for the treatment of tumors. Further, the present invention relates to enhancers for activity of an antitumor agent.

BACKGROUND ART

As staurosporin derivatives effective for the treatment of tumors, UCN-1 in WO89/7105, CGP41251 in EP657164A, etc. are described.

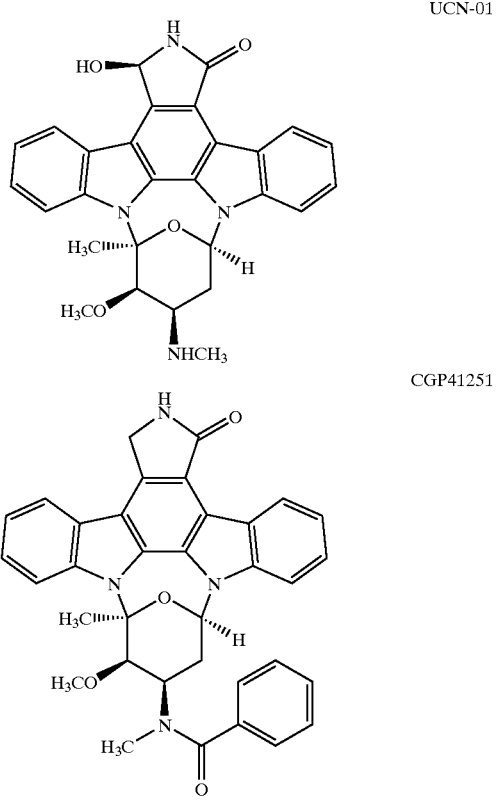

The staurosporin derivatives as described in the above two literatures, Japanese Published unexamined Application No.62-220196, WO94/20106, WO95/32974, WO95/32975, WO95/32976, EP624590A, etc. are characterized in that in the general formula (I) described below, both of $R^2$ and $R^3$ are hydrogen.

As the staurosporin derivatives wherein in the general formula (I) described below, at least one of $R^2$ and $R^3$ is not hydrogen, compounds described in Japanese Published Unexamined Application No.3-72485, Japanese. Published. Unexamined Application No.3-220194 and Japanese Published Unexamined Application No. 4-364186, compounds described in WO94/6799, and compounds described in WO97/5141 are known. However, Japanese Published Unexamined Application No.3-72485, Japanese Published Unexamined Application No.3-220194 and Japanese Published Unexamined Application No.4-364186 disclose only compounds wherein in the general formula (I) described below, $R^1$ is hydrogen, and $R^2$ and $R^3$ are hydrogen, nitro, amino, formyl, carboxy, lower alkoxycarbonyl, hydroxymethyl or hydroxy, and these compounds are used for inhibition of platelet aggregation, and their effect on the treatment of malignant tumors is not shown. WO94/6799 disclose only compounds wherein in the general formula (I) described below, $R^1$ is hydrogen, and $R^2$ and $R^3$ are hydrogen, halogen, formyl, lower alkanoyl or lower alkoxy, and these compounds are used for the treatment of thrombocytopenia, and their effect on the treatment of malignant tumors is not shown. Further, the compounds described in WO97/5141 are characterized in that in the general formula (I) described below, compounds are the derivatives which have a ketone or an oxime at the 11-position, and there are neither specific compounds nor synthetic intermediates thereof wherein in the general formula (I) described below, at least one of $R^2$ and $R^3$ is not hydrogen.

On the other hand, it is known that some of these compounds in the prior art have strong affinity for human $\alpha_1$ acidic glycoprotein (hereinafter referred to as $h\alpha_1 AGP$), which is contained in human plasma [Pharmacogenetics, 6, 411 (1996)]. The pharmacokinetics etc. of such compounds can be influenced by the strong affinity for $h\alpha_1 AGP$ and the expected efficacy of the compounds upon administration into humans can also be influenced. Thus, staurosporin derivatives with low affinity for $h\alpha_1 AGP$ are desired. The above-described staurosporin derivatives wherein in the general formula (I) described below, both of $R^2$ and $R^3$ are hydrogen are shown to have strong bonding to $h\alpha_1 AGP$ [Abstracts of $118^{th}$ The Pharmaceutical Society of Japan Annual Meeting, 4, 43 (1998)].

On the other hand, it is known that UCN-01 shows a synergistic effect when combined with known anticancer agents having actions on DNA or antimetabolites, such as Cisplatin, Mitomycin C or 5-Fluorouracil, in vitro and in vivo [Proc. Am. Assoc. Cancer Res., 33, 514 (Publication No. 3072) (1992) and Cancer Chemotherapy Pharmacology, 32, 183 (1993)]. The mechanism of bringing about the is estimated as follows: when DNA in cancer cells is damaged by anticancer agents having actions on DNA or by antimetabolites, the cancer cells act for repairing the DNA damage by stopping their cell cycle at the G2 or S stage (accumulation action at the G2 or S stage), and UCN-01 abrogates this accumulation action, thus promoting progress of the cell cycle, thereby depriving the cancer cells of a chance to repair the DNA damage and leading the cancer cells to apoptosis [Clinical Cancer Res., 2, 791 (1996), Cell Growth and Differentiation, 8, 779 (1997), J. Natl. Cancer Inst., 88, 956 (1996), Proc. Am. Assoc. Cancer Res., 39, 70 (Publication No. 476) (1998)]. This action is called abrogation action on accumulation action at the G2 or S stage, and caffeine is known as a known chemical having this abrogation action, but its concentration for inducing action is as very high as mmol/L level, and so there is little clinical usefulness. [Cancer Res., 55, 1643 (1995)].

Among such compounds, UCN-01, which can abrogate accumulation action at the G2 or S stage at a low concentration of 100 mmol/L or less, is considered to be the strongest abrogation inducer known so far.

On the other hand, UCN-01 binds strongly to $h\alpha_1 AGP$ to lose its biological activity, thus making administration of a large amount of UCN-01 clinically necessary and simultaneously necessitating attention to the interaction among chemicals on $h\alpha_1 AGP$, and therefore it is anticipated that the possibility of using UCN-01 as an abrogation inducer on accumulation action at the G2 and S stage is limited [Cancer Res., 58, 3248 (1998)].

Accordingly, there is demand for enhancers for activity of antitumor agents, which are capable of exerting abrogation

DISCLOSURE OF THE INVENTION

An object of the present invention is to provide staurosporin derivatives or pharmaceutically acceptable salts thereof, which are useful for the treatment of tumors. Another object is to provide enhancers for activity of antitumor agents.

The present invention relates to antitumor agents comprising a staurosporin derivative or a pharmaceutically acceptable salt thereof, as an active ingredient, which is represented by the general formula (I):

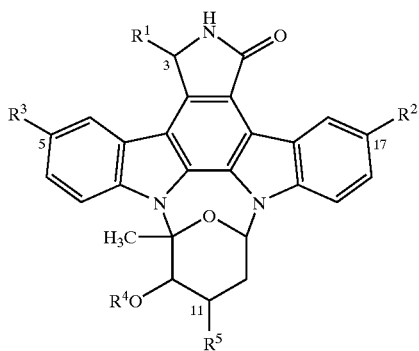

(I)

wherein $R^1$ represents hydrogen, hydroxy, or lower alkoxy;

$R^2$ represents hydrogen, substituted or unsubstituted lower alkyl, substituted or unsubstituted lower alkenyl, substituted or unsubstituted lower alkadienyl, substituted or unsubstituted lower alkynyl, substituted or unsubstituted aryl, a substituted or unsubstituted heterocyclic group, halogen, nitro, formyl, $COR^6$ <wherein $R^6$ represents substituted or unsubstituted lower alkyl, substituted or unsubstituted aryl, a substituted or unsubstituted heterocyclic group, $NR^7R^8$ {wherein $R^7$ and $R^8$ are the same or different and represent hydrogen, substituted or unsubstituted lower alkyl, substituted or unsubstituted lower alkenyl, cycloalkyl, substituted or unsubstituted aryl, or a substituted or unsubstituted heterocyclic group, or are combined with their adjacent N to form a substituted or unsubstituted heterocyclic group (the heterocyclic group formed by $R^7$ and $R^8$ together with their adjacent N may contain an oxygen atom, a sulfur atom, or another nitrogen atom)}, $OR^9$ (wherein $R^9$ represents hydrogen, substituted or unsubstituted lower alkyl, substituted or unsubstituted lower alkenyl, cycloalkyl, or substituted or unsubstituted aryl), or $SR^{10}$ (wherein $R^{10}$ represents substituted or unsubstituted lower alkyl, or substituted or unsubstituted aryl)>, $NR^{11}R^{12}$ <wherein $R^{11}$ and $R^{12}$ are the same or different and represent hydrogen, substituted or unsubstituted lower alkyl, substituted or unsubstituted lower alkenyl, cycloalkyl, $COR^{13}$ {wherein $R^{13}$ represents substituted or unsubstituted lower alkyl, substituted or unsubstituted lower alkenyl, lower alkoxycarbonyl, substituted or unsubstituted aryl, a substituted or unsubstituted heterocyclic group, $OR^{9A}$ (wherein $R^{9A}$ has the same meaning as defined for $R^9$ above) $NR^{7A}R^{8A}$ (wherein $R^{7A}$ and $R^{8A}$ have the same meaning as defined for $R^7$ and $R^8$ above, respectively)}, $CSR^{13A}$ (wherein $R^{13A}$ has the same meaning as defined for $R^{13}$ above), $SO_2R^{13B}$ (wherein $R^{13B}$ has the same meaning as defined for $R^{13}$ above), or a residue of an amino acid, excluding a hydroxyl group in a carboxylic group of the amino acid (a functional group in the amino acid may be protected with a protective group)>, or $OR^{14}$ {wherein $R^{14}$ represents hydrogen, substituted or unsubstituted lower alkyl, substituted or unsubstituted lower alkenyl, cycloalkyl, substituted or unsubstituted lower alkanoyl, substituted or unsubstituted aroyl, or $CONR^{7B}R^{8B}$ (wherein $R^{7B}$ and $R^{8B}$ have the same meanings as defined for $R^7$ and $R^8$ above, respectively)};

$R^4$ represents hydrogen or substituted or unsubstituted lower alkyl;

$R^5$ represents $NR^{11A}R^{12A}$ (wherein $R^{11A}$ and $R^{12A}$ have the same meanings as defined for $R^{11}$ and $R^{12}$ above, respectively); and $R^3$ has the same meaning as defined for $R^2$, with the proviso that $R^2$ and $R^3$ are not simultaneously hydrogen.

Further, the present invention relates to staurosporin derivatives or pharmaceutically acceptable salts thereof, which are represented by the general formula (IA):

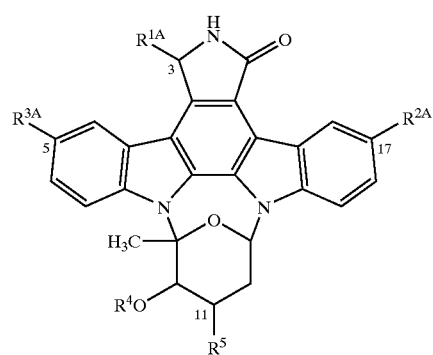

(IA)

wherein $R^{2A}$ represents hydrogen, hydroxy, halogen, formyl, nitro, amino, $COR^{6A1}$ (wherein $R^{6A1}$ represents substituted or unsubstituted lower alkyl, hydroxy, or substituted or unsubstituted lower alkoxy), $OR^{14A1}$ (wherein $R^{14A1}$ represents substituted or unsubstituted lower alkyl), lower alkyl, substituted lower alkyl, substituted or unsubstituted lower alkenyl, substituted or unsubstituted lower alkadienyl, substituted or unsubstituted lower alkynyl, substituted or unsubstituted aryl, a substituted or unsubstituted heterocyclic group, $COR^{6A3}$ (wherein $R^{6A3}$ has the same meaning as defined for $R^{6A2}$ below), $NR^{11A2}R^{12A2}$ (wherein $R^{11A2}$ and $R^{12A2}$ have the same meanings as defined for $R^{11A1}$ and $R^{12A1}$ below, respectively), or $OR^{14A3}$ (wherein $R^{14A3}$ has the same meaning as defined for $R^{14A2}$ below);

when $R^{2A}$ represents hydrogen, hydroxymethyl, hydroxy, halogen, formyl, nitro, amino, $COR^{6A1}$ (wherein $R^{6A1}$ represents substituted or unsubstituted lower alkyl, hydroxy, or substituted or unsubstituted lower alkoxy), or $OR^{14A1}$ (wherein $R^{14A1}$ represents substituted or unsubstituted lower alkyl), $R^{3A}$ represents lower alkyl, substituted lower alkyl (the substituted lower alkyl is not hydroxymethyl), substituted or unsubstituted lower alkenyl, substituted or unsubstituted lower alkadienyl, substituted or unsubstituted lower alkynyl, substituted or unsubstituted aryl, a substituted or unsubstituted heterocyclic group, $COR^{6A2}$ <wherein $R^{6A2}$ represents substituted or unsubstituted aryl, a substituted or unsubstituted heterocyclic group, $NR^{7A1}R^{8A1}$ (wherein $R^{7A1}$ and $R^{8A1}$ have the same meanings as defined for $R^7$ and $R^8$ above, respectively), $OR^{9A1}$ (wherein $R^{9A1}$ represents substituted or unsubstituted lower alkenyl, cycloalkyl, or substituted or unsubstituted aryl), or $SR^{10A1}$ (wherein $R^{10A1}$ has the same meaning as defined for $R^{10}$ above)>, $NR^{11A1}R^{12A1}$ (wherein $NR^{11A1}$ and $R^{12A1}$ have the same meanings as defined for $R^{11}$ and $R^{12}$ above, respectively, with the proviso that $R^{11A1}$ and $R^{12A1}$ are not simultaneously hydrogen), or $OR^{14A2}$ {wherein $R^{14A2}$ represents substituted or unsubstituted lower alkenyl, cycloalkyl, substituted or unsubstituted lower alkanoyl, substituted or unsubstituted aroyl, or $CONR^{7B1}R^{8B1}$ (wherein $R^{7B1}$ and $R^{8B1}$ have the same meanings as defined for $R^7$ and $R^8$ above, respectively)};

when $R^{2A}$ represents lower alkyl, substituted lower alkyl (the substituted lower alkyl is not hydroxymethyl), substituted or unsubstituted lower alkenyl, substituted or unsubstituted lower alkadienyl, substituted or unsubstituted lower alkynyl, substituted or unsubstituted aryl, a substituted or unsubstituted heterocyclic group, $COR^{6A3}$ (wherein $R^{6A3}$ has the same meaning as defined for $R^{6A2}$ above), $NR^{11A2}R^{12A2}$ (wherein $R^{11A2}$ and $R^{12A2}$ have the same meanings as defined for $R^{11A1}$ and $R^{12A1}$ above, respectively), or $OR^{14A3}$ (wherein $R^{14A3}$ has the same meaning as defined for $R^{14A2}$ above), $R^{3A}$ represents substituted or unsubstituted lower alkyl substituted or unsubstituted lower alkenyl, substituted or unsubstituted lower alkadienyl, substituted or unsubstituted lower alkynyl, substituted or unsubstituted aryl, a substituted or unsubstituted heterocyclic group, halogen, nitro, formyl, $COR^{6A4}$ [wherein $R^{6A4}$ represents substituted or unsubstituted lower alkyl, substituted or unsubstituted aryl, a substituted or unsubstituted heterocyclic group, $NR^{7A2}R^{8A2}$ {wherein $R^{7A2}$ and $R^{8A2}$ have the same meanings as defined for $R^7$ and $R^8$ above, respectively}, $OR^{9A2}$ (wherein $R^{9A2}$ has the same meaning as defined for $R^9$ above), or $SR^{10A2}$ (wherein $R^{10A2}$ has the same meaning as defined for $R^{10}$ above)], $NR^{11A3}R^{12A3}$ (wherein $R^{11A3}$ and $R^{12A3}$ have the same meanings as defined for $R^{11}$ and $R^{12}$ above, respectively), or $OR^{14A4}$ (wherein $R^{14A4}$ has the same meaning as defined for $R^{14}$ above);

$R^{1A}$ has the same meaning as defined for $R^1$ above; and $R^4$ and $R^5$ have the same meanings as defined above, respectively.

In particular, the staurosporin derivatives or the pharmaceutically acceptable salts thereof, wherein $R^{1A}$ is hydroxy, are preferable.

Further, the present invention relates to staurosporin derivatives or pharmaceutically acceptable salts thereof, which are represented by the general formula (IB):

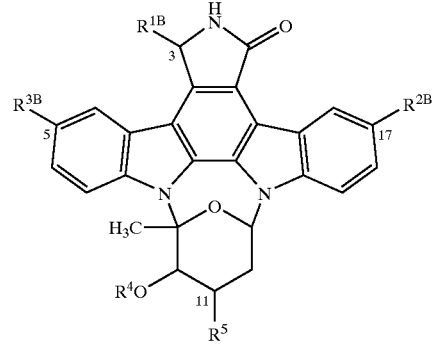

(IB)

wherein $R^{1B}$, $R^{2B}$ and $R^{3B}$ represent groups defined for the above $R^1$, $R^2$ and $R^3$, respectively, except when $R^1$ is hydrogen and $R^2$ and $R^3$ are the same or different and represent hydrogen, nitro, amino, carboxy, lower alkoxycarbonyl, hydroxy or hydroxymethyl, and when $R^1$ is hydrogen and $R^2$ and $R^3$ are the same or different and represent hydrogen, halogen, formyl, lower alkanoyl or lower alkoxy; and $R^4$ and $R^5$ have the same meanings as defined above, respectively.

In particular, the staurosporin derivatives or the pharmaceutically acceptable salts thereof, wherein $R^{1B}$ is hydroxy, are preferable.

Further, the present invention relates to staurosporin derivatives or pharmaceutically acceptable salts thereof, wherein in the general formula (IA), $R^{2A}$ represents amino, halogen, formyl or hydroxy, and $R^{3A}$ represents substituted or unsubstituted lower alkenyl, substituted or unsubstituted lower alkynyl, lower alkyl, substituted lower alkyl (the substituted lower alkyl is not hydroxymethyl), or $NHCOR^{13A1}$ (wherein $R^{12A1}$ has the same meaning as defined for $R^{13}$ above); or $R^{2A}$ represents substituted or unsubstituted lower alkenyl, a substituted or unsubstituted lower alkynyl, lower alkyl, substituted lower alkyl (the substituted lower alkyl is not hydroxymethyl), or $NHCOR^{13A2}$ (wherein $R^{13A2}$ has the same meaning as defined for $R^{13}$ above), and $R^{3A}$ represents substituted or unsubstituted lower alkenyl, substituted or unsubstituted lower alkynyl, amino, substituted or unsubstituted lower alkyl, or $NHCOR^{13A}$ (wherein $R^{13A}$ has the same meaning as defined for $R^{13}$ above).

In particular, the staurosporin derivatives or the pharmaceutically acceptable salts thereof, wherein $R^{1A}$ is hydroxy, are preferable.

Further, the present invention relates to the staurosporin derivatives or the pharmaceutically acceptable salts thereof, wherein in the general formula (IB), $R^{2B}$ and $R^{3B}$ are the same or different and represent substituted or unsubstituted lower alkenyl, substituted or unsubstituted lower alkynyl, amino, halogen, formyl, hydroxy, substituted or unsubstituted lower alkyl, or $NHCOR^{13}$ (wherein $R^{13}$ has the same meaning as defined above).

In particular, the staurosporin derivatives or the pharmaceutically acceptable salts thereof, Wherein $R^{1B}$ is hydroxy, are preferable.

Further, the present invention relates to a pharmaceutical composition comprising at least one staurosporin derivative or pharmaceutically acceptable salt thereof, represented by the general formula (IA) or (IB), and a pharmaceutically acceptable carrier.

Further, the present invention relates to enhancers for activity of an antitumor agent, comprising the staurosporin derivative represented by the general formula (I) or the pharmaceutically acceptable salt thereof, as an active ingredient. Further, the present invention relates to the enhancers for activity enhancing the activity of an antitumor agent by abrogating accumulation action at the G2 or S stage of the cell cycle.

Further, the present invention relates to agents for abrogating accumulation action at the G2 or S stage of the cell cycle, comprising the staurosporin derivative represented by the general formula (I) or the pharmaceutically acceptable salt thereof, as an active ingredient.

Further, the present invention relates to enhancers for activity of an antitumor agent, comprising the staurosporin derivative represented by the general formula (IA) or (IB) or the pharmaceutically acceptable salt, as an active ingredient. Further, the present invention relates to the enhancers for activity enhancing the activity of an antitumor agent by abrogating accumulation action at the G2 or S stage of the cell cycle.

Further, the present invention relates to agents for abrogating accumulation action at the G2 or S stage of the cell cycle, comprising the staurosporin derivative represented by the general formula (IA) or (IB) or the pharmaceutically acceptable salt, as an active ingredient.

Further, the present invention relates to antitumor agents comprising at least one staurosporin derivative or pharmaceutically acceptable salt thereof, represented by the general formula (IA) or (IB).

Further, the present invention relates to a pharmaceutical composition comprising at least one staurosporin derivative or pharmaceutically acceptable salt thereof, represented by the general formula (IA) or (IB).

Further, the present invention relates to a method for treating a malignant tumor, comprising the step of administering a therapeutically effective amount of the staurosporin derivative represented by the general formula (I) or the pharmaceutically acceptable salt thereof.

Further, the present invention relates to a method for enhancing the activity of an antitumor agent, comprising the step of administering a therapeutically effective amount of the staurosporin derivative represented by the general formula (I) or the pharmaceutically acceptable salt thereof.

Further, the present invention relates to a method for abrogating accumulation action at the G2 or S stage of the cell cycle, comprising the step of administering a therapeutically effective amount of the staurosporin derivative represented by the general formula (I) or the pharmaceutically acceptable salt thereof.

Further, the present invention relates to use of the staurosporin derivative represented by the general formula (I) or the pharmaceutically acceptable salt thereof for the manufacture of an antitumor agent.

Further, the present invention relates to use of the staurosporin derivative represented by the general formula (I) or the pharmaceutically acceptable salt thereof for the manufacture of an enhancer for activity of an antitumor agent.

Further, the present invention relates to use of the staurosporin derivative represented by the general formula (I) or the pharmaceutically acceptable salt thereof for the manufacture of an agent for abrogating accumulation action at the G2 or S stage of the cell cycle.

Further, the present invention relates to a method for treating a malignant tumor, comprising the step of administering a therapeutically effective amount of the staurosporin derivative represented by the general formula (IA) or (IB) or the pharmaceutically acceptable salt thereof.

Further, the present invention relates to a method for enhancing the activity of an antitumor agent, comprising the step of administering a therapeutically effective amount of the staurosporin derivative represented by the general formula (IA) or (IB) or the pharmaceutically acceptable salt thereof.

Further, the present invention relates to a method for abrogating accumulation action at the G2 or S stage of the cell cycle, comprising the step of administering a therapeutically effective amount of the staurosporin derivative represented by the general formula (IA) or (IB) or the pharmaceutically acceptable salt thereof.

Further, the present invention relates to use of the staurosporin derivative represented by the general formula (IA) or (IB) or the pharmaceutically acceptable salt thereof for the manufacture of an antitumor agent.

Further, the present invention relates to use of the staurosporin derivative represented by the general formula (IA) or (IB) or the pharmaceutically acceptable salt thereof for the manufacture of an enhancer for activity of an antitumor agent.

Further, the present invention relates to use of the staurosporin derivative represented by the general formula (IA) or (IB) or the pharmaceutically acceptable salt thereof for the manufacture of an agent for abrogating accumulation action at the G2 or S stage of the cell cycle.

Hereinafter, the compound represented by the general formula (I) is referred to as Compound (I). The compounds of other formula numbers are referred to in the same manner.

In the definition of each group in Compound (I), Compound (IA) and Compound (IB), the lower alkyl means the straight-chain or branched alkyl having 1 to 8 carbon atoms, for example, methyl, ethyl, propyl, isopropyl, butyl, isobutyl, sec-butyl, tert-butyl, pentyl, neopentyl, hexyl, heptyl, octyl, etc.

The lower alkyl moieties of the lower alkoxy and lower alkoxycarbonyl have the same meaning as defined for the lower alkyl described above.

The cycloalkyl means the cycloalkyl having 3 to 6 carbon atoms, for example, cyclopropyl, cyclobutyl, cyclopentyl, cyclohexyl, etc.

The lower alkenyl means the straight-chain or branched alkenyl having 2 to 6 carbon atoms, for example, vinyl, allyl, butenyl, pentenyl, hexenyl, etc.

The lower alkadienyl means the straight-chain or branched alkadienyl having 5 to 8 carbon atoms, for example, pentadienyl, hexadienyl, heptadienyl, octadienyl, etc.

The lower alkynyl means the straight-chain or branched alkynyl having 2 to 8 carbon atoms, for example, ethynyl, propynyl, butynyl, pentynyl, hexynyl, heptynyl, octynyl, etc.

The lower alkanoyl means the straight-chain or branched alkanoyl having 2 to 9 carbon atoms, for example, acetyl, propionyl, butyryl, isobutyryl, valeryl, isovaleryl, pivaloyl, hexanoyl, heptanoyl, octanoyl, etc.

The aryl and the aryl moiety of the aroyl mean, for example, phenyl, naphthyl, etc.

The heterocyclic group means, for example, aliphatic heterocyclic groups such as pyrrolidinyl, imidazolidinyl, piperidinyl, morpholinyl, thiomorpholinyl, piperidino, morpholino and piperadinyl, or aromatic heterocyclic groups such as furyl, thienyl, pyrrolyl, imidazolyl, triazolyl, oxazolyl, thiazolyl, pyridyl, pyrimidinyl, indolyl, quinolyl, isoquinolyl and quinazolinyl.

The heterocyclic group formed together with their adjacent N (the heterocyclic group formed together with their adjacent N may contain oxygen, sulfur, or other nitrogen atoms) means pyrrolidinyl, morpholino, thiomorpholino, N-methylpiperadinyl, pyrazolidinyl, piperidino, piperadinyl, homopiperadinyl, indolyl, isoindolyl, etc.

The halogen means an atom of fluorine, chlorine, bromine or iodine atom.

The amino acid means α-amino acids such as glycine, alanine, proline, glutamic acid, lysine, serine, cysteine, cystine, threonine, valine, methionine, leucine, isoleucine, norleucine, phenylalanine, tyrosine, thyroxine, hydroxyproline, tryptophan, aspartic acid, arginine, ornithine and histidine. The protective group for a functional group in the amino acid is the one used usually in peptide synthesis, and means, for example, benzyloxycarbonyl, tert-butoxycarbonyl, benzyloxy, tert-butoxy, methoxybenzenesulfonyl, etc.

The substituents in the substituted lower alkyl and substituted lower alkoxy include 1 to 3 substituents which are the same or different, for example, halogen, carboxy, lower alkoxycarbonyl, lower alkanoyl, aryl, substituted aryl (the substituents in the substituted aryl have the same meanings as defined for the substituents in the substituted aryl described below), a heterocyclic group, a substituted heterocyclic group (the substituents in the substituted heterocyclic group have the same meanings as defined for the substituents in the substituted heterocyclic group described below), $CONR^{15}R^{16}$ {wherein $R^{15}$ and $R^{16}$ are the same or different and represent hydrogen, hydroxy, aralkyl, lower alkyl, lower alkenyl, aryl, substituted aryl (the substituents in the substituted aryl have the same meanings as defined for the substituents in the substituted aryl described below), a heterocyclic group, or a substituted heterocyclic group (the substituents in the substituted heterocyclic group have the same meanings as the substituents in the substituted heterocyclic group described below), or are combined with their adjacent N to form a heterocyclic group (the heterocyclic group formed together with their adjacent N may contain oxygen, sulfur, or other nitrogen atoms)}, $NR^{17}R^{18}$ (wherein $R^{17}$ and $R^{18}$ are the same or different and represent hydrogen, lower alkyl, lower alkenyl, lower alkanoyl, aroyl, aryl, substituted aryl (the substituents in the substituted aryl have the same meanings as defined for the substituents in the substituted aryl described below), a heterocyclic group, a substituted heterocyclic group (the substituents in the substituted heterocyclic group have the same meanings as the substituents in the substituted heterocyclic group described below), substituted lower alkyl {the substituted lower alkyl is replaced by at least one of hydroxy, lower alkoxy, $O(CH_2CH_2O)_nR^{19}$ (wherein n is an integer of 1 to 15, and $R^{19}$ is lower alkyl), oxo, carboxy, lower alkoxycarbonyl, aryl, substituted aryl (the substituents in the substituted aryl have the same meanings as defined for the substituents in the substituted aryl described below), a heterocyclic group, a substituted heterocyclic group (the substituents in the substituted heterocyclic group have the same meanings as defined for the substituents in the substituted heterocyclic group described below), $CONR^{15A}R^{16A}$ (wherein $R^{15A}$ and $R^{16A}$ have the same meanings as defined for $R^{15}$ and $R^{16}$ described above, respectively), amino, lower alkylamino, and di(lower alkyl)amino}, cycloalkyl, or aralkyloxycarbonyl, are combined with their adjacent N to form a heterocyclic group (the heterocyclic group formed together with their adjacent N may contain oxygen, sulfur, or other nitrogen atoms), or are combined with their adjacent N to form a substituted heterocyclic group (the substituted heterocyclic group formed together with their adjacent N may contain oxygen, sulfur, or other nitrogen atoms, and the substituents in the substituted heterocyclic group formed together with their adjacent N have the same meanings as defined for the substituents in the substituted heterocyclic group formed together with their adjacent N described below)], $N^+R^{20}R^{21}R^{22}X^-$ {wherein $R^{20}$ and $R^{21}$ are the same or different and represent lower alkyl, or are combined with their adjacent N to form a heterocyclic group (the heterocyclic group formed together with their adjacent N may contain oxygen, sulfur, or other nitrogen atoms), $R^{22}$ is lower alkyl, and X is an atom of chlorine, bromine or iodine}, $OR^{23}$ {wherein $R^{23}$ represents hydrogen, lower alkyl, lower alkanoyl, substituted lower alkyl {the substituted lower alkyl is replaced by at least one of hydroxy, lower alkoxy, $O(CH_2CH_2O)_{nA}R^{19A}$ (wherein nA is an integer of 1 to 15, and $R^{19A}$ is lower alkyl), oxo, carboxy, lower alkoxycarbonyl, aryl, substituted aryl (the substituents in the substituted aryl have the same meanings as defined for the substituents in the substituted aryl described below), a heterocyclic group, a substituted heterocyclic group (the substituents in the substituted heterocyclic group have the same meanings as defined for the substituents in the substituted heterocyclic group described below), $CONR^{15B}R^{16B}$ {wherein $R^{15B}$ and $R^{16B}$ have the same meanings as defined for $R^{15}$ and $R^{16}$ described above, respectively}, amino, lower alkylamino, and di(lower alkyl)amino}, aryl, substituted aryl (the substituents in the substituted aryl have the same meanings as defined for the substituents in the substituted aryl described below), a heterocyclic group, and a substituted heterocyclic group (the substituents in the substituted heterocyclic group have the same meanings as defined for the substituents in the substituted heterocyclic group described below)}, $SR^{23A}$ (wherein $R^{23A}$ has the same meaning as defined for $R^{23}$ described above) or $SO_2R^{23B}$ (wherein $R^{23B}$ is lower alkyl), etc. The lower alkyl moieties of the lower alkyl, lower alkoxy, lower alkoxycarbonyl, lower alkylamino and di(lower alkyl)amino have the same meanings as defined for the lower alkyl described above. The cycloalkyl and the lower alkenyl have the same meanings as defined for the cycloalkyl and lower alkenyl described above, respectively. The lower alkanoyl has the same meaning as defined for the lower alkanoyl described above. The aryl and the aryl moiety of the aroyl have the same meanings as defined for the aryl described above, and the aralkyl and the aralkyl moiety of the aralkyloxycarbonyl mean the aralkyl having 7 to 15 carbon atoms, for example, benzyl, phenetyl, benzhydryl, naphthylmethyl, etc. The heterocyclic group has the same meaning as defined for the heterocyclic group described above, and the heterocyclic group formed together with their adjacent N has the same meaning as defined for the heterocyclic group formed together with their adjacent N described above. The halogen has the same meaning as defined the halogen/described above.

The substituents in the substituted lower alkenyl, substituted lower alkadienyl and substituted lower alkynyl include oxo in addition to the substituents in the substituted lower alkyl described above.

The substituents in the substituted lower alkanoyl include 1 to 3 substituents which are the same or different, for example, halogen, $NR^{17A}R^{18A}$ (wherein $R^{17A}$ and $R^{18A}$ have the same meanings as defined for $R^{17}$ and $R^{18}$ described above, respectively), etc.

The substituents in the substituted aryl and substituted aroyl include 1 to 3 substituents which are the same or different, for example, halogen, lower alkyl, substituted lower alkyl (the substituents in the substituted lower alkyl are halogen, oxo, carboxy, lower alkoxycarbonyl, amino, lower alkylamino, di(lower alkyl)amino, hydroxy or lower alkoxy), nitro, hydroxy, lower alkoxy, amino, lower alkylamino, di(lower alkyl)amino, lower alkanoyl, cyano, etc. The lower alkyl moieties in the lower alkyl, lower alkoxycarbonyl, lower alkoxy, lower alkylamino or di(lower alkyl)amino have the same meaning as defined for the lower alkyl described above. The lower alkanoyl has the same meaning as defined for the lower alkanoyl described above. The halogen has the same meaning as defined for the halogen described above.

The substituents in the substituted heterocyclic group and substituted heterocyclic group formed together with their adjacent N include oxo in addition to the substituents in the substituted aryl and the substituted aroyl described above.

The pharmaceutically acceptable salts of Compound (I) include pharmaceutically acceptable acid addition salts, metal salts, ammonium salts, organic amine addition salts, amino acid addition salts, etc. The acid addition salts include inorganic acid salts such as hydrochloride, sulfate and phosphate and organic acid salts such as methane sulfonate, acetate, maleate, fumarate, tartrate, citrate and lactate; the metal salts include alkali metal salts such as sodium salt and potassium salt, alkaline earth metal salts such as magnesium salt and calcium salt, aluminum salt, zinc salt, etc.; the ammonium salts include salts of ammonium, tetramethylammonium, etc.; the organic amine addition salts include addition salts of morpholine, piperidine, etc.; and the amino acid addition salts include addition salts of lysine, glycine, phenylalanine, aspartic acid, glutamic acid, etc.

The antitumor agent, which can be used in combination with the enhancers for activity provided by the present invention, includes anticancer agents having actions on DNA, for example, platina preparations such as Cisplatin and Carboplatin, Mitomycin type drugs, nitrogen mustard type drugs, nitrosourea type drugs, Camptothecine derivatives (topoisomerase I inhibitors) such as CPT-11 and Topotecan, and Etoposide (topoisomerase II inhibitor), etc., and antimetabolites, for example, 5-Fluorouracil derivatives, Cytidine derivatives such as Cytosine arabinoside (Ara-C) and Gemcitabine, Adenosine derivatives such as Fludarabine, Methotrexate derivatives, TS (thymidylic acid synthase) inhibitors such as Toumidex, etc.

Hereinafter, the processes for the production of Compound (I) are described.

Unless otherwise specified, each group in the reaction steps described below has the same meaning as defined above.

Compound (I) can be produced by the following reaction steps.

In the processes shown below, if the defined groups are changed under the conditions of the practical process or are not appropriate for the practice of the process, the objective compounds can be obtained using the methods for introducing and eliminating protective groups ordinarily used in synthetic organic chemistry [for example, T. W. Greene: Protective Groups in Organic Synthesis, John Wiley & Sons Inc. (1981)]. And also, the order of the reaction steps such as introduction of the substituents etc., can be altered, if necessary.

Process 1

Compound (Ia) that is, Compound (I) wherein $R^1$ is hydrogen, can be produced in a known method [for example, the compound, wherein $R^2$ or $R^3$ is substituted or unsubstituted lower alkyl, substituted or unsubstituted lower alkenyl, substituted or unsubstituted lower alkynyl, substituted or unsubstituted aryl, a substituted or unsubstituted heterocyclic group, halogen, nitro, formyl, $COR^6$ (wherein $R^6$ has the same meaning as defined above), $NR^{11}R^{12}$ (wherein $R^{11}$ and $R^{12}$ have the same meanings as defined above, respectively), etc., can be obtained in a method described in WO88/7045, WO97/46565, etc. and the compound, wherein, $R^2$ or $R^3$ is formyl, lower alkanoyl, carboxy, lower alkoxycarbonyl, $OR^{14}$ (wherein $R^{14}$ has the same meaning as defined above), etc., can be obtained in a method described in Japanese Published Unexamined Application No.3-220194, WO94/6799, etc.] or in a method similar thereto, from Compound (II), which can be obtained in a known method [J. Am. Chem. Soc., 117, 552 (1995), J. Antibiotics, 30, 275 (1977), J. Chem. Soc., Chem. Comm., 800 (1978), etc.]

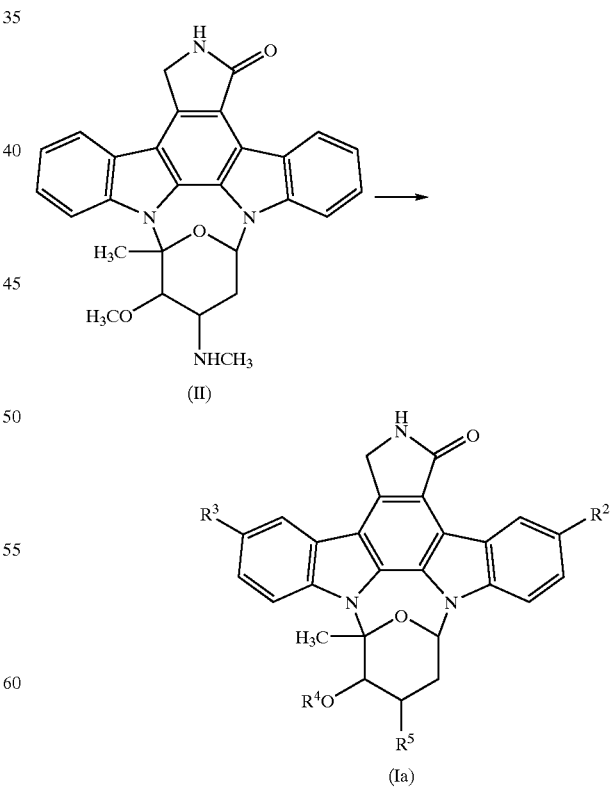

(wherein $R^2$, $R^3$, $R^4$ and $R^5$ have the same meanings as defined above, respectively).

Process 2

Compound (Ib), that is, Compound (I) wherein $R^1$ is hydroxy or lower alkoxy, can be produced in a known method (for example, the compound, wherein $R^1$ is hydroxy, can be obtained in a method described in WO89/7105, Japanese Published Unexamined Application No.1-168689, Japanese Published Unexamined Application No.6-9645, etc., and the compound, wherein $R^1$ is lower alkoxy, can be obtained in a method described in WO89/7105, Japanese Published Unexamined Application No.1-168689, etc.) or in a method similar thereto, from Compound (Ia).

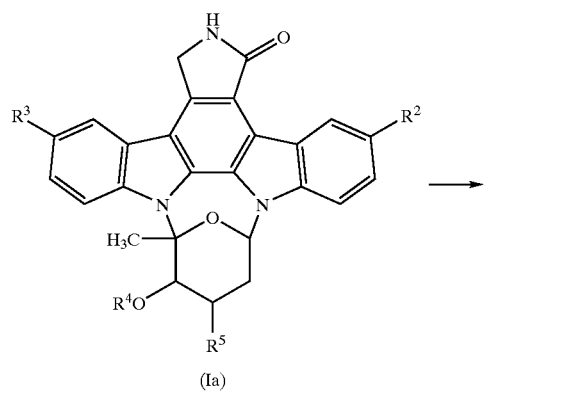

(Ia)

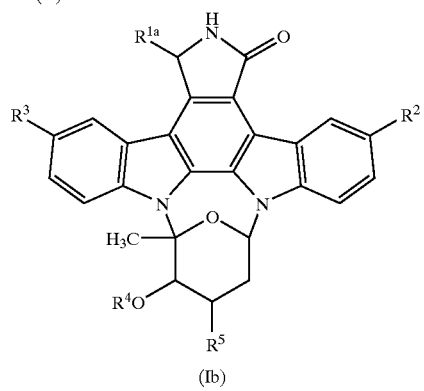

(Ib)

(wherein $R^{1a}$ is hydroxy or lower alkoxy, and $R^2$, $R^3$, $R^4$ and $R^5$ have the same meanings as defined above, respectively).

Transformations of functional groups, contained in substituents in $R^1$, $R^2$, $R^3$, $R^4$ or $R^5$ in Compound (I), obtained in the Examples, and the compounds, obtained in the Reference Examples, can also be conducted by other methods known in the art [for example, R. C. Larock: Comprehensive Organic Transformations (1989)], in addition to the method described above.

By a suitable combination of the methods described above, Compound (I) having objective functional groups at objective positions can be obtained.

The objective products in the processes described above can be isolated and purified by a suitable combination of techniques used in ordinary organic synthesis, such as filtration, extraction, washing, drying, concentration, crystallization and various kinds of chromatography. Further, the intermediates can also be subjected to the subsequent reaction without particular purification.

Compound (I) can exist as isomers such as regioisomers, geometrical isomers, tautomers or optical isomers, and in the present invention, all possible isomers or the mixture thereof in any ratio can be used as the antitumor agents, the enhancers for activity of an antitumor agent, and the agents for abrogating accumulation action at the G2 or S stage of the cell cycle.

Among Compound (I), compounds having the same configuration at the 9-, 10-, 11- and 13-positions as in a staurosporin shown in the following formula, are more preferred.

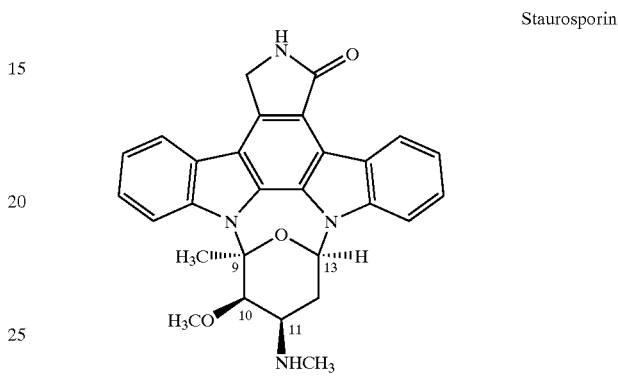

Staurosporin

In the case where a salt of Compound (I) is desired, when Compound (I) is obtained in the form of the salt, it may be directly purified, while when Compound (I) is obtained in its free form, it may be dissolved or suspended in a suitable solvent, and converted into the salt followed by adding an acid or a base thereto.

Compound (I) or pharmaceutically acceptable salts thereof may exist in the form of adducts with water or various solvents, and these adducts also fall under the scope of the present invention.

Specific examples of Compound (I) are shown in Table 1, and the compounds described in the Reference Examples are shown in Table 2. With respect to stereochemistry based on the substituent $R^1$ at the 3-position, (a), (b) and (c) in the tables indicate an isomer of longer retention time, an isomer of shorter retention time, and a mixture of the two isomers, respectively, under the following conditions for high performance liquid chromatography (HPLC).

HPLC analysis was conducted as follows.

Column: YMC AM312 (50×6 mm I.D.)

Mobile phase: Starting from 50% methanol-a 0.02 mol/L phosphate buffer (pH=7), the concentration of methanol was increased at a predetermined rate over 15 minutes to 100% methanol, and thereafter, the sample was eluted with 100% methanol.

TABLE 1

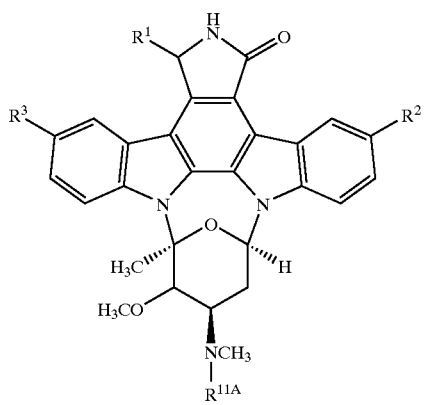

| Example No. | Compound No. | $R^2$ | $R^3$ | $R^{11A}$ | $R^1$ |
|---|---|---|---|---|---|
| 1 | 1 | $NH_2$ | H | H | OH(a) |
| 1 | 2 | $NH_2$ | H | H | OH(b) |
| 2 | 3 | $NH_2$ | $NH_2$ | H | OH(a) |
| 2 | 4 | $NH_2$ | $NH_2$ | H | OH(b) |
| 3 | 5 | $N(CH_3)_2$ | H | H | H |
| 4 | 6 | $N(CH_3)_2$ | H | H | OH(a) |
| 4 | 7 | $N(CH_3)_2$ | H | H | OH(b) |
| 5 | 8 | $N(CH_3)_2$ | $N(CH_3)_2$ | H | OH(a) |
| 5 | 9 | $N(CH_3)_2$ | $N(CH_3)_2$ | H | OH(b) |
| 6 | 10 | CHO | H | H | OH(c) |
| 7 | 11 | CHO | CHO | H | OH(a) |
| 7 | 12 | CHO | CHO | H | OH(b) |
| 8 | 13 | $CH_2OH$ | H | H | OH(a) |
| 8 | 14 | $CH_2OH$ | H | H | OH(b) |
| 9 | 15 | $CH_2OH$ | $CH_2OH$ | H | OH(a) |
| 9 | 16 | $CH_2OH$ | $CH_2OH$ | H | OH(b) |
| 10 | 17 | $CH_3$ | H | H | H |
| 11 | 18 | $CH_3$ | H | H | OH(c) |
| 12 | 19 | $CH_3$ | $CH_3$ | H | H |
| 13 | 20 | $CH_3$ | $CH_3$ | H | OH(c) |
| 14 | 21 | OH | H | H | OH(b) |
| 15 | 22 | OH | OH | H | OH(a) |
| 15 | 23 | OH | OH | H | OH(b) |
| 16 | 24 | Br | H | H | OH(c) |
| 17 | 25 | Br | Br | H | OH(c) |
| 18 | 26 | I | I | $COCF_3$ | $OCH_3$(c) |
| 19 | 27 | I | I | H | $OCH_3$(c) |
| 20 | 28 | I | I | H | OH(c) |
| 21 | 29 | Br | $NO_2$ | $COCF_3$ | H |
| 22 | 30 | Br | $NO_2$ | H | H |
| 23 | 31 | Br | $NH_2$ | $COCF_3$ | H |
| 24 | 32 | H | $NH_2$ | H | OH(a) |
| 24 | 33 | H | $NH_2$ | H | OH(b) |
| 25 | 34 | $NH_2$ | Br | H | H |
| 26 | 35 | $C\equiv CC(CH_3)_2OH$ | H | $COCF_3$ | H |
| 27 | 36 | $C\equiv CC(CH_3)_2OH$ | H | H | H |
| 28 | 37 | $C\equiv CC(CH_3)_2OH$ | H | H | OH(b) |
| 28 | 38 | $C\equiv CC(CH_3)_2OH$ | H | H | OH(a) |
| 29 | 39 | $C\equiv CCH_2CH_2OH$ | H | $COCF_3$ | H |
| 30 | 40 | $C\equiv CCH_2CH_2OH$ | H | H | H |
| 31 | 41 | $C\equiv CCH_2CH_2OH$ | H | H | OH(b) |
| 31 | 42 | $C\equiv CCH_2CH_2OH$ | H | H | OH(a) |
| 32 | 43 | $C\equiv CH$ | H | $COCF_3$ | H |
| 32 | 44 | $C\equiv CH$ | H | H | H |
| 33 | 45 | $C\equiv CH$ | H | H | OH(b) |
| 33 | 46 | $C\equiv CH$ | H | H | OH(a) |
| 34 | 47 | $C\equiv CC_6H_5$ | H | $COCF_3$ | H |
| 35 | 48 | $C\equiv CC_6H_5$ | H | H | H |
| 36 | 49 | $C\equiv CCH_2N(CH_3)_2$ | H | $COCF_3$ | H |
| 36 | 50 | $C\equiv CCH_2N(CH_3)_2$ | H | H | H |
| 37 | 51 | $C\equiv CCH_2N(CH_3)_2$ | H | H | OH(b) |
| 37 | 52 | $C\equiv CCH_2N(CH_3)_2$ | H | H | OH(a) |
| 38 | 53 | $C\equiv CCH_2OCH_3$ | H | $COCF_3$ | H |
| 39 | 54 | $C\equiv CCH_2OCH_3$ | H | H | H |
| 40 | 55 | $CH=CHCO_2CH_3$ | H | $COCF_3$ | H |
| 41 | 56 | $CH=CHCO_2CH_3$ | H | H | H |

TABLE 1-continued

| Example No. | Compound No. | R² | R³ | R¹¹ᴬ | R¹ |
|---|---|---|---|---|---|
| 42 | 57 | CH=CH₂ | H | COCF₃ | H |
| 43 | 58 | CH=CH₂ | H | H | H |
| 44 | 59 | CH=CH—N-pyrrolidinone (2-oxo) | H | COCF₃ | H |
| 45 | 60 | CH=CH—N-pyrrolidinone (2-oxo) | H | H | H |
| 46 | 61 | CH=CH-(2-pyridyl) | H | COCF₃ | H |
| 47 | 62 | CH=CH-(2-pyridyl) | H | H | H |
| 48 | 63 | CH=CH—N-imidazolyl | H | COCF₃ | H |
| 49 | 64 | CH=CH—N-imidazolyl | H | H | H |
| 50 | 65 | CH=CH—N-imidazolyl | H | H | OH(c) |
| 51 | 66 | CH=CH-(4-pyridyl) | H | COCF₃ | H |
| 52 | 67 | CH=CH-(4-pyridyl) | H | H | H |
| 53 | 68 | CH=CH-(4-pyridyl) | H | H | OH(b) |

TABLE 1-continued

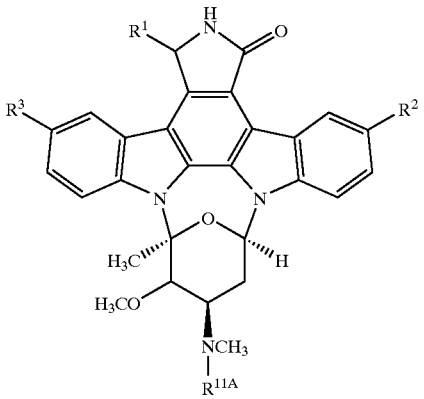

| Example No. | Compound No. | R² | R³ | R¹¹ᴬ | R¹ |
|---|---|---|---|---|---|
| 53 | 69 | CH=CH—(4-pyridyl) | H | H | OH(a) |
| 54 | 70 | CH=CH—(4-methylthiazol-5-yl) | H | H | H |
| 55 | 71 | CH=CH—(1,2,4-triazol-1-yl) | H | H | H |
| 56 | 72 | CH=CHCONH₂ | H | H | H |
| 57 | 73 | CH=CHCO₂C(CH₃)₃ | H | H | H |
| 58 | 74 | CH=CHCO₂H | H | COCF₃ | H |
| 59 | 75 | CH=CH—CO-piperidinyl | H | H | H |
| 60 | 76 | CH=CH—CO-thiomorpholinyl | H | H | H |
| 61 | 77 | CH=CHSO₂CH₃ | H | H | H |
| 62 | 78 | CH=CHCOCH₃ | H | H | H |
| 63 | 79 | CH=CH—(2-pyridyl) | CH=CH—(2-pyridyl) | H | H |
| 64 | 80 | CH=CHCO₂CH₃ | CH=CHCO₂CH₃ | H | H |
| 65 | 81 | CH₂CH₂—(2-pyridyl) | H | COCF₃ | H |
| 66 | 82 | CH₂CH₂—(2-pyridyl) | H | H | H |
| 67 | 83 | CH₂CH₂—(imidazol-1-yl) | H | H | H |

TABLE 1-continued

| Example No. | Compound No. | R² | R³ | R¹¹ᴬ | R¹ |
|---|---|---|---|---|---|
| 68 | 84 | CH₂CH₂CO₂CH₃ | H | H | H |
| 69 | 85 | C₆H₅ | H | COCF₃ | H |
| 70 | 86 | C₆H₅ | H | H | H |
| 71 | 87 | 3-pyridyl (CH₂ linked) | H | COCF₃ | H |
| 72 | 88 | 3-pyridyl (CH₂ linked) | H | H | H |
| 73 | 89 | CH₂N(CH₃)₂ | H | H | H |
| 74 | 90 | CH₂N(CH₃)₂ | H | H | OH(c) |
| 75 | 91 | CH₂N(CH₃)₂ | CH₂N(CH₃)₂ | H | H |
| 76 | 92 | CH₂N(CH₃)₂ | CH₂N(CH₃)₂ | H | OH(c) |
| 77 | 93 | CH₂NHCH₂C₆H₅ | H | H | H |
| 78 | 94 | CH₂NH(CH₂)₃CH₃ | H | H | H |
| 79 | 95 | CH₂NHCH₃ | H | H | H |
| 80 | 96 | CH₂NHC(CH₃)₃ | H | H | H |
| 81 | 97 | CH₂NHCH₂CH₂OH | H | H | H |
| 82 | 98 | CH₂NHCH₂CH₂N(CH₃)₂ | H | H | H |
| 83 | 99 | CH₂NHCH₂CH₂OCH₃ | H | H | H |
| 84 | 100 | CH₂NHC₆H₅ | H | H | H |
| 85 | 101 | CH₂NH—(4-Cl-C₆H₄) | H | H | H |
| 86 | 102 | CH₂OCH₃ | H | H | H |
| 87 | 103 | CH₂OCH₃ | H | H | OH(a) |
| 87 | 104 | CH₂OCH₃ | H | H | OH(b) |
| 88 | 105 | CH₂OCH₂CH₃ | H | COCF₃ | H |
| 89 | 106 | CH₂OCH₂CH₃ | H | H | H |
| 90 | 107 | CH₂OCH₃ | CH₂OCH₃ | COCF₃ | H |
| 91 | 108 | CH₂OCH₃ | CH₂OCH₃ | H | H |
| 92 | 109 | CH₂OCH₃ | CH₂OCH₃ | H | OH(a) |
| 92 | 110 | CH₂OCH₃ | CH₂OCH₃ | H | OH(b) |
| 93 | 111 | CH₂SCH₂CH₃ | H | H | H |
| 94 | 112 | CH₂SCH₂CH₃ | H | H | OH(a) |
| 94 | 113 | CH₂SCH₂CH₃ | H | H | OH(b) |
| 95 | 114 | CH₂SCH₂CH₃ | CH₂SCH₂CH₃ | H | H |
| 96 | 115 | CH₂SCH₂CH₃ | CH₂SCH₂CH₃ | H | OH(a) |
| 96 | 116 | CH₂SCH₂CH₃ | CH₂SCH₂CH₃ | H | OH(b) |
| 97 | 117 | CH₂SO₂CH₂CH₃ | H | H | H |
| 98 | 118 | CH₂SO₂CH₂CH₃ | H | H | OH(a) |
| 98 | 119 | CH₂SO₂CH₂CH₃ | H | H | OH(b) |
| 99 | 120 | CH₂SO₂CH₂CH₃ | CH₂SO₂CH₂CH₃ | H | H |
| 100 | 121 | CH₂SO₂CH₂CH₃ | CH₂SO₂CH₂CH₃ | H | OH(a) |
| 100 | 122 | CH₂SO₂CH₂CH₃ | CH₂SO₂CH₂CH₃ | H | OH(b) |
| 101 | 123 | NHCONHCH₂CH₃ | NHCONHCH₂CH₃ | H | H |
| 102 | 124 | NHCONHC₆H₅ | NHCONHC₆H₅ | H | H |

TABLE 1-continued

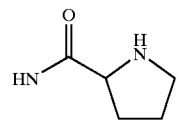

| Example No. | Compound No. | R² | R³ | R¹¹ᴬ | R¹ |
|---|---|---|---|---|---|
| 103 | 125 | NHCONH₂ | H | H | H |
| 104 | 126 | NHCONH₂ | H | H | OH(c) |
| 105 | 127 | NHCONHCH₂CH₃ | H | COCF₃ | H |
| 106 | 128 | NHCONHCH₂CH₃ | H | H | H |
| 107 | 129 | NHCONHCH₂CH₃ | H | H | OH(c) |
| 108 | 130 | NHCONHCH₂CH=CH₂ | H | H | H |
| 109 | 131 | NHCONHC₆H₅ | H | COCF₃ | H |
| 110 | 132 | NHCONHC₆H₅ | H | H | H |
| 111 | 133 | NHCONHC₆H₅ | H | H | OH(c) |
| 112 | 134 | NHCOCH₂NH₂ | H | H | H |
| 113 | 135 | NHCOCH₂NH₂ | H | H | OH(c) |
| 114 | 136 | NHCO(CH₂)₂NH₂ | H | H | H |
| 115 | 137 | NHCSNHC₆H₅ | H | H | H |
| 116 | 138 | NHCSNHCH₂CH₃ | H | H | H |
| 117 | 139 | NHCSNHCH₂CH₃ | H | H | OH(c) |
| 118 | 140 |  | H | H | H |
| 119 | 141 | NHCOC₆H₅ | H | COCF₃ | H |
| 120 | 142 | NHCOC₆H₅ | H | H | H |
| 121 | 143 | 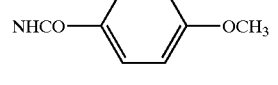 | H | COCF₃ | H |
| 122 | 144 | 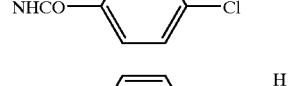 | H | H | H |
| 123 | 145 | 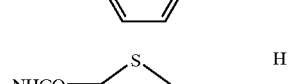 | H | COCF₃ | H |
| 124 | 146 | 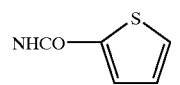 | H | H | H |
| 125 | 147 | 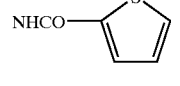 | H | H | H |
| 126 | 148 | 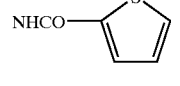 | H | H | OH(b) |

TABLE 1-continued

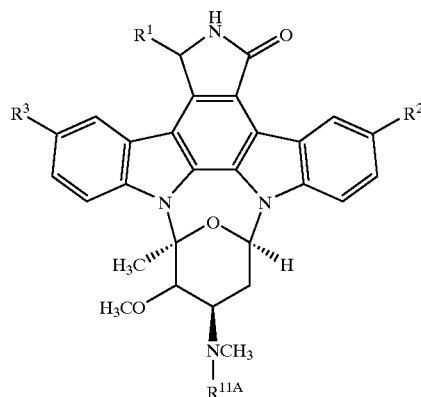

| Example No. | Compound No. | R² | R³ | R¹¹ᴬ | R¹ |
|---|---|---|---|---|---|
| 126 | 149 | NHCO-(2-thienyl) | H | H | OH(a) |
| 127 | 150 | NHCO-(2-thienyl) | Br | H | H |
| 128 | 151 | NHCO(CH$_2$)$_2$CO$_2$CH$_3$ | H | COCF$_3$ | H |
| 129 | 152 | NHCO-(2-Cl-C$_6$H$_4$) | H | H | H |
| 130 | 153 | NHCOC(CH$_3$)$_3$ | H | H | H |
| 131 | 154 | NHCO-(2-OCH$_3$-C$_6$H$_4$) | H | H | H |
| 132 | 155 | NHCOCH=CH$_2$ | H | H | H |
| 133 | 156 | NHCO(CH$_2$)$_6$CH$_3$ | H | H | H |
| 134 | 157 | NHCO-(2,6-Cl$_2$-C$_6$H$_3$) | H | H | H |
| 135 | 158 | NHCO$_2$CH$_2$CH(CH$_3$)$_2$ | H | H | H |
| 136 | 159 | NHSO$_2$CH$_3$ | H | H | H |
| 137 | 160 | NHSO$_2$C$_6$H$_5$ | H | H | H |
| 138 | 161 | NHCOCH$_3$ | H | H | H |
| 139 | 162 | Br | NHCOC$_6$H$_5$ | H | H |
| 140 | 163 | Br | NHCO-(4-Cl-C$_6$H$_4$) | COCF$_3$ | H |
| 141 | 164 | Br | NHCOCO$_2$CH$_3$ | COCF$_3$ | H |
| 142 | 165 | Br | NHCO-(2-thienyl) | H | H |

TABLE 1-continued

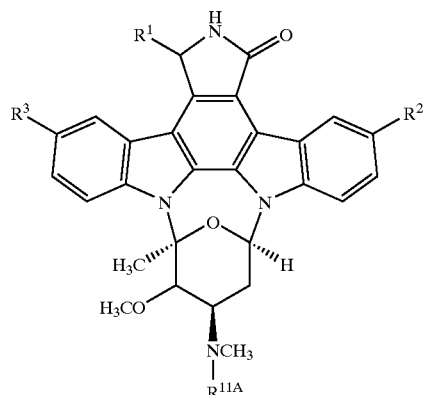

| Example No. | Compound No. | R² | R³ | R¹¹ᴬ | R¹ |
|---|---|---|---|---|---|
| 143 | 166 | Br | NHCO—⟨C₆H₄⟩—OCH₃ | H | H |
| 144 | 167 | Br | NHCO—⟨C₆H₄⟩—OCH₃ | H | OH(b) |
| 144 | 168 | Br | NHCO—⟨C₆H₄⟩—OCH₃ | H | OH(a) |
| 145 | 169 | Br | NHCO—⟨C₆H₄⟩—OCH₃ | H | H |
| 146 | 170 | CH=CHCO₂CH₃ | NHCO—⟨C₆H₄⟩—OCH₃ | H | H |
| 147 | 171 | NH₂ | NHCO—⟨C₆H₄⟩—OCH₃ | H | H |
| 148 | 172 | Br | NHCO(CH₂)₂CO₂CH₃ | H | H |
| 149 | 173 | H | NHCOC₆H₅ | H | H |
| 150 | 174 | H | NHCO—⟨C₆H₄⟩—OCH₃ | H | H |
| 151 | 175 | H | NHCO(CH₂)₂CONH₂ | H | H |
| 152 | 176 | H | NHCO—⟨C₆H₄⟩—Cl | H | H |
| 153 | 177 | H | NHCONHCH₂CH₃ | H | H |
| 154 | 178 | H | NHCONH₂ | H | H |
| 155 | 179 | H | NHCONHCH₂CH=CH₂ | H | H |
| 156 | 180 | H | imidazolidin-2-one | H | H |

TABLE 1-continued

| Example No. | Compound No. | R² | R³ | R¹¹ᴬ | R¹ |
|---|---|---|---|---|---|
| 157 | 181 | CONH(CH₂)₃CH₃ | H | H | H |
| 158 | 182 | CONHCH₃ | H | H | H |
| 159 | 183 | CONHCH₂C₆H₅ | H | H | H |
| 160 | 184 | CONHCH₃ | H | H | OH(b) |
| 160 | 185 | CONHCH₃ | H | H | OH(a) |
| 161 | 186 | CONH(CH₂)₂OH | H | H | H |
| 162 | 187 | CONH(CH₂)₂N(CH₃)₂ | H | H | H |
| 163 | 188 | CON-piperidine | H | H | H |
| 164 | 189 | CON-morpholine | H | H | H |
| 165 | 190 | CON-(N-methylpiperazine) | H | H | H |
| 166 | 191 | CON-pyrrolidine | H | H | H |
| 167 | 192 | CON(CH₃)₂ | H | H | H |
| 168 | 193 | CONHCH₂CONH₂ | H | H | H |
| 169 | 194 | CONH₂ | H | H | H |
| 170 | 195 | CONHC(CH₃)₃ | H | H | H |
| 171 | 196 | CONHCH₂CO₂CH₂CH₃ | H | H | H |
| 171 | 197 | CONHCH₂CO₂H | H | H | H |
| 172 | 198 | CONH-(4-methoxyphenyl) | H | H | H |
| 173 | 199 | CONH-(4-chlorophenyl) | H | H | H |
| 174 | 200 | CONH(CH₂)₃CH₃ | CONH(CH₂)₃CH₃ | H | H |
| 175 | 201 | CON(CH₃)₂ | CON(CH₃)₂ | H | H |
| 176 | 202 | CONHCH₂CH₂OH | CONHCH₂CH₂OH | H | H |
| 177 | 203 | CONHCH₃ | CONHCH₃ | H | H |

TABLE 2

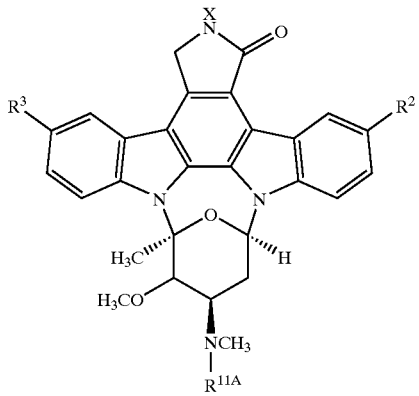

| Reference Example No. | Compound No. | R² | R³ | R¹¹ᴬ | X |
|---|---|---|---|---|---|
| 1 | a | H | H | COCF₃ | H |
| 2 | b | H | H | COOCH₂C₆H₅ | H |
| 3 | c | NO₂ | H | COCF₃ | H |
| 4 | d | NH₂ | H | COCF₃ | H |
| 5 | e | NH₂ | NH₂ | COCF₃ | H |
| 6 | f | NO₂ | NO₂ | COOCH₂C₆H₅ | H |
| 7 | g | CHO | H | COCF₃ | H |
| 7 | h | CHO | CHO | COCF₃ | H |
| 8 | i | H | H | COCF₃ | COCH₃ |
| 9 | j | CHO | H | COCF₃ | COCH₃ |
| 9 | k | CHO | CHO | COCF₃ | COCH₃ |
| 10 | m | CH₂OH | H | COCF₃ | COCH₃ |
| 11 | n | CH₂OH | CH₂OH | COCF₃ | COCH₃ |
| 12 | p | CH₂OH | H | H | H |
| 13 | q | CH₂OH | CH₂OH | H | H |
| 14 | r | OH | H | H | H |
| 15 | s | OH | OH | H | H |
| 16 | t | CO₂H | H | COCF₃ | COCH₃ |
| 17 | u | CO₂H | CO₂H | COCF₃ | COCH₃ |
| 18 | v | CO₂H | H | H | H |
| 19 | w | CO₂H | CO₂H | H | H |
| 20 | y | Br | H | COCF₃ | H |
| 21 | z | Br | H | H | H |
| 22 | aa | Br | Br | COCF₃ | H |
| 23 | ab | Br | Br | H | H |
| 24 | ac | I | H | COCF₃ | H |
| 25 | ad | I | I | COCF₃ | H |
| 26 | ae | I | I | H | H |

Compound (I) or pharmaceutically acceptable salts thereof can be used as it is or in various pharmaceutical forms, depending on the pharmacological action thereof and the object of administration. The pharmaceutical compositions of the present invention can be produced by uniformly mixing an effective amount of Compound (I) or a pharmaceutically acceptable salt thereof as an active ingredient with a pharmaceutically acceptable carrier. The carrier can be in various forms depending on the form of a preparation desirable for administration. These pharmaceutical compositions are desirably in a unit administration form being suitable for oral administration or parenteral administration such as an ointment or injection.

For the preparation of tablets, for example, an excipient such as lactose, glucose, sucrose, mannitol or methyl cellulose, a disintegrator such as starch, sodium alginate, carboxymethyl cellulose calcium or crystalline cellulose, a lubricant such as magnesium stearate or talc, a binder such as gelatin, polyvinylalcohol, polyvinylpyrrolidone, hydroxypropyl cellulose or methyl cellulose, or a surfactant such as a sucrose fatty acid ester or a sorbitol fatty acid ester may be used in a usual manner. Tablets containing 1 to 200 mg of an active ingredient per tablet are preferred.

For the preparation of granules, for example, an excipient such as lactose or sucrose, a disintegrator such as starch, or a binder such as gelatin may be used in a usual manner.

For the preparation of powders, for example, an excipient such as lactose or mannitol may be used in a usual manner.

For the preparation of capsules, for example, gelatin, water, sucrose, gum Arabia, sorbitol, glycerin, crystalline cellulose, magnesium stearate, talc, etc., may be used in a usual manner. Capsules containing 0.1 to 200 mg of an active ingredient per capsule are preferred.

For the preparation of syrups, for example, a sugar such as sucrose, water, ethanol, etc., may be used in a usual manner.

For the preparation of ointments, for example, an ointment base such as vaseline, liquid paraffin, lanoline or Macrogol, or an emulsifier such as sodium lauryl lactate, benzalkonium chloride, a sorbitan mono-fatty acid ester, carmellose sodium, or gum Arabia, etc., may be used in a usual manner.

For the preparation of injections, for example, water, physiological saline, a vegetable oil (olive oil, peanut oil, etc.), a solvent (ethyl oleate, propylene glycol, polyethylene glycol, etc.), a solubilizing agent (sodium benzoate, sodium salicylate, urethane, etc.), an isotonizing agent (sodium chloride, glucose, etc.), a preservative (phenol, cresol, p-hydroxybenzoic acid ester, chlorobutanol, etc.), or an antioxidant (ascorbic acid, sodium pyrosulfite, etc.), may be used in a usual manner.

Compound (I) or pharmaceutically acceptable salts thereof can be administered orally or parenterally as an ointment or injection, and generally preferred to be administered in a dose of 0.1 to 200 mg/kg per day, although the effective dose and frequency of administration are varied depending on the administration form, patient's age or weight, symptoms, etc.

Hereinafter, the activity of Compound (I) is described by reference to Test Examples.

TEST EXAMPLE 1

Test for Inhibitory Activity on Cell Growth in Human Lung Cancer Cell Line A-549

A human lung cancer cell line A-549, which was prepared at a density of $1.0 \times 10^4$ cells/mL in a Roswell Park Memorial Institute's Medium (PRMI) 1640 medium containing 10% fetal bovine serum and Penicillin/Streptomycin, was put in an amount of 0.1 mL/well on a 96 MicroWell™ plate (Catalog No. 167008, produced by Nunc). The cells were cultured at 37° C. for 20 hours in a $CO_2$ gas incubator, a 10 mmol/L solution of each test compound in dimethyl sulfoxide (DMSO) was diluted with the culture medium, the diluted mixture was added into each well in an amount of 0.05 mL/well, the mixture was diluted stepwise by pipetting on the plate, and the cells were cultured at 37° C. for 72 hours in a $CO_2$ gas incubator.

After the removal of the culture supernatant, a medium containing 1 mg/ML of 3-(4,5-dimethylthiazol-2-yl)-2,5-diphenyltetrazolium bromide (Sigma) was added into each well in an amount of 0.05 mL/well and the cells were cultured at 37° C. for 5 hours in a $CO_2$ gas incubator. Then, the medium was removed, and DMSO was added into each well in an amount of 0.1 mL/well. The plate was vigorously stirred using a plate mixer, and then the absorbance of each cell at 550 nm was measured by a microplate reader (Wako Pure Chemical Industries, Ltd.) The inhibitory activity on cell growth was calculated as a 50% inhibitory concentration ($IC_{50}$) by use of the formula in measurement software (Soft Max Pro) attached to the microplate reader.

TEST EXAMPLE 2

Test for Affinity with Human AGP Using Dextran Coated Charcoal (DCC)

A solution of the test compound in DMSO was added to an isotonic phosphate buffer (PBS, pH=7.4) containing human AGP, to prepare an equimolar solution (20 μmol/L) of the test compound and human AGP. The solution was pre-incubated at 37° C. for 15 minutes and then mixed with an equal volume of 4 mg/mL of DCC in PBS, and incubation was further continued. After two hours from mixing, a part of the solution was sampled and centrifuged (4° C., 20000× g, 2 minutes) to precipitate the charcoal, and the supernatant was subjected to HPLC analysis. Separately, an equimolar solution (20 μmol/L) of the test compound and human AGP was mixed with an equal volume of PBS (pH=7.4), and then the mixed solution was subjected as a DCC-untreated sample to HPLC analysis. The ratio of the peak area of the DCC-treated sample to the average peak area of the DCC-untreated sample (the solution mixed with PBS) was calculated as the degree of binding (%). A compound showing a lower degree of binding was regarded as a compound having a lower binding activity to human AGP.

The results in Test Examples 1 and 2 are shown in Table 3.

TABLE 3

| Compound No. | Inhibitory activity on cell growth ($IC_{50}$/μmol/L) | Degree of binding to $h\alpha_1 AGP$ (%) |
|---|---|---|
| UCN-01 | 0.018 | 76.8 |
| 2 | 0.015 | 20.5 |
| 3 | 0.059 | 10.6 |
| 11 | 0.053 | 5.8 |
| 15 | 0.074 | 18.0 |
| 36 | 0.076 | 36.1 |
| 40 | 0.024 | 33.5 |
| 44 | 0.0051 | 16.4 |
| 64 | 0.026 | 19.8 |
| 102 | 0.0092 | 37.7 |
| 129 | 0.11 | 18.4 and 9.6 |
| 147 | 0.19 | 36.9 |
| 172 | 0.14 | 18.0 |
| 176 | 0.034 | 21.2 |

TEST EXAMPLE 3

Action of the Compound on Abrogation of Accumlation Action at the G2 Stage and S Stage of the Cell Cycle The action of the compound on abrogation of accumulation action at G2 stage and S stage of the cell cycle was examined by using human epidermal cancer cell line A431 (hereinafter referred to as A431 cells). A suspension of A431 cells, which was prepared at a density of $3 \times 10^4$ cells/mL in DMEM medium containing 10% fetal bovine serum (hereinafter referred to as medium A, produced by Nissui), was pipetted in a volume of 10 mL onto a 10 cm Petri dish (Catalog No. 3003, produced by Falcon). The Petri dish was incubated at 37° C. for 24 hours in a $CO_2$ gas incubator. Then, Cisplatin (Sigma) prepared at a final concentration of 20 μmol/L in medium A, was added into the Petri dish and the Petri dish was further incubated at 37° C. for 1 hour in a $CO_2$ gas incubator.

After the removal of the medium, the cells were washed with PBS(−) [phosphate buffered saline (not containing calcium ions), produced by Dainippon Pharmaceutical Co., Ltd.], then medium A was further added into the Petri dish, and the cells were cultured at 37° C. for 15 hours in a $CO_2$ gas incubator. The test compound diluted appropriately with medium A was added into the Petri dish, and then the cells were cultured at 37° C. for 8 hours in a $CO_2$ gas incubator. After the removal of the culture supernatant, the cells were washed with PBS(−), detached in an aqueous solution of 0.25% of Trypsin (GIBCO BRL) and 0.02% of ethylenediaminetetraacetic acid (Wako Pure Chemical Industries, Ltd.), then fixed at a density of $10^6$ cells/mL with a 70% aqueous solution of ethanol and stored in a cold room at 4° C. Ethanol was removed by centrifugation from the fixed cells, and then the fixed cells were washed with PBS(−). The cells were treated at 37° C. for 30 minutes with a 0.25 mg/mL PBS(−)solution of ribonuclease A type 1-A (Sigma) containing 0.1% of Nonidet P-40 (Nacalai Tesque, Inc.), and then a solution of propidiumiodide (Sigma) in 0.1% NP-40/PBS(−) was added into the cells at a final concentration of 50 μg/mL, and the cells were stained in ice for at least 20 minutes.

A DNA histogram was taken by EPICS ELITE Flow Cytometer, and the cell cycle distribution was analyzed by use of MultiCycle Program.

The results are shown in Table 4. In the method shown in Test Example 3, the G2 stage and the M stage of the cell cycle can not be distinguished from each other, and thus the distrubution of the G2 stage combined with that of the M stage (G2 stage+M stage) is expressed in percentage. However, the M stage accounts for only 1% of the whole (100%), so the ratio of the distrubution of (G2 stage+M stage) is considered almost identical with that of the G2 stage.

TABLE 4

| | C II cycl distributi n (%) | | |
|---|---|---|---|
| | G1 stage | S stage | G2 stage + M stage |
| Non-treatment | 36.1 | 49.9 | 14.0 |
| Cisplatin(20 μmo/L) | 5.5 | 77.0 | 17.5 |
| Cisplatin(20 μmo/L) + UCN-01 (50 nmol/L) | 31.9 | 40.5 | 27.6 |
| Cisplatin (20 μmo/L) + Compound 3(200 nmol/L) | 22.0 | 55.3 | 22.7 |
| Cisplatin (20 μmo/L) + Compound 11(200 nmol/L) | 28.5 | 54.0 | 17.5 |
| Cisplatin (20 μmo/L) + Compound 22(200 nmol/L) | 15.7 | 46.3 | 38.1 |
| Cisplatin (20 μmo/L) + Compound 52(200 nmol/L) | 22.9 | 63.7 | 13.4 |

An increase in the S stage, an increase in (G2 stage+M stage) and a decrease in the G1 stage (prevention of progress toward the next cell cycle, that is, accumulation action at the G2 stage or S stage) were recognized in the cell cycle distribution in the group, which was treated with only Cisplatin (20 μmol/L), in comparison to the cell cycle distribution in the untreated group.

When UCN-01 (50 mmol/L) was used in combination with Cisplatin (20 μmol/L), a decrease in the S stage and an increase in the G1 stage (abrogation of accumulation action at the G2 stage and S stage) were recognized.

Also when Compound 3, 11, 22 or 52 (each 200 mmol/L) was used in combination with Cisplatin, the action of abrogating accumulation action at the G2 stage and S stage was also similarly confirmed. Accordingly, it was suggested that the compounds of the present invention abrogate accumulation action at the G2 stage and S stage, thus enhancing the cell-killing effect of Cisplatin.

BEST MODE FOR CARRYING OUT THE INVENTION

Hereinafter, the present invention is described in more detail by the Examples.

In proton nuclear magnetic resonance spectrum ($^1$H-NMR) used in the Examples, an exchangeable hydrogen may not clearly be measured depending on the compound used and measurement conditions. Signal multiplicity is expressed in conventional terms where br is indicative of an apparently broad signal.

EXAMPLE 1

Compounds 1 and 2

Step 1

1.01 g (1.68 mmol) of Compound b obtained in Reference Example 2 was dissolved in 100 mL of methylene chloride followed by adding 0.30 mL (6.9 mmol) of fuming nitric acid, and then the mixture was stirred for 10 minutes. The reaction mixture was neutralized with a saturated aqueous solution of sodium bicarbonate, and subjected to extraction with chloroform. The organic layer was washed with water and then with a saturated saline solution, and dried over anhydorus sodium sulfate. After the solvent was distilled away, the residue was purified by silica gel column chromatography (eluted with chloroform/methanol=40/1) and triturated in methanol to give 800 mg of 17-nitro-11-N-benzyloxycarbonyl staurosporin (73%).

$^1$H-NMR (270 M Hz, DMSO-$d_6$) δ (ppm): 10.24 (1H, brs), 8.48 (1H, s), 8.34 (1H, dd, J=8.6, 1.7 Hz), 8.08 (1H, d, J=7.9 Hz), 7.95 (1H, d, J=8.6 Hz), 7.78 (1H, brd, J=9.2 Hz), 7.53 (1H, dd, J=7.9, 7.6 Hz), 7.44–7.12 (6H, m), 7.10 (1H, m), 5.24 (1H, d, J=13.2 Hz), 5.18 (1H, d, J=12.5 Hz), 5.08 (2H, s), 4.68 (1H, m), 4.26 (1H, brs), 2.83 (1H, m), 2.75 (3H, s), 2.64 (3H, s), 2.35 (1H, m), 2.32 (3H, s).

MS (FAB, m/z): 646 (M+1)$^+$.

Step 2

205 mg (0.318 mmol) of 17-nitro-11-N-benzyloxycarbonyl staurosporin was dissolved in 20 mL of N,N-dimethylformamide and, subjected to catalytic reduction in an atmosphere of hydrogen in the presence of 206 mg of palladium hydroxide at ordinary temperature under normal pressure for 2 hours. After the reaction mixture was filtered with Celite, the solvent was removed under reduced pressure, and the residue was purified by preparative thin-layer chromatography (developed with chloroform/methanol=4/1), to give 114 mg of 17-aminostaurosporin (75%).

$^1$H-NMR (270 M Hz, DMSO-$d_6$) δ (ppm): 8.48 (1H, d, J=1.3 Hz), 8.43 (1H, s), 7.99–7.92 (2H, m), 7.40 (1H, dd, J=8.6, 7.3 Hz), 7.29–7.24 (2H, m), 6.85 (1H, dd, J=8.6, 1.3 Hz), 6.61 (1H, m), 4.90 (2H, s), 4.10 (1H, brs), 3.26 (1H, m), 3.18 (3H, brs), 2.41 (2H, m), 2.31 (3H, s), 1.66 (3H, brs).

MS (FAB, m/z): 482 (M+1)$^+$.

Step 3

108 mg (0.224 mmol) of 17-aminostaurosporin was dissolved in dimethyl sulfoxide followed by adding 2.0 mL of a 6 mol/L aqueous solution of sodium hydroxide, and then the mixture was stirred at room temperature for 1 hour. After the reaction was completed, the reaction mixture was diluted with an iced water, and treated with HP-20 resin (Mitsubishi Kagaku Diaion HP20) to remove the dimethyl sulfoxide by washing with water. And the components absorbed were eluted with methanol and then with acetone, and the solvent was distilled away under reduced pressure. The residue was separated and purified by preparative thin-layer chromatography (developed with chloroform/methanol/28% ammonia water=40/10/1) and then by preparative thin-layer chromatography (developed with chloroform/methanol=4/1) and triturated in a mixed solvent of ethyl acetate and diisopropyl ether to give 19.1 mg of Compound 1 (17%) and 26.1 mg of Compound 2 (23%). The ratio of the respective diastereoisomers based on their hydroxyl group by HPLC was as follows: Compound 1 (96% d.e.) and Compound 2 (95% d.e.)

Compound 1

$^1$H-NMR (270 M Hz, DMSO-$d_6$) δ (ppm): 8.65 (1H, s), 8.42 (1H, d, J=2.2 Hz), 8.40 (1H, d, J=8.6 Hz), 7.94 (1H, d, J=8.3 Hz), 7.37 (1H, ddd, J=8.3, 7.5, 0.8 Hz), 6.84 (1H, dd, J=8.6, 2.2 Hz), 7.30–7.20 (2H, m), 6.56 (1H, m), 6.39 (1H, d, J=10.0 Hz), 6.34 (1H, d, J=10.0 Hz), 4.86 (2H, brm), 4.08 (1H, brd, J=3.0 Hz), 3.27 (3H, brs), 3.33 (1H, m), 2.50 (2H, m), 2.27 (3H, s), 1.67 (3H, brs).

MS (FAB, m/z): 498 (M+1)$^+$.

Compound 2

$^1$H-NMR (270 M Hz, DMSO-$d_6$) δ (ppm): 8.65 (1H, s), 8.42 (1H, d, J=2.0 Hz), 8.34 (1H, dd, J=7.9, 0.8 Hz), 7.95 (1H, d, J=8.6 Hz), 7.37 (1H, ddd, J=8.6, 7.9, 0.8 Hz), 7.29–7.20 (2H, m), 6.84 (1H, dd, J=8.6, 2.0 Hz), 6.57 (1H, m), 6.34 (2H, s), 4.08 (1H, m), 3.33 (1H, m), 3.25 (3H, brs), 2.43 (2H, m), 2.28 (3H, s), 1.60 (3H, brs).

MS (FAB, m/z): 498 (M+1)$^+$.

EXAMPLE 2

Compounds 3 and 4

Step 1

In a manner similar to that in step 2 of Example 1, 210 mg (0.305 mmol) of Compound f obtained in Reference Example 6 was subjected to catalytic reduction in an atmosphere of hydrogen in the presence of 211 mg of palladium hydroxide to give 116 mg of 5,17-diaminostaurosporin (77%).

$^1$H-NMR (270 M Hz, DMSO-$d_6$) δ (ppm): 8.45 (1H, d, J=2.0 Hz), 8.33 (1H, s), 7.64 (1H, d, J=9.2 Hz), 7.23 (1H, d, J=8.6 Hz), 7.10 (1H, s), 6.82 (1H, dd, J=8.6, 2.0 Hz), 6.76 (1H, d, J=9.2 Hz), 6.55 (1H, m), 4.80 (2H, s), 4.77 (4H, brm), 4.02 (1H, brs), 3.34 (1H, m), 3.11 (3H, brs), 2.68 (1H, m), 2.50 (1H, m), 2.24 (3H, s), 1.76 (3H, brs).

MS (FAB, m/z): 497 (M+1)$^+$.

Step 2

In a manner similar to that in step 3 of Example 1, 9.9 mg of Compound 3 (11%) and 11.4 mg of Compound 4 (13%) were obtained from 87.1 mg (0.170 mmol) of 5,17-diaminostaurosporin, dimethyl sulfoxide, and 1.7 mL of a 6 mol/L aqueous solution of sodium hydroxide. The ratio of the respective diastereoisomers based on their hydroxyl group by HPLC was as follows: Compound 3 (90% d.e.) and Compound 4 (91% d.e.)

Compound 3

$^1$H-NMR (270 M Hz, DMSO-$d_6$) δ (ppm): 8.55 (1H, s), 8.40 (1H, d, J=2.3 Hz), 7.62 (1H, d, J=8.8 Hz), 7.59 (1H, brs), 7.24 (1H, d, J=8.8 Hz), 6.81 (1H, dd, J=8.8, 2.2 Hz), 6.75 (1H, dd, J=8.8, 2.3 Hz), 6.53 (1H, m), 6.22 (1H, d, J=10.5 Hz), 6.21 (1H, d, J=10.5 Hz), 4.81 (4H, brm), 4.01 (1H, brs), 3.33 (1H, m), 3.18 (3H, brs), 2.38 (2H, m), 2.20 (3H, s), 1.77 (3H, brs).

MS (FAB, m/z): 513 (M+1)$^+$.

Compound 4

$^1$H-NMR (270 M Hz, DMSO-d$_6$) δ (ppm): 8.57 (1H, s), 8.40 (1H, d, J=2.0 Hz), 7.63 (1H, d, J=8.7 Hz), 7.54 (1H, brs), 7.23 (1H, d, J=8.7 Hz), 6.82 (1H, dd, J=8.7, 2.3 Hz), 6.75 (1H, dd, J=8.7, 2.0 Hz), 6.54 (1H, m), 6.24 (1H, d, J=10.4 Hz), 6.18 (1H, d, J=10.4 Hz), 4.85 (4H, m), 4.03 (1H, brs), 3.34 (1H, m), 3.11 (3H, brm), 2.50 (1H, m), 2.32 (1H, m), 2.24 (3H, s), 1.77 (3H, brs).

MS (FAB, m/z): 513 (M+1)$^+$.

EXAMPLE 3

Compound 5

Step 1

115 mg (0.183 mmol) of Compound d obtained in Reference Example 4 was dissolved in 14 mL of dichloroethane followed by adding 0.20 mL (2.5 mmol) of a 37% aqueous solution of formaldehyde, 515 mg (2.43 mmol) of sodium triacetoxyborohydride and 0.15 mL (2.5 mmol) of acetic acid, under an atmosphere of argon, and then the mixture was stirred at room temperature for 20 minutes. The reaction was terminated by adding water, and the reaction mixture was neutralized with a saturated aqueous solution of sodium bicarbonate, and subjected to extraction with chloroform. The organic layer was washed with a saturated saline solution and dried over anhydrous sodium sulfate. After the solvent was distilled away under reduced pressure, the residue was purified by preparative thin-layer chromatography (developed with chloroform/methanol=15/1) to give 90.4 mg of 17-dimethylamino-11-N-trifluoroacetyl staurosporin (62%).

$^1$H-NMR (270 M Hz, DMSO-d$_6$) δ (ppm): 8.89 (1H, brs), 8.56 (1H, brs), 8.06–7.95 (2H, m), 7.64–7.20 (4H, m), 6.99 (1H, brs), 4.99 (2H, s), 4.90 (1H, m), 4.43 (1H, brs), 2.97 (6H, s), 2.89 (3H, s), 2.84 (1H, m), 2.77 (3H, s), 2.50 (1H, m), 2.37 (3H, s).

MS (FAB, m/z): 606 (M+1)$^+$.

Step 2

90.1 mg (0.149 mmol) of 17-dimethylamino-11-N-trifluoroacetyl staurosporin was dissolved in a: mixed solvent of 20 mL of chloroform and 10 mL of methanol followed by adding 3 mL of a 6 mol/L aqueous solution of sodium hydroxide, and then the mixture was stirred at room temperature for 30 minutes. After neutralization with 1 mol/L hydrochloric acid, there action mixture was made weakly alkaline with a saturated aqueous solution of sodium bicarbonate, and subjected to extraction with chloroform. The organic layer was washed with a saturated saline solution, and dried over anhydrous sodium sulfate. The solvent was distilled away under reduced pressure, and the residue was purified by preparative thin-layer chromatography (developed with chloroform/methanol=15/1) to give 58.2 mg of Compound 5 (77%).

$^1$H-NMR (270 M Hz, DMSO-d$_6$) δ (ppm): 8.81 (1H, d, J=2.5 Hz), 8.41 (1H, s), 7.99–7.93 (2H, m), 7.45–7.37 (2H, m), 7.26 (1H, t, J=7.3 Hz), 7.08 (1H, dd, J=8.9, 2.5 Hz), 6.63 (1H, m), 4.92 (2H, s), 4.07 (1H, brs), 3.34 (1H, m), 3.28 (3H, brs), 2.95 (6H, s), 2.50 (2H, m), 2.30 (3H, s), 1.53 (3H, brs).

MS (FAB, m/z): 509 (M)$^+$.

EXAMPLE 4

Compounds 6 and 7

In a manner similar to that in step 3 of Example 1, 7.4 mg of Compound 6 (15%), and 12.1 mg of Compound 7 (24%) were obtained from 48.0 mg (0.094 mmol) of Compound 5, dimethyl sulfoxide and 1.0 mL of a 6 mol/L aqueous solution of sodium hydroxide. The ratio of the respective diastereoisomers based on their hydroxyl group by HPLC was as follows: Compound 6 (95% d.e.) and Compound 7 (91% d.e.)

Compound 6

$^1$H-NMR (270 M Hz, DMSO-d$_6$) δ (ppm): 8.75 (1H, d, J=2.3 Hz), 8.65 (1H, s), 8.40 (1H, d, J=7.9 Hz), 7.94 (1H, d, J=8.7 Hz), 7.44 (1H, d, J=9.0 Hz), 7.37 (1H, dd, J=8.7, 7.4 Hz), 7.23 (1H, dd, J=7.9, 7.4 Hz), 7.09 (1H, dd, J=9.0, 2.3 Hz), 6.60 (1H, m), 6.42 (1H, d, J=9.9 Hz), 6.36 (1H, d, J=9.9 Hz), 4.06 (1H, brs), 3.34 (4H, m), 2.95 (6H, s), 2.50 (2H, m), 2.27 (3H, s), 1.57 (3H, brs).

MS (FAB, m/z): 526 (M+1)$^+$.

Compound 7

$^1$H-NMR (270 M Hz, DMSO-d$_6$) δ (ppm): 8.75 (1H, d, J=2.3 Hz), 8.66 (1H, s), 8.35 (1H, d, J=7.6 Hz), 7.95 (1H, d, J=8.4 Hz), 7.44 (1H, d, J=8.9 Hz), 7.38 (1H, dd, J=8.4, 7.3 Hz), 7.23 (1H, dd, J=7.6, 7.3 Hz), 7.09 (1H, dd, J=8.9, 2.3 Hz), 6.61 (1H, m), 6.36 (2H, s), 4.06 (1H, brs), 3.34 (1H, m), 3.28 (3H, brm), 2.95 (6H, s), 2.50 (2H, m), 2.28 (3H, s), 1.48 (3H, brs).

MS (FAB, m/z): 526 (M+1)$^+$.

EXAMPLE 5

Compounds 8 and 9

Step 1

1.02 g (1.48 mmol) of Compound f obtained in Reference Example 6 was dissolved in a mixed solvent of 50 mL of tetrahydrofuran and 50 mL of ethanol followed by adding 4.42 g (19.6 mmol) of tin (II) chloride.2H$_2$O, and then the mixture was heated to 60° C. A solution of 169 mg (4.47 mmol) of sodium borohydride in a mixed solvent of 10 mL of tetrahydrofuran and 10 mL of ethanol was added to the above mixture, and the mixture was stirred for 7 hours. After the reaction was completed, the reaction mixture was diluted with tetrahydrofuran and ethyl acetate, and then neutralized by the gradual addition of a saturated aqueous solution of sodium bicarbonate. The resulting precipitates were separated by filtration. The filtrate was subjected to extraction with ethyl acetate, the extract was washed with a saturated saline solution and dried over anhydrous sodium sulfate, and then the solvent was distilled away under reduced pressure. The residue was purified by silica gel column chromatography (eluted with chloroform/methanol/acetic acid=9/1/0.1) and triturated in ethyl acetate to give 388 mg of 5,17-diamino-11-N-benzyloxycarbonyl staurosporin (44%).

$^1$H-NMR (270 M Hz, DMSO-d$_6$) δ (ppm): 8.48 (1H, s), 8.09 (1H, brs), 7.55 (1H, d, J=7.9 Hz), 7.43–7.41 (5H, m), 7.26–7.18 (2H, m), 6.83–6.74 (3H, m), 5.26 (1H, d, J=12.1 Hz), 5.16 (1H, d, J=12.1 Hz), 4.83 (2H, s), 4.66 (1H, m), 4.08 (1H, s), 2.73 (3H, s), 2.63 (3H, s), 2.50 (2H, m), 2.21 (3H, s).

MS (FAB, m/z): 631 (M+1)$^+$.

Step 2

In a manner similar to that in step 1 of Example 3, 114 mg of 5,17-bis(dimethylamino)-11-N-benzyloxycarbonyl staurosporin (91%) was obtained from 115 mg (0.183 mmol) of 5,17-diamino-11-N-benzyloxycarbonyl staurosporin, 0.30 mL (3.7 mmol) of a 37% aqueous solution of formaldehyde, 777 mg (3.67 mmol) of sodium triacetoxyborohydride and 0.22 mL (3.7 mmol) of acetic acid.

¹H-NMR (270 M Hz, DMSO-d₆) δ (ppm): 8.95 (1H, brs), 8.17 (1H, brm), 7.74 (1H, brm), 7.19–7.43 (9H, m), 6.86 (1H, m), 5.19–5.26 (2H, m), 5.14 (2H, s), 4.65 (1H, m), 4.13 (1H, brs), 3.03 (14H, m), 2.74 (3H, s), 2.62 (3H, s), 2.25 (3H, s).

MS (FAB, m/z): 687 (M+1)⁺.

Step 3

In a manner similar to that in step 2 of Example 1, 111 mg (0.162 mmol) of 5,17-bis(dimethylamino)-11-N-benzyloxycarbonyl staurosporin was subjected to catalytic reduction in an atmosphere of hydrogen in the presence of 113 mg of 10% palladium carbon (50% hydrous product) to give 55.6 mg of 5,17-bis(dimethylamino)staurosporin (62%).

¹H-NMR (270 M Hz, DMSO-d₆) δ (ppm): 8.82 (1H, d, J=2.0 Hz), 7.83 (1H, m), 7.41 (1H, m), 7.17 (1H, m), 7.11–6.99 (2H, m), 6.67 (1H, m), 5.12 (2H, brs), 4.13 (1H, m), 3.35 (1H, m), 3.01–2.95 (15H, m), 2.50 (2H, m), 2.31 (3H, s), 1.94 (3H, brm).

MS (FAB, m/z): 553 (M+1)⁺.

Step 4

In a manner similar to that in step 3 of Example 1, 3.5 mg of Compound 8 (5%) and 14.8 mg of Compound 9 (20%) were obtained from 72.1 mg (0.130 mmol) of 5,17-bis (dimethylamino)staurosporin, dimethyl sulfoxide and 1.5 mL of a 6 mol/L aqueous solution of sodium hydroxide. The ratio of the respective diastereoisomers based on their hydroxyl group by HPLC was as follows: Compound 8 (99% d.e.) and Compound 9 (97% d.e.)

Compound 8

¹H-NMR (270 M Hz, DMSO-d₆) δ (ppm): 8.74 (1H, d, J=2.6 Hz), 8.57 (1H, s), 7.83–7.70 (2H, m), 7.41 (1H, d, J=9.2 Hz), 7.09–6.97 (2H, m), 6.58 (1H, m), 6.39 (2H, m), 4.03 (1H, brs), 3.35 (1H, m), 3.27 (3H, brm), 2.95 (12H, s), 2.50 (2H, m), 2.23 (3H, s), 1.65 (3H, brs).

MS (FAB, m/z): 569 (M+1)⁺.

Compound 9

¹H-NMR (270 M Hz, DMSO-d₆) δ (ppm): 8.73 (1H, d, J=2.6 Hz), 8.61 (1H, s), 7.80–7.71 (2H, m), 7.41 (1H, d, J=8.8 Hz), 7.07 (1H, dd, J=8.9, 2.6 Hz), 6.99 (1H, dd, J=8.8, 2.6 Hz), 6.59 (1H, m), 6.35 (2H, brs), 4.01 (1H, brs), 3.35 (1H, m), 3.28 (3H, brs), 2.95 (12H, s), 2.50 (2H, m), 2.23 (3H, s), 1.53 (3H, brs).

MS (FAB, m/z): 569 (M+1)⁺.

EXAMPLE 6

Compound 10

In a manner similar to that in step 3 of Example 1, 9.5 mg of Compound 10 (20%) was obtained from 12.4 mg (0.0216 mmol) of Compound g obtained in Reference Example 7, dimethyl sulfoxide and 0.2 mL of a 6 mol/L aqueous solution of sodium hydroxide. The resulting product was a mixture (1:1) of isomers based on their hydroxyl group by HPLC.

¹H-NMR (270 MHz, DMSO-d₆) δ (ppm): 10.09 (1H, s), 9.74 (1H, brs), 8.90 (1H, brs), 8.43 and 8.37 (Total 1H, 2d, J=7.6 Hz), 8.01 (1H, d, J=8.6 Hz), 8.01 (1H, d, J=8.6 Hz), 7.80 (1H, d, J=8.6 Hz), 7.42 (1H, dd, J=8.2, 7.6 Hz), 7.26 (1H, dd, J=7.6, 6.9 Hz), 6.79 (1H, brs), 6.60–6.36 (2H, m), 4.10 (1H, d, J=3.3 Hz), 3.38 (3H, s), 3.34–3.26 (1H, m), 2.64–2.40 (2H, m), 2.29 (3H, s), 1.46 and 1.38 (Total 3H, 2brs).

MS (FAB, m/z): 511 (M+1)⁺.

EXAMPLE 7

Compounds 11 and 12

In a manner similar to that in step 3 of Example 1, 9.7 mg of Compound 11 (24%) and 7.1 mg of Compound 12 (18%) were obtained from 46.5 mg (0.0752 mmol) of Compound h obtained in Reference Example 7, dimethyl sulfoxide and 0.20 mL of a 6 mol/L aqueous solution of sodium hydroxide. The ratio of the respective diastereoisomers based on their hydroxyl group by HPLC was as follows: Compound 11 (89.9% d.e.) and Compound 12 (85.4% d.e.)

Compound 11

¹H-NMR (270 MHz, DMSO-d₆) δ (ppm): 10.10 (1H, s), 10.09 (1H, s), 9.76 (1H, d, J=1.3 Hz), 9.03 (1H, brs), 8.98 (1H, d, J=1.3 Hz), 8.15 (1H, d, J=8.9 Hz), 8.03 (1H, dd, J=8.6, 1.3 Hz), 7.94 (1H, dd, J=8.9, 1.7 Hz), 7.83 (1H, d, J=8.6 Hz), 6.81 (1H, brs), 6.68 (1H, d, J=9.9 Hz), 6.51 (1H, d, J=9.9 Hz), 4.14 (1H, d, J=3.3 Hz), 3.42 (3H, s), 3.34–3.26 (1H, m), 2.70–2.40 (2H, m), 2.32 (3H, s), 1.39 (3H, brs).

MS (FAB, m/z): 539 (M+1)⁺.

Compound 12

¹H-NMR (270 MHz, DMSO-d₆) δ (ppm): 10.10 (1H, s), 10.09 (1H, s), 9.76 (1H, d, J=1.3 Hz), 9.04 (1H, brs), 8.92 (1H, d, J=1.3 Hz), 8.16 (1H, d, J=8.9 Hz), 8.04 (1H, dd, J=8.6, 1.3 Hz), 7.94 (1H, dd, J=8.9, 1.3 Hz), 7.84 (1H, d, J=8.6 Hz), 6.81 (1H, brs), 6.68 (1H, d, J=9.9 Hz), 6.51 (1H, d, J=9.9 Hz), 4.14 (1H, d, J=3.3 Hz), 3.42 (3H, s), 3.34–3.26 (1H, m), 2.70–2.40 (2H, m), 2.32 (3H, s), 1.39 (3H, brs).

MS (FAB, m/z): 539 (M+1)⁺.

EXAMPLE 8

Compounds 13 and 14

In a manner similar to that in step 3 of Example 1, 10.6 mg of Compound 13 (24%) and 7.1 mg of Compound 14 (16%) were obtained from 43.3 mg (0.0866 mmol) of Compound p obtained in Reference Example 12, dimethyl sulfoxide and 0.10 mL of a 6 mol/L aqueous solution of sodium hydroxide. The ratio of the respective diastereoisomers based on their hydroxyl group by HPLC was as follows: Compound 13 (76.8% d.e.) and Compound 14 (90.3% d.e.)

Compound 13

¹H-NMR (270 MHz, DMSO-d₆) δ (ppm): 9.14 (1H, brs), 8.74 (1H, brs), 8.41 (1H, d, J=7.6 Hz), 7.95 (1H, d, J=8.6 Hz), 7.55 (1H, d, J=8.6 Hz), 7.45 (1H, dd, J=8.3, 1.0 Hz), 7.38 (1H, dd, J=7.9, 7.6 Hz), 7.23 (1H, dd, J=7.6, 7.6 Hz), 6.66 (1H, brs), 6.52–6.30 (2H, m), 5.17 (1H, t, J=5.3 Hz), 4.65 (2H, d, J=5.3 Hz), 4.08 (1H, d, J=3.3 Hz), 3.34–3.26 (4H, m), 2.52–2.46 (2H, m), 2.27 (3H, s), 1.52 (3H, brs).

MS (FAB, m/z): 513 (M+1)⁺.

Compound 14

¹H-NMR (270 MHz, DMSO-d₆) δ (ppm): 9.13 (1H, brs), 8.75 (1H, brs), 8.32 (1H, d, J=7.3 Hz), 7.95 (1H, d, J=8.3 Hz), 7.54 (1H, d, J=8.6 Hz), 7.45 (1H, dd, J=8.6, 1.3 Hz), 7.38 (1H, dd, J=7.6, 7.3 Hz), 7.23 (1H, dd, J=7.6, 7.3 Hz), 6.68 (1H, dd, J=3.3, 3.0 Hz), 6.50–6.30 (2H, m), 5.18 (1H, t, J=5.6 Hz), 4.66 (2H, d, J=5.6 Hz), 4.07 (1H, d, J=3.3 Hz), 3.34–3.26 (4H, m), 2.52–2.46 (2H, m), 2.28 (3H, s), 1.45 (3H, brs).

MS (FAB, m/z): 513 (M+1)⁺.

EXAMPLE 9

Compounds 15 and 16

In a manner similar to that in step 3 of Example 1, 4.0 mg of Compound 15 (6%) and 6.3 mg of Compound 16 (9%) were obtained from 68.6 mg (0.130 mmol) of Compound q obtained in Reference Example 13, dimethyl sulfoxide and 0.20 mL of a 6 mol/L aqueous solution of sodium hydroxide. The ratio of the respective diastereoisomers based on their hydroxyl group by HPLC was as follows: Compound 15 (99.3% d.e.) and Compound 16 (94.7% d.e.)

Compound 15

$^1$H-NMR (270 MHz, DMSO-$d_6$) δ (ppm): 9.14 (1H, brs), 8.69 (1H, brs), 8.29 (1H, brs), 7.91 (1H, d, J=8.9 Hz), 7.53 (1H, d, J=8.3 Hz), 7.45 (1H, dd, J=8.3, 1.3 Hz), 7.37 (1H, dd, J=8.6, 1.0 Hz), 6.69 (1H, brs), 6.50–6.30 (2H, m), 5.13 (1H, t, J=5.6 Hz), 5.12 (1H, t, J=5.6 Hz), 4.84–4.56 (4H, m), 4.08 (2H, d, J=2.6 Hz), 3.36 (3H, s), 3.34–3.26 (1H, m), 2.52–2.46 (2H, m), 2.29 (3H, s), 1.53 (3H, brs).

MS (FAB, m/z): 543 (M+1)$^+$.

Compound 16

$^1$H-NMR (270 MHz, DMSO-$d_6$) δ (ppm): 9.14 (1H, brs), 8.68 (1H, brs), 8.34 (1H, brs), 7.90 (1H, d, J=8.9 Hz), 7.53 (1H, d, J=8.2 Hz), 7.44 (1H, dd, J=8.3, 1.3 Hz), 7.37 (1H, dd, J=8.6, 1.3 Hz), 6.65 (1H, brs), 6.41 (2H, brs), 5.22–5.02 (2H, m), 4.66 (2H, d, J=5.3 Hz), 4.64 (2H, d, J=5.9 Hz), 4.06 (1H, d, J=3.6 Hz), 3.39 (3H, s), 3.34–3.26 (1H, m), 2.52–2.46 (2H, m), 2.27 (3H, s), 1.53 (3H, brs).

MS (FAB, m/z): 543 (M+1)$^+$.

EXAMPLE 10

Compound 17

2 mL of methylene chloride, 1.0 mL (13 mmol) of trifluoroacetic acid and 0.10 mL (0.63 mmol) of triethylsilane were added to 124 mg (0.211 mmol) of Compound g obtained in Reference Example 7, and then the mixture was stirred at room temperature for 20 minutes. The solvent was distilled away under reduced pressure, and the residue was purified by preparative thin-layer chromatography (developed with chloroform/ethyl acetate=1/1) and then treated with a 6 mol/L aqueous solution of sodium hydroxide in accordance with step 2 of Example 3 to give 34.0 mg of Compound 17 (32%).

$^1$H-NMR (270 MHz, DMSO-$d_6$) δ (ppm): 9.05 (1H, brs), 8.48 (1H, brs), 7.98 (1H, d, J=8.6 Hz), 7.93 (1H, d, J=7.9 Hz), 7.47 (1H, d, J=8.3 Hz), 7.39 (1H, ddd, J=8.9, 7.6, 1.3 Hz), 7.30–7.20 (2H, m), 6.65 (1H, dd, J=3.6, 2.6 Hz), 4.92 (2H, s), 4.05 (1H, d, J=3.3 Hz), 3.36 (3H, s), 3.34–3.26 (1H, m), 2.52–2.46 (5H, m), 2.28 (3H, s), 1.43 (3H, s).

MS (FAB, m/z): 481 (M+1)$^+$.

EXAMPLE 11

Compound 18

In a manner similar to that in step 3 of Example 1, 8.8 mg of Compound 18 (28%) was obtained from 30.3 mg (0.0631 mmol) of Compound 17, dimethyl sulfoxide and 0.20 mL of a 6 mol/L aqueous solution of sodium hydroxide. The resulting product was a mixture (1.39:1) of isomers based on their hydroxyl group by HPLC.

$^1$H-NMR (270 MHz, DMSO-$d_6$) δ (ppm): 9.00 (1H, brs), 8.72 (1H, brs), 8.40 and 8.34 (Total 1H, 2d, J=6.9 Hz), 7.94 (1H, d, J=8.3 Hz), 7.48 (1H, d, J=8.3 Hz), 7.38 (1H, dd, J=8.2, 7.3 Hz), 7.28 (1H, dd, J=8.3, 1.3 Hz), 7.23 (1H, dd, J=7.9, 7.3 Hz), 6.63 (1H, brs), 6.50–6.30 (2H, m), 4.07 (1H, d, J=3.3 Hz), 3.40 (3H, s), 3.34–3.26 (1H, m), 2.52–2.46 (2H, m), 2.53 (3H, s), 2.27 and 2.26 (Total 3H, 2s), 1.53 and 1.45 (Total 3H, 2s).

MS (FAB, m/z): 497 (M+1)$^+$.

EXAMPLE 12

Compound 19

In a manner similar to that in Example 10, 111 mg (0.180 mmol) of Compound h obtained in Reference Example 7 was treated with 1.0 mL (13 mmol) of trifluoroacetic acid and 0.15 mL (0.90 mmol) of triethylsilane, followed by treatment with a 6 mol/L aqueous solution of sodium hydroxide, to give 34.6 mg of Compound 19 (41%).

$^1$H-NMR (270 MHz, DMSO-$d_6$) δ (ppm): 9.04 (1H, brs), 8.46 (1H, brs), 7.83 (1H, d, J=8.6 Hz), 7.71 (1H, brs), 7.45 (1H, d, J=8.6 Hz), 7.25 (1H, dd, J=8.2, 1.3 Hz), 7.20 (1H, dd, J=8.9, 1.3 Hz), 6.64 (1H, dd, J=3.6, 3.0 Hz), 4.90 (2H, s), 4.02 (1H, d, J=3.3 Hz), 3.39 (3H, s), 3.34–3.26 (1H, m), 2.52–2.46 (8H, m), 2.25 (3H, s), 1.43 (3H, s).

MS (FAB, m/z): 495 (M+1)$^+$.

EXAMPLE 13

Compound 20

In a manner similar to that in step 3 of Example 1, 15.0 mg of Compound 20 (52%) was obtained from 28.0 mg (0.0567 mmol) of Compound 19, dimethyl sulfoxide and 0.20 mL of a 6 mol/L aqueous solution of sodium hydroxide. The resulting product was a mixture (1.10:1) of isomers based on their hydroxyl group by HPLC.

$^1$H-NMR (270 MHz, DMSO-$d_6$) δ (ppm): 8.99 (1H, brs), 8.70 (1H, brs), 8.20 and 8.14 (Total 1H, 2brs), 7.82 and 7.82 (Total 1H, 2d, J=8.6 Hz), 7.46 (1H, d, J=8.6 Hz), 7.27 (1H, dd, J=8.6, 1.3 Hz), 7.20 (1H, dd, J=8.9, 1.7 Hz), 6.63 (1H, m), 6.50–6.30 (2H, m), 4.04 (1H, d, J=2.6 Hz), 3.40 (3H, s), 3.34–3.26 (1H, m), 2.52–2.46 (8H, m), 2.25 and 2.24 (Total 3H, 2s), 1.55 and 1.46 (Total 3H, 2s).

MS (FAB, m/z): 511 (M+1)$^+$.

EXAMPLE 14

Compound 21

In a manner similar to that in step 3 of Example 1, 5.9 mg of compound 21 (20%) was obtained from 28.0 mg (0.0581 mmol) of Compound r obtained in Reference Example 14, dimethyl sulfoxide and 0.10 mL of a 6 mol/L aqueous solution of sodium hydroxide. The ratio of the diastereoisomers based on their hydroxyl group by HPLC was. (93.5% d.e.)

$^1$H-NMR (270 MHz, DMSO-$d_6$) δ (ppm): 9.03 (1H, brs), 8.71 (1H, brs), 8.62 (1H, d, J=2.3 Hz), 8.33 (1H, d, J=7.3 Hz), 7.94 (1H, d, J=8.6 Hz), 7.44–7.32 (2H, m), 7.22 (1H, dd, J=7.6, 6.9 Hz), 6.94 (1H, dd, J=8.6, 2.3 Hz), 6.60 (1H, brs), 6.44–6.30 (2H, m), 4.06 (1H, d, J=3.3 Hz), 3.34–3.26 (1H, m), 3.28 (3H, s), 2.52–2.46 (2H, m), 2.27 (3H, s), 1.51 (3H, brs).

MS (FAB, m/z): 499 (M+1)$^+$.

EXAMPLE 15

Compounds 22 and 23

In a manner similar to that in step 3 of Example 1, 7.5 mg of Compound 22 (18%) and 11.9 mg of Compound 23 (29%)

were obtained from 39.4 mg (0.0791 mmol) of Compound s obtained in Reference Example 15, dimethyl sulfoxide and 0.20 mL of a 6 mol/L aqueous solution of sodium hydroxide. The ratio of the respective diastereoisomers based on their hydroxyl group by HPLC was as follows: Compound 22 (85.8% d.e.) and Compound 23 (67.3% d.e.)

Compound 22

$^1$H-NMR (270 MHz, DMSO-d$_6$) δ (ppm): 9.07 (1H, brs), 9.01 (1H, brs), 8.63 (1H, brs), 8.61 (1H, d, J=2.3 Hz), 7.78 (1H, d, J=2.3 Hz), 7.72 (1H, d, J=9.2 Hz), 7.35 (1H, d, J=8.9 Hz), 6.98–6.80 (2H, m), 6.56 (1H, brs), 6.31 (1H, d, J=10.2 Hz), 6.25 (1H, d, J=10.6 Hz), 4.01 (1H, d, J=3.0 Hz), 3.36 (3H, s), 3.34–3.26 (1H, m), 2.50–2.35 (2H, m), 2.20 (3H, s), 1.63 (3H, brs).

MS (FAB, m/z): 515 (M+1)$^+$.

Compound 23

$^1$H-NMR (270 MHz, DMSO-d$_6$) δ (ppm): 9.07 (1H, brs), 9.00 (1H, brs), 8.64 (1H, brs), 8.60 (1H, d, J=2.3 Hz), 7.73 (1H, d, J=8.6 Hz), 7.71 (1H, d, J=3.0 Hz), 7.34 (1H, d, J=8.6 Hz), 7.00–6.80 (2H, m), 6.57 (1H, brs), 6.32–6.20 (2H, m), 4.01 (1H, d, J=3.0 Hz), 3.34–3.26 (1H, m), 3.25 (3H, s), 2.58–2.36 (2H, m), 2.21 (3H, s), 1.56 (3H, brs).

MS (FAB, m/z): 515 (M+1)$^+$.

EXAMPLE 16

Compound 24

In a manner similar to that in step 3 of Example 1, 20.5 mg of Compound 24 (23%) was obtained from 100 mg (0.156 mmol) of Compound z obtained in Reference Example 21, dimethyl sulfoxide and 0.3 mL of a 6 mol/L aqueous solution of sodium hydroxide. The resulting product was a mixture (1.22:1) of isomers based on their hydroxyl group by HPLC.

$^1$H-NMR (270 MHz, DMSO-d$_6$) δ (ppm): 9.39 (1H, brs), 8.84 (1H, brs), 8.42 and 8.36 (Total 1H, 2d, J=7.6 Hz), 7.97 (1H, d, J=8.6 Hz), 7.61 (2H, m), 7.41 (1H, dd, J=7.9, 7.3 Hz), 7.26 (1H, dd, J=7.6, 7.3 Hz), 6.71 (1H, m), 6.47 (1H, m), 6.42 (1H, m), 4.08 (1H, d, J=3.3 Hz), 3.37 and 3.36 (Total 3H, 2s), 3.32 (1H, m), 2.51 (2H, m), 2.29 and 2.30 (Total 3H, 2s), 1.49 and 1.41 (Total 3H, 2s).

MS (FAB, m/z): 563, 561 (M+1)$^+$.

EXAMPLE 17

Compound 25

In a manner similar to that in step 3 of Example 1, 19.1 mg of Compound 25 (21%) was obtained from 100 mg (0.139 mmol) of Compound ab obtained in Reference Example 23, dimethyl sulfoxide and 0.3 mL of a 6 mol/L aqueous solution of sodium hydroxide. The resulting product was a mixture (1:2.2) of isomers based on their hydroxyl group by HPLC.

$^1$H-NMR (270 MHz, DMSO-d$_6$) δ (ppm): 9.39 (1H, brs), 8.89 (1H, brs), 8.57 and 8.49 (Total 1H, 2d, J=2.0 Hz), 7.93 (1H, d, J=9.2 Hz), 7.63 (2H, m), 7.52 (1H, dd, J=8.9, 2.0 Hz), 6.72 (1H, m), 6.56 (1H, m), 6.41 (1H, m), 4.07 (1H, brs), 3.42 (1H, m), 3.40 and 3.39 (Total 3H, 2s), 2.51 (2H, m), 2.27 (3H, s), 1.43 and 1.35 (Total 3H, 2s).

MS (FAB, m/z): 483 (M+1)$^+$.

EXAMPLE 18

Compound 26

Compound 26 (4%: yield from Compound a) was obtained as a by-product, when Compound ad was obtained in Reference Example 25.

$^1$H-NMR (270 MHz, CDCl$_3$) δ (ppm): 9.65 (1H, d, J=1.3 Hz), 8.38 (1H, d, J=2.0 Hz), 8.32 (1H, brs), 7.70 (1H, dd, J=8.9, 1.7 Hz), 7.56 (1H, dd, J=8.6, 1.7 Hz), 7.48 (1H, d, J=8.9 Hz), 6.69 (1H, dd, J=8.6, 2.3 Hz), 6.41 (1H, dd, J=9.2, 3.3 Hz), 6.29 (1H, s), 4.98 (1H, m), 3.79 (1H, s), 3.34 (3H, s), 2.89 (3H, s), 2.58 (3H, s), 2.54 (1H, m), 2.35 (1H, m), 2.06 (3H, s).

MS (FAB, m/z): 845 (M+1)$^+$.

EXAMPLE 19

Compound 27

37.9 mg (0.0449 mmol) of Compound 26 was dissolved in a mixed solvent 1.1 mL of a 7 mol/L methanolic solution of ammonia and 0.23 mL of chloroform and the mixture was stirred at room temperature for 17.5 hours. The solvent was distilled away under reduced pressure, and the residue was purified by preparative thin-layer chromatography (developed with chloroform/methanol=15/1) to give 26.3 mg of Compound 27 (78%).

$^1$H-NMR (270 MHz, DMSO-d$_6$) δ (ppm): 9.55 (1H, s), 9.06 (1H, brs), 8.53 (1H, s), 7.82 (1H, d, J=8.9 Hz), 7.76 (1H, d, J=8.6 Hz), 7.66 (1H, d, J=9.2 Hz), 7.52 (1H, d, J=8.6 Hz), 6.70 (1H, m), 6.49 (1H, s), 4.04 (1H, d, J=3.0 Hz), 3.33 (3H, s), 3.23 (1H, m), 3.21 (3H, s), 2.47 (2H, m), 2.27 (3H, s), 1.34 (3H, s).

MS (FAB, m/z): 749 (M+1)$^+$.

EXAMPLE 20

Compound 28

In a manner similar to that in step 3 of Example 1, 16.1 mg of Compound 28 (11%) was obtained from 168 mg (0.206 mmol) of Compound ae obtained in Reference Example 26, dimethyl sulfoxide and 0.40 mL of a 6 mol/L aqueous solution of sodium hydroxide. The resulting product was a mixture (1:1.35) of isomers based on their hydroxyl group by HPLC.

$^1$H-NMR (270 MHz, DMSO-d$_6$) δ (ppm): 9.57 (1H, s), 8.87 (1H, brs), 8.75 and 8.67 (Total 1H, 2s), 7.81 (1H, d, J=8.6 Hz), 7.75 (1H, d, J=8.6 Hz), 7.66 (1H, d, J=8.6 Hz), 7.52 (1H, d, J=8.6 Hz), 6.69 (1H, m), 6.55 (1H, m), 6.39 (1H, m), 4.06 (1H, brs), 3.38 (3H, s), 3.25 (1H, m), 2.55 (2H, m), 2.25 (3H, s), 1.44 and 1.36 (Total 3H, 2s).

MS (FAB, m/z): 735 (M+1)$^+$.

EXAMPLE 21

Compound 29

In a manner similar to that in step 1 of Example 1, 3.96 g of Compound 29 (64%) was obtained from 5.40 g (8.95 mmol) of Compound y obtained in Reference Example 20 and 1.5 mL (36 mmol) of fuming nitric acid.

$^1$H-NMR (270 MHz, CDCl$_3$+CD$_3$OD) δ (ppm): 9.42 (1H, d, J=2.0 Hz), 8.73 (1H, d, J=2.1 Hz), 8.38 (1H, dd, J=9.6, 2.1 Hz), 7.79 (1H, d, J=9.6 Hz), 7.48 (1H, dd, J=8.7, 2.0 Hz), 7.10 (1H, d, J=8.7 Hz), 6.77 (1H, dd, J=9.2, 4.9 Hz), 5.06 (1H, d, J=17.7 Hz), 5.01 (1H, d, J=17.7 Hz), 4.99 (1H, m), 4.09 (1H, brs), 3.01 (3H, s), 2.74 (1H, m), 2.57 (1H, m), 2.52 (3H, s), 2.47 (3H, s).

MS (FAB, m/z): 686 (M+1)$^+$.

EXAMPLE 22

Compound 30

In a manner similar to that in Example 19, 50.0 mg (0.0728 mmol) of Compound 29 was treated with a 7 mol/L methanolic solution of ammonia, to give 12.3 mg of Compound 30 (29%).

$^1$H-NMR (270 MHz, DMSO-d$_6$) δ (ppm): 9.47 (1H, d, J=1.9 Hz), 8.75 (1H, d, J=2.4 Hz), 8.73 (1H, brs), 8.29 (1H, dd, J=9.5, 2.4 Hz), 8.17 (1H, d, J=9.5 Hz), 7.68 (1H, d, J=8.7 Hz), 7.62 (1H, dd, J=8.7, 1.9 Hz), 6.75 (1H, d, J=4.2 Hz), 5.08 (2H, s), 4.12 (1H, d, J=3.5 Hz), 3.44 (3H, s), 3.32 (1H, m), 2.54 (2H, m), 2.33 (3H, s), 1.27 (3H, s).

MS (FAB, m/z): 590 (M+1)$^+$.

EXAMPLE 23

Compound 31

In a manner similar to that in step 1 of Example 5, 12.3 mg of Compound 31 (29%) was obtained from 1.64 g (2.39 mmol) of Compound 29, 6.58 g (29.1 mmol) of tin (II) chloride.2H$_2$O and 271 mg (7.16 mmol) of sodium borohydride.

$^1$H-NMR (270 MHz, DMSO-d$_6$) δ (ppm): 9.43 (1H, s), 8.60 (1H, brs), 7.70 (1H, d, J=8.9 Hz), 7.59 (2H, m), 7.21 (1H, s), 7.01 (1H, m), 6.85 (1H, d, J=8.9 Hz), 4.89 (2H, s), 4.84 (1H, m), 4.32 (1H, brs), 4.09 (2H, brs), 3.32 (1H, m), 2.95 (3H, s), 2.82 (2H, m), 2.70 (3H, s), 2.30 (3H, s).

MS (FAB, m/z): 656 (M+1)$^+$.

EXAMPLE 24

Compounds 32 and 33

Step 1

In a manner similar to that in step 2 of Example 1, 3.00 g (4.37 mmol) of Compound 29 was subjected to catalytic reduction in an atmosphere of hydrogen in the presence of 3.00 g of palladium hydroxide, to give 1.53 g of 5-amino-11-N-trifluoroacetyl staurosporin (60%).

MS (FAB, m/z): 577 (M)$^+$.

Step 2

In a manner similar to that in step 3 of Example 1, 13.6 mg of Compound 32 (12%) and 8.5 mg of Compound 33 (7%) were obtained from 136 mg (0.235 mmol) of 5-amino-11-N-trifluoroacetyl staurosporin, dimethyl sulfoxide and 0.40 mL of a 6 mol/L aqueous solution of sodium hydroxide. The ratio of the respective diastereoisomers based on their hydroxyl group by HPLC was as follows: Compound 32 (31.9% d.e.) and Compound 33 (91.6% d.e.)

Compound 32

$^1$H-NMR (270 MHz, DMSO-d$_6$) δ (ppm): 9.19 (1H, d, J=7.9 Hz), 8.62 (1H, brs), 7.64 (1H, d, J=9.2 Hz), 7.62 (1H, d, J=2.3 Hz), 7.55 (1H, d, J=7.6 Hz), 7.43 (1H, dd, J=7.6, 7.3 Hz), 7.24 (1H, dd, J=7.9, 7.3 Hz), 6.77 (1H, dd, J=9.2, 2.3 Hz), 6.65 (1H, m), 6.27 (2H, s), 4.02 (1H, d, J=3.6 Hz), 3.32 (1H, m), 3.29 (3H, s), 2.50 (2H, m), 2.22 (3H, s), 1.63 (3H, s).

MS (FAB, m/z): 498 (M+1)$^+$.

Compound 33

$^1$H-NMR (270 MHz, DMSO-d$_6$) δ (ppm): 9.19 (1H, d, J=7.9 Hz), 8.64 (1H, brs), 7.65 (1H, d, J=9.1 Hz), 7.55 (1H, d, J=2.3 Hz), 7.54 (1H, d, J=7.6 Hz), 7.43 (1H, dd, J=7.6, 7.3 Hz), 7.24 (1H, dd, J=7.9, 7.3 Hz), 6.77 (1H, dd, J=9.1, 2.3 Hz), 6.66 (1H, m), 6.25 (2H, m), 4.02 (1H, d, J=3.3 Hz), 3.32 (1H, m), 3.26 (3H, s), 2.50 (2H, m), 2.23 (3H, s), 1.56 (3H, s).

MS (FAB, m/z): 498 (M+1)$^+$.

EXAMPLE 25

Compound 34

Step 1

In a manner similar to that in Reference Example 20, 870 mg of 5-bromo-17-nitro-11-N-trifluoroacetyl staurosporin (82%) was obtained from 938 mg (1.54 mmol) of Compound c obtained in Reference Example 3 and 282 mg (1.58 mmol) of N-bromosuccinimide.

$^1$H-NMR (270 MHz, DMSO-d$_6$) δ (ppm): 10.18 (1H, d, J=2.3 Hz), 8.79 (1H, brs), 8.34 (1H, dd, J=8.9, 2.3 Hz), 8.17 (1H, d, J=1.7 Hz), 7.99 (1H, d, J=9.2 Hz), 7.78 (1H, d, J=8.9 Hz), 7.63 (1H, dd, J=9.2, 1.7 Hz), 7.14 (1H, dd, J=8.6, 6.3 Hz), 5.04 (2H, s), 4.90 (1H, brm), 4.43 (1H, brs), 3.30 (3H, s), 2.67 (3H, s), 2.42 (2H, m), 2.37 (3H, s).

MS (FAB, m/z): 686 (M+1)$^+$.

Step 2

In a manner similar to that in step 1 of Example 5, 46.3 mg of Compound 34 (56%) was obtained from 101 mg (0.147 mmol) of 5-bromo-17-nitro-11-N-trifluoroacetyl staurosporin, 277 mg (1.47 mmol) of tin (II) chloride.2H$_2$O and 55 mg (1.5 mmol) of sodium borohydride.

$^1$H-NMR (270 MHz, DMSO-d$_6$) δ (ppm): 8.47 (1H, s), 8.45 (1H, brs), 8.02 (1H, s), 7.91 (1H, d, J=8.9 Hz), 7.49 (1H, d, J=9.2 Hz), 7.30 (1H, d, J=8.4 Hz), 6.85 (1H, d, J=8.4 Hz), 6.57 (1H, brm), 4,92 (2H, s), 4.74 (2H, brs), 4.03 (1H, d, J=2.3 Hz), 3.31 (3H, s), 3.25 (1H, m), 2.46 (2H, m), 2.25 (3H, s), 1.45 (3H, s).

MS (FAB, m/z): 560 (M+1)$^+$.

EXAMPLE 26

Compound 35

500 mg (0.726 mmol) of Compound ac obtained in Reference Example 24 was dissolved in 15 mL of diethylamine followed by adding 26 mg (0.036 mmol) of Pd[P(C$_6$H$_5$)$_3$]$_2$Cl$_2$, 345 mg (0.18 mmol) of copper iodide (CuI) and 1.4 mL (15 mmol) of 2-methyl-3-butyn-2-ol, and the mixture was stirred under an atmosphere of argon at room temperature for 2 hours. Water was added to the reaction mixture, and then the mixture was extracted with chloroform. The organic layer was washed with a saturated saline solution and dried over anhydrous sodium sulfate. The solvent was distilled away under reduced pressure. The residue was purified by silica gel column chromatography (eluted with chloroform/methanol=from 50/1 to 30/1) to give 429 mg of Compound 35 (92%).

$^1$H-NMR (270 MHz, CDCl$_3$) δ (ppm): 9.48 (1H, brs), 7.83 (1H, d, J=7.9 Hz), 7.69 (1H, d, J=8.6 Hz), 7.44 (1H, dd, J=8.3, 7.6 Hz), 7.42 (1H, d, J=8.3 Hz), 7.30 (1H, dd, J=7.6, 7.3 Hz), 7.02 (1H, d, J=8.6 Hz), 6.91 (1H, brs), 6.62 (1H, dd, J=8.6, 4.6 Hz), 4.99 (1H, m), 4.94 (2H, s), 4.00 (1H, brs), 2.96 (3H, s), 2.68 (1H, m), 2.58 (1H, m), 2.47 (3H, s), 2.40 (3H, s), 1.71 (6H, s).

MS (FAB, m/z): 645 (M+1)$^+$.

EXAMPLE 27

Compound 36

In a manner similar to that in Example 19, 50.0 mg (0.078 mmol) of Compound 35 was treated with a 7 mol/L methanolic solution of ammonia, to give 39.1 mg of Compound 36 (92%).

$^1$H-NMR (270 MHz, DMSO-d$_6$) δ (ppm): 9.33 (1H, brs), 8.57 (1H, brs), 7.99 (1H, d, J=7.9 Hz), 7.96 (1H, d, J=6.3 Hz), 7.60 (1H, d, J=8.6 Hz), 7.46 (1H, d, J=8.3 Hz), 7.43

(1H, dd, J=8.3, 7.6 Hz), 7.29 (1H, dd, J=7.6, 7.3 Hz), 6.72 (1H, m), 4.95 (2H, s), 4.07 (1H, d, J=3.0 Hz), 3.34 (3H, s), 3.27 (1H, m), 2.51 (2H, m), 2.31 (3H, s), 1.53 (6H, s), 1.44 (3H, s).

MS (FAB, m/z): 549 (M+1)+.

EXAMPLE 28

Compounds 37 and 38

In a manner similar to that in step 3 of Example 1, 6.8 mg of Compound 37 (4.3%) and 6.4 mg of Compound 38 (4.1%) were obtained from 180 mg (0.279 mmol) of Compound 35, dimethyl sulfoxide and 0.55 mL of a 6 mol/L aqueous solution of sodium hydroxide. The ratio of the respective diastereoisomers based on their hydroxyl group by HPLC was as follows: Compound 37 (90.0% d.e.) and Compound 38 (97.6% d.e.)

Compound 37

$^1$H-NMR (270 MHz, DMSO-$d_6$) δ (ppm): 9.26 (1H, brs), 8.81 (1H, s), 8.37 (1H, d, J=7.9 Hz), 7.97 (1H, d, J=8.6 Hz), 7.60 (1H, d, J=8.6 Hz), 7.47 (1H, d, J=8.6 Hz), 7.41 (1H, dd, J=8.6, 7.3 Hz), 7.26 (1H, dd, J=7.6, 7.3 Hz), 6.71 (1H, m), 6.41 (2H, m), 5.48 (1H, s), 4.08 (1H, d, J=3.3 Hz), 3.32 (3H, s), 3.30 (1H, m), 2.51 (2H, m), 2.30 (3H, s), 1.53 (6H, s), 1.44 (3H, s).

MS (FAB, m/z): 565 (M+1)+.

Compound 38

$^1$H-NMR (270 MHz, DMSO-$d_6$) δ (ppm): 9.27 (1H, brs), 8.81 (1H, s), 8.42 (1H, d, J=7.9 Hz), 7.96 (1H, d, J=8.9 Hz), 7.60 (1H, d, J=8.3 Hz), 7.47 (1H, dd, J=8.6, 1.7 Hz), 7.41 (1H, dd, J=8.6, 7.3 Hz), 7.25 (1H, dd, J=7.6, 7.3 Hz), 6.69 (1H, m), 6.48 (1H, m), 6.40 (1H, m), 5.49 (1H, s), 4.08 (1H, d, J=3.3 Hz), 3.33 (3H, s), 3.30 (1H, m), 2.51 (2H, m), 2.29 (3H, s), 1.53 (9H, s).

MS (FAB, m/z): 565 (M+1)+.

EXAMPLE 29

Compound 39

In a manner similar to that in Example 26, 75.5 mg of Compound 39 (83%) was obtained from 100 mg (0.145 mmol) of Compound ac obtained in Reference Example 24, 5.1 mg (0.0073 mmol) of Pd[P($C_6H_5$)$_3$]$_2Cl_2$, 6.9 mg (0.036 mmol) of copper iodide (CuI) and 0.22 mL (2.9 mmol) of 3-butyn-1-ol.

$^1$H-NMR (270 MHz, CDCl$_3$) δ (ppm): 9.40 (1H, d, J=1.3 Hz), 7.82 (1H, d, J=7.6 Hz), 7.74 (1H, d, J=8.3 Hz), 7.47 (1H, dd, J=7.6, 7.3 Hz), 7.46 (1H, dd, J=8.3, 1.7 Hz), 7.33 (1H, dd, J=8.3, 7.3 Hz), 7.08 (1H, d, J=8.2 Hz), 6.61 (1H, dd, J=9.1, 4.8 Hz), 4.99 (1H, m), 4.92 (1H, d, J=17.5 Hz), 4.83 (1H, d, J=17.5 Hz), 4.02 (1H, brs), 3.86 (2H, t, J=6.6 Hz), 2.99 (3H, s), 2.74 (2H, t, J=6.6 Hz), 2.67 (1H, m), 2.54 (1H, ddd, J=15.2, 12.9, 4.6 Hz), 2.49 (3H, s), 2.40 (3H, s).

MS (FAB, m/z): 631 (M+1)+.

EXAMPLE 30

Compound 40

In a manner similar to that in Example 19, 49.3 mg (0.0782 mmol) of compound 39 was treated with a 7 mol/L methanolic solution of ammonia, to give 33.7 mg of Compound 40 (81%)

$^1$H-NMR (270 MHz, DMSO-$d_6$) δ (ppm): 9.32 (1H, d, J=1.0 Hz), 8.57 (1H, brs), 7.99 (1H, d, J=7.9 Hz), 7.96 (1H, d, J=6.3 Hz), 7.58 (1H, d, J=8.6 Hz), 7.47 (1H, dd, J=8.3, 1.7 Hz), 7.42 (1H, dd, J=7.6, 7.3 Hz), 7.28 (1H, dd, J=7.6, 7.3 Hz), 6.71 (1H, m), 4.95 (2H, s), 4.07 (1H, d, J=3.3 Hz), 3.63 (1H, t, J=6.6 Hz), 3.33 (3H, s), 3.28 (1H, m), 2.62 (2H, t, J=6.6 Hz), 2.51 (2H, m), 2.30 (3H, s), 1.44 (3H, s).

MS (FAB, m/z): 535 (M+1)+.

EXAMPLE 31

Compounds 41 and 42

In a manner similar to that in step 3 of Example 1, 16.1 mg of Compound 41 (10.4%) and 11.2 mg of Compound 42 (7.2% were obtained from 177 mg (0.281 mmol) of Compound 39, dimethyl sulfoxide and 0.55 mL of a 6 mol/L aqueous solution of sodium hydroxide. The ratio of the respective diastereoisomers based on their hydroxyl group by HPLC was as follows: Compound 41 (81.3% d.e.), and Compound 42 (77.2% d.e.)

Compound 41

$^1$H-NMR (270 MHz, DMSO-$d_6$) δ (ppm): 9.26 (1H, s), 8.83 (1H, s), 8.36 (1H, d, J=7.3 Hz), 7.97 (1H, d, J=8.6 Hz), 7.58 (1H, d, J=8.6 Hz), 7.48 (1H, dd, J=8.4, 1.5 Hz), 7.41 (1H, dd, J=7.3, 7.3 Hz), 7.25 (1H, dd, J=7.6, 7.3 Hz), 6.70 (1H, m), 6.44 (1H, m), 6.38 (1H, m), 4.93 (1H, m), 4.07 (1H, d, J=3.3 Hz), 3.63 (2H, t, J=6.8 Hz), 3.34 (3H, s), 3.26 (1H, m), 2.62 (2H, t, J=6.8 Hz), 2.51 (2H, m), 2.29 (3H, s), 1.43 (3H, s).

MS (FAB, m/z): 551 (M+1)+.

Compound 42

$^1$H-NMR (270 MHz, DMSO-$d_6$) δ (ppm): 9.27 (1H, d, J=1.3 Hz), 8.82 (1H, s), 8.42 (1H, d, J=7.6 Hz), 7.96 (1H, d, J=8.6 Hz), 7.58 (1H, d, J=8.3 Hz), 7.48 (1H, dd, J=8.4, 1.5 Hz), 7.40 (1H, dd, J=7.3, 7.3 Hz), 7.25 (1H, dd, J=7.6, 7.6 Hz), 6.69 (1H, m), 6.48 (1H, m), 6.40 (1H, m), 4.93 (1H, m), 4.08 (1H, d, J=3.3 Hz), 3.63 (2H, t, J=6.9 Hz), 3.35 (3H, s), 3.28 (1H, m), 2.62 (2H, t, J=6.9 Hz), 2.51 (2H, m), 2.28 (3H, s), 1.51 (3H, s).

MS (FAB, m/z): 551 (M+1)+.

EXAMPLE 32

Compounds 43 and 44

46.5 mg (0.0721 mmol) of Compound 35 was dissolved in 2.3 mL toluene followed by adding 2.9 mg (0.072 mmol) of sodium hydride, and the mixture was heated under reflux for 7.5 hours. Water was added to the reaction mixture, and then the mixture was extracted with chloroform. The organic layer was washed with a saturated saline solution and dried over anhydrous sodium sulfate. The solvent was distilled away under reduced pressure.

The residue was purified by preparative thin-layer chromatography (developed with chloroform/methanol=14/1) to give 9.5 mg of Compound 43 (22%) and 8.8 mg of Compound 44 (25%).

Compound 43

$^1$H-NMR (270 MHz, CDCl$_3$) δ (ppm): 9.64 (1H, brs), 7.95 (1H, d, J=8.3 Hz), 7.75 (1H, d, J=8.3 Hz), 7.62 (1H, dd, J=8.6, 1.7 Hz), 7.49 (1H, dd, J=7.3, 6.9 Hz), 7.38 (1H, dd, J=7.6, 6.9 Hz), 7.18 (1H, d, J=6.3 Hz), 6.78 (1H, dd, J=8.2, 5.6 Hz), 6.30 (1H, m), 5.08 (1H, m), 5.04 (2H, s), 4.11 (1H, brs), 3.09 (1H, s), 3.04 (3H, s), 2.70 (2H, m), 2.54 (3H, s), 2.51 (3H, s).

MS (FAB, m/z): 587 (M+1)$^+$.

Compound 44

$^1$H-NMR (270 MHz, DMSO-d$_6$) δ (ppm): 9.42 (1H, d, J=1.0 Hz), 8.59 (1H, brs), 7.99 (1H, d, J=7.2 Hz), 7.96 (1H, d, J=6.9 Hz), 7.62 (1H, d, J=8.6 Hz), 7.54 (1H, dd, J=8.6, 1.7 Hz), 7.42 (1H, dd, J=8.3, 7.6 Hz), 7.29 (1H, dd, J=7.6, 7.3 Hz), 6.73 (1H, m), 4.96 (2H, s), 4.07 (1H, d, J=3.3 Hz), 4.05 (1H, s), 3.35 (3H, s), 3.28 (1H, m), 2.52 (2H, m), 2.30 (3H, s), 1.42 (3H, s).

MS (FAB, m/z): 491 (M+1)$^+$.

EXAMPLE 33

Compounds 45 and 46

In a manner similar to that in step 3 of Example 1, 13.2 mg of Compound 45 (13%) and 11.0 mg of Compound 46 (11%) were obtained from 105 mg (0.201 mmol) of a mixture containing Compound 43 and Compound 44, dimethyl sulfoxide and 0.39 mL of a 6 mol/L aqueous solution of sodium hydroxide. The ratio of the respective diastereoisomers based on their hydroxyl group by HPLC was as follows: Compound 45 (84.3% d.e.) and Compound 46 (89.6% d.e.)

Compound 45

$^1$H-NMR (270 MHz, DMSO-d$_6$) δ (ppm): 9.36 (1H, s), 8.84 (1H, s), 8.37 (1H, d, J=7.6 Hz), 7.97 (1H, d, J=8.6 Hz), 7.63 (1H, d, J=8.6 Hz), 7.55 (1H, dd, J=8.4, 1.5 Hz), 7.41 (1H, dd, J=8.3, 7.3 Hz), 7.26 (1H, dd, J=7.6, 7.6 Hz), 6.72 (1H, m), 6.45 (1H, m), 6.39 (1H, m), 4.08 (1H, brs), 4.07 (1H, s), 3.35 (3H, s), 3.31 (1H, m), 2.51 (2H, m), 2.30 (3H, s), 1.41 (3H, s).

MS (FAB, m/z): 507 (M+1)$^+$.

Compound 46

$^1$H-NMR (270 MHz, DMSO-d$_6$) δ (ppm): 9.37 (1H, s), 8.84 (1H, s), 8.43 (1H, d, J=7.6 Hz), 7.97 (1H, d, J=8.9 Hz), 7.63 (1H, d, J=8.6 Hz), 7.55 (1H, dd, J=8.4, 1.5 Hz), 7.41 (1H, dd, J=8.3, 7.3 Hz), 7.25 (1H, dd, J=7.6, 7.3 Hz), 6.70 (1H, m), 6.49 (1H, m), 6.40 (1H, m), 4.08 (1H, d, J=3.6 Hz), 4.07 (1H, s), 3.37 (3H, s), 3.32 (1H, m), 2.51 (2H, m), 2.29 (3H, s), 1.49 (3H, s).

MS (FAB, m/z): 507 (M+1)$^+$.

EXAMPLE 34

Compound 47

In a manner similar to that in Example 26, 75.3 mg of Compound 47 (78%) was obtained from 100 mg (0.145 mmol) of Compound ac obtained in Reference Example 24, 5.1 mg (0.0073 mmol) of Pd[P(C$_6$H$_5$)$_3$]$_2$Cl$_2$, 5.5 mg (0.029 mmol) of copper iodide (CuI) and 0.32 mL (2.9 mmol) of phenyl acetylene.

$^1$H-NMR (270 MHz, CDCl$_3$) δ (ppm): 9.60 (1H, d, J=1.3 Hz), 7.78 (1H, d, J=6.9 Hz), 7.71 (1H, d, J=8.6 Hz), 7.63 (2H, dd, J=7.9, 1.7 Hz), 7.52 (1H, dd, J=8.2, 1.7 Hz), 7.44 (1H, dd, J=7.3, 7.3 Hz), 7.37 (3H, m), 7.29 (1H, dd, J=7.6, 7.6 Hz), 7.04 (1H, d, J=8.3 Hz), 7.02 (1H, brs), 6.61 (1H, dd, J=8.9, 4.3 Hz), 4.97 (1H, m), 4.92 (1H, d, J=17.5 Hz), 4.83 (1H, d, J=16.2 Hz), 3.97 (1H, brs), 2.96 (3H, s), 2.64 (1H, m), 2.56 (1H, m), 2.50 (3H, s), 2.32 (3H, s).

MS (FAB, m/z): 663 (M+1)$^+$.

EXAMPLE 35

Compound 48

In a manner similar to that in Example 19, 44.9 mg (0.0678 mmol) of Compound 47 was treated with a 7 mol/L methanolic solution of ammonia, to give 31.9 mg of Compound 48 (83%).

$^1$H-NMR (270 MHz, DMSO-d$_6$) δ (ppm): 9.48 (1H, brs), 8.62 (1H, brs), 7.99 (1H, d, J=8.3 Hz), 7.97 (1H, d, J=7.0 Hz), 7.63 (4H, m), 7.44 (4H, m), 7.29 (1H, dd, J=7.6, 7.3 Hz), 6.75 (1H, m), 4.97 (2H, s), 4.08 (1H, d, J=3.6 Hz), 3.33 (3H, s), 3.28 (1H, m), 2.52 (2H, m), 2.31 (3H, s), 1.43 (3H, s).

MS (FAB, m/z): 491 (M+1)$^+$.

EXAMPLE 36

Compounds 49 and 50

In a manner similar to that in Example 26, 30.9 mg of Compound 49 (33%) and 7.1 mg of Compound 50 (9%) were obtained from 100 mg (0.145 mmol) of Compound ac obtained in Reference Example 24, 5.1 mg (0.0073 mmol) of Pd[P(C$_6$H$_5$)$_3$]$_2$Cl$_2$, 5.5 mg (0.029 mmol) of copper iodide (CuI) and 0.31 mL (2.9 mmol) of 1-dimethylamino-2-propyne.

Compound 49

$^1$H-NMR (270 MHz, CDCl$_3$) δ (ppm): 9.56 (1H, brs), 7.82 (1H, d, J=7.6 Hz), 7.71 (1H, d, J=8.3 Hz), 7.51 (1H, d, J=8.2 Hz), 7.45 (1H, dd, J=8.3, 7.3 Hz), 7.32 (1H, dd, J=7.6, 7.3 Hz), 7.06 (1H, d, J=8.2 Hz), 6.90 (1H, brs), 6.61 (1H, dd, J=8.6, 4.6 Hz), 4.99 (1H, m), 4.95 (1H, d, J=16.8 Hz), 4.86 (1H, d, J=16.5 Hz), 4.00 (1H, brs), 3.56 (2H, s), 2.98 (3H, s), 2.65 (1H, m), 2.54 (1H, m), 2.49 (3H, s), 2.46 (6H, s), 2.39 (3H, s).

MS (FAB, m/z): 644 (M+1)$^+$.

Compound 50

$^1$H-NMR (270 MHz, CDCl$_3$) δ (ppm): 9.55 (1H, brs), 7.91 (1H, d, J=8.9 Hz), 7.88 (1H, d, J=8.9 Hz), 7.55 (1H, d, J=8.6 Hz), 7.42 (1H, dd, J=7.6, 7.3 Hz), 7.31 (1H, dd, J=7.6, 7.3 Hz), 7.20 (1H, d, J=8.6 Hz), 6.52 (1H, brd, J=5.3 Hz), 6.32 (1H, brs), 5.01 (2H, s), 3.86 (1H, d, J=3.3 Hz), 3.57 (2H, s), 3.42 (3H, s), 3.33 (1H, m), 2.72 (1H, m), 2.44 (6H, s), 2.41 (1H, m), 2.35 (3H, s), 1.51 (3H, s).

MS (FAB, m/z): 548 (M+1)$^+$.

EXAMPLE 37

Compounds 51 and 52

In a manner similar to that in step 3 of Example 1, 17.0 mg of Compound 51 (7.6%) and 6.1 mg of Compound 52 (2.7%) were obtained from 254 mg (0.3$^9$5 mmol) of a mixture containing Compound 49 and Compound 50, dimethyl sulfoxide and 0.77 mL of a 6 mol/L aqueous solution of sodium hydroxide. The ratio of the respective diastereoisomers based on their hydroxyl group by HPLC was as follows: Compound 51 (61.2% d.e.) and Compound 52 (94.9% d.e.)

Compound 51

$^1$H-NMR (270 MHz, DMSO-d$_6$) δ (ppm): 9.32 (1H, s), 8.82 (1H, s), 8.37 (1H, d, J=7.6 Hz), 7.97 (1H, d, J=8.2 Hz), 7.61 (1H, d, J=8.6 Hz), 7.52 (1H, dd, J=8.4, 1.5 Hz), 7.41 (1H, dd, J=8.3, 7.3 Hz), 7.26 (1H, dd, J=7.6, 7.3 Hz), 6.71 (1H, m), 6.40 (2H, m), 4.08 (1H, d, J=3.3 Hz), 3.51 (2H, s), 3.36 (3H, s), 3.27 (1H, m), 2.51 (2H, m), 2.30 (9H, s), 1.42 (3H, s).

MS (FAB, m/z): 564 (M+1)$^+$.

Compound 52

$^1$H-NMR (270 MHz, DMSO-d$_6$) δ (ppm): 9.33 (1H, s), 8.82 (1H, s), 8.43 (1H, d, J=7.9 Hz), 7.97 (1H, d, J=8.2 Hz), 7.61 (1H, d, J=8.6 Hz), 7.52 (1H, dd, J=8.3, 1.7 Hz), 7.42 (1H, dd, J=8.6, 6.9 Hz), 7.26 (1H, dd, J=7.6, 7.3 Hz), 6.71 (1H, m), 6.50 (1H, m), 6.41 (1H, m), 4.10 (1H, d, J=3.3 Hz), 3.53 (2H, s), 3.32 (3H, s), 3.25 (1H, m), 2.51 (2H, m), 2.31 (6H, s), 2.30 (3H, s), 1.56 (3H, s).

MS (FAB, m/z): 564 (M+1)$^+$.

EXAMPLE 38

Compound 53

In a manner similar to that in Example 26, 54.2 mg of Compound 53 (59%) was obtained from 100 mg (0.1.45 mmol) of w Compound ac obtained in Reference Example 24, 5.1 mg (0.0073 mmol) of Pd[P(C$_6$H$_5$)$_3$]$_2$Cl$_2$, 5.5 mg (0.029 mmol) of copper iodide (CuI) and 0.25 mL (2.9 mmol) of methyl propargyl ether.

$^1$H-NMR (270 MHz, CDCl$_3$) δ (ppm): 9.54 (1H, s), 7.78 (1H, d, J=7.6 Hz), 7.71 (1H, d, J=8.3 Hz), 7.47 (1H, dd, J=8.3, 1.7 Hz), 7.44 (1H, dd, J=7.6, 6.9 Hz), 7.30 (1H, dd, J=7.6, 7.3 Hz), 7.17 (1H, brs), 7.01 (1H, d, J=8.6 Hz), 6.57 (1H, dd, J=8.9, 4.3 Hz), 4.98 (1H, m), 4.92 (1H, d, J=16.8 Hz), 4.82 (1H, d, J=16.5 Hz), 4.42 (2H, s), 3.96 (1H, brs), 3.54 (3H, s), 2.95 (3H, s), 2.63 (1H, m), 2.56 (1H, m), 2.50 (3H, m), 2.32 (3H, s).

MS (FAB, m/z): 535 (M+1)$^+$.

EXAMPLE 39

Compound 54

In a manner similar to that in Example 19, 34.4 mg (0.0545 mmol) of Compound 53 was treated with a 7 mol/L methanolic solution of ammonia, to give 24.4 mg of Compound 54 (84%).

$^1$H-NMR (270 MHz, DMSO-d$_6$+CD$_3$OD) δ (ppm): 9.38 (1H, s), 8.17 (1H, s), 7.98 (1H, d, J=9.2 Hz), 7.94 (1H, d, J=7.9 Hz), 7.56 (1H, d, J=8.3 Hz), 7.55 (1H, dd, J=7.6, 7.3 Hz), 7.41 (1H, dd, J=7.6, 7.3 Hz), 7.28 (1H, d, J=8.6 Hz), 6.68 (1H, m), 4.94 (2H, s), 4.36 (2H, s), 4.03 (1H, m), 3.66 (3H, s), 3.38 (3H, s), 3.26 (1H, m), 2.45 (2H, m), 2.30 (3H, s), 1.44 (3H, s).

MS (FAB, m/z): 631 (M+1)$^+$.

EXAMPLE 40

Compound 55

80 mg (0.12 mmol) of Compound ac obtained in Reference Example 24 was dissolved in 2.4 mL of N,N-dimethylformamide followed by adding 1.3 mg (0.0058 mmol) of palladium acetate, 7.1 mg (0.023 mmol) of tri-o-tolylphosphine, 0.053 mL (0.58 mmol) of methyl acrylate and 0.32 mL (2.3 mmol) of triethylamine, and the mixture was stirred at 60° C. for 8 hours under an atmosphere of argon. Water was added to the reaction mixture, and then the mixture was extracted with ethyl acetate. The organic layer was washed with a saturated saline solution and dried over anhydrous sodium sulfate. The solvent was distilled away under reduced pressure. The residue was purified by preparative thin-layer chromatography (developed with chloroform/acetone=3/1 and then with hexane/ethyl acetate=1/2) to give 51.6 mg of Compound 55 (69%).

$^1$H-NMR (270 MHz, CDCl$_3$) δ (ppm): 9.54 (1H, brs), 7.96 (1H, d, J=16.2 Hz), 7.90 (1H, d, J=7.9 Hz), 7.71 (1H, d, J=8.2 Hz), 7.57 (1H, d, J=8.6 Hz), 7.47 (1H, dd, J=7.9, 7.3 Hz), 7.35 (1H, dd, J=7.6, 6.9 Hz), 7.13 (1H, d, J=8.6 Hz), 6.95 (1H, brs), 6.73 (1H, dd, J=8.9, 4.6 Hz), 6.51 (1H, d, J=15.8 Hz), 5.05 (1H, m), 5.01 (2H, s), 4.02 (1H, brs), 3.86 (3H, s), 2.99 (3H, s), 2.69 (1H, m), 2.58 (1H, m), 2.52 (3H, s), 2.39 (3H, s).

MS (FAB, m/z): 647 (M+1)$^+$.

EXAMPLE 41

Compound 56

In a manner similar to that in Example 19, 37 mg (0.0572 mmol) of Compound 55 was treated with a 7 mol/L methanolic solution of ammonia, to give 28.1 mg of Compound 56 (89%).

$^1$H-NMR (270 MHz, DMSO-d$_6$) δ (ppm): 9.53 (1H, d, J=1.3 Hz), 8.58 (1H, brs), 7.99 (1H, d, J=8.6 Hz), 7.97 (1H, d, J=6.3 Hz), 7.87 (1H, dd, J=7.9, 1.7 Hz), 7.86 (1H, d, J=16.2 Hz), 7.67 (1H, d, J=8.6 Hz), 7.43 (1H, dd, J=7.6, 7.3 Hz), 7.29 (1H, dd, J=7.6, 7.3 Hz), 6.75 (1H, m), 6.58 (1H, d, J=15.8 Hz), 4.97 (2H, s), 4.08 (1H, d, J=3.3 Hz), 3.76 (3H, s), 3.37 (3H, s), 3.28 (1H, m), 2.51 (2H, m), 2.31 (3H, s), 1.42 (3H, s).

MS (FAB, m/z): 551 (M+1)$^+$.

EXAMPLE 42

Compound 57

100 mg (0.145 mmol) of Compound ac obtained in Reference Example 24 was dissolved in 3 mL of toluene followed by adding 8.4 mg (0.0073 mmol) of tetrakistriphenylphosphine palladium and 0.051 mL (0.17 mmol) of vinyl tributyl tin, and the mixture was stirred at 60° C. for 2 hours under an atmosphere of argon. A 5% aqueous solution of ammonium fluoride was added to the reaction mixture, and then the mixture was extracted with ethyl acetate. The organic layer was washed with a saturated saline solution and dried over anhydrous sodium sulfate. The solvent was distilled away under reduced pressure. The residue was purified by preparative thin-layer chromatography (developed with hexane/ethyl acetate=1/2) to give 49.4 mg of Compound 57 (58%)

$^1$H-NMR (270 MHz, CDCl$_3$ MHz) δ (ppm): 9.46 (1H, brs), 7.84 (1H, d, J=7.3 Hz), 7.70 (1H, d, J=8.6 Hz), 7.54 (1H, dd, J=8.6, 1.7 Hz), 7.44 (1H, dd, J=8.3, 7.3 Hz), 7.32 (1H, dd, J=7.6, 7.3 Hz), 7.04 (1H, d, J=8.3 Hz), 7.02 (1H, dd, J=17.2, 10.9 Hz), 6.80 (1H, m), 6.57 (1H, dd, J=8.6, 5.3 Hz), 5.85 (1H, d, J=17.5 Hz), 5.25 (1H, d, J=10.9 Hz), 4.97 (1H, m), 4.96 (1H, d, J=16.2 Hz), 4.88 (1H, d, J=16.8 Hz), 3.99 (1H, brs), 2.95 (3H, s), 2.71 (1H, m), 2.59 (1H, m), 2.46 (3H, s), 2.38 (3H, s).

MS (FAB, m/z): 589 (M+1)$^+$.

EXAMPLE 43

Compound 58

In a manner similar to that in Example 19, 49.4 mg (0.0839 mmol) of Compound 57 was treated with a 7 mol/L methanolic solution of ammonia, to give 27.8 mg of Compound 58 (67%).

$^1$H-NMR (270 MHz, DMSO-$d_6$) δ (ppm): 9.34 (1H, brs), 8.51 (1H, brs), 7.98 (1H, d, J=7.9 Hz), 7.95 (1H, d, J=7.3 Hz), 7.63 (1H, dd, J=8.3, 1.7 Hz), 7.57 (1H, d, J=8.3 Hz), 7.41 (1H, dd, J=7.6, 7.6 Hz), 7.28 (1H, dd, J=7.6, 7.3 Hz), 6.92 (1H, dd, J=17.8, 10.9 Hz), 6.71 (1H, m), 5.80 (1H, d, J=17.5 Hz), 5.21 (1H, d, J=11.2 Hz), 4.95 (2H, s), 4.07 (1H, d, J=3.6 Hz), 3.35 (3H, s), 3.27 (1H, m), 2.51 (2H, m), 2.30 (3H, s), 1.43 (3H, s).

MS (FAB, m/z): 493 (M+1)$^+$.

EXAMPLE 44

Compound 59

In a manner similar to that in Example 40, 103 mg of Compound 59 (53%) was obtained from 200 mg (0.291 mmol) of Compound ac obtained in Reference Example 24, 3.3 mg (0.015 mmol) of palladium acetate, 18 mg (0.058 mmol) of tri-o-tolylphosphine, 0.16 mL (1.5 mmol) of N-vinyl-2-pyrrolidinone and 0.81 mL (5.8 mmol) of triethylamine.

$^1$H-NMR (270 MHz, CDCl$_3$) δ (ppm): 9.44 (1H, d, J=1.7 Hz), 7.76 (1H, d, J=8.6 Hz), 7.70 (1H, d, J=7.6 Hz), 7.51 (1H, dd, J=8.6, 1.7 Hz), 7.46 (1H, dd, J=8.9, 7.6 Hz), 7.34 (1H, dd, J=7.6, 7.3 Hz), 6.97 (1H, d, J=8.6 Hz), 6.38 (1H, brs), 6.28 (1H, dd, J=9.2, 3.6 Hz), 5.63 (1H, s), 5.30 (1H, s), 4.96 (1H, m), 4.66 (1H, d, J=16.5 Hz), 4.17 (1H, d, J=16.8 Hz), 3.88 (1H, brs), 3.84 (2H, m), 2.90 (3H, s), 2.73 (3H, m) 2.57 (3H, s), 2.39 (1H, ddd, J=14.7, 12.5, 4.0 Hz), 2.38 (2H, m), 2.17 (3H, s).

MS (FAB, m/z): 672 (M+1)$^+$.

EXAMPLE 45

Compound 60

In a manner similar to that in Example 19, 35.0 mg (0.0521 mmol) of Compound 59 was treated with a 7 mol/L methanolic solution of ammonia, to give 28.6 mg of Compound 60 (95%).

$^1$H-NMR (270 MHz, DMSO-$d_6$) δ (ppm): 9.31 (1H, brs), 8.53 (1H, brs), 7.99 (1H, d, J=7.9 Hz), 7.96 (1H, d, J=6.6 Hz), 7.58 (1H, d, J=9.2 Hz), 7.54 (1H, d, J=9.6 Hz), 7.42 (1H, dd, J=8.3, 7.3 Hz), 7.28 (1H, dd, J=7.6, 7.3 Hz), 6.71 (1H, m), 5.50 (1H, s), 5.20 (1H, s), 4.95 (2H, br), 4.07 (1H, d, J=3.3 Hz), 3.66 (2H, m), 3.34 (3H, s), 3.28 (1H, m), 2.51 (2H, m), 2.30 (3H, s), 2.18 (2H, m), 1.45 (3H, s).

MS (FAB, m/z): 576 (M+1)$^+$.

EXAMPLE 46

Compound 61

In a manner similar to that in Example 40, 125 mg of Compound 61 (86%) was obtained from 150 mg (0.218 mmol) of Compound ac obtained in Reference Example 24, 3.9 mg (0.017 mmol) of palladium acetate, 21 mg (0.070 mmol) of tri-o-tolylphosphine, 0.12 mL (1.1 mmol) of 2-vinyl pyridine and 0.61 mL (4.4 mmol) of triethylamine.

$^1$H-NMR (270 MHz, CDCl$_3$+CD$_3$OD) δ (ppm): 9.52 (1H, brs), 8.55 (1H, brd, J=4.0 Hz), 7.83 (1R, d, J=9.2 Hz), 7.74 (2H, m), 7.74 (1H, d, J=7.9 Hz), 7.72 (1H, d, J=16.2 Hz), 7.59 (1H, d, J=7.9 Hz), 7.45 (1H, dd, J=7.6, 6.9 Hz), 7.31 (1H, dd, J=7.6, 6.9 Hz), 7.28 (1H, d, J=16.2 Hz), 7.19 (1H, ddd, J=6.9, 5.6, 1.0 Hz), 7.17 (1H, d, J=8.6 Hz), 6.67 (1H, dd, J=9.2, 4.6 Hz), 5.00 (1H, m), 4.95 (1H, d, J=17.8 Hz), 4.88 (1H, d, J=17.2 Hz), 4.02 (1H, brs), 2.99 (3H, s), 2.70 (1H, m), 2.56 (1H, ddd, J=15.2, 12.9, 4.6 Hz), 2.50 (3H, s), 2.38 (3H, s).

MS (FAB, m/z): 570 (M+1)$^+$.

EXAMPLE 47

Compound 62

In a manner similar to that in Example 19, 25.9 mg (0.0389 mmol) of Compound 61 was treated with a 7 mol/L methanolic solution of ammonia, to give 17.9 mg of Compound 62 (81%).

$^1$H-NMR (270 MHz, DMSO-$d_6$) δ (ppm): 9.52 (1H, brs), 8.59 (1H, brd, J=5.6 Hz), 8.57 (1H, brs), 7.99 (1H, d, J=8.3 Hz), 7.97 (1H, d, J=6.3 Hz), 7.90 (1H, d, J=16.2 Hz), 7.83 (1H, d, J=7.6 Hz), 7.79 (1H, ddd, J=7.6, 7.6, 1.7 Hz), 7.64 (1H, d, J=8.6 Hz), 7.59 (1H, d, J=7.9 Hz), 7.42 (1H, dd, J=7.9, 7.6 Hz), 7.29 (1H, dd, J=7.6, 7.3 Hz), 7.27 (1H, d, J=16.2 Hz), 7.24 (1H, dd, J=7.6, 5.4 Hz), 6.73 (1H, m), 4.97 (2H, s), 4.07 (1H, d, J=3.0 Hz), 3.35 (3H, s), 3.27 (1H, m), 2.51 (2H, m), 2.31 (3H, s), 1.44 (3H, s).

MS (FAB, m/z): 666 (M+1)$^+$.

EXAMPLE 48

Compound 63

In a manner similar to that in Example 40, 153 mg of Compound 63 (54%) was obtained from 300 mg (0.436 mmol) of Compound ac obtained in Reference Example 24, 9.8 mg (0.044 mmol) of palladium acetate, 53 mg (0.17 mmol) of tri-o-tolylphosphine, 0.20 mL (2.2 mmol) of 1-vinylimidazole and 1.2 mL (8.7 mmol) of triethylamine.

$^1$H-NMR (270 MHz, CDCl$_3$) δ (ppm): 9.42 (1H, brs), 7.85 (1H, d, J=8.9 Hz), 7.84 (1H, s), 7.70 (1H, d, J=8.3 Hz), 7.46 (1H, d, J=8.3 Hz), 7.42 (1H, d, J=14.9 Hz), 7.41 (1H, dd, J=8.6, 8.3 Hz), 7.34 (1H, brs), 7.31 (1H, dd, J=8.3, 7.3 Hz), 7.17 (1H, brs), 7.10 (1H, d, J=8.6 Hz), 6.93 (1H, d, J=14.5 Hz), 6.85 (1H, brs), 6.68 (1H, dd, J=8.7, 4.8 Hz), 5.01 (1H, m), 4.98 (2H, s), 4.01 (1H, brs), 2.97 (3H, s), 2.64 (1H, m), 2.56 (1H, ddd, J=15.4, 12.9, 5.0 Hz), 2.48 (3H, s), 2.39 (3H, s).

MS (FAB, m/z): 655 (M+1)$^+$.

EXAMPLE 49

Compound 64

In a manner similar to that in Example 19, 70.1 mg (0.107 mmol) of Compound 63 was treated with a 7 mol/L methanolic solution of ammonia, to give 36.2 mg of Compound 64 (61%).

$^1$H-NMR (270 MHz, CDCl$_3$) δ (ppm): 9.35 (1H, brs), 8.54 (1H, brs), 8.12 (1H, s), 7.99 (1H, d, J=7.9 Hz), 7.96 (1H, d, J=6.3 Hz), 7.83 (1H, brs), 7.78 (1H, d, J=14.9 Hz), 7.71 (1H, d, J=8.6 Hz), 7.63 (1H, d, J=8.6 Hz), 7.42 (1H, dd, J=8.6, 7.3 Hz), 7.28 (1H, dd, J=7.6, 6.3 Hz), 7.24 (1H, d, J=14.5 Hz), 7.06 (1H, brs), 6.72 (1H, m), 4.96 (2H, s), 4.07 (1H, d, J=3.0 Hz), 3.35 (3H, s), 3.27 (1H, m), 2.51 (2H, m), 2.31 (3H, s), 1.45 (3H, s).

MS (FAB, m/z): 559 (M+1)$^+$.

EXAMPLE 50

Compound 65

In a manner similar to that in step 3 of Example 1, 7.2 mg of Compound 65 (11%) was obtained from 75.0 mg (0.115 mmol) of Compound 63, dimethyl sulfoxide, and 0.23 mL of a 6 mol/L aqueous solution of sodium hydroxide. The resulting product was a mixture (1.19:1) of isomers based on their hydroxyl group by HPLC.

$^1$H-NMR (270 MHz, DMSO-d$_6$) δ (ppm): 9.29 (1H, s), 8.77 (1H, s), 8.44 and 8.37 (Total 1H, 2d, J=7.6 Hz), 8.12 (1H, s), 7.97 (1H, d, J=8.2 Hz), 7.83 (1H, s), 7.78 (1H, d, J=14.5 Hz), 7.72 (1H, d, J=9.2 Hz), 7.64 (1H, d, J=8.6 Hz), 7.40 (1H, dd, J=7.9, 7.6 Hz), 7.25 (1H, m), 7.24 (1H, d, J=14.5 Hz), 7.06 (1H, s), 6.71 (1H, m), 6.41 (1H, m), 4.08 (1H, brs), 3.37 and 3.35 (Total 3H, 2s), 3.32 (1H, m), 2.50 (2H, m), 2.30 and 2.29 (Total 3H, 2s), 1.54 and 1.46 (Total 3H, 2s).

MS (FAB, m/z): 575 (M+1)$^+$.

EXAMPLE 51

Compound 66

In a manner similar to that in Example 40, 89.4 mg of Compound 66 (77%) was obtained from 120 mg (0.174 mmol) of Compound ac obtained in Reference Example 24, 4.0 mg (0.017 mmol) of palladium acetate, 21.0 mg (0.070 mmol) of tri-o-tolylphosphine, 0.094 mL (0.87 mmol) of 4-vinylpyridine and 0.49 mL (3.5 mmol) of triethylamine.

$^1$H-NMR (270 MHz, CDCl$_3$) δ (ppm): 9.54 (1H, brs), 8.56 (2H, d, J=5.9 Hz), 7.83 (1H, d, J=7.6 Hz), 7.69 (1H, d, J=8.6 Hz), 7.54 (1H, dd, J=8.6, 1.7 Hz), 7.53 (1H, d, J=16.2 Hz), 7.44 (1H, dd, J=7.3, 7.3 Hz), 7.40 (2H, d, J=6.3 Hz), 7:31 (1H, dd, J=7.6, 7.3 Hz), 7.05 (1H, d, J=8.2 Hz), 7.03 (1H, d, J=16.5 Hz), 6.92 (1H, brs), 6.61 (1H, dd, J=8.6, 5.0 Hz), 4.97 (2H, s), 4.91 (1H, m), 3.98 (1H, brs), 2.96 (3H, s), 2.62 (1H, m), 2.58 (1H, ddd, J=14.7, 12.2, 5.0 Hz), 2.47 (3H, s), 2.36 (3H, s).

MS (FAB, m/z): 666 (M+1)$^+$.

EXAMPLE 52

Compound 67

In a manner similar to that in Example 19, 57.2 mg (0.0859 mmol) of Compound 66 was treated with a 7 mol/L methanolic solution of ammonia, to give 48.4 mg of Compound 67 (99%).

$^1$H-NMR (270 MHz, DMSO-d$_6$) δ (ppm): 9.51 (1H, brs), 8.55 (1H, brs), 8.54 (2H, d, J=5.9 Hz), 7.99 (1H, d, J=7.9 Hz), 7.97 (1H, d, J=5.9 Hz), 7.85 (1H, d, J=8.6 Hz), 7.74 (1H, d, J=16.2 Hz), 7.66 (1H, d, J=8.9 Hz), 7.62 (2H, d, J=5.9 Hz), 7.43 (1H, dd, J=8.3, 7.3 Hz), 7.29 (1H, dd, J=7.6, 7.3 Hz), 7.19 (1H, d, J=16.5 Hz), 6.74 (1H, m), 4.97 (2H, s), 4.08 (1H, d, J=3.6 Hz), 3.36 (3H, s), 3.31 (1H, m), 2.54 (2H, m), 2.31 (3H, s), 1.45 (3H, s).

MS (FAB, m/z): 570 (M+1)$^+$.

EXAMPLE 53

Compounds 68 and 69

In a manner similar to that in step 3 of Example 1, 11.8 mg of Compound 68 (5.2%) and 9.4 mg of Compound 69 (4.2%) were obtained from 257 mg (0.386 mmol) of Compound 66, dimethyl sulfoxide and 0.76 mL of a 6 mol/L aqueous solution of sodium hydroxide. The ratio of the respective diastereoisomers based on their hydroxyl group by HPLC was as follows: Compound 68 (90.1% d.e.) and Compound 69 (96.7% d.e.)

Compound 68

$^1$H-NMR (270 MHz, DMSO-d$_6$) δ (ppm): 9.45 (1H, s), 8.81 (1H, s), 8.54 (2H, d, J=5.0 Hz), 8.38 (1H, d, J=7.9 Hz), 7.97 (1H, d, J=8.6 Hz), 7.86 (1H, d, J=8.3 Hz), 7.75 (1H, d, J=16.2 Hz), 7.66 (1H, d, J=8.4 Hz), 7.63 (2H, d, J=5.6 Hz), 7.41 (1H, dd, J=7.9, 7.3 Hz), 7.26 (1H, dd, J=10.9, 7.3 Hz), 7.19 (1H, d, J=16.5 Hz), 6.73 (1H, m), 6.45 (2H, m), 4.08 (1H, brs), 3.36 (3H, s), 3.31 (1H, m), 2.54 (2H, m), 2.30 (3H, s), 1.44 (3H, s).

MS (FAB, m/z): 586 (M+1)$^+$.

Compound 69

$^1$H-NMR (270 MHz, DMSO-d$_6$) δ (ppm): 9.46 (1H, s), 8.80 (1H, s), 8.54 (2H, d, J=5.3 Hz), 8.43 (1H, d, J=7.9 Hz), 7.97 (1H, d, J=8.6 Hz), 7.86 (1H, d, J=8.3 Hz), 7.75 (1H, d, J=16.2 Hz), 7.66 (1H, d, J=8.4 Hz), 7.63 (2H, d, J=5.6 Hz), 7.41 (1H, dd, J=8.3, 7.3 Hz), 7.25 (1H, dd, J=9.2, 7.6 Hz), 7.19 (1H, d, J=16.5 Hz), 6.72 (1H, m), 6.50 (1H, m), 6.43 (1H, m), 4.08 (1H, brs), 3.38 (3H, s), 3.31 (1H, m), 2.51 (2H, m), 2.29 (3H, s), 1.52 (3H, s).

MS (FAB, m/z): 586 (M+1)$^+$.

EXAMPLE 54

Compound 70

Step 1

In a manner similar to that in Example 40, 78.4 mg of 17-[2-(4-methyl-1,3-thiazol-5-yl)vinyl]-11-N-trifluoroacetyl staurosporin (79%) was obtained from 100 mg (0.145 mmol) of Compound ac obtained in Reference Example 24, 2.6 mg (0.012 mmol) of palladium acetate, 14 mg (0.046 mmol) of tri-o-tolylphosphine, 0.083 mL (0.73 mmol) of 4-methyl-5-vinyl-1,3-thiazole and 0.40 mL (2.9 mmol) of triethylamine.

$^1$H-NMR (270 MHz, CDCl$_3$) δ (ppm): 9.50 (1H, s), 8.57 (1H, s), 7.88 (1H, d, J=7.3 Hz), 7.72 (1H, d, J=8.6 Hz), 7.61 (1H, dd, J=8.6, 1.7 Hz), 7.46 (1H, dd, J=7.3, 7.3 Hz), 7.34 (1H, dd, J=7.6, 7.6 Hz), 7.27 (1H, d, J=15.8 Hz), 7.17 (1H, d, J=8.6 Hz), 7.10 (1H, d, J=16.2 Hz), 6.73 (1H, dd, J=8.6, 5.3 Hz), 6.56 (1H, s), 5.04 (1H, m,), 4.99 (2H, s), 4.06 (1H, brs), 3.00 (3H, s), 2.70 (1H, m), 2.65 (1H, s), 2.62 (3H, s), 2.50 (3H, s), 2.47 (3H, s).

MS (FAB, m/z): 686 (M+1)$^+$.

Step 2

In a manner similar to that in Example 19, 40.0 mg (0.0583 mmol) of 17-[2-(4-methyl-1,3-thiazol-5-yl)vinyl]-11-N-trifluoroacetyl staurosporin was treated with a 7 mol/L methanolic solution of ammonia, to give 25.7 mg of Compound 70 (75%).

$^1$H-NMR (270 MHz, DMSO-d$_6$) δ (ppm): 9.41 (1H, s), 8.89 (1H, s), 8.54 (1H, s), 7.97 (2H, m), 7.85 (1H, d, J=8.6 Hz), 7.62 (1H, d, J=8.6 Hz), 7.42 (1H, dd, J=7.6, 7.3 Hz), 7.38 (1H, d, J=15.8 Hz), 7.28 (1H, dd, J=7.6, 7.3 Hz), 7.05 (1H, d, J=15.8 Hz), 6,73 (1H, m), 4.96 (2H, s), 4.07 (1H, d, J=3.3 Hz), 3.33 (3H, s), 3.28 (1H, m), 2.54 (3H, s), 2.51 (2H, m), 2.31 (3H, s), 1.44 (3H, s).

MS (FAB, m/z): 590 (M+1)$^+$.

EXAMPLE 55

Compound 71

Step 1

In a manner similar to that in Example 40, 54.2 mg of 17-[2-(1,2,4-triazol-1-yl)vinyl]-11-N-trifluoroacetyl staurosporin (57%) was obtained from 100 mg (0.145 mmol) of Compound ac obtained in Reference Example 24, 2.6 mg (0.0116 mmol) of palladium acetate, 14 mg (0.046 mmol) of tri-o-tolylphosphine, 0.063 mL (0.73 mmol) of 1-vinyl-1,2,4-triazole and 0.40 mL (2.9 mmol) of triethylamine.

$^1$H-NMR (270 MHz, CDCl$_3$) δ (ppm): 9.46 (1H, brs), 8.44 (1H, s), 8.08 (1H, s), 7.84 (1H, d, J=7.3 Hz), 7.67 (1H, d, J=8.6 Hz), 7.61 (1H, d, J=14.5 Hz), 7.42 (1H, d, J=14.5 Hz), 7.39 (1H, dd, J=9.9, 8.9 Hz), 7.29 (3H, m), 7.05 (1H, d, J=8.2 Hz), 6.66 (1H, dd, J=8.9, 4.6 Hz), 5.04 (1H, d, J=16.5 Hz), 4.98 (1H, m), 4.95 (1H, d, J=16.5 Hz), 3.97 (1H, brs), 2.96 (3I, s), 2.63 (1H, m), 2.55 (1H, m), 2.49 (3H, s), 2.32 (3H, s).

MS (FAB, m/z): 656 (M+1)$^+$.

Step 2

In a manner similar to that in Example 19, 37.0 mg (0.0564 mmol) of 17-[2-(1,2,4-triazol-1-yl)vinyl]-11-N-trifluoroacetyl staurosporin was treated with a 7 mol/L methanolic solution of ammonia, to give 28.3 mg of Compound 71 (90%).

$^1$H-NMR (270 MHz, DMSO-d$_6$) δ (ppm): 9.41 (1H, brs), 8.97 (1H, s), 8.56 (1H, s), 8.19 (1H, s), 7.99 (1H, m), 7.97 (1H, d, J=14.5 Hz), 7.96 (1H, d, J=7.9 Hz), 7.76 (1H, d, J=8.9 Hz), 7.66 (1H, d, J=8.6 Hz), 7.46 (1H, d, J=14.5 Hz), 7.42 (1H, m), 7.28 (1H, dd, J=7.6, 7.6 Hz), 6.73 (1H, m), 4.96 (2H, s), 4.08 (1H, d, J=3.3 Hz), 3.36 (3H, s), 3.29 (1H, m), 2.51 (2H, m), 2.31 (3H, s), 1.44 (3H, s).

MS (FAB, m/z): 560 (M+1)$^+$.

EXAMPLE 56

Compound 72

Step 1

In a manner similar to that in Example 40, 52.8 mg of 17-(2-carbamoylvinyl)-11-N-trifluoroacetyl staurosporin (58%) was obtained from 100 mg (0.145 mmol) of Compound ac obtained in Reference Example 24, 1.6 mg (0.0073 mmol) of palladium acetate, 8.8 mg (0.029 mmol) of tri-o-tolylphosphine, 0.052 mg (0.73 mmol) of acrylamide and 0.40 mL (2.9 mmol) of triethylamine.

$^1$H-NMR (270 MHz, CDCl$_3$+CD$_3$OD) δ (ppm): 9.59 (1H, s), 7.82 (1H, d, J=15.5 Hz), 7.81 (1H, d, J=7.9 Hz), 7.71 (1H, d, J=8.6 Hz), 7.47 (1H, dd, J=8.3, 6.3 Hz), 7.45 (1H, d, J=8.3 Hz), 7.33 (1H, dd, J=8.6, 7.6 Hz), 7.05 (1H, d, J=8.2 Hz), 6.74 (1H, d, J=15.5 Hz), 6.61 (1H, dd, J=8.9, 4.6 Hz), 4.96 (1H, m), 4.92 (2H, s), 3.98 (1H, s), 2.96 (3H, s), 2.69 (1H, m), 2.60 (1H, m), 2.51 (3H, s), 2.33 (3H, s).

MS (FAB, m/z): 632 (M+1)$^+$.

Step 2

In a manner similar to that in Example 19, 40.0 mg (0.0633 mmol) of 17-(2-carbamoylvinyl)-11-N-trifluoroacetyl staurosporin was treated with a 7 mol/L methanolic solution of ammonia, to give 29.2 mg of Compound 72 (86%).

$^1$H-NMR (270 MHz, DMSO-d$_6$) δ (ppm): 9.51 (1H, s), 8.57 (1H, s), 7.99 (1H, d, J=8.3 Hz), 7.97 (1H, d, J=7.3 Hz), 7.65 (4H, m), 7.42 (1H, dd, J=8.3, 7.6 Hz), 7.28 (1H, dd, J=7.6, 7.3 Hz), 7.02 (1H, brs), 6.73 (1H, m), 6.63 (1H, d, J=15.8 Hz), 4.97 (2H, s), 4.07 (1H, d, J=3.3 Hz), 3.29 (1H, m), 2.51 (2H, m), 2.30 (3H, s), 1.43 (3H, s).

MS (FAB, m/z): 536 (M+1)$^+$.

EXAMPLE 57

Compound 73

Step 1

In a manner similar to that in Example 40, 1.36 g of 17-(2-tert-butoxycarbonylvinyl)-11-N-trifluoroacetyl staurosporin (91%) was obtained from 1.50 g (2.18 mmol) of Compound ac obtained in Reference Example 24, 39 mg (0.17 mmol) of palladium acetate, 212 mg (0.697 mmol) of tri-o-tolylphosphine, 1.6 mg (11 mmol) of tert-butyl acrylate and 6.1 mL (44 mmol) of triethylamine.

$^1$H-NMR (270 MHz, CDCl$_3$) δ (ppm): 9.47 (1H, s), 7.86 (1H, d, J=7.6 Hz), 7.83 (1H, d, J=15.8 Hz), 7.68 (1H, d, J=8.2 Hz), 7.48 (1H, d, J=8.3 Hz), 7.44 (1H, dd, J=7.9, 6.6 Hz), 7.32 (1H, dd, J=7.6, 7.6 Hz), 7.04 (1H, d, J=8.6 Hz), 6.67 (1H, dd, J=8.2, 4.6 Hz), 6.41 (1H, d, J=15.8 Hz), 4.99 (1H, m), 4.98 (2H, s), 3.96 (1H, s), 2.96 (3H, s), 2.67 (1H, m), 2.60 (1H, m), 2.52 (3H, s), 2.30 (3H, s), 1.62 (9H, s).

MS (FAB, m/z): 689 (M+1)$^+$.

Step 2

In a manner similar to that in Example 19, 39.0 mg (0.0566 mmol) of 17-(2-tert-butoxycarbonylvinyl)-11-N-trifluoroacetyl staurosporin was treated with a 7 mol/L methanolic solution of ammonia, to give 26.5 mg of Compound 73 (62%).

$^1$H-NMR (270 MHz, DMSO-d$_6$) δ (ppm): 9.51 (1H, s), 8.57 (1H, s), 7.99 (2H, m), 7.83 (1H, d, J=8.6 Hz), 7.74 (1H, d, J=15.8 Hz), 7.64 (1H, d, J=8.6 Hz), 7.43 (1H, dd, J=8.3, 7.3 Hz), 7.29 (1H, dd, J=7.3, 7.3 Hz), 6.74 (1H, m), 6.47 (1H, d, J=15.8 Hz), 4.97 (2H, s), 4.07 (1H, brs), 3.35 (3H, s), 3.29 (1H, m), 2.50 (2H, m), 2.30 (3H, s), 1.53 (9H, s), 1.42 (3H, s).

MS (FAB, m/z): 593 (M+1)$^+$.

EXAMPLE 58

Compound 74

1.36 g (1.97 mmol) of 17-(2-tert-butoxycarbonylvinyl)-11-N-trifluoroacetyl staurosporin was dissolved in 41 mL dichloromethane followed by adding 1.5 mL (20 mmol) of trifluoroacetic acid, and the mixture was stirred at room temperature for 24 hours. The solvent was distilled away under reduced pressure from the reaction mixture, and the residue was purified by silica gel column chromatography (eluted with chloroform/methanol=from 30/1 to 20/1), to give 883 mg of Compound 74 (71%).

$^1$H-NMR (270 MHz, CDCl$_3$+CD$_3$OD) δ (ppm): 9.48 (1H, s), 7.95 (1H, d, J=15.8 Hz), 7.83 (1H, d, J=7.3 Hz), 7.71 (1H, d, J=8.6 Hz), 7.56 (1H, d, J=8.3 Hz), 7.46 (1H, dd, J=7.3, 7.3 Hz), 7.33 (1H, dd, J=7.6, 7.6 Hz), 7.11 (1H, d, J=8.3 Hz), 6.69 (1H, dd, J=8.9, 4.3 Hz), 6.55 (1H, d, J=15.8 Hz), 5.01 (1H, m), 4.92 (2H, s), 3.98 (1H, brs), 2.97 (3H, s), 2.68 (1H, m), 2.55 (1H, m), 2.5 (3H, s), 2.32 (3H, s).

MS (FAB, m/z): 633 (M+1)$^+$.

EXAMPLE 59

Compound 75

Step 1

30.0 mg (0.0474 mmol) of Compound 74 was dissolved in 1.5 mL of dichloromethane followed by adding 36 mg (0.14 mmol) of 2-chloro-1-methylpyridinium iodide, 0.028 mL (0.28 mmol) of piperidine and 0.040 mL (0.28 mmol) of triethylamine, and the mixture was heated under reflux for 4.5 hours. A saturated aqueous solution of sodium bicarbonate was added to the reaction mixture, and then the mixture was extracted with chloroform. The organic layer was washed with a saturated saline solution and dried over anhydrous sodium sulfate. The solvent was distilled away under reduced pressure. The residue was purified by preparative thin-layer chromatography (developed with chloroform/methanol=15/1) to give 18.0 mg of 17-(2-piperidinocarbonylvinyl)-11-N-trifluoroacetyl staurosporin (54%).

Major component [E isomer]

$^1$H-NMR (270 MHz, CDCl$_3$) δ (ppm): 9.65 (1H, s), 7.94 (1H, d, J=15.2 Hz), 7.85 (1H, d, J=7.6 Hz), 7.72 (1H, d, J=8.6 Hz), 7.54 (1H, d, J=8.6 Hz), 7.46 (1H, dd, J=7.3, 6.9 Hz), 7.33 (1H, dd, J=7.6, 7.3 Hz), 7.20 (1H, br), 7.11 (1H, d, J=8.3 Hz), 7.08 (1H, d, J=15.5 Hz), 6.68 (1H, dd, J=8.9, 4.6 Hz), 5.02 (1H, m), 4.94 (2H, m), 4.01 (1H, brs), 3.73 (4H, br), 2.98 (3H, s), 2.68 (1H, m), 2.53 (1H, m), 2.52 (3H, s), 2.39 (3H, s), 1.92 (2H, br), 1.70 (4H, br).

MS (FAB, m/z): 700 (M+1)$^+$.

Step 2

In a manner similar to that in Example 19, 29.0 mg (0.0414 mmol) of 17-(2-piperidinocarbonylvinyl)-11-N-trifluoroacetyl staurosporin was treated with a 7 mol/L methanolic solution of ammonia, to give 17.9 mg of Compound 75 (72%). The resulting product was a mixture (E/Z=91/9) of isomers based on their olefin moiety by $^1$H-NMR and HPLC.

Major component [E isomer]

$^1$H-NMR (270 MHz, DMSO-d$_6$) δ (ppm): 9.44 (1H, brs), 8.57 (1H, s), 7.99 (1H, d, J=8.6 Hz), 7.93 (2H, d, J=8.6 Hz), 7.70 (1H, d, J=15.5 Hz), 7.64 (1H, d, J=8.6 Hz), 7.42 (1H, dd, J=8.6, 7.3 Hz), 7.29 (1H, dd, J=7.6, 7.3 Hz), 7.18 (1H, d, J=15.2 Hz), 6.75 (1H, m), 4.96 (2H, s), 4.08 (1H, d, J=3.6 Hz), 3.62 (4H, br), 3.33 (3H, s), 3.31 (1H, m), 2.51 (2H, m), 2.31 (3H, s), 1.59 (6H, br), 1.42 (3H, s).

MS (FAB, m/z): 604 (M+1)$^+$.

EXAMPLE 60

Compound 76

Step 1

In a manner similar to that in step 1 of Example 59, 41.4 mg of 17-[2-(1,4-thiomorpholinocarbonyl)vinyl]-11-N-trifluoroacetyl staurosporin (37%) was obtained from 100 mg (0.158 mmol) of Compound 74, 121 mg (0.474%) mol) of 2-chloro-1-methylpyridinium iodide, 0.095 mL (0.95 mmol) of thiomorpholine and 0.013 mL (0.96 mmol) of triethylamine.

Major component [E isomer]

$^1$H-NMR (270 MHz, CDCl$_3$) δ (ppm): 9.63 (1H, s), 7.97 (1H, d, J=15.2 Hz), 7.77 (1H, d, J=7.6 Hz), 7.70 (1H, d, J=8.3 Hz), 7.65 (1H, br), 7.51 (1H, d, J=8.2 Hz), 7.44 (1H, dd, J=8.3, 7.3 Hz), 7.31 (1H, m), 7.06 (1H, d, J=8.6 Hz), 7.00 (1H, d, J=15.2 Hz), 6.60 (1H, m), 5.01 (1H, m), 4.95 (2H, s), 4.06 (4H, br), 3.96 (1H, brs), 2.95 (3H, s), 2.74 (4H, br), 2.64 (1H, m), 2.57 (1H, m), 2.53 (3H, s), 2.31 (3H, s).

MS (FAB, m/z): 718 (M+1)$^+$.

Step 2

In a manner similar to that in Example 19, 30.0 mg (0.0418 mmol) of 17-[2-(1,4-thiomorpholinocarbonyl)vinyl]-11-N-trifluoroacetyl staurosporin was treated with a 7 mol/L methanolic solution of ammonia, to give 17.9 mg of Compound 76 (69%). The resulting product was a mixture (E/Z=89/11) of isomers based on their olefin moiety by $^1$H-NMR and HPLC.

Major component [E isomer]

$^1$H-NMR (270 MHz, DMSO-d$_6$) δ (ppm): 9.43 (1H, s), 8.58 (1H, s), 7.98 (3H, m), 7.72 (1H, d, J=15.5 Hz), 7.66 (1H, d, J=8.6 Hz), 7.42 (1H, d, J=8.6 Hz), 7.28 (1H, dd, J=7.6, 6.9 Hz), 7.18 (1H, d, J=15.5 Hz), 6.76 (1H, m), 4.96 (2H, s), 4.08 (1H, d, J=3.0 Hz), 3.91 (4H, br), 3.36 (3H, s), 3.30 (1H, m), 2.66 (4H, br), 2.51 (2H, m), 2.31 (3H, 8), 1.42 (3H, s)

MS (FAB, m/z): 622 (M+1)$^+$.

EXAMPLE 61

Compound 77

Step 1

In a manner similar to that in Example 40, 64.1 mg of 17-(2-methanesulfonylvinyl)-11-N-trifluoroacetyl staurosporin (66%) was obtained from 100 mg (0.145 mmol) of Compound ac obtained in Reference Example 24, 3.3 mg (0.015 mmol) of palladium acetate, 18 mg (0.058 mmol) of tri-o-tolylphosphine, 0.13 mL (1.5 mmol) of methyl vinyl sulfone and 0.40 mL (2.9 mmol) of triethylamine.

$^1$H-NMR (270 MHz, CDCl$_3$) δ (ppm): 9.40 (1H, s), 7.85 (1H, d, J=7.6 Hz), 7.75 (1H, d, J=15.2 Hz), 7.75 (1H, brs), 7.66 (1H, d, J=8.2 Hz), 7.45 (1H, dd, J=7.9, 7.3 Hz), 7.35 (1H, dd, J=7.6, 7.3 Hz), 7.34 (1H, d, J=7.3 Hz), 7.04 (1H, d, J=8.6 Hz), 6.97 (1H, d, J=15.2 Hz), 6.76 (1H, dd, J=9.2, 4.0 Hz), 4.98 (3H, m), 3.92 (1H, brs), 3.14 (3H, s), 2.94 (3H, s), 2.68 (1H, m), 2.52 (3H, s), 2.50 (1H, m), 2.23 (3H, s).

MS (FAB, m/z): 667 (M+1)$^+$.

Step 2

In a manner similar to that in Example 19, 48.0 mg (0.072 mmol) of 17-(2-methanesulfonylvinyl)-11-N-trifluoroacetyl staurosporin was treated with a 7 mol/L methanolic solution of ammonia, to give 27.6 mg of Compound 77 (67%).

$^1$H-NMR (270 MHz, DMSO-d$_6$) δ (ppm): 9.50 (1H, s), 8.62 (1H, s), 7.99 (1H, d, J=8.6 Hz), 7.97 (1H, d, J=7.6 Hz), 7.89 (1H, d, J=8.6 Hz), 7.72 (1H, d, J=8.6 Hz), 7.64 (1H, d, J=15.5 Hz), 7.43 (1H, dd, J=8.6, 7.3 Hz), 7.35 (1H, d, J=15.5 Hz), 7.29 (1H, dd, J=7.6, 7.3 Hz), 6.76 (1H, m), 4.97 (2H, s), 4.08 (1H, d, J=3.0 Hz), 3.35 (3H, br), 3.33 (3H, s), 2.51 (2H, m), 2.31 (3H, s), 1.40 (3H, s).

MS (FAB, m/z): 571 (M+1)$^+$.

EXAMPLE 62

Compound 78

Step 1

In a manner similar to that in Example 40, 26.9 mg of 17-(3-oxo-1-buten-1-yl)-11-N-trifluoroacetyl staurosporin (29%) was obtained from 100 mg (0.145 mmol) of Compound ac obtained in Reference Example 24, 3.3 mg (0.015 mmol) of palladium acetate, 18 mg (0.058 mmol) of tri-o-tolylphosphine, 0.12 mL (1.5 mmol) of methyl vinyl ketone and 0.40 mL (2.9 mmol) of triethylamine.

$^1$H-NMR (270 MHz, CDCl$_3$+CD$_3$OD) δ (ppm): 9.47 (1H, d, J=1.3 Hz), 7.88 (1H, d, J=7.3 Hz), 7.77 (1H, d, J=16.2 Hz), 7.73 (1H, d, J=8.3 Hz), 7.64 (1H, dd, J=8.6, 1.3 Hz), 7.47 (1H, dd, J=7.3, 6.9 Hz), 7.35 (1H, dd, J=7.6, 7.3 Hz), 7.20 (1H, d, J=8.6 Hz), 6.79 (1H, d, J=16.2 Hz), 6.75 (1H, dd, J=10.1, 4.0 Hz), 5.04 (1H, m), 4.97 (2H, s), 4.04 (1H, s), 3.00 (3H, s), 2.74 (1H, m), 2.58 (1H, ddd, J=15.2, 12.9, 4.6 Hz), 2.50 (3H, s), 2.45 (3H, s), 2.40 (3H, s).

MS (FAB, m/z): 631 (M+1)$^+$.

Step 2

In a manner similar to that in Example 19, 25.0 mg (0.0396 mmol) of 17-(3-oxo-1-buten-1-yl)-11-N-trifluoroacetyl staurosporin was treated with a 7 mol/L methanolic solution of ammonia, to give 12.1 mg of Compound 78 (57%).

$^1$H-NMR (270 MHz, DMSO-d$_6$) δ (ppm): 9.57 (1H, s), 8.59 (1H, s), 7.99 (1H, d, J=8.3 Hz), 7.96 (1H, d, J=6.3 Hz), 7.86 (1H, d, J=7.3 Hz), 7.82 (1H, d, J=15.8 Hz), 7.68 (1H, d, J=8.6 Hz), 7.43 (1H, dd, J=8.3, 7.6 Hz), 7.29 (1H, dd, J=7.6, 7.6 Hz), 6.79 (1H, d, J=16.5 Hz), 6.76 (1H, m), 4.97 (2H, s), 4.08 (1H, d, J=3.3 Hz), 3.36 (3H, s), 3.26 (1H, m), 2.50 (2H, m), 2.40 (3H, s), 2.31 (3H, s), 1.42 (3H, s).

MS (FAB, m/z): 535 (M+1)$^+$.

EXAMPLE 63

Compound 79

Step 1

In a manner similar to that in Example 40, 30.4 mg of 5,17-bis[2-(2-pyridyl)vinyl]-11-N-trifluoroacetyl staurosporin (41%) was obtained from 70.0 mg (0.0972 mmol) of Compound aa obtained in Reference Example 22, 3.5 mg (0.016 mmol) of palladium acetate, 19 mg (0.063 mmol) of tri-o-tolylphosphine, 0.13 mL (1.2 mmol) of 2-vinylpyridine and 0.41 mL (2.9 mmol) of triethylamine.

$^1$H-NMR (270 MHz, CDCl$_3$) δ (ppm): 9.61 (1H, s), 8.58 (2H, br), 7.91 (1H, d, J=16.2 Hz), 7.76 (1H, brs), 7.68 (1H, d, J=15.2 Hz), 7.58–7.60 (4H, m), 7.53 (1H, dd, J=7.6, 7.3 Hz), 7.41 (1H, d, J=7.9 Hz), 7.35 (1H, d, J=7.6 Hz), 7.19 (1H, d, J=15.8 Hz), 7.11 (1H, d, J=16.5 Hz), 7.10 (1H, dd, J=7.3, 5.0 Hz), 7.00 (1H, dd, J=7.3, 5.0 Hz), 6.93 (1H, d, J=8.6 Hz), 6.49 (1H, dd, J=9.1, 3.8 Hz), 5.08 (1H, d, J=16.8 Hz), 5.02 (1H, m), 4.94 (1H, d, J=16.5 Hz), 3.83 (1H, s), 2.90 (3H, s), 2.54 (1H, m), 2.43 (1H, ddd, J=13.8, 13.0, 3.6 Hz), 2.14 (3H, s).

MS (FAB, m/z): 769 (M+1)$^+$.

Step 2

In a manner similar to that in Example 19, 26.4 mg (0.0343 mmol) of 5,17-bis[2-(2-pyridyl)vinyl]-11-N-trifluoroacetyl staurosporin was treated with a 7 mol/L methanolic solution of ammonia, to give 19.2 mg of Compound 79 (83%).

$^1$H-NMR (270 MHz, DMSO-d$_6$) δ (ppm): 9.53 (1H, s), 8.65 (1H, brs), 8.591 (2H, d, J=4.3 Hz), 8.21 (1H, s), 8.00 (1H, d, J=8.9 Hz), 7.94 (1H, d, J=16.2 Hz), 7.90 (1H, d, J=16.2 Hz), 7.77–7.85 (4H, m), 7.65 (1H, d, J=8.9 Hz), 7.59 (2H, m), 7.38 (1H, d, J=16.2 Hz), 7.27 (1H, d, J=16.2 Hz), 7.22 (2H, m), 6.74 (1H, br), 5.07 (2H, s), 4.09 (1H, d, J=3.0 Hz), 3.33 (3H, s), 3.31 (1H, m), 2.51 (2H, m), 2.32 (3H, s), 1.43 (3H, s).

MS (FAB, m/z): 673 (M+1)$^+$.

EXAMPLE 64

Compound 80

Step 1

In a manner similar to that in Example 40, 15.6 mg of 5,17-bis(2-methoxycarbonylvinyl)-11-N-trifluoroacetyl staurosporin (19%) was obtained from 80.0 mg (0.111 mmol) of Compound aa obtained in Reference Example 22, 5.0 mg (0.022 mol) of palladium acetate, 27 mg (0.089 mmol) of tri-o-tolylphosphine, 0.20 mL (2.2 mmol) of methyl acrylate and 0.46 mL (3.3 mmol) of triethylamine.

$^1$H-NMR (270 MHz, CDCl$_3$) δ (ppm): 9.46 (1H, d), 7.94 (1H, brs), 7.91 (1H, d, J=15.8 Hz), 7.78 (1H, d, J=15.8 Hz), 7.70 (1H, s), 7.66 (1H, d, J=8.9 Hz), 7.59 (1H, d, J=8.9 Hz), 7.44 (1H, d, J=8.6 Hz), 6.91 (1H, d, J=8.6 Hz), 6.55 (1H, dd, J=9.2, 4.0 Hz), 6.44 (1H, d, J=16.2 Hz), 6.43 (1H, d, J=15.8 Hz), 5.10 (1H, d, J=16.8 Hz), 5.02 (1H, m), 4.95 (1H, d, J=17.2 Hz), 3.90 (3H, s), 3.85 (1H, brs), 3.83 (3H, s), 2.91 (3H, s), 2.63 (1H, m), 2.59 (3H, s), 2.41 (1H, ddd, J=14.5, 12.9, 4.0 Hz), 2.14 (3H, s).

MS (FAB, m/z): 731 (M+1)$^+$.

Step 2

In a manner similar to that in Example 19, 15.0 mg (0.0205 mmol) of 5,17-bis(2-methoxycarbonylvinyl)-11-N-trifluoroacetyl staurosporin was treated with a 7 mol/L methanolic solution of ammonia, to give 6.8 mg of Compound 80 (52%).

$^1$H-NMR (270 MHz, DMSO-d$_6$) δ (ppm): 9.53 (1H, d, J=1.3 Hz), 8.68 (1H, s), 8.29 (1H, s), 7.99 (1H, d, J=9.2 Hz), 7.92 (1H, d, J=15.8 Hz), 7.89 (1H, d, J=8.0 Hz), 7.85 (1H, d, J=15.8 Hz), 7.80 (1H, d, J=10.2 Hz), 7.67 (1H, d, J=8.6 Hz), 6.75 (1H, br), 6.72 (1H, d, J=16.2 Hz), 6.57 (1H, d, J=15.8 Hz), 5.03 (2H, s), 4.08 (1H, d, J=3.3 Hz), 3.76 (3H, s), 3.75 (3H, s), 3.33 (3H, s), 3.27 (1H, m), 2.51 (2H, m), 2.31 (3H, s), 1.36 (3H, s).

MS (FAB, m/z): 635 (M+1)$^+$.

EXAMPLE 65

Compound 81

In a manner similar to that in step 2 of Example 1, 69.0 mg (0.104 mmol) of Compound 61 was subjected to catalytic reduction in an atmosphere Of hydrogen in the presence of 20 mg of 10% palladium carbon (50% hydrous product), to give 56.1 mg of Compound 81 (81%).

$^1$H-NMR (270 MHz, CDCl$_3$) δ (ppm): 9.37 (1H, s), 8.60 (1H, brd, J=5.0 Hz), 7.84 (1H, d, J=7.6 Hz), 7.70 (1H, d, J=8.6 Hz), 7.60 (1H, ddd, J=7.9, 7.6, 2.0 Hz), 7.43 (1H, dd, J=8.3, 7.3 Hz), 7.34 (1H, dd, J=8.3, 1.7 Hz), 7.30 (1H, dd, J=7.9, 7.3 Hz), 7.25 (1H, d, J=8.6 Hz), 7.13 (1H, dd, J=7.3, 5.0 Hz), 7.10 (1H, d, J=8.3 Hz), 6.94 (1H, brs), 6.62 (1H, dd, J=7.9, 5.6 Hz), 5.02 (1H, m), 4.97 (2H, s), 4.02 (1H, d, J=2.0 Hz), 3.30 (4H, m), 2.98 (3H, s), 2.65 (2H, m), 2.47 (3H, s), 2.43 (3H, s).

MS (FAB, m/z): 668 (M+1)$^+$.

EXAMPLE 66

Compound 82

In a manner similar to that in Example 19, 38.5 mg (0.0577 mmol) of Compound 81 was treated with a 7 mol/L methanolic solution of ammonia, to give 22.8 mg of Compound 82 (69%).

$^1$H-NMR (270 MHz, DMSO-d$_6$) δ (ppm): 9.17 (1H, d, J=1.3 Hz), 8.54 (1H, brd, J=4.0 Hz), 8.50 (1H, brs), 7.98 (1H, d, J=8.3 Hz), 7.95 (1H, d, J=6.6 Hz), 7.68 (1H, ddd, J=7.6, 7.6, 2.0 Hz), 7.48 (1H, d, J=8.6 Hz), 7.41 (1H, dd, J=7.9, 7.6 Hz), 7.33 (1H, dd, J=8.3, 1.7 Hz), 7.32 (1H, d, J=8.9 Hz), 7.27 (1H, dd, J=7.9, 7.6 Hz), 7.21 (1H, dd, J=6.6, 5.0 Hz), 6.66 (1H, dd, J=3.6, 3.3 Hz), 4.94 (2H, s), 4.05 (1H, d, J=3.3 Hz), 3.32 (3H, s), 3.25 (1H, m), 3.17 (4H, br), 2.49 (2H, m), 2.29 (3H, s), 1.46 (3H, s).

MS (FAB, m/z): 572 (M+1)$^+$.

EXAMPLE 67

Compound 83

Step 1

In a manner similar to that in step 2 of Example 1, 50.0 mg (0.0764 mmol) of Compound 63 was subjected to catalytic reduction in an atmosphere of hydrogen in the presence of 40 mg of 10% palladium carbon (50% hydrous product), to give 17.5 mg of 17-[2-(1,3-imidazol-1-yl)ethyl]-11-N-trifluoroacetyl staurosporin (35%).

$^1$H-NMR (270 MHz, CDCl$_3$) δ (ppm): 9.32 (1H, 8), 7.90 (1H, d, J=7.6 Hz), 7.72 (1H, d, J=8.6 Hz), 7.46 (1H, dd, J=7.3, 7.3 Hz), 7.37 (1H, s), 7.35 (1H, dd, J=7.3, 6.9 Hz), 7.11 (1H, d, J=8.3 Hz), 7.05 (1H, brs), 7.02 (1H, dd, J=8.3, 1.7 Hz), 6.98 (1H, brs), 6.70 (1H, dd, J=8.1, 5.8 Hz), 6.57 (1H, br), 5.06 (1H, m), 5.02 (2H, s), 4.32 (2H, t, J=7.1 Hz), 4.07 (1H, d, J=2.0 Hz), 3.29 (2H, t, J=7.1 Hz), 3.01 (3H, s), 2.70 (1H, m), 2.60 (1H, m), 2.50 (3H, s), 2.48 (3H, s).

MS (FAB, m/z): 657 (M+1)$^+$.

Step 2

In a manner similar to that in Example 19, 24.4 mg (0.0372 mmol) of 17-[2-(1,3-imidazol-1-yl)ethyl]-11-N-trifluoroacetyl staurosporin was treated with a 7 mol/L methanolic solution of ammonia, to give 7.8 mg of Compound 83 (37%).

$^1$H-NMR (270 MHz, DMSO-d$_6$) δ (ppm): 9.14 (1H, s), 8.50 (1H, s), 7.98 (1H, d, J=8.3 Hz), 7.95 (1H, d, J=7.3 Hz), 7.60 (1H, s), 7.52 (1H, d, J=8.6 Hz), 7.41 (1H, dd, J=7.6, 7.6 Hz), 7.29 (1H, d, J=6.9 Hz), 7.27 (1H, dd, J=9.6, 6.9 Hz), 7.24 (1H, s), 6.86 (1H, s), 6.68 (1H, m), 4.94 (2H, s), 4.32 (2H, t, J=7.3 Hz), 4.07 (1H, d, J=3.3 Hz), 3.33 (2H, s), 3.27 (1H, m), 3.23 (2H, t, J=7.3 Hz), 2.51 (2H, m), 2.30 (3H, s), 1.46 (3H, s).

MS (FAB, m/z): 561 (M+1)$^+$.

EXAMPLE 68

Compound 84

Step 1

In a manner similar to that in step 2 of Example 1, 50.0 mg (0.0773 mmol) of Compound 55 was subjected to catalytic reduction in an atmosphere of hydrogen in the presence of 20 mg of 10% palladium carbon (50 hydrous product), to give 35.8 mg of 17-(2-methoxycarbonylethyl)-11-N-trifluoroacetyl staurosporin (71%).

$^1$H-NMR (270 MHz, CDCl$_3$) δ (ppm): 9.28 (1H, s), 7.89 (1H, d, J=7.3 Hz), 7.71 (1H, d, J=8.6 Hz), 7.45 (1H, dd, 7.5 7.3, 7.3 Hz), 7.34 (1H, dd, d=7.6, 6.6 Hz), 7.32 (1H, d, J=7.9 Hz), 7.12 (1H, d, J=8.3 Hz), 6.74 (1H, br), 6.66 (1H, dd, J=8.3, 5.3 Hz), 5.02 (1H, m), 4.97 (2H, s), 4.04 (1H, d, J=1.7 Hz), 3.73 (3H, s), 3.21 (2H, t, J=7.9 Hz), 2.99 (3H, s), 2.80 (2H, t, J=7.9 Hz), 2.68 (1H, m), 2.58 (1H, m), 2.48 (3H, s), 2.44 (3H, s).

MS (FAB, m/z): 649 (M+1)$^+$.

Step 2

In a manner similar to that in Example 19, 27.0 mg (0.0416 mmol) of 17-(2-methoxycarbonylethyl)-11-N-trifluoroacetyl staurosporin was treated with a 7 mol/L methanolic solution of ammonia, to give 14.4 mg of Compound 84 (63%).

$^1$H-NMR (270 MHz, DMSO-d$_6$) δ (ppm): 9.11 (1H, s), 8.49 (1H, d), 7.98 (1H, d, J=8.6 Hz), 7.95 (1H, d, J=6.9 Hz), 7.50 (7H, d, J=8.6 Hz), 7.41 (1H, dd, J=8.3, 7.3 Hz), 7.33 (1H, d, J=8.6 Hz), 7.27 (1H, dd, J=7.6, 7.3 Hz), 6.67 (1H, m), 4.94 (2H, s), 4.06 (1H, d, J=3.3 Hz), 3.62 (3H, s), 3.33 (3H, s), 3.25 (1H, m), 3.06 (2H, t, J=7.6 Hz), 2.73 (2H, t, J=7.6 Hz), 2.49 (2H, m), 2.29 (3H, s), 1.45 (3H, s).

MS (FAB, m/z): 553 (M+1)$^+$.

EXAMPLE 69

Compound 85

50.0 mg (0.0780 mmol) of Compound y obtained in Reference Example 20 was dissolved in a mixed solvent of 1.2 mL of toluene and 0.3 mL of ethanol followed by adding 4.5 mg (0.0039 mmol) of tetrakistriphenylphosphine palladium, 11 mg (0.098 mmol) of phenylboric acid and 0.16 mL of a 1 mol/L aqueous solution of sodium carbonate, and the mixture was stirred at 60° C. for 1.5 hours under an atmosphere of argon. Water was added to the reaction mixture, and then the mixture was extracted with chloroform. The organic layer was washed with a saturated saline solution and dried over anhydrous sodium sulfate. The solvent was distilled away under reduced pressure. The residue was purified by preparative thin-layer chromatography (developed with chloroform/methanol=15/1) to give 37.9 mg of Compound 85 (76%).

$^1$H-NMR (270 MHz, CDCl$_3$) δ (ppm): 9.78 (1H, t, J=1.7 Hz), 7.79 (3H, m), 7.69 (1H, d, J=8.6 Hz), 7.61 (1H, dd, J=8.6, 2.0 Hz), 7.47 (3H, m), 7.36 (1H, dd, J=8.6, 7.6 Hz), 7.28 (1H, dd, J=7.6, 7.3 Hz), 7.05 (1H, d, J=8.6 Hz), 6.79 (1H, brs), 6.50 (1H, dd, J=6.9, 6.6 Hz), 4.91 (1H, d, J=16.5 Hz), 4.83 (1H, m), 4.83 (1H, d, J=16.2 Hz), 3.95 (1H, d, J=1.7 Hz), 2.92 (3H, s), 2.52 (2H, m), 2.44 (3H, s), 2.32 (3H, s).

MS (FAB, m/z): 639 (M+1)$^+$.

EXAMPLE 70

Compound 86

In a manner similar to that in Example 19, 21.6 mg (0.0338 mmol) of Compound 85 was treated with a 7 mol/L methanolic solution of ammonia, to give 16.5 mg of Compound 86 (90%).

$^1$H-NMR (270 MHz, DMSO-d$_6$) δ (ppm): 9.63 (1H, d, J=1.3 Hz), 8.51 (1H, brs), 7.99 (1H, d, J=7.9 Hz), 7.97 (1H, d, J=7.3 Hz), 7.76 (3H, d, J=7.3 Hz), 7.67 (1H, d, J=8.6 Hz), 7.52 (1H, dd, J=7.9, 7.6 Hz), 7.42 (1H, dd, J=7.9, 7.6 Hz), 7.35 (1H, dd, J=7.6, 7.3 Hz), 7.29 (1H, dd, J=7.6, 7.3 Hz), 6.73 (1H, m), 4.97 (2H, s), 4.07 (1H, d, J=3.3 Hz), 3.35 (3H, s), 3.29 (1H, m), 2.53 (2H, m), 2.31 (3H, s), 1.47 (3H, s).

MS (FAB, m/z): 543 (M+1)$^+$.

EXAMPLE 71

Compound 87

In a manner similar to that in Example 69, 49.8 mg of Compound 87 (54%) was obtained from 100 mg (0.145 mmol) of Compound ac obtained in Reference Example 24, 8.4 mg (0.0073 mmol) of tetrakistriphenylphosphine palladium, 26 mg (0.17 mmol) of diethyl (3-pyridyl)borane and 0.29 mL of a 1 mol/L aqueous solution of sodium carbonate.

$^1$H-NMR (270 MHz, CDCl$_3$) δ (ppm): 9.69 (1H, d, J=1.7 Hz), 9.01 (1H, d, J=2.0 Hz), 8.59 (1H, dd, J=4.8, 1.5 Hz), 8.08 (1H, ddd, J=7.9, 2.3, 1.7 Hz), 7.81 (1H, d, J=7.6 Hz), 7.69 (1H, d, J=8.6 Hz), 7.61 (1H, dd, J=8.4, 1.8 Hz), 7.42 (1H, dd, J=7.3, 7.3 Hz), 7.39 (1H, dd, J=7.9, 4.6 Hz), 7.27 (1H, dd, J=7.6, 7.3 Hz), 7.19 (1H, d, J=8.6 Hz), 7.00 (1H, brs), 6.69 (1H, dd, J=8.9, 4.6 Hz), 5.00 (1H, m), 4.93 (2H, s), 3.99 (1H, brs), 2.96 (3H, s), 2.67 (1H, m), 2.57 (1H, ddd, J=15.2, 12.9, 4.6 Hz), 2.49 (3H, s), 2.34, (3H, s).

MS (FAB, m/z): 640 (M+1)$^+$.

EXAMPLE 72

Compound 88

In a manner similar to that in Example 19, 31.2 mg (0.0488 mmol) of Compound 87 was treated with a 7 mol/L methanolic solution of ammonia, to give 20.7 mg of Compound 88 (78%).

$^1$H-NMR (270 MHz, DMSO-d$_6$) δ (ppm): 9.66 (1H, d, J=2.0 Hz), 8.99 (1H, d, J=1.7 Hz), 8.57 (1H, dd, J=4.8, 1.5 Hz), 8.53 (1H, brs), 8.14 (1H, ddd, J=7.9, 2.3, 1.7 Hz), 8.00 (1H, d, J=8.3 Hz), 7.98 (1H, d, J=6.3 Hz), 7.83 (1H, dd, J=8.6, 2.0 Hz), 7.73 (1H, d, J=8.6 Hz), 7.54 (1H, ddd, J=7.9, 5.0, 0.7 Hz), 7.43 (1H, ddd, J=8.6, 7.3, 1.3 Hz), 7.29 (1H, dd, J=7.6, 7.3 Hz), 6.76 (1H, m), 4.97 (2H, s), 4.08 (1H, d, J=3.3 Hz), 3.36 (3H, s), 3.29 (1H, m), 2.53 (2H, m), 2.32 (3H, s), 1.46 (3H, s).

MS (FAB, m/z): 544 (M+1)$^+$.

EXAMPLE 73

Compound 89

100 mg (0.170 mmol) of Compound g obtained in Reference Example 7 was dissolved in 8 mL of 1,2-dichloroethane followed by adding 1.2 mL (1.7 mmol) of 1.5 mol/L dimethylamine in 1,2-dichloroethane, 364 mg (1.72 mmol) of sodium triacetoxyborohydride and 0.12 mL (2.1 mmol) of acetic acid, and the mixture was stirred at room temperature for 12 hours. A saturated aqueous solution of sodium bicarbonate was added to the reaction mixture, and then the mixture was extracted with tetrahydrofuran. The organic layer was washed with a saturated saline solution and dried over anhydrous sodium sulfate. The solvent was distilled away under reduced pressure. The residue was purified by preparative thin-layer chromatography (developed with chloroform/methanol/water=80/30/3) and then treated with a 7 mol/L methanolic solution of ammonia in a manner similar to that in Example 19, to give 4.4 mg of Compound 89 (5%).

$^1$H-NMR (270 MHz, DMSO-d$_6$) δ (ppm): 9.38 (1H, brs), 8.68 (1H, brs), 8.09 (1H, d, J=7.9 Hz), 8.09 (1H, d, J=7.9 Hz), 7.80–7.60 (2H, m), 7.60–7.50 (1H, m), 7.50–7.40 (1H, m), 6.92 (1H, brs), 5.01 (2H, s), 4.60–4.38 (3H, m), 3.37 (3H, s), 3.34–3.26 (1H, m), 2.77 (6H, s), 2.80–2.00 (8H, m).

MS (FAB, m/z): 524 (M+1)$^+$.

EXAMPLE 74

Compound 90

In a manner similar to that in step 3 of Example 1, 7.5 mg of Compound 90 (16%) was obtained from 45.4 mg (0.0868 mmol) of Compound 89, dimethyl sulfoxide and 0.10 mL of a 6 mol/L aqueous solution of sodium hydroxide. The resulting product was a mixture (1:1) of isomers based on their hydroxyl group by HPLC.

$^1$H-NMR (270 MHz, DMSO-d$_6$) δ (ppm): 9.12 (1H, brs), 8.74 (1H, brs), 8.41 and 8.35 (Total 1H, 2d, J=7.6 Hz), 7.96 (1H, d, J=8.6 Hz), 7.56 (1H, d, J=8.6 Hz), 7.44 (1H, dd, J=8.3, 1.3 Hz), 7.39 (1H, dd, J=8.6, 8.3 Hz), 7.24 (1H, dd, J=7.6, 7.3 Hz), 6.80–6.60 (1H, m), 6.50–6.32 (2H, m), 4.08 (1H, d, J=3.0 Hz), 3.69 (2H, brs), 3.34–3.26 (4H, m), 2.52–2.46 (2H, m), 2.28 (3H, s), 2.27 (6H, s), 1.23 (3H, s).

MS (FAB, m/z): 497 (M+1)$^+$.

EXAMPLE 75

Compound 91

In a manner similar to that in Example 73, 12.0 mg of Compound 91 (12%) was obtained from 95.3 mg (0.154 mmol) of Compound h obtained in Reference Example 7, 1.1 mL (1.6 mmol) of 1.5 mol/L dimethylamine in 1,2-dichloroethane, 324 mg (1.53 mmol) of sodium triacetoxyborohydride, 0.11 mL (1.9 mmol) of acetic acid and a 7 mol/L methanolic solution of ammonia.

$^1$H-NMR (270 MHz, DMSO-d$_6$) δ (ppm): 9.33 (1H, brs), 8.69 (1H, brs), 8.20–8.00 (2H, m), 7.72 (1H, d, J=7.6 Hz), 7.62–7.46 (2H, m), 6.80 (1H, brs), 4.98 (2H, s), 4.56–4.10 (5H, m), 3.34–3.26 (4H, m), 2.71 (12H, brs), 2.52–2.46 (2H, m), 2.36 (3H, s), 1.50 (3H, brs).

MS (FAB, m/z): 581 (M+1)$^+$.

EXAMPLE 76

Compound 92

In a manner similar to that in step 3 of Example 1, 24.4 mg of Compound 92 (26%) was obtained from 92.2 mg (0.159 mmol) of Compound 91, dimethyl sulfoxide and 0.20 mL of a 6 mol/L aqueous solution of sodium hydroxide. The resulting product was a mixture (1:1) of isomers based on their hydroxyl group by HPLC.

$^1$H-NMR (270 MHz, DMSO-d$_6$) δ (ppm): 9.10 (1H, brs), 8.73 (1H, d, J=2.3 Hz), 8.32 and 8.26 (Total 1H, 2brs), 7.90 (1H, d, J=8.6 Hz), 7.54 (1H, d, J=8.3 Hz), 7.42 (1H, dd, J=8.3, 1.3 Hz), 7.33 (1H, dd, J=8.6, 1.0 Hz), 6.70–6.60 (1H, m), 6.50–6.30 (2H, m), 4.07 (1H, d, J=3.0 Hz), 3.62 (2H, s), 3.58 (2H, s), 3.34 (3H, s), 3.34–3.26 (1H, m), 2.52–2.46 (2H, m), 2.27 (3H, s), 2.24 (6H, s), 2.23 (6H, s), 1.54 and 1.48 (Total 3H, 2s).

MS (FAB, m/z): 597 (M+1)$^+$.

EXAMPLE 77

Compound 93

In a manner similar to that in Example 73, 13.4 mg of Compound 93 (59%) was obtained from 53.0 mg (0.0839 mmol) of Compound j obtained in Reference Example 9, 0.087 mL (0.80 mmol) of benzylamine, 171 mg (0.810 mmol) of sodium triacetoxyborohydride, 0.055 mL (0.96 mmol) of acetic acid and a 7 mol/L methanolic solution of ammonia.

$^1$H-NMR (270 MHz, DMSO-d$_6$) δ (ppm): 9.22 (1H, brs), 8.61 (1H, brs), 7.97 (1H, d, J=8.3 Hz), 7.94 (1H, d, J=7.6 Hz), 7.60–7.20 (9H, m), 6.69 (1H, brs), 4.93 (2H, s), 4.06 (1H, d, J=3.3 Hz), 3.94 (2H, s), 3.85 (2H, s), 3.34–3.26 (4H, m), 2.52–2.46 (2H, m), 2.29 (3H, s), 1.44 (3H, s).

MS (FAB, m/z): 586 (M+1)$^+$.

EXAMPLE 78

Compound 94

In a manner similar to that in Example 73, 15.8 mg of Compound 94 (44%) was obtained from 1.3 mL (0.065 mmol) of 50 mmol/L Compound j obtained in Reference Example 9 in 1,2-dichloroethane, 0.058 mL (0.58 mmol) of butylamine, 126 mg (0.592 mmol) of sodium triacetoxyborohydride, 0.045 mL (0.78 mmol) of acetic acid and a 7 mol/L methanolic solution of ammonia.

$^1$H-NMR (270 MHz, DMSO-d$_6$) δ (ppm): 9.19 (1H, brs), 8.48 (1H, brs), 7.97 (1H, d, J=8.6 Hz), 7.94 (1H, d, J=7.3 Hz), 7.56 (1H, d, J=8.6 Hz), 7.48 (1H, dd, J=8.3, 1.7 Hz), 7.40 (1H, ddd, J=8.3, 6.9, 1.3 Hz), 7.26 (1H, dd, J=7.6, 7.3 Hz), 6.68 (1H, dd, J=3.6, 3.3 Hz), 4.93 (2H, s), 4.06 (1H, d, J=3.6 Hz), 3.94 (2H, s), 3.34 (3H, s), 3.34–3.26 (1H, m), 2.52–2.46 (2H, m), 2.66 (2H, t, J=6.9 Hz), 2.29 (3H, s), 1.56–1.26 (4H, m), 1.43 (3H, s), 0.87 (3H, t, J=7.3 Hz).

MS (FAB, m/z): 552 (M+1)$^+$.

EXAMPLE 79

Compound 95

In a manner similar to that in Example 73, 5.2 mg of Compound 95 (16%) was obtained from 1.3 mL (0.065 mmol) of 50 mmol/L Compound j obtained in Reference Example 9 in 1,2-dichloroethane, 0.50 mL (0.59 mmol) of 0.86 mol/L methylamine in 1,2-dichloroethane, 126 mg (0.592 mmol) of sodium triacetoxyborohydride, 0.045 mL (0.78 mmol) of acetic acid and a 7 mol/L methanolic solution of ammonia.

$^1$H-NMR (270 MHz, DMSO-d$_6$) δ (ppm): 9.24 (1H, d, J=1.3 Hz), 8.50 (1H, brs), 7.98 (1H, d, J=8.3 Hz), 7.95 (1H, d, J=7.3 Hz), 7.61 (1H, d, J=8.6 Hz), 7.52 (1H, dd, J=8.6, 1.7 Hz), 7.41 (1H, ddd, J=8.6, 7.3, 1.3 Hz), 7.27 (1H, dd, J=7.6, 7.3 Hz), 6.70 (1H, dd, J=3.6, 3.0 Hz), 4.94 (2H, s), 4.07 (1H, d, J=3.6 Hz), 4.04 (2H, s), 3.35 (3H, s), 3.34–3.26 (4H, m), 2.52–2.46 (2H, m), 2.29 (3H, s), 1.41 (3H, s).

MS (FAB, m/z): 510 (M+1)$^+$.

EXAMPLE 80

Compound 96

In a manner similar to that in Example 73, 16.8 mg of Compound 96 (47%) was obtained from 1.3 mL (0.065 mmol) of 50 mmol/L Compound j obtained in Reference Example 9 in 1,2-dichloroethane, 0.066 mL (0.59 mmol) of tert-butylamine, 118 mg (0.557 mmol) of sodium triacetoxyborohydride, 0.045 mL (0.78 mmol) of acetic acid and a 7 mol/L methanolic solution of ammonia.

$^1$H-NMR (270 MHz, DMSO-d$_6$) δ (ppm): 9.26 (1H, brs), 8.49 (1H, brs), 7.98 (1H, d, J=8.6 Hz), 7.95 (1H, d, J=7.3 Hz), 7.63 (1H, d, J=8.3 Hz), 7.53 (1H, dd, J=8.6, 1.3 Hz), 7.41 (1H, ddd, J=8.3, 6.0, 1.3 Hz), 7.27 (1H, dd, J=7.6, 7.3 Hz), 6.71 (1H, brs), 6.74–6.60 (1H, m), 4.94 (2H, s), 4.14–4.00 (3H, m), 3.34–3.26 (1H, m), 3.30 (3H, s), 2.52–2.46 (2H, m), 2.29 (3H, s), 1.39 (3H, s), 1.30 (9H, s).

MS (FAB, m/z): 552 (M+1)$^+$.

EXAMPLE 81

Compound 97

In a manner similar to that in Example 79, 14.6 mg of Compound 97 (42%) was obtained from 1.3 mL (0.065 mmol) of 50 mmol/L Compound j obtained in Reference Example 9 in 1,2-dichloroethane, 0.035 mL (0.59 mmol) of ethanolamine, 117 mg (0.552 mmol) of sodium triacetoxyborohydride, 0.045 mL (0.78 mmol) of acetic acid and a 7 mol/L methanolic solution of ammonia.

$^1$H-NMR (270 MHz, DMSO-d$_6$) δ (ppm): 9.19 (1H, brs), 8.48 (1H, brs), 7.97 (1H, d, J=8.6 Hz), 7.94 (1H, d, J=7.6 Hz), 7.56 (1H, d, J=8.3 Hz), 7.49 (1H, dd, J=8.6, 1.3 Hz), 7.40 (1H, ddd, J=7.6, 7.3, 0.7 Hz), 7.26 (1H, dd, J=7.6, 7.3 Hz), 6.69 (1H, brs), 4.93 (2H, s), 4.63 (1H, brs), 4.06 (1H, d, J=3.3 Hz), 3.97 (2H, s), 3.54 (2H, t, J=5.6 Hz), 3.34–3.26 (4H, m), 2.74 (2H, t, J=5.6 Hz), 2.52–2.46 (2H, m), 2.29 (3H, s), 1.43 (3H, s).

MS (FAB, m/z): 540 (M+1)$^+$.

EXAMPLE 82

Compound 98

In a manner similar to that in Example 73, 10.3 mg of Compound 98 (28%) was obtained from 1.3 mL (0.065 mmol) of 50 mmol/L Compound j obtained in Reference Example 9 in 1,2-dichloroethane, 0.064 mL (0.59 mmol) of N,N-dimethylethylenediamine, 118 mg (0.557 mmol) of sodium triacetoxyborohydride, 0.045 mL (0.78 mmol) of acetic acid and a 7 mol/L methanolic solution of ammonia.

$^1$H-NMR (270 MHz, DMSO-d$_6$) δ (ppm): 9.20 (1H, d, J=1.3 Hz), 8.48 (1H, brs), 7.97 (1H, d, J=8.6 Hz), 7.94 (1H, d, J=7.3 Hz), 7.57 (1H, d, J=8.6 Hz), 7.48 (1H, dd, J=8.3, 1.7 Hz), 7.40 (1H, ddd, J=8.6, 7.3, 1.3 Hz), 7.26 (1H, dd, J=7.6, 7.6 Hz), 6.69 (1H, dd, J=3.6, 3.3 Hz), 4.93 (2H, s), 4.06 (1H, d, J=3.3 Hz), 3.98 (2H, s), 3.34 (3H, s), 3.34–3.26 (1H, m), 2.75 (2H, t, J=6.3 Hz), 2.52–2.46 (2H, m), 2.42 (2H, t, J=6.3 Hz), 2.29 (3H, s), 2.15 (6H, s), 1.42 (3H, s).

MS (FAB, m/z): 567 (M+1)$^+$.

EXAMPLE 83

Compound 99

In a manner similar to that in Example 73, 21.7 mg of Compound 99 (60%) was obtained from 1.3 mL (0.065 mmol) of 50 mmol/L Compound j obtained in Reference Example 9 in 1,2-dichloroethane, 0.051 mL (0.59 mmol) of 2-methoxyethylamine, 122 mg (0.575 mmol) of sodium triacetoxyborohydride, 0.045 mL (0.78 mmol) of acetic acid and a 7 mol/L methanolic solution of ammonia.

$^1$H-NMR (270 MHz, DMSO-d$_6$) δ (ppm): 9.18 (1H, d, J=0.7 Hz), 8.48 (1H, brs), 7.97 (1H, d, J=8.6 Hz), 7.94 (1H, d, J=7.3 Hz), 7.55 (1H, d, J=8.6 Hz), 7.47 (1H, dd, J=8.3, 1.7 Hz), 7.40 (1H, ddd, J=8.3, 6.9, 1.2 Hz), 7.26 (1H, dd, J=7.6, 7.3 Hz), 6.68 (1H, dd, J=3.6, 3.0 Hz), 4.93 (2H, s), 4.06 (1H, d, J=3.3 Hz), 3.95 (2H, s), 3.46 (2H, t, J=5.6 Hz), 3.34–3.26 (4H, m), 3.25 (3H, s), 2.80 (2H, t, J=5.6 Hz), 2.52–2.46 (2H, m), 2.29 (3H, s), 1.43 (3H, s).

MS (FAB, m/z): 553 (M+1)$^+$.

EXAMPLE 84

Compound 100

In a manner similar to that in Example 73, 8.4 mg of Compound 100 (23%) was obtained from 1.3 mL (0.065 mmol) of 50 mmol/L Compound j obtained in Reference Example 9 in 1,2-dichloroethane, 0.053 mL (0.59 mmol) of aniline, 122 mg (0.575 mmol) of sodium triacetoxyborohydride, 0.045 mL (0.78 mmol) of acetic acid and a 7 mol/L methanolic solution of ammonia.

$^1$H-NMR (270 MHz, DMSO-d$_6$) δ (ppm): 9.27 (1H, brs), 8.49 (1H, brs), 7.98 (1H, d, J=8.3 Hz), 7.95 (1H, d, J=6.6 Hz), 7.55 (1H, d, J=8.6 Hz), 7.48 (1H, dd, J=8.4, 1.5 Hz), 7.41 (1H, brdd, J=7.3, 7.6 Hz), 7.27 (1H, dd, J=7.6, 7.3 Hz), 7.03 (2H, dd, J=8.3, 7.3 Hz), 6.72–6.65 (1H, m), 6.65 (2H, d, J=7.9 Hz), 6.49 (1H, brt, J=7.3 Hz), 6.17 (1H, brdd, J=5.3, 5.9 Hz), 4.93 (2H, s), 4.39 (2H, d, J=5.3 Hz), 4.09 (1H, d, J=3.0 Hz), 3.30 (3H, s), 3.34–3.26 (1H, m), 2.52–2.46 (2H, m), 2.30 (3H, s), 1.53 (3H, brs).

MS (FAB, m/z): 572 (M+1)$^+$.

EXAMPLE 85

Compound 101

In a manner similar to that in Example 73, 15.1 mg of Compound 101 (38%) was obtained from 1.3 mL (0.065 mmol) of 50 mmol/L Compound j obtained in Reference Example 9 in 1,2-dichloroethane, 73.1 mg (0.590 mmol) of p-chloroaniline, 125 mg (0.590 mmol) of sodium triacetoxyborohydride, 0.045 mL (0.78 mmol) of acetic acid, 3.0 of a 7 mol/L methanolic solution of ammonia and chloroform.

$^1$H-NMR (270 MHz, DMSO-d$_6$) δ (ppm): 9.25 (1H, brs), 8.48 (1H, brs), 7.98 (1H, d, J=8.3 Hz), 7.98 (1H, d, J=6.9 Hz), 7.54 (1H, d, J=8.6 Hz), 7.45 (1H, dd, J=8.7, 1.5 Hz), 7.39 (1H, brdd, J=6.9, 8.2 Hz), 7.27 (1H, dd, J=7.6, 7.3 Hz), 7.10–7.02 (2H, m), 6.72–6.60 (3H, m), 6.42 (1H, t, J=5.6 Hz), 4.93 (2H, s), 4.39 (2H, d, J=5.3 Hz), 4.09 (1H, d, J=2.6 Hz), 3.34–3.26 (1H, m), 3.31 (3H, s), 2.52–2.46 (2H, m), 2.30 (3H, s), 1.52 (3H, brs).

MS (FAB, m/z): 606, 608 (M+1)$^+$.

EXAMPLE 86

Compound 102

127 mg (0.200 mmol) of Compound m obtained in Reference Example 10 was dissolved in 2 mL of chloroform followed by adding 4 mL of methanol and 234 mg (1.00 mmol) of DL-camphor-10-sulfonic acid, and the mixture was heated under reflux for 3 hours. After cooling the reaction mixture to room temperature, a saturated aqueous solution of sodium bicarbonate was added thereto and the mixture was extracted with chloroform. The organic layer was washed with a saturated saline solution and dried over anhydrous sodium sulfate. The solvent was distilled away under reduced pressure. The residue was purified by preparative thin-layer chromatography (developed with chloroform/methanol=20/1) and then treated with a 6 mol/L aqueous solution of sodium hydroxide in a manner similar to that in step 2 of Example 3, to give 67.8 mg of Compound 102 (66%).

¹H-NMR (270 MHz, DMSO-d₆) δ (ppm): 9.21 (1H, d, J=1.0 Hz), 8.49 (1H, brs), 7.97 (1H, d, J=8.3 Hz), 7.94 (1H, d, J=7.6 Hz), 7.56 (1H, d, J=8.3 Hz), 7.45–7.35 (2H, m), 7.27 (1H, dd, J=7.6, 7.3 Hz), 6.70 (1H, dd, J=3.3, 3.3 Hz), 4.93 (2H, s), 4.57 (2H, s), 4.06 (1H, d, J=3.3 Hz), 3.33 (3H, s), 2.29 (3H, s), 1.44 (3H, s).

MS (FAB, m/z): 511 (M+1)⁺.

EXAMPLE 87

Compounds 103 and 104

In a manner similar to that in step 3 of Example 1, 15.8 mg of Compound 103 (29%) and 17.4 mg of Compound 104 (32%) were obtained from 52.2 mg (0.102 mmol) of Compound 102, dimethyl sulfoxide and 0.50 mL of a 6 mol/L aqueous solution of sodium hydroxide. The ratio of the respective diastereoisomers based on their hydroxyl group by HPLC was as follows: Compound 103 (83.1% d.e.) and Compound 104 (64.0% d.e.)

Compound 103

¹H-NMR (270 MHz, DMSO-d₆) δ (ppm): 9.16 (1H, d, J=1.0 Hz), 8.71 (1H, brs), 8.41 (1H, d, J=7.9 Hz), 7.95 (1H, d, J=8.3 Hz), 7.57 (1H, d, J=8.3 Hz), 7.46–7.34 (2H, m), 7.23 (1H, dd, J=7.3, 7.3 Hz), 6.67 (1H, dd, J=3.6, 3.3 Hz), 6.48–6.34 (2H, m), 4.57 (2H, s), 4.07 (1H, d, J=3.3 Hz), 3.35 (3H, s), 3.34–3.26 (1H, m), 3.33 (3H, s), 2.52–2.46 (2H, m), 2.27 (3H, s), 1.52 (3H, s).

MS (FAB, m/z): 527 (M+1)⁺.

Compound 104

¹H-NMR (270 MHz, DMSO-d₆) δ (ppm): 9.15 (1H, d, J=1.0 Hz), 8.73 (1H, brs), 8.35 (1H, d, J=7.6 Hz), 7.96 (1H, d, J=8.6 Hz), 7.57 (1H, d, J=8.3 Hz), 7.47–7.34 (2H, m), 7.24 (1H, dd, J=7.9, 7.3 Hz), 6.68 (7H, dd, J=3.6, 2.3 Hz), 6.42–6.36 (2H, m), 4.57 (2H, s), 4.06 (1H, d, J=3.6 Hz), 3.34 (3H, s), 3.34–3.26 (1H, m), 3.33 (3H, s), 2.52–2.46 (2H, m), 2.28 (3H, s), 1.43 (3H, s).

MS (FAB, m/z): 527 (M+1)⁺.

EXAMPLE 88

Compound 105

42.4 mg (0.0669 mmol) of Compound m obtained in Reference Example 10 was dissolved in 5 mL of chloroform followed by adding 10 mL of ethanol and 91 mg (0.39 mmol) of DL-camphor-10-sulfonic acid, and the mixture was heated under reflux for 7 hours. After cooling the reaction mixture to room temperature, a saturated aqueous solution of sodium bicarbonate was added thereto and the mixture was extracted with chloroform. The organic layer was washed with a saturated saline solution and dried over anhydrous sodium sulfate. The solvent was distilled away under reduced pressure. The residue was purified by preparative thin-layer chromatography (developed with chloroform/methanol=20/1), to give 10.7 mg of Compound 105 (26%) and 28.9 mg of 2-acetyl-17-ethoxymethyl-11-N-trifluoroacetyl staurosporin (65%) (the compound wherein hydrogen on a nitrogen atom in the lactam moiety of Compound 105 was replaced by an acetyl group).

Compound 105

¹H-NMR (270 MHz, DMSO-d₆) δ (ppm): 9.23 (1H, d, J=1.0 Hz), 8.59 (1H, brs), 8.05 (1H, d, J=7.9 Hz), 8.00 (1H, d, J=8.6 Hz), 7.60 (1H, d, J=8.3 Hz), 7.54–7.44 (2H, m), 7.27 (1H, dd, J=7.6, 7.3 Hz), 7.04 (1H, dd, J=8.3, 6.3 Hz), 4.99 (2H, s), 4.96–4.84 (1H, m), 4.62 (2H, s), 4.43 (1H, brs), 3.53 (2H, q, J=6.9 Hz), 2.52–2.46 (2H, m), 2.96 (3H, brs), 2.75 (3H, s), 2.36 (3H, s), 1.17 (3H, t, J=6.9 Hz).

MS (FAB, m/z): 621 (M+1)⁺.

2-Acetyl-17-ethoxymethyl-11-N-trifluoroacetyl staurosporin

¹H-NMR (270 MHz, CDCl₃) δ (ppm): 9.23 (1H, d, J=1.0 Hz), 8.02 (1H, dd, J=7.6, 0.7 Hz), 7.75 (1H, d, J=8.6 Hz), 7.59 (1H, dd, J=8.3, 1.3 Hz), 7.49 (1H, ddd, J=7.3, 7.3, 1.0 Hz), 7.40 (1H, dd, J=7.6, 7.3 Hz), 7.25 (1H, d, J=7.3 Hz), 6.73 (1H, dd, J=8.9, 5.0 Hz), 5.32 (1H, d, J=17.8 Hz), 5.22 (1H, d, J=17.8 Hz), 5.04 (1H, ddd, J=12.9, 5.6, 2.0 Hz), 4.77 (2H, s), 4.05 (1H, brs), 3.65 (2H, q, J=6.9 Hz), 3.00 (3H, brs), 2.80–2.50 (2H, m), 2.80 (3H, s), 2.52 (3H., s), 2.44 (3H, s), 1.29 (3H, t, J=6.9 Hz).

MS (FAB, m/z): 663 (M+1)⁺.

EXAMPLE 89

Compound 106

In a manner similar to that in step 2 of Example 3, 28.9 mg (0.0437 mmol) of 2-acetyl-17-ethoxymethyl-11-N-trifluoroacetyl staurosporin obtained in Example 88 was treated with 0.5 mL of a 6 mol/L aqueous solution of sodium hydroxide, to give 19.8 mg of Compound 106 (86%).

¹H-NMR (270 MHz, DMSO-d₆) δ (ppm): 9.21 (1H, d, J=1.0 Hz), 8.49 (1H, brs), 7.97 (1H, d, J=8.3 Hz), 7.94 (1H, d, J=7.9 Hz), 7.56 (1H, d, J=8.2 Hz), 7.45–7.35 (2H, m), 7.26 (1H, dd, J=7.6, 7.3 Hz), 6.69 (1H, brs), 4.93 (2H, s), 4.61 (2H, s), 4.06 (1H, d, J=3.3 Hz), 3.54 (2H, q, J=6.9 Hz), 3.34 (3H, s), 3.34–3.26 (1H, m), 2.52–2.46 (2H, m), 2.29 (3H, s), 1.43 (3H, s), 1.18 (3H, t, J=6.9 Hz).

MS (FAB, m/z): 525 (M+1)⁺.

EXAMPLE 90

Compound 107

In a manner similar to that in Example 88, 112 mg (0.168 mmol) of Compound n obtained in Reference Example 11 was treated with 20 mL of methanol and 585 mg (2.52 mmol) of DL-camphor-10-sulfonic acid, 36.8 mg out of 179 mg of the resulting crude product was purified by preparative thin-layer chromatography (developed with chloroform/methanol=20/1 and then developed with chloroform/methanol/28% aqueous ammonia=100/10/1), to give 8.2 mg of Compound 107 (36%).

¹H-NMR (270 MHz, DMSO-d₆) δ (ppm): 9.23 (1H, brs), 8.61 (1H, brs), 8.03–7.94 (2H, m), 7.60 (1H, d, J=8.6 Hz), 7.50–7.40 (2H, m), 7.05 (1H, dd, J=7.6, 6.6 Hz), 4.99 (2H, s), 4.95–4.86 (1H, m), 4.61 (2H, s), 4.58 (2H, s), 4.43 (1H, brs), 3.36 (3H, s), 3.32 (3H, s), 2.96 (3H, s), 2.75 (3H, s), 2.52–2.46 (2H, m), 2.36 (3H, s).

MS (FAB, m/z): 651 (M+1)⁺.

EXAMPLE 91

Compound 108

In a manner similar to that in Example 86, 554 mg (0.834 mmol) of Compound n obtained in Reference Example 11 was treated with 20 mL of methanol and 1.90 g (8.20 mmol) of DL-camphor-10-sulfonic acid. Then in a manner similar to that in step 2 of Example 3, the reaction mixture was treated with a 6 mol/L aqueous solution of sodium hydroxide, to give 328 mg of Compound 108 (71%).

$^1$H-NMR (270 MHz, DMSO-d$_6$) δ (ppm): 9.21 (1H, brs), 8.50 (1H, brs), 7.92 (1H, d, J=8.9 Hz), 7.87 (1H, brs), 7.56 (1H, d, J=8.3 Hz), 7.42 (1H, dd, J=8.3, 1.3 Hz), 7.3.7 (1H, brd, J=8.6 Hz), 6.70 (1H, brs), 4.94 (2H, s), 4.58 (2H, s), 4.57 (2H, s), 4.06 (1H, d, J=3.0 Hz), 3.35 (3H, s), 3.35 (3H, s), 3.34–3.26 (1H, m), 3.33 (3H, s), 2.52–2.46 (2H, m), 2.29 (3H, s), 1.45 (3H, s).

MS (FAB, m/z): 555 (M+1)$^+$.

EXAMPLE 92

Compounds 109 and 110

In a manner similar to that in step 3 of Example 1, 15.0 mg of Compound 109 (29%) and 12.8 mg of Compound 110 (25%) were obtained from 50.7 mg (0.0915 mmol) of Compound 108, dimethyl sulfoxide and 0.50 mL of a 6 mol/L aqueous solution of sodium hydroxide. The ratio of the respective diastereoisomers based on their hydroxyl group by HPLC was as follows: Compound 109 (16.4% d.e.) and Compound 110 (49.8% d.e.)

Compound 109

$^1$H-NMR (270 MHz, DMSO-d$_6$) δ (ppm): 9.16 (1H, brs), 8.72 (1H, brs), 8.36 (1H, brs), 7.92 (1H, d, J=8.9 Hz), 7.56 (1H, d, J=8.6 Hz), 7.43 (1H, dd, J=8.3, 1.7 Hz), 7.35 (1H, dd, J=8.6, 1.7 Hz), 6.72–6.64 (1H, m), 6.48–6.36 (2H, m), 4.57 (2H, 9), 4.55 (2H, s), 4.07 (1H, d, J=3.3 Hz), 3.35 (3H, s), 3.34 (3H, s), 3.34–3.26 (1H, m), 3.33 (3H, s), 2.52–2.46 (2H, m), 2.27 (3H, s), 1.51 (3H, s).

MS (FAB, m/z): 571 (M+1)$^+$.

Compound 110

$^1$H-NMR (270 MHz, DMSO-d$_6$) δ (ppm): 9.16 (1H, brs), 8.73 (1H, brs), 8.30 (1H, brs), 7.93 (1H, d, J=8.9 Hz), 7.56 (1H, d, J=8.3 Hz), 7.43 (1H, dd, J=8.3, 1.3 Hz), 7.35 (1H, dd, J=8.6, 1.3 Hz), 6.68 (1H, brs), 6.45–6.34 (2H, m), 4.57 (2H, s), 4.55 (2H, s), 4.06 (1H, d, J=3.3 Hz), 3.34 (3H, s), 3.34–3.26 (1H, m), 3.33 (3H, s), 3.33 (3H, s), 2.52–2.46 (2H, m), 2.28 (3H, s), 1.43 (3H, s).

MS (FAB, m/z): 571 (M+1)$^+$.

EXAMPLE 93

Compound 111

Step 1

190 mg (0.305 mmol) of Compound m obtained in Reference Example 10 was dissolved in 10 mL of methylene chloride followed by adding 0.21 mL (1.5 mmol) of trifluoroacetic anhydride and 0.23 mL (3.1 mmol) of ethanethiol, and the mixture was stirred at room temperature for 6 hours. A saturated aqueous solution of sodium bicarbonate was added to the reaction mixture, and the mixture was extracted with chloroform. The organic layer was washed with a saturated saline solution and dried over anhydrous sodium sulfate. The solvent was distilled away under reduced pressure. The residue was purified by silica gel column chromatography (eluted with chloroform) to give 185 mg of 2-acetyl-17-ethylthiomethyl-11-N-trifluoroacetyl staurosporin (90%).

Rf=0.11 (CHCl$_3$)

Step 2

In a manner similar to that in step 2 of Example 3, 84.4 mg (0.124 mmol) of 2-acetyl-17-ethylthiomethyl-11-N-trifluoroacetyl staurosporin was treated with 0.5 mL of a 6 mol/L aqueous solution of sodium hydroxide to give 61.3 mg of Compound 111 (92%).

$^1$H-NMR (270 MHz, DMSO-d$_6$) δ (ppm): 9.18 (1H, brs), 8.46 (1H, brs), 7.97 (1H, d, J=8.6 Hz), 7.94 (1H, d, J=7.3 Hz), 7.53 (1H, d, J=8.2 Hz), 7.41 (1H, d, J=7.6 Hz), 7.40 (1H, dd, J=7.6, 7.3 Hz), 7.27 (1H, dd, J=7.6, 7.3 Hz), 6.68 (1H, dd, J=3.3, 3.3 Hz), 4.93 (2H, s), 4.06 (1H, d, J=3.3 Hz), 3.94 (2H, s), 3.34–3.26 (4H, m), 2.52–2.46 (2H, m), 2.48 (2H, q, J=7.3 Hz), 2.29 (3H, s), 1.46 (3H, s), 1.22 (3H, t, J=7.3 Hz).

MS (FAB, m/z): 541 (M+1)$^+$.

EXAMPLE 94

Compounds 112 and 113

In a manner similar to that in step 3 of Example 1, 11.0 mg of Compound 112 (25%) and 14.7 mg of Compound 113 (34%) were obtained from 42.0 mg (0.0780 mmol) of Compound 111, dimethyl sulfoxide and 0.50 mL of a 6 mol/L aqueous solution of sodium hydroxide. The ratio of the respective diastereoisomers based on their hydroxyl group by HPLC was as follows: Compound 112 (77.4% d.e.) and Compound 113 (84.8% d.e.)

Compound 112

$^1$H-NMR (270 MHz, DMSO-d$_6$) δ (ppm): 9.13 (1H, d, J=1.3 Hz), 8.71 (1H, brs), 8.41 (1H, d, J=7.6 Hz), 7.95 (1H, d, J=8.6 Hz), 7.54 (1H, d, J=8.6 Hz), 7.42 (1H, dd, J=8.3, 1.3 Hz), 7.38 (1H, brdd, J=7.3, 7.6 Hz), 7.23 (1H, dd, J=7.6, 7.3 Hz), 6.65 (1H, dd, J=3.6, 3.0 Hz), 6.48–6.36 (2H, m), 4.07 (1H, d, J=3.3 Hz), 3.94 (2H, s), 3.35 (3H, s), 3.34–3.26 (1H, m), 2.52–2.46 (2H, m), 2.49 (1H, q, J=7.6 Hz), 2.27 (3H, s), 1.53 (3H, s), 1.22 (3H, t, J=7.6 Hz).

MS (FAB, m/z): 557 (M+1)$^+$.

Compound 113

$^1$H-NMR (270 MHz, DMSO-d$_6$) δ (ppm): 9.13 (1H, d, J=1.3 Hz), 8.72 (1H, brs), 8.35 (1H, d, J=7.6 Hz), 7.96 (1H, d, J=8.6 Hz), 7.54 (1H, d, J=8.2 Hz), 7.47–7.34 (2H, m), 7.24 (1H, dd, J=7.6, 7.3 Hz), 6.67 (1H, dd, J=3.6, 3.0 Hz), 6.44–6.36 (2H, m), 4.06 (1H, d, J=3.6 Hz), 3.94 (2H, s), 3.34–3.26 (1H, m), 3.33 (3H, s), 2.52–2.46 (2H, m), 2.47 (1H, q, J=7.6 Hz), 2.28 (3H, s), 1.45 (3H, s), 1.22 (3H, t, J=7.6 Hz).

MS (FAB, m/z): 557 (M+1)$^+$.

EXAMPLE 95

Compound 114

Step 1

In a manner similar to that in step 1 of Example 93, 148 mg of 2-acetyl-5,17-bis(ethylthiomethyl)-11-N-trifluoroacetyl staurosporin (77%) was obtained from 171 mg (0.257 mmol) of Compound n obtained in Reference Example 11, 0.18 mL (1.3 mmol) of trifluoroacetic anhydride and 0.19 mL (2.6 mmol) of ethanethiol.

$^1$H-NMR (270 MHz, CDCl$_3$) δ (ppm): 9.22 (1H, d, J=1.0 Hz), 7.92 (1H, brs), 7.68 (1H, d, J=8.9 Hz), 7.57 (1H, dd, J=8.3, 1.7 Hz), 7.49 (1H, dd, J=8.6, 1.7 Hz), 7.23 (1H, d, J=8.6 Hz), 6.69 (1H, dd, J=8.6, 5.0 Hz), 5.36 (1H, d, J=17.8 Hz), 5.26 (1H, d, J=17.8 Hz), 5.04 (1H, ddd, J=12.5, 5.9, 2.0 Hz), 4.08 (1H, d, J=5.9 Hz), 4.04 (2H, s), 3.98 (2H, s), 3.02 (3H, brs), 2.84 (3H, s), 2.57 (2H, q, J=7.6 Hz), 2.56 (2H, q, J=7.6 Hz), 2.52–2.46 (2H, m), 2.50 (3H, s), 2.49 (3H, s), 1.32 (3H, t, J=7.3 Hz), 1.30 (3H, t, J=7.3 Hz).

MS (FAB, m/z): 753 (M+1)$^+$.

Step 2

In a manner similar to that in step 2 of Example 3, 75.1 mg (0.0999 mmol) of 2-acetyl-5,17-bis(ethylthiomethyl)-

11-N-trifluoroacetyl staurosporin was treated with an aqueous solution of sodium hydroxide, to give 44.4 mg of Compound 114 (72%).

$^1$H-NMR (270 MHz, DMSO-$d_6$) δ (ppm): 9.17 (1H, d, J=1.0 Hz), 8.46 (1H, brs), 7.91 (1H, d, J=8.6 Hz), 7.84 (1H, brs), 7.53 (1H, d, J=8.2 Hz), 7.41 (1H, dd, J=8.6, 1.3 Hz), 7.36 (1H, d, J=8.9 Hz), 6.67 (1H, brs), 4.91 (2H, s), 4.05 (1H, d, J=3.3 Hz), 3.94 (4H, s), 3.34–3.26 (4H, m), 2.52–2.46 (2H, m), 2.27 (3H, s), 1.45 (3H, s), 1.23 (3H, t, J=7.6 Hz), 1.21 (3H, t, J=7.3 Hz).

MS (FAB, m/z): 615 (M+1)$^+$.

EXAMPLE 96

Compounds 115 and 116

In a manner similar to that in step 3 of Example 1, 8.0 mg of Compound 115 (37%) and 8.0 mg of Compound 116 (37%) were obtained from 21.0 mg (0.0342 mmol) of Compound 114, dimethyl sulfoxide and 0.50 mL of a 6 mol/L aqueous solution of sodium hydroxide. The ratio of the respective diastereoisomers based on their hydroxyl group by HPLC was as follows: Compound 115 (77.5% d.e.) and Compound 116 (97.2% d.e.)

Compound 115

$^1$H-NMR (270 MHz, DMSO-$d_6$) δ (ppm): 9.12 (1H, d, J=0.7 Hz), 8.70 (1H, brs), 8.31 (1H, brs), 7.89 (1H, d, J=8.9 Hz), 7.53 (1H, d, J=8.6 Hz), 7.42 (1H, dd, J=6.3, 1.3 Hz), 7.35 (1H, brd, J=8.6 Hz), 6.70–6.62 (1H, m), 6.47–6.33 (2H, m), 4.06 (1H, d, J=3.3 Hz), 3.94 (2H, s), 3.90 (2H, s), 3.35 (3H, s), 3.34–3.26 (1H, m), 2.52–2.46 (2H, m), 2.26 (3H, s), 1.52 (3H, s), 1.30–1.18 (6H, m).

MS (FAB, m/z): 631 (M+1)$^+$.

Compound 116

$^1$H-NMR (270 MHz, DMSO-$d_6$) δ (ppm): 9.12 (1H, brs), 8.71 (1H, brs), 8.26 (1H, brs), 7.90 (1H, d, J=8.9 Hz), 7.53 (1H, d, J=8.2 Hz), 7.42 (1H, brd, J=8.3 Hz), 7.35 (1H, brd, J=8.9 Hz), 6.66 (1H, brs), 6.43–6.30 (2H, m), 4.05 (1H, d, J=3.0 Hz), 3.94 (2H, s), 3.91 (2H, s), 3.34–3.26 (4H, m), 2.52–2.46 (2H, m), 2.26 (3H, s), 1.44 (3H, s), 1.30–1.18 (6H, m).

MS (FAB, m/z): 631 (M+1)$^+$.

EXAMPLE 97

Compound 117

94.0 mg (0.139 mmol) of 2-acetyl-17-ethylthiomethyl-11-N-trifluoroacetyl staurosporin obtained in step 1 of Example 93 was dissolved in 5 mL of chloroform followed by adding 245 mg (1.42 mmol) of p-chloroperbenzoic acid, and the mixture was stirred at room temperature for 2 hours. A saturated aqueous solution of sodium bicarbonate was added to the reaction mixture, and then the mixture was extracted with chloroform. The organic layer was washed with a saturated aqueous solution of sodium thiosulfate and with a saturated saline solution, and then dried over anhydrous sodium sulfate. The solvent was distilled away under reduced pressure. The residue was purified by preparative thin-layer chromatography (developed with chloroform/methanol=20/1) and then treated with a 7 mol/L methanolic solution of ammonia in a manner similar to that in Example 19, to give 55.0 mg of Compound 117 (69%)

$^1$H-NMR (270 MHz, DMSO-$d_6$) δ (ppm): 9.21 (1H, d, J=1.3 Hz), 8.49 (1H, brs), 7.98 (1H, d, J=8.6 Hz), 7.95 (1H, d, J=7.6 Hz), 7.62 (1H, d, J=8.3 Hz), 7.48 (1H, dd, J=8.3, 1.7 Hz), 7.41 (1H, ddd, J=8.3, 7.0, 1.3 Hz), 7.27 (1H, dd, J=7.6, 7.3 Hz), 6.71 (1H, dd, J=3.3, 3.3 Hz), 4.94 (2H, s), 4.59 (2H, s), 4.07 (1H, d, J=3.6 Hz), 3.34–3.26 (4H, m), 3.09 (2H, q, J=7.3 Hz), 2.52–2.46 (2H, m), 2.30 (3H, s), 1.45 (3H, s), 1.28 (3H, t, J=7.6 Hz).

MS (FAB, m/z): 573 (M+1)$^+$.

EXAMPLE 98

Compounds 118 and 119

In a manner similar to that in step 3 of Example 1, 6.4 mg of Compound 118 (12%) and 11.5 mg of Compound 119 (22%) were obtained from 50.2 mg (0.0878 mmol) of Compound 117, dimethyl sulfoxide and 0.20 mL of a 6 mol/L aqueous solution of sodium hydroxide. The ratio of the respective diastereoisomers based on their hydroxyl group by HPLC was as follows: Compound 118 (82.4% d.e.) and Compound 119 (58.5% d.e.)

Compound 118

$^1$H-NMR (270 MHz, DMSO-$d_6$) δ (ppm): 9.23 (1H, d, J=1.3 Hz), 8.72 (1H, brs), 8.42 (1H, d, J=7.9 Hz), 7.96 (1H, d, J=8.6 Hz), 7.62 (1H, d, J=8.6 Hz), 7.49 (1H, dd, J=8.3, 1.7 Hz), 7.39 (1H, ddd, J=8.6, 7.3, 1.3 Hz), 7.24 (1H, dd, J=7.6, 7.3 Hz), 6.69 (1H, dd, J=3.6, 3.0 Hz), 6.46 (1H, d, J=9.6 Hz), 6.39 (1H, d, J=9.6 Hz), 4.10 (2H, s), 4.08 (1H, d, J=3.3 Hz), 3.35 (3H, s), 3.34–3.26 (1H, m), 3.08 (2H, q, J=7.3 Hz), 2.58–2.46 (2H, m), 2.28 (3H, s), 1.53 (3H, s), 1.28 (3H, t, J=7.3 Hz).

MS (FAB, m/z): 589 (M+1)$^+$.

Compound 119

$^1$H-NMR (270 MHz, DMSO-$d_6$) δ (ppm): 9.22 (1H, d, J=1.3 Hz), 8.73 (1H, brs), 8.36 (1H, d, J=7.6 Hz), 7.96 (1H, d, J=8.6 Hz), 7.62 (1H, d, J=8.6 Hz), 7.49 (1H, dd, J=8.6, 1.7 Hz), 7.40 (1H, ddd, J=8.6, 7.3, 1.3 Hz), 7.24 (1H, dd, J=7.6, 7.3 Hz), 6.70 (1H, brs), 6.42–6.36 (2H, m), 4.60 (2H, s), 4.08 (1H, d, J=3.3 Hz), 3.34 (3H; s), 3.34–3.26 (1H, m), 3.08 (2H, q, J=7.6 Hz), 2.56–2.46 (2H, m), 2.29 (3H, s), 1.45 (3H, s), 1.28 (3H, t, J=7.6 Hz).

MS (FAB, m/z): 589 (M+1)$^+$.

EXAMPLE 99

Compound 120

In a manner similar to that in Example 97, 32.0 mg of Compound 120 (57%) was obtained from 62.4 mg (0.0830 mmol) of 2-acetyl-5,17-bis(ethylthiomethyl)-11-N-trifluoroacetyl staurosporin obtained in step 1 of Example 95, 285 mg (1.65 mmol) of m-chloroperbenzoic acid and a 7 mol/L methanolic solution of ammonia.

$^1$H-NMR (270 MHz, DMSO-$d_6$) δ (ppm): 9.27 (1H, d, J=1.3 Hz), 8.52 (1H, brs), 8.02–7.94 (2H, m), 7.63 (1H, d, J=8.3 Hz), 7.49 (1H, dd, J=8.6, 1.7 Hz), 7.43 (1H, dd, J=8.9, 1.7 Hz), 6.71 (1H, brs), 4.90 (2H, s), 4.62 (2H, s), 4.59 (2H, s), 4.07 (1H, d, J=3.6 Hz), 3.36 (3H, s), 3.34–3.26 (1H, m), 3.09 (2H, q, J=7.6 Hz), 3.08 (2H, q, J=7.6 Hz), 2.56–2.46 (2H, m), 2.30 (3H, s), 1.41 (3H, s), 1.28 (3H, t, J=7.3 Hz), 1.27 (3H, t, J=7.3 Hz).

MS (FAB, m/z): 679 (M+1)$^+$.

EXAMPLE 100

Compounds 121 and 122

In a manner similar to that in step 3 of Example 1, 7.3 mg of Compound 121 (36%) and 10.3 mg of Compound 122

(42%) were obtained from 24.1 mg (0.0355 mmol) of Compound 120, dimethyl sulfoxide and 0.50 mL of a 6 mol/L aqueous solution of sodium hydroxide. The ratio of the respective diastereoisomers based on their hydroxyl group by HPLC was as follows: Compound 121 (98.2% d.e.) and Compound 122 (73.7 d.e.)

Compound 121

$^1$H-NMR (270 MHz, DMSO-d$_6$) δ (ppm): 9.23 (1H, d, J=1.0 Hz), 8.75 (1H, brs), 8.43 (1H, brs), 7.97 (1H, d, J=8.9 Hz), 7.63 (1H, d, J=8.6 Hz), 7.54–7.34 (2H, m), 6.73–6.66 (1H, m), 6.47–6.33 (2H, m), 4.68–4.48 (4H, m), 4.08 (1H, d, J=3.3 Hz), 3.39 (3H, s), 3.34–3.26 (1H, m), 3.16–3.02 (4H, m), 2.58–2.46 (2H, m), 2.28 (3H, s), 1.48 (3H, s), 1.28 (6H, t, J=7.3 Hz).

MS (FAB, m/z): 695 (M+1)$^+$.

Compound 122

$^1$H-NMR (270 MHz, DMSO-d$_6$) δ (ppm): 9.22 (1H, d, J=1.0 Hz), 8.77 (1H, brs), 8.38 (1H, brs), 7.98 (1H, d, J=8.9 Hz), 7.63 (1H, d, J=8.6 Hz), 7.50 (1H, dd, J=8.3, 1.3 Hz), 7.42 (1H, dd, J=8.9, 1.3 Hz), 6.71 (1H, brs), 6.47–6.28 (2H, m), 4.67–4.50 (4H, m), 4.08 (1H, d, J=3.3 Hz), 3.38 (3H, s), 3.34–3.26 (1H, m), 3.11 (2H, q, J=7.6 Hz), 3.08 (2H, q, J=7.6 Hz), 2.57–2.50 (2H, m), 2.29 (3H, s), 1.40 (3H, s), 1.29 (3H, t, J=7.6 Hz), 1.28 (3H, t, J=7.6 Hz).

MS (FAB, m/z): 695 (M+1)$^+$.

EXAMPLE 101

Compound 123

Step 1

22.5 mg (0.0380 mmol) of Compound e obtained in Reference Example 5 was dissolved in 4 mL of methylene chloride followed by adding 0.053 mL (0.38 mmol) of triethylamine and 0.038 mL (0.48 mmol) of ethyl isocyanate under an atmosphere of argon, and the mixture was stirred overnight. Water was added to the reaction mixture, and then the mixture was extracted with methylene chloride. The organic layer was washed with a saturated saline solution and dried over anhydrous sodium sulfate. The solvent was distilled away under reduced pressure, and the residue was purified by preparative thin-layer chromatography (developed with chloroform/methanol=9/1) to give 12.2 mg of 5,17-bis(3-ethylureido)-11-N-trifluoroacetyl staurosporin (44%).

$^1$H-NMR (270 MHz, DMSO-d$_6$) δ (ppm): 8.91 (1H, s), 8.56 (2H, s), 8.49 (1H, s), 8.19 (1H, s), 7.91–7.83 (2H, m), 7.49 (1H, d, J=10.4 Hz), 7.40 (1H, d, J=9.9 Hz), 6.97 (1H, t, J=7.3 Hz), 6.14 (1H, brs), 6.03 (1H, brs), 4.91 (3H, m), 4.36 (1H, brs), 3.17 (4H, brm), 2.90 (3H, s), 2.88 (2H, m), 2.74 (3H, s), 2.34 (3H, s), 1.10 (3H, t, J=7.1 Hz), 1.09 (3H, t, J=7.1 Hz).

MS (FAB, m/z): 735 (M+1)$^+$.

Step 2

In a manner similar to that in step 2 of Example 3, 12.2 mg (0.017 mmol) of 5,17-bis(3-ethylureido)-11-N-trifluoroacetyl staurosporin was treated with a 6 mol/L solution of sodium hydroxide, to give 5.4 mg of Compound 123 (51%).

$^1$H-NMR (270 MHz, DMSO-d$_6$) δ (ppm): 8.88 (1H, d, J=2.0 Hz), 8.54 (1H, s), 8.49 (1H, s), 8.45 (1H, s), 8.10 (1H, s), 7.86–7.82 (2H, m), 7.45 (1H, d, J=8.9 Hz), 7.33 (1H, brd, J=8.6 Hz), 6.69 (1H, m), 6.16 (1H, t, J=5.8 Hz), 6.03 (1H, t, J=5.3 Hz), 4.85 (2H, s), 4.11 (1H, brs), 3.35 (1H, m), 3.18–3.11 (7H, m), 2.50 (2H, m), 2.29 (3H, s), 1.69 (3H, brs), 1.08 (3H, t, J=7.1 Hz), 1.07 (3H, t, J=7.1 Hz).

MS (FAB, m/z): 639 (M+1)$^+$.

EXAMPLE 102

Compound 124

Step 1

In a manner similar to that in step 1 of Example 101, 107 mg of 5,17-bis(3-phenylureido)-11-N-trifluoroacetyl staurosporin (74%) was obtained from 103 mg (0.174 mmol) of Compound e obtained in Reference Example 5, 0.12 mL (0.86 mmol) of triethylamine and 0.19 mL (1.8 mmol) of phenyl isocyanate.

$^1$H-NMR (270 MHz, DMSO-d$_6$) δ (ppm): 9.04 (1H, d, J=2.0 Hz), 8.80 (2H, s), 8.73 (1H, s), 8.62 (2H, s), 8.26 (1H, d, J=2.0 Hz), 7.97–7.92 (2H, m), 7.59–7.48 (6H, m), 7.34–7.26 (4H, m), 7.05–6.94 (3H, m), 4.96 (2H, s), 4.89 (1H, m), 4.40 (1H, brs), 2.99 (3H, s), 2.86 (1H, m), 2.78 (3H, s), 2.37 (3H, s), 2.31 (1H, m).

MS (FAB, m/z): 831 (M+1)$^+$.

Step 2

In a manner similar to that in step 2 of Example 3, 98.4 mg (0.118 mmol) of 5,17-bis (3-phenylureido)-11-N-trifluoroacetyl staurosporin was treated with a 6 mol/mL solution of sodium hydroxide, to give 75.5 mg of Compound 124 (83%).

$^1$H-NMR (27 0 MHz, DMSO-d$_6$) δ (ppm): 9.00 (1H, s), 8.75 (2H, s), 8.64 (1H, s), 8.52 (1H, s), 8.16 (1H, s), 7.91–7.88 (2H, m), 7.55–7.48 (5H, m), 7.39–7.26 (6H, m), 7.00–6.96 (2H, m), 6.69 (1H, mm), 4.90 (2H, s), 4.06 (1H, brs), 3.35 (4H, m), 2.50 (2H, m), 2.29 (3H, s), 1.52 (3H, brs).

MS (FAB, m/z): 735 (M+1)$^+$.

EXAMPLE 103

Compound 125

Step 1

105 m g (0.182 mmol) of Compound d obtained in Reference Example 4 was dissolved in 10 mL of tetrahydrofuran and 1 mL of acetic acid followed by adding 151 mg (1.86 mmol) of potassium cyanate dissolved in 1 mL of water, and the mixture was stirred at room temperature for 1 0 minutes. The solvent was distilled away, an then the residue was purified by preparative thin-layer chromatography (developed with chloroform/methanol=9/1) to give 68.6 mg 17-ureido-11-N-trifluoroacetyl staurosporin (61%).

$^1$H-NMR (270 MHz, DMSO-d$_6$) δ (ppm): 8.91 (1H, d, J=2.0 Hz), 8.63 (1H, s), 8.60 (1H, s), 8.05 (1H, d, J=7.6 Hz), 8.00 (1H, d, J=8.3 Hz), 7.92 (1H, dd, J=8.9, 2.0 Hz), 7.61–7.46 (2H, m), 7.36 (1H, dd, J=7.6, 7.3 Hz), 7.03–6.97 (1H, m), 5.78 (2H, s), 4.99 (2H, s), 4.90 (1H, m), 4.44 (1H, brs), 2.97 (3H, s), 2.84 (1H, m), 2.77 (3H, s), 2.36 (3H, s), 2.32 (1H, m).

MS (FAB, m/z): 621 (M+1)$^+$.

Step 2.

In a manner similar to that in step 2 of Example 3, 63.0 mg (0.102 mmol) of 17-ureido-11-N-trifluoroacetyl staurosporin was treated with a 6 mol/L solution of sodium hydroxide, to give 50.9 mg of Compound 125 (95%).

$^1$H-NMR (270 MHz, DMSO-d$_6$) δ (ppm): 8.89 (1H, s), 8.53 (1H, s), 8.52 (1H, d, J=2.3 Hz), 8.33–7.85 (3H, m), 7.47 (1H, d, J=8.9 Hz), 7.40 (1H, dd, J=8.6, 7.1 Hz), 7.27 (1H, dd, J=7.3, 7.1 Hz), 6.65 (1H, m), 5.76 (2H, brs), 4.93 (2H, s), 4.07 (1H, brs), 3.35 (4H, m), 2.50 (2H, m), 2.30 (3H, s), 1.47 (3H, brs).

MS (FAB, m/z): 525 (M+1)$^+$.

EXAMPLE 104

Compound 126

In a manner similar to that in step 3 of Example 1, 18.4 mg of Compound 126 (41%) was obtained from 44.0 mg (0.0840 mmol) of Compound 125, dimethyl sulfoxide and 1.0 mL of a 6 mol/L solution of sodium hydroxide. The resulting product was a mixture (1:1) of isomers based on their hydroxyl group by $^1$H-NMR.

$^1$H-NMR (270 MHz, DMSO-d$_6$) δ (ppm): 8.84 (1H, s), 8.76 (1H, s), 8.56 (1H, s), 8.41 and 8.35 (Total 1H, 2d, J=7.6 Hz), 7.96 (1H, d, J=8.6 Hz), 7.88 (1H, d, J=7.8 Hz), 7.47 (1H, d, J=8.6 Hz), 7.39 (1H, dd, J=7.8, 7.1 Hz), 7.24 (1H, dd, J=7.6, 7.1 Hz), 6.65 (1H, m), 6.45 (2H, m), 5.77 (2H, s), 4.09 (1H, brs), 3.35 (4H, m), 2.50 (2H, m), 2.29 (3H, s), 1.57 and 1.49 (Total 3H, 2brs).

MS (FAB, m/z): 541 (M+1)$^+$.

EXAMPLE 105

Compound 127

In a manner similar to that in step 1 of Example 101, 114 mg of Compound 127 (75%) was obtained from 135 mg (0.234 mmol) of Compound d obtained in Reference Example 4, 0.16 mL (1.1 mmol) of triethylamine and 0.088 mL (1.1 mmol) of ethyl isocyanate.

$^1$H-NMR (270 MHz, DMSO-d$_6$) δ (ppm): 8.92 (1H, brs), 8.60 (1H, s), 8.48 (1H, s), 8.05 (1H, d, J=7.8 Hz), 8.00 (1H, d, J=8.6 Hz), 7.90 (1H, dd, J=8.9, 2.0 Hz), 7.36 (1H, dd, J=7.8, 7.3 Hz), 7.52–7.46 (2H, m), 7.00 (1H, m), 6.02 (1H, t, J=5.5 Hz), 4.99 (2H, s), 4.90 (1H, brs), 4.43 (1H, brs), 3.15 (2H, m), 2.97 (3H, s), 2.85 (1H, m), 2.76 (3H, s), 2.37 (3H, s), 2.30 (1H, m), MS (FAB, m/z): 649 (M+1)$^+$.

EXAMPLE 106

Compound 128

In a manner similar to that in step 2 of Example 3, 110 mg (0.170 mmol) of Compound 127 was treated with a 6 mol/L solution of sodium hydroxide, to give 76.7 mg of Compound 128 (82%).

$^1$H-NMR (270 MHz, DMSO-d$_6$) δ (ppm): 8.89 (1H, d, J=1.7 Hz), 8.50 (1H, s), 8.42 (1H, s), 8.00–7.94 (2H, m), 7.85 (1H, d, J=8.4 Hz), 7.47 (1H, d, J=8.9 Hz), 7.41 (1H, dd, J=8.4, 7.3 Hz), 7.27 (1H, t, J=7.3 Hz), 6.66 (1H, m), 6.03 (1H, t, J=5.8 Hz), 4.93 (2H, s), 4.08 (1H, brs), 3.34 (4H, m), 3.14 (2H, m), 2.50 (2H, m), 2.30 (3H, s), 1.51 (3H, brs), 1.08 (3H, t, J=6.9 Hz).

MS (FAB, m/z): 553 (M+1)$^+$.

EXAMPLE 107

Compound 129

In a manner similar to that in step 3 of Example 1, 30.4 mg of Compound 129+(50%) was obtained from 58.6 mg (0.106 mmol) of Compound 128, dimethyl sulfoxide and 1.0 mL of a 6 mol/L solution of sodium hydroxide. The resulting product was a mixture (1.2:1) of isomers based on their hydroxyl group by HPLC.

$^1$H-NMR (270 MHz, DMSO-d$_6$) δ (ppm): 8.85 (1H, d, J=1.7 Hz), 8.71 (1H, s), 8.43 (1H, s), 8.35 and 8.41 (Total 1H, 2d, J=8.3 Hz), 7.95 (1H, d, J=8.7 Hz), 7.85 (1H, d, J=8.3 Hz), 7.47 (1H, d, J=8.7 Hz), 7.37 (1H, dd, J=8.3, 7.6 Hz), 7.24 (1H, dd, J=8.3, 7.6 Hz), 6.63 (1H, m), 6.44–6.35 (2H, m), 6.02 (1H, t, J=5.6 Hz), 4.07 (1H, brs), 3.32 (4H, m), 3.14 (2H, m), 2.50 (2H, m), 2.28 (3H, s), 1.52 (3H, s), 1.08 (3H, t, J=7.1 Hz).

MS (FAB, m/z): 569 (M+1)$^+$.

EXAMPLE 108

Compound 130

Step 1

50 mg (0.087 mmol) of Compound d obtained in Reference Example 4 was dissolved in 1 mL of chloroform followed by adding 55 mg of polyvinylpyridine and 0.031 mL (0.35 mmol) of allyl isocyanate, and the mixture was shaken for 1 hour. After the reaction was completed, J=36 mg of polyvinylpyridine and 420 mg of aminomethyl resin were added thereto and the mixture was further shaken overnight. The polymer was separated by filtration and the solvent was distilled away under reduced pressure. The residue was purified by preparative thin-layer chromatography (developed with chloroform/methanol=5/1) to give 42.5 mg of 17-(3-allylureido)-11-N-trifluoroacetyl staurosporin (74%).

$^1$H-NMR (270 MHz, CDCl$_3$) δ (ppm): 9.18 (1H, s), 8.16 (1H, brs), 8.01 (1H, brs), 7.86 (1H, d, J=8.6 Hz), 7.61 (2H, m), 7.34 (1H, t, J=7.4.Hz), 7.17 (1H, t, J=7.4 Hz), 7.06 (1H, d, J=8.6 Hz), 6.51 (1H, m), 5.82 (1H, m), 5.55 (1H, brs), 5.15 (1H, d, J=17.2 Hz), 4.98 (1H, d, J=10.2 Hz), 4.85 (1H, m), 4.78 (2H, s), 3.87 (2H, d, J=5.3 Hz), 3.84 (1H, brs), 2.86 (3H, s), 2.55 (2H, m), 2.40 (3H, s), 2.15 (3H, s).

MS (FAB, m/z): 660 (M)$^+$.

Step 2

In a manner similar to that in Example 19, 42.0 mg (0.064 mmol) of 17-(3-allylureido)-11-N-trifluoroacetyl staurosporin was treated with a 7 mol/L methanolic solution of ammonia, to give 28.0 mg of Compound 130 (78%).

$^1$H-NMR (270 MHz, DMSO-d$_6$) δ (ppm): 8.91 (1H, d, J=2.3 Hz), 8.53 (1H, brs), 8.49 (1H, brs), 7.97 (1H, d, J=8.4 Hz), 7.94 (1H, d, J=7.6 Hz), 7.86 (1H, dd, J=8.9, 2.3 Hz), 7.48 (1H, d, J=8.9 Hz), 7.40 (1H, dd, J=8.4, 7.6 Hz), 7.27 (1H, t, J=7.6 Hz), 6.65 (1H, brm), 6.18 (1H, t, J=5.6 Hz), 5.91 (1H, m), 5.21 (1H, dd, J=1.7, 17.3 Hz), 5.09 (1H, dd, J=1.7, 10.2 Hz), 4.93 (2H, s), 4.06 (1H, d, J=3.3 Hz), 3.77 (2H, brt, J=5.6 Hz), 3.31 (3H, s), 3.27 (1H, m), 2.50 (2H, m), 2.29 (3H, s), 1.47 (3H, s).

MS (FAB, m/z): 565 (M+1)$^+$.

EXAMPLE 109

Compound 131

In a manner similar to that in step 1 of Example 101, 115 mg of Compound 131 (70%) was obtained from 136 mg (0.236 mmol) of Compound d obtained in Reference Example 4, 0.16 mL (1.1 mmol) of triethylamine and 0.12 mL (1.1 mmol) of phenyl isocyanate.

$^1$H-NMR (270 MHz, DMSO-d$_6$) δ (ppm): 9.05 (1H, d, J=2.0 Hz), 8.79 (1H, s), 8.62 (2H, s), 8.06 (1H, d, J=7.9 Hz), 8.01 (1H, d, J=8.6 Hz), 7.95 (1H, dd, J=8.9, 2.0 Hz), 7.57 (1H, d, J=8.9 Hz), 7.51–7.47 (3H, m), 7.39–7.26 (3H, m), 7.05–6.94 (2H, m), 5.00 (2H, s), 4.91 (1H, m), 4.44 (1H, brs), 2.98 (3H, 8), 2.86 (1H, m), 2.77 (3H, s), 2.38 (3H, s), 2.31 (1H, s).

MS (FAB, m/z): 697 (M+1)$^+$.

EXAMPLE 110

Compound 132

In a manner similar to that in step 2 of Example 3, 109 mg (0.156 mmol) of Compound 131 was treated with a 6 mol/L solution of sodium hydroxide, to give 60.0 mg of Compound 132 (64%).

$^1$H-NMR (270 MHz, DMSO-d$_6$) δ (ppm): 9.01 (1H, d, J=2.0 Hz), 8.74 (1H, s), 8.65 (1H, s), 8.53 (1H, s), 8.00–7.89

(3H, m), 7.56–7.39 (4H, m), 7.32–7.26 (3H, m), 6.96 (1H, t, J=7.3 Hz), 6.69 (1H, m), 4.94 (2H, s), 4.09 (1H, brs), 3.34 (4H, m), 2.50 (2H, m), 2.31 (3H, s), 1.51 (3H, brs).

MS (FAB, m/z): 601 (M+1)$^+$.

EXAMPLE 111

Compound 133

In a manner similar to that in step 3 of Example 1, 17.4 mg of Compound 133 (44%) was obtained from 38.9 mg (0.0650 mmol) of Compound 132, dimethyl sulfoxide and 0.8 mL of a 6 mol/L solution of sodium hydroxide. The resulting product was a mixture of isomers (1:1.3) based on their hydroxide group by HPLC.

$^1$H-NMR (270 MHz, DMSO-d$_6$) δ (ppm): 8.97 (1H, s), 8.76 (2H, s), 8.64 (1H, s), 8.36 and 8.42 (Total 1H, 2d, J=7.9 Hz), 7.98–7.90 (2H, m), 7.56–7.48 (3H, m), 7.39 (1H, dd, J=8.3, 7.6 Hz), 7.32–7.22 (3H, m), 6.96 (1H, t, J=7.3 Hz), 6.67 (1H, m), 6.41 (2H, m), 4.08 (1H, brd), 3.33 (4H, m), 2.50 (2H, m), 2.28 and 2.29 (Total 3H, 2s), 1.48 and 1.56 (Total 3H, 2s).

MS (FAB, m/z): 617 (M+1)$^+$.

EXAMPLE 112

Compound 134

Step 1

201 mg (0.347 mmol) of Compound d obtained in Reference Example 4 was dissolved in 20 mL of tetrahydrofuran followed by adding 97 mg (0.56 mmol) of tert-butoxycarbonyl glycine, 107 mg (0.559 mmol) of 3-(3-dimethylaminopropyl)-1-ethylcarbodiimide hydrochloride and 68 mg (0.56 mmol) of 4-dimethylaminopyridine under an atmosphere of argon, and the mixture was stirred at room temperature for 2 hours. The reaction was terminated by adding water thereto, and the reaction mixture was diluted with ethyl acetate, neutralized with a saturated aqueous solution of sodium bicarbonate, and subjected to extraction with ethyl acetate. The organic layer was washed with a saturated saline solution and dried over anhydrous sodium sulfate. The solvent was distilled away under reduced pressure, and then the residue was purified by preparative thin-layer chromatography (developed with chloroform/methanol=15/1) to give 174 mg of 17-tert-butoxycarbonylglycylamino-11-N-trifluoroacetyl staurosporin (68%).

$^1$H-NMR (270 MHz, DMSO-d$_6$) δ (ppm): 10.04 (1H, s), 9.18 (1H, brs), 8.61 (1H, s), 8.06 (1H, d, J=7.8 Hz), 8.01 (1H, d, J=8.6 Hz), 7.89 (1H, dd, J=7.8, 2.0 Hz), 7.57 (1H, d, J=7.8 Hz), 7.49 (1H, dd, J=8.6, 7.3 Hz), 7.36 (1H, dd, J=7.8, 7.3 Hz), 7.05–7.00 (2H, m), 4.99 (2H, s), 4.91 (1H, m), 4.44 (1H, brs), 3.80 (2H, d, J=5.9 Hz), 2.98 (3H, s), 2.77 (3H, s), 2.50 (2H, m), 2.37 (3H, s), 1.42 (9H, s).

MS (FAB, m/z): 734 (M)$^+$.

Step 2

171 mg (0.233 mmol) of 17-tert-butoxycarbonylglycylamino-11-N-trifluoroacetyl staurosporin was dissolved in 10 mL of trifluoroacetic acid and the mixture was stirred at room temperature for 10 minutes under an atmosphere of argon. After the reaction was completed, the solvent was distilled away, and the residue was purified by preparative thin-layer chromatography (developed with chloroform/methanol/28% aqueous ammonia=60/10/1) to give 122 mg of 17-glycylamino-11-N-trifluoroacetyl staurosporin (83%).

$^1$H-NMR (270 MHz, DMSO-d$_6$) δ (ppm): 9.18 (1H, d, J=2.0 Hz), 8.62 (1H, s), 8.06 (1H, d, J=7.8 Hz), 8.01 (1H, d, J=8.3 Hz), 7.95 (1H, dd, J=8.9, 2.0 Hz), 7.58 (1H, d, J=8.9 Hz), 7.50 (1H, dd, J=8.3, 7.3 Hz), 7.36 (1H, dd, J=7.8, 7.3 Hz), 7.03 (1H, m), 5.00 (2H, s), 4.91 (1H, m), 4.44 (1H, brs), 3.34 (2H, m), 2.98 (3H, s), 2.76 (3H, s), 2.50 (2H, m), 2.37 (3H, s).

MS (FAB, m/z): 635 (M+1)$^+$.

Step 3

In a manner similar to that in step 2 of Example 3, 118 mg (0.187 mmol) of 17-glycylamino-11-N-trifluoroacetyl staurosporin was treated with a 6 mol/L solution of sodium hydroxide, to give 97.6 mg of Compound 134 (97%).

$^1$H-NMR (270 MHz, DMSO-d$_6$) δ (ppm): 9.92 (1H, brm), 9.15 (1H, d, J=2.2 Hz), 8.50 (1H, s), 8.00–7.94 (2H, m), 7.91 (1H, dd, J=8.9, 2.2 Hz), 7.60 (1H, d, J=8.6 Hz), 7.40 (1H, dd, J=8.6, 7.9 Hz), 7.27 (1H, dd, J=7.9, 7.6 Hz), 6.68 (1H, m), 4.94 (2H, s), 4.07 (1H, brd, J=3.3 Hz), 3.35 (6H, m), 2.50 (2H, m), 2.30 (3H, s), 1.16 (3H, brs).

MS (FAB, m/z): 539 (M+1)$^+$.

EXAMPLE 113

Compound 135

In a manner similar to that in step 3 of Example 1, 19.2 mg of Compound 135 (24%) was obtained from 79.0 mg (0.147 mmol) of Compound 134, dimethyl sulfoxide and 1.0 mL of a 6 mol/L solution of sodium hydroxide. The product was a mixture (1.1:1) of isomers based on their hydroxyl group by HPLC.

$^1$H-NMR (270 MHz, DMSO-d$_6$) δ (ppm): 10.15 (1H, brs), 9.14 (1H, s), 8.75 (1H, s), 8.36 and 8.42 (Total 1H, 2d, J=7.9 Hz), 7.97 (1H, d, J=8.3 Hz), 7.90 (1H, d, J=8.4 Hz), 7.57 (1H, d, J=8.6 Hz), 7.40 (1H, dd, J=8.4, 7.6 Hz), 7.25 (1H, dd, J=7.9, 7.6 Hz), 6.68 (1H, m), 6.40 (2H, brm), 4.08 (1H, brs), 3.36 (6H, m), 2.50 (2H, m), 2.29 (3H, s), 1.46 and 1.54 (Total 3H, 2s).

MS (FAB, m/z): 555 (M+1)$^+$.

EXAMPLE 114

Compound 136

Step 1

In a manner similar to that in step 1 of Example 112, 334 mg of 17-tert-butoxycarbonyl-β-alanylamino-11-N-trifluoroacetyl staurosporin (85%) was obtained from 303 mg (0.525 mmol) of Compound d obtained in Reference Example 4, 161 mg (0.850 mmol) of tert-butoxycarbonyl-β-alanine, 161 mg (0.837 mmol) of 3-(3-dimethylaminopropyl)-1-ethylcarbodiimide hydrochloride and 104 mg (0.847 mmol) of 4-dimethylaminopyridine.

$^1$H-NMR (270 MHz, DMSO-d$_6$) δ (ppm): 10.08 (1H, s), 9.18 (1H, d, J=2.0 Hz), 8.60 (1H, s), 8.06 (1H, d, J=7.4 Hz), 8.00 (1H, d, J=8.4 Hz), 7.91 (1H, dd, J=8.9, 2.0 Hz), 7.56 (1H, d, J=8.9 Hz), 7.50 (1H, dd, J=8.4, 7.3 Hz), 7.36 (1H, dd, J=7.4, 7.3 Hz), 7.02 (1H, m), 6.87 (1H, brm), 4.99 (2H, s), 4.90 (1H, m), 4.44 (1H, brs), 3.34 (4H, m), 2.97 (3H, d, J=1.3 Hz), 2.85 (1H, m), 2.77 (3H, s), 2.50 (1H, m), 2.36 (3H, s), 1.40 (9H, s).

MS (FAB, m/z): 748 (M)$^+$.

Step 2

In a manner similar to that in step 2 of Example 112, 409 mg of 17-β-alanylamino-11-N-trifluoroacetyl staurosporin (quant.) was obtained from 328 mg (0.438 mmol) of 17-tert-butoxycarbonyl-β-alanylamino-11-N-trifluoroacetyl staurosporin and 20 mL of trifluoroacetic acid.

$^1$H-NMR (270 MHz, DMSO-d$_6$) δ (ppm): 10.31 (1H, s), 9.23 (1H, d, J=2.0 Hz), 8.60 (1H, s), 8.06 (1H, d, J=7.4 Hz), 8.01 (1H, d, J=8.6 Hz), 7.89 (1H, dd, J=8.9, 2.0 Hz), 7.52

(1H, d, J=8.9 Hz), 7.50 (1H, dd, J=8.6, 7.3 Hz), 7.37 (1H, dd, J=7.4, 7.3 Hz), 7.20 (2H, brs), 7.03 (1H, m), 5.00 (2H, s), 4.91 (1H, m), 4.45 (1H, brs), 3.15 (2H, t, J=6.6 Hz), 2.97 (3H, s), 2.82 (2H, m), 2.77 (3H, s), 2.50 (1H, m), 2.37 (3H, s), 2.31 (1H, m).

MS (FAB, m/z): 649 (M+1)$^+$.

Step 3

In a manner similar to that in step 2 of Example 3, 398 mg (0.613 mmol) of 17-β-alanylamino-11-N-trifluoroacetyl staurosporin was treated with a 6 mol/L solution of sodium hydroxide, to give 243 mg of Compound 136 (72%).

$^1$H-NMR (270 MHz, DMSO-d$_6$) δ (ppm): 10.26 (1H, s), 9.22 (1H, d, J=2.0 Hz), 8.53 (1H, s), 8.04–8.00 (2H, m), 7.89 (1H, dd, J=8.6, 2.0 Hz), 7.79 (2H, brm), 7.58–7.43 (2H, m), 7.33 (1H, t, J=7.6 Hz), 6.77 (1H, m), 4.96 (2H, s), 4.21 (1H, brs), 3.32 (4H, m), 3.14 (2H, t, J=6.0 Hz), 2.77 (2H, t, J=6.0 Hz), 2.50 (2H, m), 2.37 (3H, s), 1.92 (3H, brm).

MS (FAB, m/z): 553 (M+1)$^+$.

EXAMPLE 115

Compound 137

Step 1

In a manner similar to that in step 1 of Example 101, 279 mg of 17-(3-phenylthioureido)-11-N-trifluoroacetyl staurosporin (75%) was obtained from 301 mg (0.521 mmol) of Compound d obtained in Reference Example 4, 0.36 mL (2.6 mmol) of triethylamine and 0.31 mL (2.6 mmol) of phenylisothiocyanate.

$^1$H-NMR (270 MHz, DMSO-d$_6$) δ (ppm): 9.92 (1H, s), 9.60 (1H, s), 9.14 (1H, s), 8.66 (1H, s), 8.07 (1H, d, J=7.6 Hz), 8.02 (1H, d, J=8.6 Hz), 7.63–7.48 (5H, m), 7.40–7.30 (3H, m), 7.15–7.03 (2H, m), 5.01 (2H, s), 4.93 (1H, m), 4.44 (1H, brs), 2.98 (3H, d, J=1.0 Hz), 2.86 (1H, m), 2.72 (3H, s), 2.50 (1H, m), 2.39 (3H, s).

MS (FAB, m/z): 713 (M+1)$^+$.

Step 2

In a manner similar to that in step 2 of Example 3, 275 mg (0.386 mmol) of 17-(3-phenylthioureido)-11-N-trifluoroacetyl staurosporin was treated with a 6 mol/L solution of sodium hydroxide, to give 34.8 mg of Compound 137 (15%).

$^1$H-NMR (270 MHz, DMSO-d$_6$) δ (ppm): 9.87 (1H, s), 9.59 (1H, s), 9.13 (1H, s), 8.55 (1H, s), 7.99 (1H, d, J=8.6 Hz), 7.96 (1H, d, J=7.6 Hz), 7.58–7.53 (4H, m), 7.45–7.28 (4H, m), 7.12 (1H, dd, J=7.6, 7.3 Hz), 6.72 (1H, m), 4.95 (2H, s), 4.09 (1H, brs), 3.32 (4H, m), 2.50 (2H, m), 2.31 (3H, s), 1.51 (3H, brs).

MS (FAB, m/z): 617 (M+1)$^+$.

EXAMPLE 116

Compound 138

Step 1

In a manner similar to that in step 1 of Example 101, 287 mg of 17-(3-ethylthioureido)-11-N-trifluoroacetyl staurosporin (82%) was obtained from 303 mg (0.524 mmol) of Compound d obtained in Reference Example 4, 0.55 mL (3.9 mmol) of triethylamine and 0.35 mL (4.0 mmol) of ethyl isothiocyanate.

$^1$H-NMR (270 MHz, DMSO-d$_6$) δ (ppm): 9.52 (1H, s), 9.08 (1H, d, J=1.7 Hz), 8.65 (1H, s), 8.07 (1H, d, J=8.3 Hz), 8.02 (1H, d, J=8.3 Hz), 7.61–7.34 (5H, m), 7.05 (1H, m), 5.01 (2H, s), 4.93 (1H, m), 4.44 (1H, brs), 3.53–3.78 (2H, m), 2.98 (3H, s), 2.89 (1H, m), 2.71 (3H, s), 2.50 (1H, m), 2.39 (3H, s), 1.12 (3H, t, J=6.8 Hz).

MS (FAB, m/z): 665 (M+1)$^+$.

Step 2

In a manner similar to that in Example 19, 99.9 mg of Compound 138 (42%) was obtained from 282 mg (0.424 mmol) of 17-(3-ethylthioureido)-11-N-trifluoroacetyl staurosporin and 5 mL of a 7 mol/L methanolic solution of ammonia.

$^1$H-NMR (270 MHz, DMSO-d$_6$) δ (ppm): 9.50 (1H, s), 9.05 (1H, d, J=2.0 Hz), 8.57 (1H, s), 8.02–7.96 (2H, m), 7.58 (1H, d, J=8.6 Hz), 7.46–7.40 (3H, m), 7.30 (1H, t, J=7.6 Hz), 6.73 (1H, m), 4.95 (2H, s), 4.12 (1H, brs), 3.48 (2H, m), 3.32 (1H, m), 3.23 (3H, brs), 2.50 (2H, m), 2.33 (3H, s), 1.61 (3H, brs), 1.12 (3H, t, J=7.1 Hz).

MS (FAB, m/z): 569 (M+1)$^+$.

EXAMPLE 117

Compound 139

In a manner similar to that in step 3 of Example 1, 21.0 mg of Compound 139 (30%) was obtained from 67.1 mg (0.118 mmol) of Compound 138, dimethyl sulfoxide and 1.0 mL of a 6 mol/L solution of sodium hydroxide.

$^1$H-NMR (270 MHz, DMSO-d$_6$) δ (ppm): 9.51 (1H, s), 9.00 (1H, d, J=2.0 Hz), 8.79 (1H, s), 8.39 (1H, m), 7.97 (1H, d, J=8.9 Hz), 7.58 (1H, d, J=8.9 Hz), 7.46–7.37 (3H, m), 7.25 (1H, dd, J=7.6, 7.3 Hz), 6.68 (1H, m), 6.50–6.38 (2H, m), 4.09 (1H, brd), 3.50 (2H, m), 3.32 (4H, m), 2.50 (2H, m), 2.29 and 2.30 (Total 3H, 2s), 1.51 and 1.58 (Total 3H, 2s), 1.12 (3H, t, J=7.1 Hz).

MS (FAB, m/z): 585 (M+1)$^+$.

EXAMPLE 118

Compound 140

Step 1

In a manner similar to that in step 1 of Example 112, 388 mg of 17-tert-butoxycarbonylprolylamino-11-N-trifluoroacetyl staurosporin (95%) was obtained from 303 mg (0.525 mmol) of Compound d obtained in Reference Example 4, 181 mg (0.842 mmol) of tert-butoxycarbonyl proline, 162 mg (0.843 mmol) of 3-(3-dimethylaminopropyl)-1-ethylcarbodiimide hydrochloride and 105 mg (0.858 mmol) of 4-dimethylaminopyridine.

$^1$H-NMR (270 MHz, DMSO-d$_6$) δ (ppm): 10.14 (1H, s), 9.18 (1H, d, J=1.6 Hz), 8.59 (1H, s), 8.06 (1H, d, J=7.6 Hz), 8.02–7.93 (2H, m), 7.58 (1H, d, J=8.9 Hz), 7.50 (1H, d, J=7.6 Hz), 7.36 (1H, t, J=7.6 Hz), 7.02 (1H, dd, J=8.1, 6.8 Hz), 5.00 (2H, s), 7.91 (1H, m), 4.44 (1H, brs), 4.34 (1H, m), 2.97 (3H, s), 2.85 (1H, m), 2.75 (3H, s), 2.50 (1H, m), 2.37 (3H, s), 2.39–2.18 (2H, m), 2.32–1.81 (4H, m), 1.42–1.33 (9H, m).

MS (FAB, m/z): 774 (M)$^+$.

Step 2

In a manner similar to that in step 2 of Example 114, 513 mg of 17-prolylamino-11-N-trifluoroacetyl staurosporin (quant.) was obtained from 379 mg (0.490 mmol) of 17-tert-butoxycarbonylprolylamino-11-N-trifluoroacetyl staurosporin and 20 mL of trifluoroacetic acid.

$^1$H-NMR (270 MHz, DMSO-d$_6$) δ (ppm): 10.71 (1H, s), 9.52 (1H, brm), 9.29 (1H, d, J=2.0 Hz), 8.62 (1H, s), 8.07 (1H, d, J=7.8 Hz), 8.02 (1H, d, J=8.3 Hz), 7.90 (1H, dd, J=8.9, 2.0 Hz), 7.63 (1H, d, J=8.9 Hz), 7.51 (1H, dd, J=8.3, 7.3 Hz), 7.37 (1H, dd, J=7.8, 7.3 Hz), 7.08 (1H, m), 5.01 (2H, s), 4.91 (1H, m), 4.45 (1H, brs), 4.42 (1H, m), 2.98 (3H, s), 2.84 (1H, m), 2.76 (3H, s), 2.50 (3H, m), 2.38 (3H, s), 2.08–1.97 (4H, m).

MS (FAB, m/z): 675 (M+1)$^+$.

Step 3

In a manner similar to that in Example 19, 8.4 mg of Compound 140 (2%) was obtained from 504 mg (0.746 mmol) of 17-prolylamino-11-N-trifluoroacetyl staurosporin and 5 mL of a 6.8 mol/L methanolic solution of ammonia.

$^1$H-NMR (270 MHz, DMSO-$d_6$) δ (ppm): 10.07 (1H, s), 9.14 (1H, d, J=2.0 Hz), 8.50 (1H, s), 8.00–7.91 (3H, m), 7.56 (1H, d, J=8.9 Hz), 7.41 (1H, dd, J=8.3, 7.6 Hz), 7.27 (1H, dd, J=7.6, 6.9 Hz), 6.68 (1H, m), 4.94 (2H, s), 4.07 (1H, d, J=3.3 Hz), 3.83 (1H, dd, J=8.6, 5.6 Hz), 3.33 (3H, s), 3.28 (1H, m), 2.99 (2H, t, J=6.4 Hz), 2.50 (2H, m), 2.30 (3H, s), 2.26–1.69 (4H, m), 1.44 (3H, brs).

MS (FAB, m/z): 579 (M+1)$^+$.

EXAMPLE 119

Compound 141

In a manner similar to that in step 1 of Example 108, 100 mg (0.173 mmol) of Compound d obtained in Reference Example 4 was reacted with 109 mg of polyvinylpyridine and 0.08.0 mL (0.69 mmol) of benzoyl chloride, followed by treatment with 216 mg of aminomethyl resin and 73 mg of polyvinylpyridine, to give 75.2 mg of Compound 141 (75%).

$^1$H-NMR (270 MHz, DMSO-$d_6$) δ (ppm): 10.45 (1H, brs), 9.39 (1H, s), 8.60 (1H, brs), 8.08–7.96 (4H, m), 7.83 (1H, d, J=8.9 Hz), 7.64–7.48 (5H, m), 7.37 (1H, t, J=7.4 Hz), 7.06 (1H, m), 5.00 (2H, 9), 4.93 (1H, brm), 4.45 (1H, brs), 2.99 (3H, s), 2.89 (1H, m), 2.78 (3H, s), 2.41 (1H, m), 2.38 (3H, s).

MS (FAB, m/z): 682 (M+1)$^+$.

EXAMPLE 120

Compound 142

In a manner similar to that in Example 19, 55.0 mg (0.0810 mmol) of Compound 141 was treated with a 7 mol/L methanolic solution of ammonia, to give 75.2 mg of Compound 142 (75%).

$^1$H-NMR (270 MHz, DMSO-$d_6$) δ (ppm): 10.40 (1H, brs), 9.35 (1H, d, J=2.0 Hz), 8.48 (1H, brs), 8.05 (2H, d, J=8.3 Hz), 7.99 (1H, d, J=7.9 Hz), 7.96 (1H, d, J=8.6 Hz), 7.78 (1H, dd, J=8.9, 2.0 Hz), 7.61–7.52 (4H, m), 7.41 (1H, dd, J=8.6, 7.3 Hz), 7.28 (1H, dd, J=7.9, 7.3 Hz), 6.71 (1H, brm), 4.94 (2H, s), 4.08 (1H, d, J=3.3 Hz), 3.36 (3H, s), 3.30 (1H, m), 2.51 (2H, m), 2.31 (3H, s), 1.47 (3H, s).

MS (FAB, m/z): 586 (M+1)$^+$.

EXAMPLE 121

Compound 143

In a manner similar to that in step 1 of Example 108, 100 mg (0.173 mmol) of Compound d obtained in Reference Example 4 was reacted with 109 mg of polyvinylpyridine and 0.098 mL (0.69 mmol) of p-methoxybenzoyl chloride, followed by treatment with 216 mg of aminomethyl resin and 73 mg of polyvinylpyridine, to give 76.0 mg of Compound 143 (64%).

$^1$H-NMR (270 MHz, DMSO-$d_6$) δ (ppm): 10.30 (1H, brs), 9.35 (1H, d, J=2.0 Hz), 8.60 (1H, brs), 8.07 (2H, d, J=8.7 Hz), 8.00 (2H, m), 7.81 (1H, dd, J=8.7, 2.0 Hz), 7.61 (1H, d, J=8.7 Hz), 7.50 (1H, t, J=7.6 Hz), 7.37 (1H, t, J=7.6 Hz), 7.08 (2H, d, J=8.7 Hz), 7.03 (1H, m), 5.00 (2H, s), 4.93 (1H, brm), 4.45 (1H, brs), 3.86 (3H, s), 2.99 (3H, s), 2.86 (1H, m), 2.78 (3H, s), 2.40 (1H, m), 2.38 (3H, s).

MS (FAB, m/z): 712 (M+1)$^+$.

EXAMPLE 122

Compound 144

In a manner similar to that of Example 19, 53.0 mg (0.0750 mmol) of Compound 143 was treated with a 7 mol/L methanolic solution of ammonia, to give 33.0 mg of Compound 144 (69%).

$^1$H-NMR (270 MHz, DMSO-$d_6$) δ (ppm): 10.25 (1H, brs), 9.32 (1H, d, J=2.1 Hz), 8.49 (1H, brs), 8.06 (2H, d, J=8.9 Hz), 7.99 (1H, d, J=8.6 Hz), 7.96 (1H, d, J=7.6 Hz), 7.77 (1H, dd, J=8.9, 2.1 Hz), 7.58 (1H, d, J=8.9 Hz), 7.41 (1H, dd, J=8.6, 7.3 Hz), 7.28 (1H, dd, J=7.6, 7.3 Hz), 7.08 (2H, d, J=8.9 Hz), 6.71 (1H, brm), 4.94 (2H, s), 4.08 (1H, d, J=3.3 Hz), 3.86 (3H, s), 3.35 (3H, s), 3.33 (1H, m), 2.51 (2H, m), 2.31 (3H, s), 1.47 (3H, s).

MS (FAB, m/z): 616 (M+1)$^+$.

EXAMPLE 123

Compound 145

In a manner similar to that in step 1 of Example 108, 100 mg (0.173 mmol) of Compound d obtained in Reference Example 4 was reacted with 109 mg of polyvinylpyridine and 0.088 mL (0.69 mmol) of p-chlorobenzoyl chloride, followed by treatment with 216 mg of aminomethyl resin and 73 mg of polyvinylpyridine, to give 73.1 mg of Compound 145 (59%).

$^1$H-NMR (270 MHz, DMSO-$d_6$) δ (ppm): 10.54 (1H, brs), 9.38 (1H, s), 8.61 (1H, brs), 8.09 (2H, d, J=8.6 Hz), 8.04 (2H, m), 7.84 (1H, d, J=6 Hz), 7.63 (3H, d, J=8.6 Hz), 7.50 (1H, t, J=7.6 Hz), 7.37 (1H, t, J=7.6 Hz), 7.06 (1H, t, J=7.6 Hz), 5.00 (2H, s), 4.92 (1H, brm), 4.45 (1H, brs), 2.99 (3H, s), 2.86 (1H, m), 2.77 (3H, s), 2.40 (1H, m), 2.38 (3H, s).

MS (FAB, m/z): 716 (M+1)$^+$.

EXAMPLE 124

Compound 146

In a manner similar to that in Example 19, 45.0 mg (0.0630 mmol) of Compound 145 was treated with a 7 mol/L methanolic solution of ammonia, to give 8.8 mg of Compound 146 (23%).

$^1$H-NMR (270 MHz, DMSO-$d_6$) δ (ppm): 10.48 (1H, brs), 9.34 (1H, d, J=2.0 Hz), 8.48 (1H, brs), 8.08 (2H, d, J=8.4 Hz), 7.99 (1H, d, J=8.4 Hz), 7.96 (1H, d, J=7.8 Hz), 7.80 (1H, brd, J=8.6 Hz), 7.63 (2H, d, J=8.4 Hz), 7.60 (1H, d, J=8.6 Hz), 7.42 (1H, dd, J=8.4, 7.3 Hz), 7.28 (1H, dd, J=7.8, 7.3 Hz), 6.71 (1H, brm), 4.94 (2H, s), 4.08 (1H, d, J=3.3 Hz), 3.36 (3H, s), 3.33 (1H, m), 2.51 (2H, m), 2.31 (3H, s), 1.46 (3H, s).

MS (FAB, m/z): 620 (M+1)$^+$.

EXAMPLE 125

Compound 147

In a manner similar to that in step 1 of Example 108, 100 mg (0.173 mmol) of Compound d obtained in Reference Example 4 was reacted with 109 mg of polyvinylpyridine and 0.088 mL (0.69 mmol) of thiophene-2-carbonyl chloride, followed by treatment with 216 mg of aminomethyl resin and 73 mg of polyvinylpyridine. Then in a manner similar to that in Example 19, the reaction mixture was treated with a 7 mol/L methanolic solution of ammonia, to give 13.4 mg of Compound 147 (13%).

$^1$H-NMR (270 MHz, DMSO-$d_6$) δ (ppm): 10.42 (1H, brs), 9.31 (1H, d, J=2.0 Hz), 8.49 (1H, brs), 8.10 (1H, brd, J=3.8 Hz), 7.99 (1H, d, J=8.6 Hz), 7.96 (1H, d, J=7.3 Hz), 7.84 (1H, dd, J=4.9, 1.0 Hz), 7.77 (1H, dd, J=8.7, 2.0 Hz), 7.59 (1H, d, J=8.7 Hz), 7.42 (1H, dd, J=8.6, 7.3 Hz), 7.28 (1H, m), 7.24 (1H, dd, J=4.9, 3.8 Hz), 6.71 (1H, m), 4.95 (2H, s), 4.08 (1H, d, J=3.3 Hz), 3.35 (3H, s), 3.33 (1H, m), 2.51 (2H, m), 2.31 (3H, s), 1.47 (3H, s).

MS (FAB, m/z): 592 (M+1)⁺.

EXAMPLE 126

Compounds 148 and 149

In a manner similar to that in step 3 of Example 1, 13.8 mg of Compound 148 (16%) and 18.0 mg of Compound 149 (21%) were obtained from 83.9 mg (0.142 mmol) of Compound 147, dimethyl sulfoxide and 0.7 mL of a 6 mol/L solution of sodium hydroxide. The ratio of the respective diastereoisomers based on their hydroxyl group by HPLC was as follows: Compound 148 (96.6% d.e.) and Compound 149 (83.2% d.e.)

Compound 148

¹H-NMR (270 MHz, DMSO-d₆) δ (ppm): 10.43 (1H, brs), 9.27 (1H, s), 8.73 (1H, brs), 8.37 (1H, d, J=7.9 Hz), 8.10 (1H, d, J=3.3 Hz), 7.97 (1H, d, J=8.3 Hz), 7.84 (1H, d, J=5.0 Hz), 7.78 (1H, d, J=8.9 Hz), 7.59 (1H, d, J=8.9 Hz), 7.40 (1H, dd, J=8.3, 7.3 Hz), 7.28–7.23 (2H, m), 6.70 (1H, brm), 6.40 (2H, brs), 4.08 (1H, d, J=3.0 Hz), 3.32 (1H, m), 3.30 (3H, s), 2.50 (2H, m), 2.30 (3H, s), 1.47 (3H, s).

MS (FAB, m/z): 608:(M+1)⁺.

Compound 149

¹H-NMR (270 MHz, DMSO-d₆) δ (ppm): 10.44 (1H, brs), 9.27 (1H, s), 8.74 (1H, brs), 8.43 (1H, d, J=7.6 Hz), 8.12 (1H, m), 7.97 (1H, d, J=8.6 Hz), 7.85 (1H, d, J=5.0 Hz), 7.80 (1H, d, J=8.7 Hz), 7.60 (1H, d, J=8.7 Hz), 7.40 (1H, dd, J=8.6, 7.3 Hz), 7.26–7.23 (2H, m), 6.70 (1H, m), 6.47 (1H, d, J=9.9 Hz), 6.39 (1H, d, J=9.9 Hz), 4.10 (1H, m), 3.34 (1H, m), 3.32 (3H, s), 2.50 (2H, m), 2.29 (3H, s), 1.55 (3H, s).

MS (FAB, m/z): 608 (M+1)⁺.

EXAMPLE 127

Compound 150

In a manner similar to that in step 1 of Example 101, 23.8 mg of Compound 150 (56%) was obtained from 35.3 mg (0.0630 mmol) of Compound 34, 0.013 mL (0.095 mmol) of triethylamine and 0.009 mL (0.008 mmol) of thiophene-2-carbonyl chloride.

¹H-NMR (270 MHz, DMSO-d₆) δ (ppm): 10.43 (1H, brs), 9.32 (1H, d, J=2.0 Hz), 8.55 (1H, brs), 8.10 (1H, brd, J=3.9 Hz), 8.07 (1H, d, J=2.0 Hz), 7.94 (1H, d, J=8.9 Hz), 7.84 (1R, dd, J=5.0, 1.0 Hz), 7.78 (1H, dd, J=8.9, 2.0 Hz), 7.61 (1H, d, J=8.9 Hz), 7.52 (1H, dd, J=8.9, 2.0 Hz), 7.24 (1H, dd, J=5.0, 3.9 Hz), 6.71 (1H, m), 4.97 (2H, s), 4.07 (1H, d, J=3.6 Hz), 3.39 (3H, s), 3.33 (1H, m), 2.50 (2H, m), 2.28 (3H, s), 1.41 (3H, s).

MS (FAB, m/z): 670 (M+1)⁺.

EXAMPLE 128

Compound 151

In a manner similar to that in step 1 of Example 108, 100 mg (0.173 mmol) of Compound d obtained in Reference Example 4 was reacted with 109 mg of polyvinylpyridine and 0.070 mL (0.69 mmol) of 3-carbomethoxypropionyl chloride, followed by treatment with 216 mg of aminomethyl resin and 73 mg of polyvinylpyridine, to give 72.5 mg of Compound 151 (61%).

¹H-NMR (270 MHz, DMSO-d₆) δ (ppm): 10.13 (1H, brs), 9.19 (1H, s), 8.60 (1H, brs), 8.06 (1H, d, J=7.8 Hz), 8.00 (1H, d, J=8.6 Hz), 7.89 (1H, d, J=8.9 Hz), 7.55 (1H, d, J=8.9 Hz), 7.50 (1H, m), 7.36 (1H, t, J=7.8 Hz), 7.02 (1H, m), 4.99 (2H, s), 4.90 (1H, brm), 4.44 (1H, brs), 3.62 (3H, s), 2.97 (3H, s), 2.85 (1H, m), 2.77 (3H, s), 2.66 (4H, m), 2.36 (3H, s), 2.32 (1H, m).

MS (FAB, m/z): 692 (M+1)⁺.

EXAMPLE 129

Compound 152

In a manner similar to that in step 1 of Example 108, 56.3 mg (0.097 mmol) of Compound d obtained in Reference Example 4 was reacted with 60.8 mg of polyvinylpyridine and 0.049 mL (0.39 mmol) of o-chlorobenzoyl chloride, followed by treatment with 675 mg of aminomethyl resin and 62 mg of polyvinylpyridine. Then in a manner similar to that in Example 19, the reaction mixture was treated with a 7 mol/L methanolic solution of ammonia, to give 10.6 mg of Compound 152 (18%).

¹H-NMR (270 MHz, DMSO-d₆) δ (ppm): 9.34 (1H, d, J=2.0 Hz), 8.44 (1H, brs), 8.00–7.92 (3H, m), 7.64–7.46 (5H, m), 7.42 (1H, t, J=7.3 Hz), 7.28 (1H, t, J=7.6 Hz), 6.71 (1H, brm), 4.94 (2H, s), 4.09 (1H, d, J=3.3 Hz), 3.32 (1H, m), 3.30 (3H, s), 2.50 (2H, m), 2.31 (3H, s), 1.46 (3H, brs).

MS (FAB, m/z): 620 (M+1)⁺.

EXAMPLE 130

Compound 153

In a manner similar to that in step 1 of Example 108, 53.3 mg (0.0920 mmol) of Compound d obtained in Reference Example 4 was reacted with 59.4 mg of polyvinylpyridine and 0.045 mL (0.37 mmol) of pivaloyl chloride, followed by treatment with 675 mg of aminomethyl resin and 62 mg of polyvinylpyridine. Then in a manner similar to that in Example 19, the reaction mixture was treated with a 7 mol/L methanolic solution of ammonia, to give 9.0 mg of Compound 153 (17%).

¹H-NMR (270 MHz, DMSO-d₆) δ (ppm): 9.35 (1H, brs), 9.17 (1H, d, J=2.0 Hz), 8.44 (1H, brs), 7.98 (1H, d, J=8.4 Hz), 7.95 (1H, d, J=7.6 Hz), 7.61 (1H, dd, J=8.9, 2.0 Hz), 7.52 (1H, d, J=8.9 Hz), 7.41 (1H, dd, J=8.4, 7.6 Hz), 7.27 (1H, t, J=7.6 Hz), 6.68 (1H, brm), 4.93 (2H, s), 4.07 (1H, d, J=3.3 Hz), 3.31 (1H, m), 3.30 (3H, s), 2.50 (2H, m), 2.30 (3H, s), 1.45 (3H, s), 1.29 (9H, s).

MS (FAB, m/z): 566 (M+1)⁺.

EXAMPLE 131

Compound 154

In a manner similar to that in step 1 of Example 108, 51.9 mg (0,0900 mmol) of Compound d obtained in Reference Example 4 was reacted with 56.3 mg of polyvinylpyridine and 0.054 mL (0.36 mmol) of o-methoxybenzoyl chloride, followed by treatment with 675 mg of aminomethyl resin and 62 mg of polyvinylpyridine. Then in a manner similar to that in Example 19, the reaction mixture was treated with a 7 mol/L methanolic solution of ammonia, to give 11.2 mg of Compound 154 (20%).

¹H-NMR (270 MHz, DMSO-d₆) δ (ppm): 10.17 (1H, brs), 9.34 (1H, d, J=2.0 Hz), 8.46 (1H, brs), 7.99 (1H, d, J=8.4 Hz), 7.96 (1H, d, J=7.3 Hz), 7.85 (1H, dd, J=8.9, 2.0 Hz), 7.76 (1H, dd, J=7.6, 2.0 Hz), 7.58 (1H, d, J=8.9 Hz), 7.52

(1H, brdd, J=6.9, 7.9 Hz), 7.41 (1H, dd, J=8.4, 7.3 Hz), 7.28 (1H, t, J=7.3 Hz), 7.21 (1H, d, J=7.9 Hz), 7.10 (1H, dd, J=7.6, 6.9 Hz), 6.71 (1H, brm), 4.94 (2H, s), 4.08 (1H, d, J=3.6 Hz), 3.97 (3H, s), 3.31 (1H, m), 3.30 (3H, s), 2.50 (2H, m), 2.31 (3H, s), 1.46 (3H, s).

MS (FAB, m/z): 616 (M+1)$^+$.

EXAMPLE 132

Compound 155

In a manner similar to that in step 1 of Example 108, 55.0 mg (0.0950 mmol) of Compound d obtained in Reference Example 4 was reacted with 60.9 mg of polyvinylpyridine and 0.031 mL (0.38 mmol) of acryloyl chloride, followed by treatment with 675 mg of aminomethyl resin and 62 mg of polyvinylpyridine. Then in a manner similar to that in Example 19, the reaction mixture was treated with a 7 mol/L methanolic solution of ammonia, to give 8.0 mg of Compound 155 (16%).

$^1$H-NMR (270 MHz, DMSO-d$_6$) δ (ppm): 10.26 (1H, brs), 9.21 (1H, d, J=1.7 Hz), 8.49 (1H, brs), 8.00–7.94 (3H, m), 7.56 (1H, d, J=9.2 Hz), 7.41 (1H, t, J=7.3 Hz), 7.27 (1H, t, J=7.3 Hz), 6.68 (1H, brm), 6.58 (1H, dd, J=17.0, 10.1 Hz), 6.27 (1H, dd, J=17.0, 2.1 Hz), 5.73 (1H, dd, J=10.1, 2.1 Hz), 4.94 (2H, s), 4.07 (1H, m), 3.32 (1H, m), 3.31 (3H, s), 2.50 (2H, m), 2.30 (3H, s), 1.46 (3H, s).

MS (FAB, m/z): 536 (M+1)$^+$.

EXAMPLE 133

Compound 156

In a manner similar to that in step 1 of Example 108, 52.0 mg (0.090 mmol) of Compound d obtained in Reference Example 4 was reacted with 57.0 mg of polyvinylpyridine and 0.061 mL (0.36 mmol) of octanoyl chloride, followed by treatment with 675 mg of aminomethyl resin and 62 mg of polyvinylpyridine. Then in a manner similar to that in Example 19, the reaction mixture was treated with a 7 mol/L methanolic solution of ammonia, to give 9.0 mg of Compound 156 (16%).

$^1$H-NMR (270 MHz, DMSO-d$_6$) δ (ppm): 9.93 (1H, brs), 9.13 (1H, d, J=1.8 Hz), 8.47 (1H, brs), 7.98 (1H, d, J=8.6 Hz), 7.95 (1H, d, J=7.8 Hz), 7.86 (1H, dd, J=8.7, 1.8 Hz), 7.51 (1H, d, J=8.7 Hz), 7.41 (1H, dd, J=8.6, 7.3 Hz), 7.27 (1H, dd, J=7.8, 7.3 Hz), 6.67 (1H, m), 4.93 (2H, s), 4.07 (1H, d, J=3.3 Hz), 3.33 (1H, m), 3.31 (3H, s), 2.50 (2H, m), 2.35 (2H, t, J=7.3 Hz), 2.30 (3H, s), 1.64 (2H, m), 1.45 (3H, s), 1.31 (8H, m), 0.88 (3H, t, J=6.8 Hz).

MS (FAB, m/z): 608 (M+1)$^+$.

EXAMPLE 134

Compound 157

In a manner similar to that in step 1 of Example 108, 52.0 mg (0.0900 mmol) of Compound d obtained in Reference Example 4 was reacted with 57.0 mg of polyvinylpyridine and 0.075 mL (0.36 mmol) of 2,6-dichlorobenzoyl chloride, followed by treatment with 1.01 g of aminomethyl resin and 87 mg of polyvinylpyridine. Then in a manner similar to that in Example 19, the reaction mixture was treated with a 7 mol/L methanolic solution of ammonia, to give 14.2 mg of Compound 157 (24%).

$^1$H-NMR (270 MHz, DMSO-d$_6$) δ (ppm): 10.83 (1H, brs), 9.29 (1H, d, J=2.0 Hz), 8.47 (1H, brs), 8.06–7.94 (3H, m), 7.64–7.37 (5H, m), 7.28 (1H, t, J=7.4 Hz), 6.72 (1H, m), 4.94 (2H, s), 4.08 (1H, d, J=3.3 Hz), 3.32 (1H, m), 3.30 (3H, s), 2.50 (2H, m), 2.31 (3H, s), 1.44 (3H, s).

MS (FAB, m/z): 654 (M+1)$^+$.

EXAMPLE 135

Compound 158

In a manner similar to that in step 1 of Example 108, 52.0 mg (0.0900 mmol) of Compound d obtained in Reference Example 4 was reacted with 57.0 mg of polyvinylpyridine and 0.047 mL (0.36 mmol) of isobutyl chloroformate, followed by treatment with 675 mg of aminomethyl resin and 65 mg of polyvinylpyridine. Then in a manner similar to that in Example 19, the reaction mixture was treated with a 7 mol/L methanolic solution of ammonia, to give 11.4 mg of Compound 158 (22%).

$^1$H-NMR (270 MHz, DMSO-d$_6$) δ (ppm): 9.47 (1H, brs), 9.18 (1H, s), 8.45 (1H, brs), 7.98 (1H, d, J=8.7 Hz), 7.95 (1H, d, J=7.8 Hz), 7.52 (2H, m), 7.41 (1H, dd, J=8.7, 7.3 Hz), 7.27 (1H, dd, J=7.8, 7.3 Hz), 6.67 (1H, m), 4.93 (2H, s), 4.07 (1H, d, J=3.6 Hz), 3.89 (2H, d, J=6.6 Hz), 3.32 (1H, m), 3.30 (3H, s), 2.50 (2H, m), 2.30 (3H, s), 1.95 (1H, m), 1.45 (3H, s), 0.97 (6H, d, J=6.9 Hz).

MS (FAB, m/z): 582 (M+1)$^+$.

EXAMPLE 136

Compound 159

In a manner similar to that in step 1 of Example 108, 52.0 mg (0.0900 mmol) of Compound d obtained in Reference Example 4 was reacted with 57.0 mg of polyvinylpyridine and 0.028 mL (0.36 mmol) of methanesulfonyl chloride, followed by treatment with 675 mg of aminomethyl resin and 65 mg of polyvinylpyridine. Then in a manner similar to that in Example 19, the reaction mixture was treated with a 7 mol/L methanolic solution of ammonia, to give 11.2 mg of Compound 159 (22%).

$^1$H-NMR (270 MHz, DMSO-d$_6$) δ (ppm): 9.49 (1H, brs), 9.18 (1H, d, J=2.0 Hz), 8.48 (1H, brs), 7.99 (1H, d, J=7.9 Hz), 7.96 (1H, d, J=7.6 Hz), 7.58 (1H, d, J=8.7 Hz), 7.42 (1H, m), 7.37 (1H, dd, J=8.7, 2.0 Hz), 7.28 (1H, d, J=7.6 Hz), 6.70 (1H, m), 4.94 (2H, s), 4.08 (1H, d, J=3.0 Hz), 3.31 (1H, m), 3.30 (3H, s), 2.97 (3H, s), 2.50 (2H, m), 2.30 (3H, s), 1.47 (3H, s).

MS (FAB, m/z): 560 (M+1)$^+$.

EXAMPLE 137

Compound 160

In a manner similar to that in step 1 of Example 108, 52.0 mg (0.0900 mmol) of Compound d obtained in Reference Example 4 was reacted with 57.0 mg of polyvinylpyridine and 0.046 mL (0.36 mmol) of benzenesulfonyl chloride, followed by treatment with 675 mg of aminomethyl resin and 65 mg of polyvinylpyridine, to give 17-methanesulfonamido-11-N-trifluoroacetyl staurosporin. Then in a manner similar to that in Example 19, the reaction mixture was treated with a 7 mol/L methanolic solution of ammonia, to give 10.0 mg of Compound 160 (18%).

$^1$H-NMR (270 MHz, DMSO-d$_6$) δ (ppm): 10.03 (1H, brs), 9.06 (1H, d, J=2.1 Hz), 8.46 (1H, brs), 7.97 (1H, d, J=7.9 Hz), 7.94 (1H, d, J=7.3 Hz), 7.78 (2H, m), 7.59–7.34 (5H, m), 7.26 (1H, t, J=7.3 Hz), 7.10 (1H, dd, J=8.6, 2.1 Hz), 6.62 (1H, m), 4.92 (2H, s), 4.05 (1H, d, J=3.3 Hz), 3.31 (1H, m), 3.30 (3H, s), 2.50 (2H, m), 2.28 (3H, s), 1.44 (3H, s).

MS (FAB, m/z): 622 (M+1)$^+$.

EXAMPLE 138

Compound 161

In a manner similar to that in step 1 of Example 108, 57.7 mg (0.100 mmol) of Compound d obtained in Reference Example 4 was reacted with 65.3 mg of polyvinylpyridine and 0.028 mL (0.40 mmol) of acetyl chloride, followed by treatment with 675 mg of aminomethyl resin and 65 mg of polyvinylpyridine. Then in a manner similar to that in Example 19, the reaction mixture was treated with a 7 mol/L methanolic solution of ammonia, to give 4.7 mg of Compound 161 (9%).

$^1$H-NMR (270 MHz, DMSO-$d_6$) δ (ppm): 10.00 (1H, brs), 9.12 (1H, d, J=2.0 Hz), 8.48 (1H, brs), 7.98 (1H, d, J=8.4 Hz), 7.95 (1H, d, J=7.6 Hz), 7.84 (1H, dd, J=8.8, 2.0 Hz), 7.51 (1H, d, J=8.8 Hz), 7.41 (1H, brdd, J=8.4, 7.6 Hz), 7.27 (1H, t, J=7.6 Hz), 6.67 (1H, m), 4.93 (2H, s), 4.07 (1H, d, J=3.3 Hz), 3.31 (1H, m), 3.30 (3H, s), 2.50 (2H, m), 2.30 (3H, s), 2.08 (3H, s), 1.48 (3H, s).

MS (FAB, m/z): 524 (M+1)$^+$.

EXAMPLE 139

Compound 162

In a manner similar to that in step 1 of Example 108, 50 mg (0.076 mmol) of Compound 31 was reacted with 100 mg of polyvinylpyridine and 0.028 mL (0.30 mmol) of benzoylchloride, followed by treatment with 385 mg of aminomethyl resin and 60 mg polyvinylpyridine. Then in a manner similar to that in Example 19, the reaction mixture was treated with a 7 mol/L methanolic solution of ammonia, to give 10.7 mg of Compound 162 (21%).

$^1$H-NMR (270 MHz, DMSO-$d_6$) δ (ppm): 10.35 (1H, brs), 9.44 (1H, s), 8.60 (1H, brs), 8.44 (1H, s), 8.04 (2H, d, J=6.6 Hz), 7.96 (1H, d, J=9.2 Hz), 7.83 (1H, brd, J=9.2 Hz), 7.64–7.57 (5H, m), 6.73 (1H, m), 4.92 (2H, s), 4.06 (1H, m), 3.37 (3H, s), 3.26 (1H, m), 2.50 (2H, m), 2.31 (3H, s), 1.42 (3H, s).

MS (FAB, m/z): 664 (M+1)$^+$.

EXAMPLE 140

Compound 163

In a manner similar to that in step 1 of Example 108, 50 mg (0.076 mmol) of Compound 31 was reacted with 100 mg of polyvinylpyridine and 0.039 mL (0.30 mmol) of p-chlorobenzoyl chloride, followed by treatment with 385 mg of aminomethyl resin and 60 mg of polyvinylpyridine, to give 7.9 mg of Compound 163 (13%).

$^1$H-NMR (270 MHz, DMSO-$d_6$) δ (ppm): 10.48 (1H, brs), 9.47 (1H, s), 8.71 (1H, brs), 8.56 (1H, s), 8.06 (2H, d, J=8.6 Hz), 7.96 (2H, m), 7.65 (4H, m), 7.07 (1H, brt, J=7.4 Hz), 4.98 (2H, s), 4.90 (1H, brm), 4.42 (1H, brs), 2.97 (3H, s), 2.84 (1H, m), 2.75 (3H, s), 2.55 (1H, m), 2.38 (3H, s).

MS (FAB, m/z): 794 (M+1)$^+$.

EXAMPLE 141

Compound 164

In a manner similar to that in step 1 of Example 108, 50 mg (0.076 mmol) of Compound 31 was reacted with 100 mg of polyvinylpyridine and 0.028 mL (0.30 mmol) of methyloxazalyl chloride, followed by treatment with 385 mg of aminomethyl resin and 60 mg of polyvinylpyridine, to give 11.3 mg of Compound 164 (20%).

$^1$H-NMR (270 MHz, DMSO-$d_6$) δ (ppm): 10.97 (1H, brs), 9.47 (1H, s), 8.72 (1H, brs), 8.52 (1H, s), 8.00 (2H, m), 7.64 (2H, m), 7.07 (1H, m), 4.94 (2H, s), 4.87 (1H, brm), 4.41 (1H, brs), 3.90 (3H, s), 3.30 (3H, s), 2.75 (2H, m), 2.54 (3H, s), 2.36 (3H, s).

EXAMPLE 142

Compound 165

In a manner similar to that in step 1 of Example 108, 50 mg (0.076 mmol) of Compound 31 was reacted with 100 mg of polyvinylpyridine and 0.033 mL (0.30 mmol) of thiophene-2-carbonyl chloride, followed by treatment with 385 mg of aminomethyl resin and 60 mg of polyvinylpyridine. Then in a manner similar to that in Example 19, the reaction mixture was treated with a 7 mol/L methanolic solution of ammonia, to give 17.9 mg of Compound 165 (35%).

$^1$H-NMR (270 MHz, DMSO-$d_6$) δ (ppm): 10.34 (1H, brs), 9.44 (1H, d, J=1.7 Hz), 8.60 (1H, brs), 8.35 (1H, d, J=2.0 Hz), 8.08 (1H, d, J=4.0 Hz), 7.97 (1H, d, J=9.1 Hz), 7.88 (1H, d, J=4.6 Hz), 7.77 (1H, brd, J=9.1 Hz), 7.63 (1H, d, J=8.6 Hz), 7.58 (1H, dd, J=8.6, 2.0 Hz), 7.26 (1H, dd, J=4.6, 4.0 Hz), 6.72 (1H, brm), 4.92 (2H, s), 4.07 (1H, d, J=3.6 Hz), 3.30 (3H, s), 3.26 (1H, m), 2.50 (2H, m), 2.31 (3H, s), 1.41 (3H, s).

MS (FAB, m/z): 670 (M+1)$^+$.

EXAMPLE 143

Compound 166

In a manner similar to that in step 1 of Example 108, 50 mg (0.076 mmol) of Compound 31 was reacted with 100 mg of polyvinylpyridine and 0.043 mL (0.30 mmol) of p-methoxybenzoyl chloride, followed by treatment with 385 mg of aminomethyl resin and 60 mg of polyvinylpyridine. Then in a manner similar to that in Example 19, the reaction mixture was treated with a 7 mol/L methanolic solution of ammonia, to give 15.9 mg of Compound 166 (30 4).

$^1$H-NMR (2701MHz, DMSO-$d_6$) δ (ppm): 10.18 (1H, brs), 9.44 (1H, d, J=1.7 Hz), 8.59 (1H, brs), 8.42 (1H, d, J=2 Hz), 8.04 (2H, d, J=8.7 Hz), 7.95 (1H, d, J=9.2 Hz), 7.81 (1H, brd, J=9.2 Hz), 7.63 (1H, d, J=8.6 Hz), 7.58 (1H, dd, J=8.6, 2.0 Hz), 7.10 (2H, d, J=8.7 Hz), 6.73 (1H, m), 4.92 (2H, s), 4.07 (1H, d, J=3.3 Hz), 3.87 (3H, s), 3.36 (3H, s), 3.17 (1H, m), 2.50 (2H, m), 2.31 (3H, s), 1.44 (3H, s).

MS (FAB, m/z): 694 (M+1)$^+$.

EXAMPLE 144

Compounds 167 and 168

In a manner similar to that in step 3 of Example 1, 93 mg of Compound 167 (14%) and 163 mg of Compound 168 (24%) were obtained from 577 mg (0.937 mmol) of Compound 166, dimethyl sulfoxide and 1.3 mL of a 6 mol/L aqueous solution of sodium hydroxide. The ratio of the respective diastereoisomers based on their hydroxyl group by HPLC was as follows: Compound 167 (91.5% d.e.) and Compound 168 (96.7% d.e.)

Compound 167

$^1$H-NMR (270 MHz, DMSO-$d_6$) δ (ppm): 10.20 (1H, brs), 9.39 (1H, s), 8.83 (1H, brs), 8.64 (1H, d, J=2.0 Hz), 8.04

(2H, d, J=8.7 Hz), 7.94 (1H, d, J=8.9 Hz), 7.72 (1H, dd, J=8.9, 2.0 Hz), 7.61 (2H, m), 7.08 (2H, d, J=8.7 Hz), 6.72 (1H, m), 6.34 (2H, s), 4.07 (1H, m), 3.86 (3H, s), 3.36 (3H, s), 3.33 (1H, m), 2.50 (2H, m), 2.30 (3H, s), 1.43 (3H, s).

MS (FAB, m/z): 710 (M+1)$^+$.

Compound 168

$^1$H-NMR (270 MHz, DMSO-d$_6$) δ (ppm): 10.20 (1H, brs), 9.39 (1H, d, J=1.7 Hz), 8.83 (1H, brs), 8.69 (1H, m), 8.04 (2H, d, J=8.9 Hz), 7.93 (1H, d, J=9.2 Hz), 7.72 (1H, m), 7.61 (2H, m), 7.08 (2H, d, J=8.9 Hz), 6.70 (1H, m), 6.36 (2H, m), 4.08 (1H, d, J=3.6 Hz), 3.86 (3H, s), 3.33 (1H, m), 3.30 (3H, s), 2.50 (2H, m), 2.29 (3H, s), 1.52 (3H, s).

MS (FAB, m/z): 710 (M+1)$^+$.

EXAMPLE 145

Compound 169

Step 1

In a manner similar to that in step 1 of Example 101, 1.00 g (1.53 mmol) of Compound 31 was reacted with 0.32 mL (2.3 mmol) of triethylamine and 0.25 mL (1.9 mmol) of p-toluoyl chloride, to give 722 mg of 17-bromo-5-(4-methylbenzamido)-11-N-trifluoroacetyl staurosporin (65%).

$^1$H-NMR (270 MHz, DMSO-d$_6$) δ (ppm): 10.32 (1H, brs), 9.47 (1H, s), 8.70 (1H, brs), 8.57 (1H, s), 7.99 (2H, m), 7.95 (2H, d, J=8.1 Hz), 7.63 (2H, m), 7.37 (2H, d, J=8.1 Hz), 7.06 (1H, m), 4.98 (2H, s), 4.90 (1H, brm), 4.41 (1H, brs), 2.97 (3H, s), 2.75 (3H, s), 2.50 (2H, m), 2.41 (3H, s), 2.38 (3H, s).

MS (FAB, m/z): 775 (M+1)$^+$.

Step 2

In a manner similar to that in Example 19, 31 mg (0.040 mmol) of 17-bromo-5-(4-methylbenzamido)-11-N-trifluoroacetyl staurosporin was treated with a 7 mol/L methanolic solution of ammonia, to give 25.5 mg of Compound 169 (94%).

$^1$H-NMR (270 MHz, DMSO-d$_6$) δ (ppm): 10.25 (1H, brs), 9.44 (1H, d, J=1.7 Hz), 8.59 (1H, brs), 8.42 (1H, d, J=2.0 Hz), 7.95 (3H, m), 7.82 (1H, dd, J=9.2, 2.0 Hz), 7.62 (1H, d, J=8.6 Hz), 7.57 (1H, dd, J=8.6, 1.7 Hz), 7.37 (2H, d, J=7.9 Hz), 6.72 (1H, m), 4.92 (2H, s), 4.07 (1H, d, J=3.3 Hz), 3.36 (3H, s), 3.34 (1H, m), 2.50 (2H, m), 2.41 (3H, s), 2.31 (3H, s), 1.43 (3H, s).

MS (FAB, m/z): 678 (M+1)$^+$.

EXAMPLE 146

Compound 170

In a manner similar to that in Example 40, 50 mg (0.065 mmol) of 17-bromo-5-(4-methylbenzamido)-11-N-trifluoroacetyl staurosporin obtained in step 1 of Example 145 was treated with 0.030 mL (0.33 mmol) of methyl acrylate, 1.1 mg (0.005 mmol) of palladium acetate, 4.3 mg (0.014 mmol) of tri-o-tolylphosphine and 0.18 mL (1.3 mmol) of triethylamine, and in a manner similar to that in Example 19, the reaction mixture was treated with a 7 mol/L methanolic solution of ammonia, to give 12.6 mg of Compound 170 (28%).

$^1$H-NMR (270 MHz, DMSO-d$_6$) δ (ppm): 10.26 (1H, brs), 9.53 (1H, d, J=1.3 Hz), 8.59 (1H, brs), 8.43 (1H, d, J=2.0 Hz), 7.96 (3H, m), 7.94–7.81 (4H, m), 7.67 (1H, d, J=8.6 Hz), 7.37 (2H, d, J=8.1 Hz), 6.76 (1H, m), 6.58 (1H, d, J=15.8 Hz), 4.93 (2H, s), 4.07 (1H, d, J=3.3 Hz), 3.76 (3H, s), 3.37 (3H, s), 3.26 (1H, m), 2.50 (2H, m), 2.41 (3H, s), 2.31 (3H, s), 1.43 (s, 3H).

MS (FAB, m/z): 684 (M+1)$^+$.

EXAMPLE 147

Compound 171

Step 1

To 2.36 g (4.08 mmol) of Compound d obtained in Reference Example 4 was added 20 mL of methylene chloride and 5.8 mL (41 mmol) of trifluoroacetic anhydride and the mixture was stirred at room temperature for 20 minutes. The reaction was terminated by adding a saturated aqueous solution of sodium bicarbonate, and the mixture was subjected to extraction with methylene chloride. The organic layer was dried over anhydrous sodium sulfate, and the solvent was distilled away under reduced pressure. The residue was purified by silica gel column chromatography (eluted with chloroform/methanol=30/1), and then triturated in a mixed solvent of ethyl acetate and diisopropyl ether, to give 912 mg of 17-trifluoroacetamido-11-N-trifluoroacetyl staurosporin (33%).

$^1$H-NMR (270 MHz, DMSO-d$_6$) δ (ppm): 11.46 (1H, brs), 9.39 (1H, d, J=2.0 Hz), 8.66 (1H, brs), 8.07 (1H, d, J=7.3 Hz), 8.02 (1H, d, J=8.6 Hz), 7.74 (1H, dd, J=8.9, 2.0 Hz), 7.66 (1H, d, J=8.9 Hz), 7.51 (1H, dd, J=8.6, 7.3 Hz), 7.37 (1H, t, J=7.3 Hz), 7.06 (1H, dd, J=8.1, 6.4 Hz), 5.01 (2H, s), 4.93 (1H, m), 4.45 (1H, brs), 2.98 (3H, s), 2.85 (1H, m), 2.75 (3H, s), 2.40 (1H, m), 2.38 (3H, s).

Step 2

In a manner similar to that in step 1 of Example 1, 28.8 mg of 5-nitro-17-trifluoroacetamido-11-N-trifluoroacetyl staurosporin (35%) was obtained from 79.4 mg (0.115 mmol) of 17-trifluoroacetamido-11-N-trifluoroacetyl staurosporin and 0.020 mL (0.47 mmol) of fuming nitric acid.

$^1$H-NMR (270 MHz, DMSO-d$_6$) δ (ppm): 11.46 (1H, brs), 9.40 (1H, d, J=1.8 Hz), 8.80 (1H, d, J=2.3 Hz), 8.74 (1H, brs), 8.33 (1H, dd, J=9.6, 2.3 Hz), 8.20 (1H, d, J=9.6 Hz), 7.76 (1H, dd, J=8.7, 1.8 Hz), 7.66 (1H, d, J=8.7 Hz), 7.06 (1H, m), 5.10 (2H, s), 4.89 (1H, m), 4.49 (1H, brs), 2.96 (3H, s), 2.86 (2H, m), 2.77 (3H, s), 2.39 (3H, s).

MS (FAB, m/z): 719 (M+1)$^+$.

Step 3

In a manner similar to that in step 2 of Example 1, 28.8 mg (0.0400 mmol) of 5-nitro-17-trifluoroacetamido-11-N-trifluoroacetyl staurosporin was subjected to catalytic reduction in an atmosphere of hydrogen in the presence of 32 mg of 10% palladium carbon (50% hydrous product), to give 16.2 mg of 5-amino-17-trifluoroacetamido-11-N-trifluoroacetyl staurosporin (59%).

$^1$H-NMR (270 MHz, DMSO-d$_6$) δ (ppm): 11.43 (1H, brs), 9.36 (1H, s), 8.53 (1H, brs), 7.70 (2H, m), 7.62 (1H, d, J=8.9 Hz), 7.21 (1H, s), 7.02 (1H, m), 6.85 (1H, d, J=8.9 Hz), 4.98 (1H, brm), 4.90 (2H, s), 4.33 (1H, brs), 2.96 (3H, s), 2.86 (2H, m), 2.72 (3H, s), 2.31 (3H, s).

Step 4

In a manner similar to that in step 1 of Example 103, 16.0 mg (0.0230 mmol) of 5-amino-17-trifluoroacetamido-11-N-trifluoroacetyl staurosporin was reacted with 0.010 mL (72 mmol) of triethylamine and 0.007 mL (0.05 mmol) of p-toluoyl chloride, and in a manner similar to that in step 2 of Example 3, the reaction mixture was treated with a 6 mol/L aqueous solution of sodium hydroxide, to give 7.8 mg of Compound 171 (55%).

$^1$H-NMR (270 MHz, DMSO-d$_6$) δ (ppm): 10.23 (1H, brs), 8.46 (1H, d, J=2.3 Hz), 8.41 (1H, brs), 8.39 (1H, d, J=2.0 Hz), 7.96 (2H, d, J=8.2 Hz), 7.92 (1H, d, J=9.2 Hz), 7.78 (1H, dd, J=9.2, 2.0 Hz), 7.37 (2H, d, J=8.2 Hz), 7.28 (1H, d, J=8.6 Hz), 6.84 (1H, dd, J=8.6, 2.3 Hz), 6.57 (1H, m), 4.86 (2H, s), 4.72 (2H, brm), 4.03 (1H, d, J=3.3 Hz), 3.33 (1H, m), 3.31 (3H, s), 2.50 (2H, m), 2.41 (3H, s), 2.28 (3H, s), 1.54 (3H, s).

MS (FAB, m/z): 615 (M+1)$^+$.

EXAMPLE 148

Compound 172

In a manner similar to that in step 1 of Example 108, 50 mg (0.076 mmol) Compound 31 was reacted with 100 mg of polyvinylpyridine and 0.031 mL (0.30 mmol) of 3-carbomethoxypropionyl chloride, followed by treatment with 385 mg of aminomethyl resin and 60 mg of polyvinylpyridine. Then in a manner similar to that in Example 19, the reaction mixture was treated with a 7 mol/L methanolic solution of ammonia, to give 5.3 mg of Compound 172 (10%).

$^1$H-NMR (270 MHz, DMSO-$d_6$) δ (ppm): 10.08 (1H, brs), 9.43 (1H, s), 8.56 (1H, brs), 8.28 (1H, s), 7.90 (1H, d, J=9.2 Hz), 7.64–7.54 (3H, m), 6.71 (1H, m), 4.88 (2H, s), 4.05 (1H, d, J=3.6 Hz), 3.62 (3H, s), 3.34 (4H, m), 2.67 (4H, m), 2.50 (2H, m), 2.28 (3H, s), 1.42 (3H, s).

MS (FAB, m/z): 674 (M+1)$^+$.

EXAMPLE 149

Compound 173

In a manner similar to that in step 1 of Example 108, 50 mg (0.087 mmol) of 5-amino-11-N-trifluoroacetyl staurosporin obtained in step 1 of Example 24 was reacted with 55 mg of polyvinylpyridine and 0.040 mL (0.35 mmol) of benzoyl chloride, followed by treatment with 420 mg of aminomethyl resin and 36 mg of polyvinylpyridine. Then in a manner similar to that in Example 19, the reaction mixture was treated with a 7 mol/L methanolic solution of ammonia, to give 13.2 mg of Compound 173 (26%).

$^1$H-NMR (270 MHz, DMSO-$d_6$) δ (ppm): 10.35 (1H, brs), 9.26 (1H, d, J=8.3 Hz), 8.52 (1H, brs), 8.44 (1H, s), 8.04 (2H, dd, J=7.8, 1.5 Hz), 7.96 (1H, d, J=9.2 Hz), 7.82 (1H, brd, J=9.2 Hz), 7.61–7.55 (4H, m), 7.46 (1H, dd, J=8.3, 6.9 Hz), 7.26 (1H, dd, J=8.3, 6.9 Hz), 6.73 (1H, brm), 4.91 (2H, s), 4.08 (1H, d, J=3.6 Hz), 3.33 (1H, m), 3.31 (3H, s), 2.50 (2H, m), 2.32 (3H, s), 1.49 (3H, brs).

MS (FAB, m/z): 586 (M+1)$^+$.

EXAMPLE 150

Compound 174

In a manner similar to that in step 1 of Example 108, 50 mg (0.087 mmol) of 5-amino-11-N-trifluoroacetyl staurosporin obtained in step 1 of Example 24 was reacted with 55 mg of polyvinylpyridine and 0.049 mL (0.35 mmol) of p-methoxybenzoyl chloride, followed by treatment with 420 mg of aminomethyl resin and 36 mg of polyvinylpyridine. Then in a manner similar to that in Example 19, the reaction mixture was treated with a 7 mol/L methanolic solution of ammonia, to give 20.8 mg of Compound 174 (39%).

$^1$H-NMR (270 MHz, DMSO-$d_6$) δ (ppm): 10.19 (1H, brs), 9.26 (1H, d, J=7.9 Hz), 8.51 (1H, brs), 8.41 (1H, s), 8.04 (1H, d, J=8.6 Hz), 7.95 (1H, d, J=9.2 Hz), 7.80 (1H, brd, J=9.2 Hz), 7.60 (1H, d, J=7.9 Hz), 7.46 (1H, t, J=7.9 Hz), 7.26 (1H, t, J=7.9 Hz), 7.10 (2H, d, J=8.6 Hz), 6.73 (1H, brm), 4.90 (2H, s), 4.08 (1H, m), 3.86 (3H, s), 3.30 (1H, m), 3.16 (3H, s), 2.50 (2H, m), 2.31 (3H, s), 1.49 (3H, brs).

MS (FAB, m/z): 616 (M+1)$^+$.

EXAMPLE 151

Compound 175

In a manner similar to that in step 1 of Example 108, 100 mg (0.173 mmol) of 5-amino-11-N-trifluoroacetyl staurosporin obtained in step 1 of Example 24 was reacted with 109 mg of polyvinylpyridine and 0.070 mL (0.69 mmol) of 3-carbomethoxypropionyl chloride, followed by treatment with 840 mg of aminomethyl resin and 73 mg of polyvinylpyridine. Then in a manner similar to that in Example 19, the reaction mixture was treated with a 7 mol/L methanolic solution of ammonia, to give 17.9 mg of Compound 175 (18%).

$^1$H-NMR (270 MHz, DMSO-$d_6$) δ (ppm): 10.02 (1H, brs), 9.25 (1H, d, J=7.6 Hz), 8.48 (1H, brs), 8.31 (1H, d, J=2.0 Hz), 7.89 (1H, d, J=9.1 Hz), 7.59 (1H, d, J=8.3 Hz), 7.56 (1H, brd, J=7.1 Hz), 7.45 (1H, dd, J=8.3, 7.6 Hz), 7.26 (1H, brd, J=7.6 Hz), 6.80 (2H, brs), 6.72 (1H, brm), 4.87 (2H, s), 4.06 (1H, d, J=4.6 Hz), 3.29 (1H, m), 3.16 (3H, s), 2.59 (2H, t, J=6.9 Hz), 2.50 (2H, m), 2.44 (2H, t, J=6.9 Hz), 2.29 (3H, s), 1.50 (3H, brs).

MS (FAB, m/z): 581 (M+1)$^+$.

EXAMPLE 152

Compound 176

In a manner similar to that in step 1 of Example 108, 50 mg (0.087 mmol) of 5-amino-11-N-trifluoroacetyl staurosporin obtained in step 1 of Example 24 was reacted with 55 mg of polyvinylpyridine and 0.044 mL (0.35 mmol) of p-chlorobenzoyl chloride, followed by treatment with 420 mg of aminomethyl resin and 36 mg of polyvinylpyridine. Then in a manner similar to that in Example 19, the reaction mixture was treated with a 7 mol/L methanolic solution of ammonia, to give 36.0 mg of Compound 176 (67%).

$^1$H-NMR (270 MHz, DMSO-$d_6$) δ (ppm): 10.42 (1H, brs), 9.26 (1H, d, J=7.9 Hz), 8.51 (1H, brs), 8.41 (1H, d, J=2.0 Hz), 8.07 (2H, d, J=8.6 Hz), 7.96 (1H, d, J=9.2 Hz), 7.79 (1H, dd, J=9.2, 2.0 Hz), 7.65 (2H, d, J=8.6 Hz), 7.60 (1H, d, J=7.9 Hz), 7.46 (1H, t, J=7.9 Hz), 7.26 (1H, t, J=7.9 Hz), 6.73 (1H, brm), 4.91 (2H, s), 4.08 (1H, d, J=3.3 Hz), 3.35 (3H, s), 3.32 (1H, m), 2.50 (2H, s), 2.32 (3H, s), 1.49 (3H, s).

MS (FAB, m/z): 620 (M+1)$^+$.

EXAMPLE 153

Compound 177

In a manner similar to that in step 1 of Example 108, 50 mg (0.087 mmol) of 5-amino-11-N-trifluoroacetyl staurosporin obtained in step 1 of Example 24 was reacted with 55 mg of polyvinylpyridine and 0.027 mL (0.35 mmol) of ethyl isocyanate, followed by treatment with 420 mg of aminomethyl resin and 36 mg of polyvinylpyridine. Then in a manner similar to that in Example 19, the reaction mixture was treated with a 7 mol/L methanolic solution of ammonia, to give 20.7 mg of Compound 177 (43%).

$^1$H-NMR (270 MHz, DMSO-$d_6$) δ (ppm): 9.25 (1H, d, J=7.9 Hz), 8.45 (1H, brs), 8.42 (1H, brs), 8.06 (1H, brs), 7.83 (1H, d, J=9.2 Hz), 7.58 (1H, d, J=8.3 Hz), 7.44 (1H, dd, J=8.3, 7.1 Hz), 7.33 (1H, brd, J=9.2 Hz), 7.25 (1H, dd, J=7.9, 7.1 Hz), 6.70 (1H, brm), 6.09 (1H, m), 4.86 (2H, s), 4.04 (1H, d, J=3.6 Hz), 3.31 (3H, s), 3.24 (1H, m), 3.16 (2H, m), 2.50 (2H, m), 2.27 (3H, s), 1.48 (3H, s), 1.09 (3H, t, J=7.1 Hz).

MS (FAB, m/z): 553 (M+1)$^+$.

EXAMPLE 154

Compound 178

In a manner similar to that in step 1 of Example 108, 100 mg (0.0870 mmol) of 5-amino-11-N-trifluoroacetyl staurosporin obtained in step 1 of Example 24 was reacted with 109 mg of polyvinylpyridine and 0.027 mL (0.35 mmol) of trimethylsilyl isocyanide, followed by treatment with 840 mg of aminomethyl resin and 73 mg of polyvinylpyridine. Then in a manner similar to that in Example 19, the reaction mixture was treated with a 7 mol/L methanolic solution of ammonia, to give 31.8 mg of Compound 178 (35%).

$^1$H-NMR (270 MHz, DMSO-$d_6$) δ (ppm): 9.26 (1H, d, J=7.8 Hz), 8.57 (1H, brs), 8.48 (1H, brs), 8.02 (1H, s), 7.85 (1H, d, J=9.2 Hz), 7.57 (1H, d, J=7.9 Hz), 7.44 (2H, m), 7.26 (1H, t, J=7.8 Hz), 6.74 (1H, brm), 5.82 (2H, s), 4.87 (2H, s), 4.09 (1H, brs), 3.31 (3H, s), 3.16 (1H, m), 2.50 (2H, m), 2.30 (3H, s), 1.66 (3H, brs).

MS (FAB, m/z): 525 (M+1)$^+$.

EXAMPLE 155

Compound 179

In a manner similar to that in step 1 of Example 108, 48 mg (0.083 mmol) of 5-amino-11-N-trifluoroacetyl staurosporin obtained in step 1 of Example 24 was reacted with 52 mg of polyvinylpyridine and 0.033 mL (0.35 mmol) of allyl isocyanate, followed by treatment with 415 mg of aminomethyl resin. Then in a manner similar to that in Example 19, the reaction mixture was treated with a 7 mol/L methanolic solution of ammonia, to give 17.7 mg of Compound 179 (38%).

$^1$H-NMR (270 MHz, DMSO-$d_6$) δ (ppm): 9.25 (1H, d, J=7.3 Hz), 8.52 (1H, brs), 8.44 (1H, brs), 8.07 (1H, d, J=2.3 Hz), 7.84 (1H, d, J=9.2 Hz), 7.58 (1H, d, J=7.9 Hz), 7.44 (1H, t, J=7.9 Hz), 7.34 (1H, dd, J=17.5, 2.0 Hz), 7.25 (1H, t, J=7.9 Hz), 6.70 (1H, brm), 6.26 (1H, t, J=5.9 Hz), 5.91 (1H, m), 5.21 (1H, dd, J=17.5, 2.0 Hz), 5.09 (1H, dd, J=10.2, 2.0 Hz), 4.86 (2H, s), 4.04 (1H, d, J=3.6 Hz), 3.79 (2H, m), 3.31 (1H, m), 3.30 (3H, s), 2.50 (2H, m), 2.27 (3H, s), 1.48 (3H, s).

MS (FAB, m/z): 565 (M+1)$^+$.

EXAMPLE 156

Compound 180

In a manner similar to that in step 1 of Example 108, 51 mg (0.088 mmol) of 5-amino-11-N-trifluoroacetyl staurosporin obtained in step 1 of Example 24 was reacted with 52 mg of polyvinylpyridine and 0.033 mL (0.35 mmol) of bromoethyl isocyanide, followed by treatment with 438 mg of aminomethyl resin. Then in a manner similar to that in Example 19, the reaction mixture was treated with a 7 mol/L methanolic solution of ammonia, to give 12.3 mg of Compound 180 (25%).

$^1$H-NMR (270 MHz, DMSO-$d_6$) δ (ppm): 9.24 (1H, d, J=7.9 Hz), 8.43 (1H, brs), 8.26 (1H, brm), 7.83 (1H, d, J=9.2 Hz), 7.62–7.50 (3H, m), 7.44 (1H, dd, J=7.9, 6.9 Hz), 7.25 (1H, dd, J=7.9, 6.9 Hz), 6.70 (1H, m), 4.85 (2H, s), 4.28 (2H, brt, J=8.3 Hz), 4.04 (1H, d, J=3.6 Hz), 3.82 (2H, brm), 3.33 (1H, m), 3.30 (3H, s), 2.50 (2H, m), 2.27 (3H, s), 1.48 (3H, s).

MS (FAB, m/z): 551 (M+1)$^+$.

EXAMPLE 157

Compound 181

35.6 mg (0.0549 mmol) of Compound t obtained in Reference Example 16 was dissolved in 5 mL of N,N-dimethylformamide followed by adding 0.82 mL (0.082 mmol) of 100 mmol/L butylamine in N,N-dimethylformamide, 28 mg (0.18 mmol) of 1-hydroxybenzotriazole.1 H$_2$O and 22 mg (0.11 mmol) of 3-(3-dimethylaminopropyl)-1-ethylcarbodiimide hydrochloride, and the mixture was stirred at room temperature for 17 hours. A saturated aqueous solution of ammonium chloride was added to the reaction mixture, and then the mixture was extracted with chloroform. The organic layer was washed with a saturated aqueous solution of sodium bicarbonate and then with a saturated saline solution, and dried over anhydrous sodium sulfate. The solvent was distilled away under reduced pressure. Then in a manner similar to that in Example 19, the residue was treated with a 7 mol/L methanolic solution of ammonia, to give 15.8 mg of Compound 181 (51%).

$^1$H-NMR (270 MHz, DMSO-$d_6$) δ (ppm): 9.71 (1H, d, J=1.3 Hz), 8.53 (1H, brs), 8.29 (1H, brt, J=4.3 Hz), 7.95 (1H, d, J=7.6 Hz), 7.95 (1H, d, J=6.9 Hz), 7.88 (1H, dd, J=8.6, 1.7 Hz), 7.62 (1H, d, J=8.6 Hz), 7.41 (1H, ddd, J=8.3, 7.3, 1.0 Hz), 7.28 (1H, dd, J=7.6, 7.6 Hz), 6.74 (1H, brs), 4.95 (2H, s), 4.08 (1H, d, J=3.3 Hz), 3.36 (3H, s), 3.34–3.26 (3H, m), 2.52–2.46 (2H, m), 2.30 (3H, s), 1.62–1.50 (2H, m), 1.46–1.30 (2H, m), 1.40 (3H, s), 0.93 (3H, t, J=7.3 Hz).

MS (FAB, m/z): 566 (M+1)$^+$.

EXAMPLE 158

Compound 182

128 mg (0.197 mmol) of Compound t obtained in Reference Example 16 was dissolved in a mixed solvent of 10 mL of N,N-dimethylformamide and 2 mL of methylene chloride followed by adding 20 mg (0.30 mmol) of methylamine hydrochloride, 0.041 mL (0.30 mmol) of triethylamine, 107 mg (0.697 mmol) of 1-hydroxybenzotriazole.1H$_2$O, and 77 mg (0.40 mmol) of 3-(3-dimethylaminopropyl)-1-ethylcarbodiimide hydrochloride, and the mixture was stirred at room temperature for 10 hours. A saturated aqueous solution of ammonium chloride was added to the reaction mixture, and then the mixture was extracted with chloroform. The organic layer was washed with a saturated aqueous solution of sodiumbicarbonate, and then with a saturated saline solution and dried over anhydrous sodium sulfate. The solvent was distilled away under reduced pressure. Then in a manner similar to that in Example 19, the residue was treated with a 7 mol/L methanolic solution of ammonia, to give 83.0 mg of Compound 182 (80%).

$^1$H-NMR (270 MHz, DMSO-$d_6$) δ (ppm): 9.70 (1H, d, J=1.3 Hz), 8.52 (1H, brs), 8.27 (1H, brq, J=4.6 Hz), 7.98 (1H, d, J=7.6 Hz), 7.96 (1H, d, J=6.9 Hz), 7.88 (1H, dd, J=8.6, 1.7 Hz), 7.63 (1H, d, J=8.6 Hz), 7.41 (1H, ddd, J=7.2, 6.9, 1.3 Hz), 7.28 (1H, dd, J=7.6, 7.3 Hz), 6.74 (1H, dd, J=3.6, 2.6 Hz), 4.95 (2H, s), 4.07 (1H, d, J=3.3 Hz), 3.36 (3H, s), 3.34–3.26 (1H, m), 2.84 (3H, d, J=4.6 Hz), 2.58 2.40 (2H, m), 2.30 (3H, s), 1.41 (3H, s).

MS (FAB, m/z): 524 (M+1)$^+$.

EXAMPLE 159

Compound 183

0.98 mL (0.098 mmol) of 100 mmol/L benzylamine in N,N-dimethylformamide, 2.0 mL (0.20 mmol) of 100 mmol/L 1-hydroxybenzotriazole monohydrate in N,N-dimethylformamide, and 1.3 mL (0.13 mmol) of 100 mmol/L 3-(3-dimethylaminopropyl)-1-ethylcarbodiimide hydrochloride in methylene chloride were added to 1.3 mL (0.065 mmol) of 50 mmol/L Compound t obtained in Reference Example 16 in N,N-dimethylformamide, and the mixture was stirred at room temperature for 6 hours. The solvent was distilled away under reduced pressure, and the residue was purified by Bondesil SCX benzenesulfonic acid column chromatography (produced by GL Sciences Inc., eluted with chloroform/methanol=4/1) and then by Bondesil SAX quarternary amine column chromatography (produced by GL Sciences Inc., eluted with chloroform/methanol=4/1). Then in a manner similar to that in Example 19, the product was treated with a 7 mol/L methanolic solution of ammonia, to give 19.7 mg of Compound 183 (51%).

$^1$H-NMR (270 MHz, DMSO-d$_6$) δ (ppm): 9.78 (1H, d, J=1.7 Hz), 8.92 (1H, brt, J=5.9 Hz), 8.54 (1H, brs), 8.02–7.92 (3H, m), 7.65 (1H, d, J=8.6 Hz), 7.46–7.20 (7H, m), 6.80–6.72 (1H, m), 4.95 (2H, s), 4.54 (2H, d, J=6.3 Hz), 4.07 (1H, d, J=3.6 Hz), 3.36 (3H, s), 3.34–3.26 (1H, m), 2.58–2.46 (2H, m), 2.30 (3H, s), 1.39 (3H, s).

MS (FAB, m/z): 600 (M+1)$^+$.

EXAMPLE 160

Compounds 184 and 185

In a manner similar to that in step 3 of Example 1, 9.0 mg of Compound 184 (14%) and 10.4 mg of Compound 185 (16%) were obtained from 63.6 mg (0.122 mmol) of Compound 182, dimethyl sulfoxide and 0.50 mL of a 6 mol/L aqueous solution of sodium hydroxide. The ratio of the respective diastereoisomers based on their hydroxyl group by HPLC was as follows: Compound 184 (56.1% d.e.) and Compound 185 (68.6% d.e.)

Compound 184

$^1$H-NMR (270 MHz, DMSO-d$_6$) δ (ppm): 9.66 (1H, d, J=1.7 Hz), 8.78 (1H, brs), 8.36 (1H, d, J=7.9 Hz), 8.28 (1H, brq, J=4.0 Hz), 7.96 (1H, d, J=8.6 Hz), 7.89 (1H, dd, J=8.6, 1.7 Hz), 7.63 (1H, d, J=8.6 Hz), 7.40 (1H, brdd, J=7.3, 7.3 Hz), 7.25 (1H, dd, J=7.6, 7.3 Hz), 6.72 (1H, brs), 6.39 (2H, brs), 4.08 (1H, d, J=3.3 Hz), 3.36 (3H, s), 3.34–3.26 (1H, m), 2.84 (3H, d, J=4.0 Hz), 2.52–2.46 (2H, m), 2.29 (3H, s), 1.39 (3H, s).

MS (FAB, m/z): 540 (M+1)$^+$.

Compound 185

$^1$H-NMR (270 MHz, DMSO-d$_6$) δ (ppm): 9.66 (1H, d, J=1.3 Hz), 8.77 (1H, brs), 8.42 (1H, d, J=7.6 Hz), 8.29 (1H, brq, J=4.0 Hz), 7.96 (1H, d, J=8.6 Hz), 7.89 (1H, dd, J=8.6, 1.7 Hz), 7.63 (1H, d, J=8.9 Hz), 7.40 (1H, brdd, J=7.6, 8.3 Hz), 7.24 (1H, dd, J=7.6, 7.3 Hz), 6.76–6.68 (1H, m), 6.40 (2H, brs), 4.08 (1H, d, J=3.3 Hz), 3.37 (3H, s), 3.34–3.26 (1H, m), 2.84 (3H, d, J=4.0 Hz), 2.52–2.46 (2H, m), 2.28 (3H, s), 1.48 (3H, s).

MS (FAB, m/z): 540 (M+1)$^+$.

EXAMPLE 161

Compound 186

In a manner similar to that in Example 157, 24.6 mg of Compound 186 (68%) was obtained from 1.3 mL (0.065 mmol) of 50 mmol/L Compound t obtained in Reference Example 16 in N,N-dimethylformamide, 0.98 mL (0.098 mmol) of 100 mmol/L ethanolamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-d$_6$) δ (ppm): 9.82 (1H, d, J=1.7 Hz), 8.62 (1H, brs), 8.34 (1H, brs), 8.12–7.98 (3H, m), 7.73 (1H, d, J=8.6 Hz), 7.52 (1H, ddd, J=8.6, 7.3, 1.3 Hz), 7.38 (1H, dd, J=7.6, 7.3 Hz), 6.84 (1H, dd, J=3.3, 3.0 Hz), 5.05 (2H, s), 4.84 (1H, brt, J=5.3 Hz), 4.18 (1H, d, J=3.3 Hz), 3.67 (2H, t, J=5.9 Hz), 3.50 (2H, dt, J=5.9, 5.9 Hz), 3.45 (3H, s), 3.34–3.26 (1H, m), 2.52–2.46 (2H, m), 2.40 (3H, s), 1.50 (3H, s).

MS (FAB, m/z): 554 (M+1)$^+$.

EXAMPLE 162

Compound 187

In a manner similar to that in Example 157, 30.9 mg of Compound 187 (82%) was obtained from 1.3 mL (0.065 mmol) of 50 mmol/L Compound t obtained in Reference Example 16 in N,N-dimethylformamide, 0.98 mL (0.098 mmol) of 100 mmol/L N,N-dimethylethylenediamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-d$_6$) δ (ppm): 9.88 (1H, d, J=1.7 Hz), 8.66 (1H, brs), 8.16–8.02 (3H, m), 7.76 (1H, d, J=8.9 Hz), 7.55 (1H, ddd, J=8.3, 7.3, 1.0 Hz), 7.41 (1H, dd, J=7.6, 7.3 Hz), 6.96–6.88 (1H, m), 5.07 (2H, s), 4.29 (1H, brs), 3.79–3.68 (2H, m), 3.34–3.14 (3H, m), 2.84 (6H, s), 2.52–2.46 (2H, m), 2.45 (3H, s), 1.84 (3H, s).

MS (FAB, m/z): 581 (M+1)$^+$.

EXAMPLE 163

Compound 188

In a manner similar to that in Example 157, 22.0 mg of Compound 188 (59%) was obtained from 1.3 mL (0.065 mmol) of 50 mmol/L Compound t obtained in Reference Example 16 in N,N-dimethylformamide, 0.98 mL, (0.098 mmol) of 100 mmol/L piperidine in N,N-dimethylformamide, 2.0 mL, (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-d$_6$) δ (ppm): 9.35 (1H, d, J=1.3 Hz), 8.54 (1H, brs), 7.99 (1H, d, J=7.9 Hz), 7.96 (1H, d, J=7.3 Hz), 7.64 (1H, d, J=8.6 Hz), 7.48 (1H, dd, J=8.3, 1.3 Hz), 7.42 (1H, brdd, J=7.3, 8.6 Hz), 7.28 (1H, dd, J=7.6, 7.3 Hz), 6.74 (1H, dd, J=3.6, 3.0 Hz), 4.95 (2H, s), 4.08 (1H, d, J=3.3 Hz), 3.64–3.46 (4H, m), 3.34–3.26 (1H, m), 3.33 (3H, s), 2.58–2.46 (2H, m), 2.30 (3H, s), 1.70–1.56 (6H, m), 1.45 (3H, s).

MS (FAB, m/z): 578 (M+1)$^+$.

EXAMPLE 164

Compound 189

In a manner similar to that in Example 157, 25.6 mg of Compound 189 (68%) was obtained from 1.3 mL (0.065 mmol) of 50 mmol/L Compound t obtained in Reference Example 16 in N,N-dimethylformamide, 0.98 mL (0.098 mmol) of 100 mmol/L morpholine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mmol/L methanolic solution of ammonia.

$^1$H-NMR (270 MHz, DMSO-$d_6$) δ (ppm): 9.39 (1H, d, J=1.7 Hz), 8.54 (1H, brs), 7.99 (1H, d, J=7.9 Hz), 7.96 (1H, d, J=6.9 Hz), 7.65 (1H, d, J=8.6 Hz), 7.53 (1H, dd, J=8.6, 1.6 Hz), 7.42 (1H, ddd, J=7.9, 6.9, 1.0 Hz), 7.28 (1H, dd, J=7.6, 7.3 Hz), 6.74 (1H, dd, J=3.6, 3.3 Hz), 4.95 (2H, s), 4.08 (1H, d, J=3.6 Hz), 3.74–3.54 (8H, m), 3.34 (3H, s), 3.34–3.26 (1H, m), 2.57–2.50 (2H, m), 2.30 (3H, s), 1.44 (3H, s).

MS (FAB, m/z): 580 (M+1)$^+$.

EXAMPLE 165

Compound 190

In a manner similar to that in Example 157, 23.9 mg of Compound 190 (62%) was obtained from 1.3 mL (0.065 mmol) of 50 mmol/L Compound t obtained in Reference Example 16 in N,N-dimethylformamide, 0.98 mL (0.098 mmol) of 100 mmol/L N-methylpiperazine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.36 (1H, d, J=1.7 Hz), 8.57 (1H, brs), 7.99 (1H, d, J=7.9 Hz), 7.96 (1H, d, J=7.3 Hz), 7.64 (1H, d, J=8.6 Hz), 7.50 (1H, dd, J=8.6, 2.0 Hz), 7.42 (1H, ddd, J=8.3, 7.3, 1.0 Hz), 7.28 (1H, dd, J=7.9, 6.9 Hz), 6.77–6.70 (1H, m), 4.95 (2H, s), 4.08 (1H, d, J=3.6 Hz), 3.66–3.50 (4H, m), 3.34–3.26 (1H, m), 3.33 (3H, s), 2.58–2.46 (2H, m), 2.46–2.36 (4H, m), 2.30 (3H, s), 2.23 (3H, s), 1.44 (3H, s).

MS (FAB, m/z): 593 (M+1)$^+$.

EXAMPLE 166

Compound 191

In a manner similar to that in Example 157, 24.1 mg of Compound 191 (66%) was obtained from 1.3 mL (0.065 mmol) of 50 mmol/L Compound t obtained in Reference Example 16 in N,N-dimethylformamide, 0.98 mL (0.098 mmol) of 100 mmol/L pyrrolidine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.51 (1H, brs), 8.53 (1H, brs), 7.99 (1H, d, J=7.9 Hz), 7.96 (1H, d, J=6.3 Hz), 7.70–7.58 (2H, m), 7.42 (1H, ddd, J=8.6, 7.3, 1.3 Hz), 7.28 (1H, dd, J=7.6, 7.3 Hz), 6.74 (1H, dd, J=3.3, 3.3 Hz), 4.95 (2H, s), 4.08 (1H, d, J=3.6 Hz), 3.64–3.50 (4H, m), 3.34–3.26 (1H, m), 3.33 (3H, s), 2.57–2.46 (2H, m), 2.30 (3H, s), 2.00–1.80 (4H, m), 1.44 (3H, s).

MS (FAB, m/z): 564 (M+1)$^+$.

EXAMPLE 167

Compound 192

In a manner similar to that in Example 158, 17.8 mg of Compound 192 (51%) was obtained from 1.3 mL (0.065 mmol) of 50 mmol/L Compound t obtained in Reference Example 16 in N,N-dimethylformamide, 0.98 mL (0.098 mmol) of 100 mmol/L dimethylamine hydrochloride in N,N-dimethylformamide, 0.098 mL (0.098 mmol) of 1.0 mol/L triethylamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.35 (1H, d, J=1.3 Hz), 8.54 (1H, brs), 7.98 (1H, d, J=7.9 Hz), 7.96 (1H, d, J=7.3 Hz), 7.63 (1H, d, J=8.3 Hz), 7.51 (1H, dd, J=8.6, 1.7 Hz), 7.42 (1H, ddd, J=8.6, 7.3, 1.3 Hz), 7.28 (1H, dd, J=7.6, 7.3 Hz), 6.74 (1H, dd, J=3.3, 3.0 Hz), 4.95 (2H, s), 4.07 (1H, d, J=3.3 Hz), 3.34 (3H, s), 3.34–3.26 (1H, m), 3.05 (6H, s), 2.58–2.46 (2H, m), 2.30 (3H, s), 1.43 (3H, s).

MS (FAB, m/z): 538 (M+1)$^+$.

EXAMPLE 168

Compound 193

In a manner similar to that in Example 158, 11.6 mg of Compound 193 (32%) was obtained from 1.3 mL (0.065 mmol) of 50 mmol/L Compound t obtained in Reference Example 16 in N,N-dimethylformamide, 0.98 mL (0.098 mmol) of 100 mmol/L glycine ethyl esterhydrochloride in N,N-dimethylformamide, 0.098 mL (0.098 mmol) of 1.0 mol/L triethylamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.76 (1H, d, J=1.7 Hz), 8.54 (1H, brs), 8.43 (1H, brt, J=5.6 Hz), 8.02–7.92 (3H, m), 7.66 (1H, d, J=8.6 Hz), 7.46–7.34 (2H, m), 7.28 (1H, dd, J=7.6, 7.3 Hz), 7.05 (1H, brs), 6.78–6.72 (1H, m), 4.95 (2H, s), 4.08 (1H, d, J=3.3 Hz), 3.88 (2H, d, J=5.9 Hz), 3.36 (3H, s), 3.34–3.26 (1H, m), 2.58–2.50 (2H, m), 2.31 (3H, s), 1.39 (3H, s).

MS (FAB, m/z): 567 (M+1)$^+$.

EXAMPLE 169

Compound 194

0.98 mL (0.098 mmol) of 100 mmol/L diisopropylamine in N,N-dimethylformamide, 2.0 mL (0.20 mmol) of 100 mmol/L 1-hydroxybenzotriazole monohydrate in N,N-dimethylformamide, and 1.3 mL (0.13 mmol) of 100 mmol/L 3-(3-dimethylaminopropyl)-1-ethylcarbodiimide hydrochloride in methylene chloride were added to 1.3 mL (0.065 mmol) of 50 mmol/L Compound t obtained in Reference Example 16 in N,N-dimethylformamide, and the mixture was stirred at room temperature for 10 hours. The solvent was distilled away under reduced pressure. The residue was dissolved in 8 mL of chloroform and the solution was washed twice with 3 mL each of a saturated aqueous solution of ammonium chloride, a saturated aqueous solution of sodium bicarbonate and a saturated saline and then dried over anhydrous sodium sulfate. The solvent was distilled away under reduced pressure. 4 mL of a 7 mol/L methanolic solution of ammonia and 4 mL of chloroform were added to the resulting residue and the mixture was stirred at room temperature form 10 hours. The solvent was distilled away under reduced pressure, and 5 mL of a 7 mol/L methanolic solution of ammonia was added again to the resulting residue and the mixture was stirred at room temperature for 30 hours. The solvent was distilled away under reduced pressure, and the resulting residue was purified by preparative thin-layer chromatography (developed with chloroform/methanol/28% aqueous ammonia=100/10/1) to give 7.8 mg of Compound 194 (24%).

$^1$H-NMR (270 MHz, DMSO-d$_6$) δ (ppm): 9.75 (1H, d, J=1.7 Hz), 8.54 (1H, brs), 8.02–7.90 (3H, m), 7.82 (1H, brs), 7.62 (1H, d, J=8.6 Hz), 7.42 (1H, ddd, J=8.6, 7.3, 1.3 Hz), 7.28 (1H, dd, J=7.6, 7.3 Hz,), 7.19 (1H, brs), 6.75 (1H, dd, J=3.3, 3.3 Hz), 4.95 (2H, s), 4.08 (1H, d, J=3.3 Hz), 3.34–3.26 (4H, m), 2.58–2.46 (2H, m), 2.31 (3H, s), 1.44 (3H, brs).

MS (FAB, m/z): 510 (M+1)$^+$.

EXAMPLE 170

Compound 195

In a manner similar to that in Example 157, 21.5 mg of Compound 195 (59%) was obtained from 1.3 mL (0.065 mmol) of 50 mmol/L Compound t obtained in Reference Example 16 in N,N-dimethylformamide, 0.98 mL (0.098 mmol) of 100 mmol/L tert-butylamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-d$_6$) δ (ppm): 9.65 (1H, d, J=1.7 Hz), 8.54 (1H, brs), 7.98 (1H, d, J=7.9 Hz), 7.95 (1H, d, J=6.3 Hz), 7.89 (1H, dd, J=8.6, 1.7 Hz), 7.64–7.56 (2H, m), 7.41 (1H, ddd, J=8.3, 7.3, 1.0 Hz), 7.27 (1H, dd, J=7.6, 7.3 Hz), 6.74 (1H, brs), 4.95 (2H, s), 4.08 (1H, d, J=3.6 Hz), 3.37 (3H, s), 3.34–3.26 (1H, m), 2.52–2.46 (2H, m), 2.30 (3H, s), 1.44 (9H, s), 1.37 (3H, s).

MS (FAB, m/z): 566 (M+1)$^+$.

EXAMPLE 171

Compounds 196 and 197

In a manner similar to that in Example 158, 1.3 mL (0.065 mmol) of 50 mmol/L Compound t obtained in Reference Example 16 in N,N-dimethylformamide was treated with 0.98 mL (0.098 mmol) of 100 mmol/L glycine ethyl ester hydrochloride in N,N-dimethylformamide, 0.098 mL (0.098 mmol) of 1.0 mol/L triethylamine in N,N-dimethylformamide, 2.0 mL (0.20 mmol) of 100 mmol/L 1-hydroxybenzotriazole monohydrate in N,N-dimethylformamide and 1.3 mL (0.13 mmol) of 100 mmol/L 3-(3-dimethylaminopropyl)-1-ethylcarbodiimide hydrochloride in methylene chloride followed by adding 1.0 mL (500 mmol) of a 500 mmol/L ethanolic solution of sodium ethoxide, and the mixture was stirred at room temperature for 1 hour. The solvent was distilled away under reduced pressure, and the resulting residue was purified by preparative thin-layer chromatography (developed with chloroform/methanol=20/1 and then with chloroform/methanol/water=5/4/1) to give 5.3 mg of Compound 196 (14%) and 14.2 mg of Compound 197 (39%).

Compound 196

$^1$H-NMR (270 MHz, DMSO-d$_6$) δ (ppm): 9.76 (1H, d, J=1.3 Hz), 8.76 (1H, brt, J=5.6 Hz), 8.55 (1H, brs), 8.02–7.90 (3H, m), 7.67 (1H, d, J=8.6 Hz), 7.42 (1H, brdd, J=7.3, 8.6 Hz), 7.28 (1H, dd, J=7.6, 7.3 Hz), 6.76 (1H, brs), 4.95 (2H, s), 4.14 (2H, q, J=7.3 Hz), 4.08 (1H, d, J=5.6 Hz), 4.04 (2H, d, J=5.6 Hz), 3.35 (3H, s), 3.34–3.26 (1H, m), 2.58–2.50 (2H, m), 2.31 (3H, s), 1.41 (3H, s), 1.23 (1H, t, J=7.3 Hz).

MS (FAB, m/z): 596 (M+1)$^+$.

Compound 197

$^1$H-NMR (270 MHz, DMSO-d$_6$) δ (ppm): 9.76 (1H, d, J=1.3 Hz), 8.59 (1H, brt, J=5.6 Hz), 8.55 (1H, brs), 8.03–7.91 (3H, m), 7.66 (1H, d, J=8.6 Hz), 7.42 (1H, brdd, J=7.3, 8.3 Hz), 7.40 (1H, brs), 7.28 (1H, dd, J=7.6, 7.3 Hz), 6.81–6.74 (1H, m), 4.95 (2H, s), 4.11 (1H, d, J=3.3 Hz), 3.96 (2H, d, J=5.3 Hz), 3.41 (3H, s), 3.34–3.26 (1H, m), 2.58–2.50 (2H, m), 2.32 (3H, s), 1.47 (3H, s).

MS (FAB, m/z): 568 (M+1)$^+$.

EXAMPLE 172

Compound 198

Step 1

51 mg (0.37 mmol) of p-nitrophenol, 7.4 mL (0.74 mmol) of 100 mmol/L 1-hydroxybenzotriazole monohydrate in N,N-dimethylformamide and 5.0 mL (0.50 mmol) of 100 mmol/L 3-(3-dimethylaminopropyl)-1-ethylcarbodiimide hydrochloride in methylene chloride were added to 161 mg (0.249 mmol) of Compound t obtained in Reference Example 16, and the mixture was stirred at room temperature for 5 hours. A saturated aqueous solution of ammonium chloride was added to the reaction mixture, and the mixture was extracted with chloroform. The organic layer was washed with a saturated aqueous solution of sodium bicarbonate and then with a saturated saline solution and dried over anhydrous sodium sulfate. The solvent was distilled away under reduced pressure. The residue was purified by silica gel column chromatography (eluted with chloroform/methanol=100/) to give 172 mg of 2-acetyl-17-(4-nitrophenyl)oxycarbonyl-11-N-trifluoroacetyl staurosporin (90%).

$^1$H-NMR (270 MHz, DMSO-d$_6$) δ (ppm): 10.04 (1H, d, J=1.6 Hz), 8.43–8.36 (2H, m), 8.30 (1H, dd, J=8.6, 1.7 Hz), 8.10 (1H, d, J=8.6 Hz), 8.07 (1H, d, J=8.6 Hz), 7.86 (1H, d, J=8.6 Hz), 7.73–7.65 (2H, m), 7.60–7.52 (1H, m), 7.47 (1H, dd, J=8.3, 8.3 Hz), 7.18 (1H, brdd, J=6.3, 7.3 Hz), 5.42 (2H, brs), 5.00–4.80 (1H, m), 4.49 (1H, brs), 3.29 (3H, s), 2.77 (3H, s), 2.68 (3H, s), 2.52–2.46 (2H, m), 2.39 (3H, s).

MS (FAB, m/z): 770 (M+1)$^+$.

Step 2

54.3 mg (0.0706 mmol) of 2-acetyl-17-(4-nitrophenyl)oxycarbonyl-11-N-trifluoroacetyl staurosporin was dissolved in 2 mL of chloroform followed by adding 83 mg (0.67 mmol) of p-methoxyaniline, and the mixture was stirred at room temperature for 17 hours. The solvent was distilled away under reduced pressure, and the residue was purified by preparative thin-layer chromatography (developed with chloroform/methanol=50/1) to give 33.5 mg of 2-acetyl-17-(4-methoxyphenyl)carbamoyl-11-N-trifluoroacetyl staurosporin. The resulting product was treated with a 7 mol/L methanolic solution of ammonia in a manner similar to that in Example 19, to give 20.8 mg of Compound 198 (63%).

$^1$H-NMR (270 MHz, DMSO-d$_6$) δ (ppm): 10.15 (1H, brs), 9.78 (1H, d, J=1.0 Hz), 8.56 (1H, brs), 8.03–7.92 (3H, m), 7.77–7.66 (3H, m), 7.42 (1H, brdd, J=7.6, 8.3 Hz), 7.28 (1H, dd, J=7.6, 7.6 Hz), 6.98–6.90 (2H, m), 6.96 (1H, brs), 4.96 (2H, s), 4.09 (1H, d, J=3.3 Hz), 3.35 (3H, s), 3.34–3.26 (4H, m), 2.63–2.46 (2H, m), 2.31 (3H, s), 1.40 (3H, s).

MS (FAB, m/z): 616 (M+1)$^+$.

EXAMPLE 173

Compound 199

In a manner similar to that in step 2 of Example 172, 15.7 mg of Compound 199 (29%) was obtained from 54.8 mg (0.0713 mmol) of 2-acetyl-17-(4-nitrophenyl)oxycarbonyl-11-N-trifluoroacetyl staurosporin obtained in step 1 of Example 172, 89 mg (0.70 mmol) of p-chloroaniline and a 7 mol/L methanolic solution of ammonia.

$^1$H-NMR (270 MHz, DMSO-$d_6$) δ (ppm): 10.43 (1H, brs), 9.81 (1H, d, J=1.7 Hz), 8.56 (1H, brs), 8.04–7.94 (3H, m), 7.92–7.84 (2H, m), 7.72 (1H, d, J=8.6 Hz), 7.48–7.38 (3H, m), 7.28 (1H, dd, J=7.6, 7.3 Hz), 6.78 (1H, brs), 4.96 (2H, s), 4.09 (1H, d, J=3.3 Hz), 3.36 (3H, s), 3.34–3.26 (1H, m), 2.62–2.45 (2H, m), 2.31 (3H, s), 1.39 (3H, s).

MS (FAB, m/z): 620, 622 (M+1)$^+$.

EXAMPLE 174

Compound 200

In a manner similar to that in Example 157, 15.8 mg of Compound 200 (72%) was obtained from 22.8 mg (0.0329 mmol) of Compound u obtained in Reference Example 17, 0.98 mL (0.098 mmol) of 100 mmol/L butylamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.72 (1H, d, J=1.7 Hz), 8.63 (1H, brs), 8.53 (1H, brt, J=5.3 Hz), 8.38 (1H, d, J=1.0 Hz), 8.31 (1H, brt, J=5.6 Hz), 8.00 (1H, d, J=8.9 Hz), 7.91 (1H, dd, J=8.9, 1.6 Hz), 7.90 (1H, dd, J=8.6, 1.7 Hz), 7.64 (1H, d, J=8.9 Hz), 6.75 (1H, brs), 5.02 (2H, s), 4.09 (1H, d, J=3.3 Hz), 3.36 (3H, s), 3.34–3.26 (5H, m), 2.52–2.46 (2H, m), 2.26 (3H, s), 1.64–1.50 (4H, m), 1.46–1.30 (4H, m), 1.36 (3H, s), 0.93 (6H, t, J=7.3 Hz).

MS (FAB, m/z): 665 (M+1)$^+$.

EXAMPLE 175

Compound 201

In a manner similar to that in Example 158, 12.9 mg of Compound 201 (64%) was obtained from 22.0 mg (0.0333 mmol) of Compound u obtained in Reference Example 17, 0.98 mL (0.098 mmol) of 100 mmol/L dimethylamine hydrochloride in N,N-dimethylformamide, 0.098 mL (0.098 mmol) of 1.0 mol/L triethylamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.36 (1H, d, J=1.0 Hz), 8.59 (1H, brs), 8.01 (1H, d, J=8.6 Hz), 7.97 (1H, d, J=1.0 Hz), 7.65 (1H, d, J=8.6 Hz), 7.52 (1H, dd, J=8.3, 1.7 Hz), 7.48 (1H, dd, J=8.6, 1.7 Hz), 6.75 (1H, brs), 4.97 (2H, s), 4.09 (1H, d, J=3.3 Hz), 3.36 (3H, s), 3.34–3.26 (1H, m), 3.06 (6H, s), 3.05 (6H, s), 2.58–2.46 (2H, m), 2.31 (3H, s), 1.40 (3H, s).

MS (FAB, m/z): 609 (M+1)$^+$.

EXAMPLE 176

Compound 202

In a manner similar to that in Example 157, 14.7 mg of Compound 202 (64%) was obtained from 23.6 mg (0.0358 mmol) of Compound u obtained in Reference Example 17, 0.98 mL (0.098 mmol) of 100 mmol/L ethanolamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.73 (1H, d, J=1.7 Hz), 8.63 (1H, brs), 8.57 (1H, brt, J=5.0 Hz), 8.41 (1H, d, J=1.3 Hz), 8.26 (1H, brt, J=5.3 Hz), 8.01 (1H, d, J=9.2 Hz), 7.98–7.88 (2H, m), 7.65 (1H, d, J=8.6 Hz), 6.75 (1H, brs), 5.03 (2H, s), 4.77 (1H, t, J=5.6 Hz), 4.75 (1H, t, J=5.6 Hz), 4.09 (1H, d, J=3.3 Hz), 3.62–3.50 (4H, m), 3.46–3.22 (4H, m), 3.36 (3H, s), 3.34–3.26 (1H, m), 2.56–2.44 (2H, m), 2.31 (3H, s), 1.37 (3H, s).

MS (FAB, m/z): 641 (M+1)$^+$.

EXAMPLE 177

Compound 203

In a manner similar to that in Example 158, 13.1 mg of Compound 203 (68%) was obtained from 21.8 mg (0.0330 mmol) of Compound u obtained in Reference Example 17, 0.98 mL (0.098 mmol) of 100 mmol/L methylamine hydrochloride in N,N-dimethylformamide, 0.098 mL (0.098 mmol) of 1.0 mol/L triethylamine in N,N-dimethylformamide, 2.0 mL (0.20 mmol) of 100 mmol/L 1-hydroxybenzotriazole monohydrate in N,N-dimethylformamide, 1.3 mL (0.13 mmol) of 100 mmol/L 3-(3-dimethylaminopropyl)-1-ethylcarbodiimide hydrochloride in methylene chloride, and a 7 mol/L methanolic solution of ammonia.

$^1$H-NMR (270 MHz, DMSO-$d_6$) δ (ppm): 9.71 (1H, d, J=1.3 Hz), 8.64 (1H, brs), 8.53 (1H, brq, J=4.6 Hz), 8.39 (1H, d, J=1.3 Hz), 8.29 (1H, brq, J=4.3 Hz), 8.01 (1H, d, J=8.9 Hz), 7.92 (1H, dd, J=5.6, 1.7 Hz), 7.88 (1H, d, J=2.0, 5.3 Hz), 7.65 (1H, d, J=8.6 Hz), 6.78–6.72 (1H, m), 5.01 (2H, s), 4.08 (1H, d, J=3.3 Hz), 3.36 (3H, s), 3.34–3.26 (1H, m), 2.87 (3H, d, J=4.6 Hz), 2.84 (3H, d, J=4.6 Hz), 2.62–2.44 (2H, m), 2.31 (3H, s), 1.36 (3H, s).

MS (FAB, m/z): 581 (M+1)$^+$.

REFERENCE EXAMPLE 1

Compound a 116.5 g (250 mmol) of staurosporin was suspended in 230 mL of methylene chloride followed by adding 350 mL (2.5 mol) of trifluoroacetic anhydride, and the mixture was stirred for 3 hours. The solvent was distilled away under reduced pressure, 500 mL of chloroform and 500 mL of methanol were added thereto and the mixture was further stirred at 40° C. for 1 hour. The solvent was distilled away under reduced pressure, and the residue was purified by silica gel column chromatography (eluted with toluene/ethyl acetate=1/1) and recrystallized from ethyl acetate to give 121.7 g of Compound a (87%).

$^1$H-NMR (270 MHz, DMSO-$d_6$) δ (ppm): 9.30 (1H, d, J=7.9 Hz), 8.62 (1H, s), 8.06 (1H, d, J=7.9 Hz), 8.00 (1H, d, J=8.6 Hz), 7.63 (1H, d, J=8.3 Hz), 7.53–7.47 (2H, m), 7.39–7.28 (2H, m), 7.06 (1H, dd, J=8.3, 6.6 Hz), 5.00 (2H, s), 4.93 (1H, m), 4.44 (1H, brs), 2.98 (3H, s), 2.85 (1H, m), 2.77 (3H, s), 2.38 (3H, s), 2.34 (1H, m).

MS (FAB, m/z): 563 (M+1)$^+$.

REFERENCE EXAMPLE 2

Compound b 10.0 g (21.4 mmol) of staurosporin was suspended in 300 mL of acetone and 200 mL of water followed by adding 9.02 g (107 mmol) of sodium bicarbonate and 4.6 mL (32 mmol) of benzyloxycarbonyl chloride under cooling on ice, and the mixture was stirred at 0° C. for 2 hours. After the reaction was completed, the product was crystallized by adding ice, purified by silica gel column chromatography (eluted with chloroform/acetone=3/2) and recrystallized from a mixed solvent of methylene chloride and methanol to give 11.9 g of Compound b (93%).

$^1$H-NMR (270 MHz, DMSO-d$_6$) δ (ppm): 9.30 (1H, d, J=7.9 Hz), 8.25 (1H, s), 8.04 (1H, d, J=7.9 Hz), 7.90 (1H, d, J=8.3 Hz), 7.58 (1H, d, J=8.3 Hz), 7.51–7.24 (9H, m), 6.96 (1H, t, J=5.9 Hz), 5.24 (1H, d, J=12.5 Hz), 5.18 (1H, d, J=12.5 Hz), 4.97 (2H, s), 4.68 (1H, m), 4.23 (1H, brs), 2.78 (1H, m), 2.75 (3H, s), 2.65 (3H, s), 2.31 (3H, s), 2.29 (1H, m).

MS (FAB, m/z): 601 (M+1)$^+$.

REFERENCE EXAMPLE 3

Compound c 6.00 g (10.7 mmol) of Compound a was dissolved in 400 mL of methylene chloride followed by adding 6.90 mL (107 mmol) of nitric acid under cooling on ice, and the mixture was stirred at room temperature for 6 hours. After the reaction suspension was dissolved in 40 mL methanol, 14.9 mL (107 mmol) of triethylamine was added thereto, and the solvent was distilled away. The residue was triturated in water to give 6.50 g of Compound c (quant.)

$^1$H-NMR (270 MHz, DMSO-d$_6$) δ (ppm): 10.21 (1H, d, J=2.3 Hz), 8.79 (1H, brs), 8.35 (1H, dd, J=9.2, 2.3 Hz), 8.08 (1H, d, J=7.8 Hz), 8.02 (1H, d, J=7.8 Hz), 7.79 (1H, d, J=9.2 Hz), 7.53 (1H, dd, J=7.8, 7.3 Hz), 7.39 (1H, dd, J=7.8, 7.3 Hz), 7.19 (1H, m), 5.04 (2H, s), 4.93 (1H, m), 4.40 (1H, m), 2.69 (3H, s), 2.50 (1H, m), 2.41 (3H, s), 2.40 (1H, m), 2.30 (3H, s).

MS (FAB, m/z): 608 (M+1)$^+$.

REFERENCE EXAMPLE 4

Compound d 6.04 g (9.95 mmol) of Compound c was dissolved in 160 mL of N,N-dimethylformamide and subjected to catalytic reduction at 40° C. for 4 hours in an atmosphere of hydrogen in the presence of 6.10 g of palladium hydroxide. After the reaction was completed, the catalyst was filtered off, and the solvent was distilled away under reduced pressure. The residue was purified by silica gel column chromatography (eluted with chloroform/methanol=20/1) and triturated in a mixed solvent of ethyl acetate and diisopropyl ether to give 2.80 g of Compound d (44%).

$^1$H-NMR (270 MHz, DMSO-d$_6$) δ (ppm): 8.53 (1H, s), 8.52 (1H, s), 8.03 (1H, d, J=7.6 Hz), 7.98 (1H, d, J=8.2 Hz), 7.47 (1H, dd, J=8.2, 7.3 Hz), 7.38–7.31 (2H, m), 6.93–6.88 (2H, m), 5.17 (2H, brs), 4.95 (2H, s), 4.89 (1H, m), 4.41 (1H, brs), 2.97 (3H, brs), 2.85 (1H, m), 2.77 (3H, s), 2.35 (3H, s), 2.28 (1H, m).

MS (FAB, m/z): 578 (M+1)$^+$.

REFERENCE EXAMPLE 5

Compound e

Step 1

3.20 mL (36.2 mmol) of trifluoromethanesulfonic acid and 1.55 mL (36.3 mmol) of fuming nitric acid were added to 80 mL of methylene chloride under cooling on ice, the mixture was stirred for 30 minutes and cooled to −78° C., a solution of 1.02 g (1.81 mmol) of Compound a in methylene chloride (20 mL) was added thereto and the mixture was stirred for 20 minutes. The reaction solution was neutralized with a saturated aqueous solution of sodium bicarbonate and subjected to extraction with a mixed solvent of chloroform and methanol. The solvent was distilled away under reduced pressure, and the residue was triturated in a mixed solvent of N,N-dimethyl formamide and water, to give 1.08 g of 5,17-dinitro-11-N-trifluoroacetyl staurosporin (91%).

$^1$H-NMR (270 MHz, DMSO-d$_6$) δ (ppm): 10.16 (1H, d, J=2.3 Hz), 8.91 (1H, s), 8.81 (1H, d, J=2.3 Hz), 8.36 (2H, dd, J=9.2, 2.3 Hz), 8.22 (1H, d, J=9.4 Hz), 7.81 (1H, d, J=9.1 Hz), 7.18 (1H, m), 5.15 (2H, s), 4.90 (m, 1H), 4.50 (1H, brs), 2.95 (1H, m), 2.95 (3H, s), 2.71 (3H, s), 2.43 (1H, m), 2.43 (3H, s).

MS (FAB, m/z): 653 (M+1)$^+$.

Step 2

In a manner similar to that in step 2 of Example 1, 1.20 g (1.84 mmol) of 5,17-dinitro-11-N-trifluoroacetyl staurosporin was subjected to catalytic reduction in an atmosphere of hydrogen in the presence of 1.21 g of palladium hydroxide, to give 623 mg of Compound e (57%).

$^1$H-NMR (270 MHz, DMSO-d$_6$) δ (ppm): 8.46 (1H, d, J=2.0 Hz), 8.45 (1H, s), 7.66 (1H, d, J=8.9 Hz), 7.29 (1H, d, J=8.6 Hz), 7.15 (1H, d, J=2.0 Hz), 6.88–6.78 (3H, m), 4.98 (4H, brs), 4.87 (1H, m), 4.84 (2H, s), 4.29 (1H, brs), 2.96 (3H, s), 2.83 (1H, m), 2.73 (3H, s), 2.27 (3H, s), 2.23 (1H, m).

MS (FAB, m/z): 593 (M+1)$^+$.

REFERENCE EXAMPLE 6

Compound f

In a manner similar to that in step 1 of Reference Example 5, 48.6 mg of Compound f (85%) was obtained from 50.0 mg (0.0830 mmol) of Compound b, 0.037 mL (0.42 mmol) of trifluoromethanesulfonic acid and 0.018 mL (0.42 mmol) of fuming nitric acid.

$^1$H-NMR (270 MHz, DMSO-d$_6$) δ (ppm): 10.23 (1H, d, J=2.0 Hz), 8.83 (1H, d, J=2.0 Hz), 8.60 (1H, brs), 8.37–8.33 (2H, m), 8.14 (1H, d, J=9.2 Hz), 7.81 (1H, d, J=9.2 Hz), 7.46–7.33 (5H, m), 7.39 (1H, m), 5.21 (2H, s), 5.12 (2H, s), 4.68 (1H, m), 4.33 (1H, brs), 2.87 (1H, m), 2.75 (3H, s), 2.71 (3H, s), 2.36 (3H, s), 2.31 (1H, m).

MS (FAB, m/z): 691 (M+1)$^+$.

REFERENCE EXAMPLE 7

Compounds g and h 9.38 g (16.7 mmol) of Compound a was dissolved in 250 mL of 1,2-dichloroethane followed by adding 7.5 mL (68 mmol) of titanium tetrachloride, and 12 mL (10 mmol) of dichloromethyl methyl ether was added thereto in 3 divided portions over 3 hours under stirring. The mixture was further stirred at room temperature for 1 hour and then cooled to 0° C., and tetrahydrofuran and a saturated aqueous solution of sodium bicarbonate were added thereto. The mixture was extracted with tetrahydrofuran, and the organic layer was washed with a saturated saline solution and dried over anhydrous sodium sulfate. The solvent was distilled away under reduced pressure. The residue was purified by silica gel column chromatography (eluted with chloroform/methanol=20/1) to give 1.75 g of Compound g (yield 18%) and 2.69 g of Compound h (yield 26%).

Compound g $^1$H-NMR (270 MHz, CDCl$_3$) δ (ppm): 10.15 (1H, s), 9.81 (1H, brs), 8.03 (1H, d, J=8.6 Hz), 7.90 (1H, d, J=7.6 Hz), 7.73 (1H, d, J=8.3 Hz), 7.50 (1H, ddd, J=8.3, 7.3, 1.0 Hz), 7.38 (1H, dd, J=7.3, 7.3 Hz), 7.30–7.20 (1H, m), 6.79 (1H, dd, J=8.9, 4.6 Hz), 6.58 (1H, brs), 5.12–4.96 (1H, m), 5.00 (2H, s), 4.05 (1H, brs), 3.01 (3H, brs), 2.52 (3H, s), 2.52–2.46 (2H, m), 2.43 (3H, s).

MS (FAB, m/z): 591 (M+1)$^+$.

Compound h $^1$H-NMR (270 MHz, DMSO-d$_6$) δ (ppm): 10.17 (1H, s), 10.08 (1H, s), 9.81 (1H, d, J=1.3 Hz), 8.86 (1H, brs), 8.64 (1H, brs), 8.20 (1H, d, J=8.9 Hz), 8.03 (1H, d, J=8.9 Hz), 8.02 (1H, d, J=8.9 Hz), 8.09 (1H, d, J=8.6 Hz), 7.16 (1H, dd, J=7.9, 6.9 Hz), 5.11 (2H, s), 4.90 (1H, ddd, J=13.5, 6.3, 3.3 Hz), 4.51 (1H, brs), 3.34–3.26 (1H, m), 2.96 (3H, s), 2.78 (3H, s), 2.42–2.28 (2H, m), 2.39 (3H, s).

MS (FAB, m/z): 619 (M+1)$^+$.

REFERENCE EXAMPLE 8

Compound i 1.21 g (2.15 mmol) of Compound a was dissolved in 50 mL of tetrahydrofuran followed by adding 4.0 mL (42 mmol) of acetic anhydride and 1.05 g (8.61 mmol) of 4-dimethylaminopyridine, and the mixture was stirred for 9 hours. Further 4.0 mL (42 mmol) of acetic anhydride and 1.06 g (8.70 mmol) of 4-dimethylaminopyridine were additionally added thereto, and the mixture was heated under reflux for 2 hours. After the reaction mixture was cooled to room temperature followed by adding 200 mL of a saturated aqueous solution of sodium bicarbonate, the mixture was extracted with chloroform. The organic layer was washed with a saturated aqueous solution of ammonium chloride and then with a saturated saline solution, and dried over anhydrous sodium sulfate. The solvent was distilled away under reduced pressure. The residue was purified by silica gel column chromatography (eluted with toluene/chloroform=1/2) to give 1.14 g of Compound i (yield 87%).

$^1$H-NMR (270 MHz, DMSO-d$_6$) δ (ppm): 9.19 (1H, d, J=8.1 Hz), 8.07 (1H, d, J=8.1 Hz), 8.04 (1H, d, J=8.1 Hz), 7.67 (1H, d, J=8.1 Hz), 7.57–7.43 (2H, m), 7.41 (1H, dd, J=8.1, 8.1 Hz), 7.35 (1H, dd, J=8.1, 8.1 Hz), 7.07 (1H, dd, J=7.7, 6.7 Hz), 5.38 (2H, s), 4.92 (1H, ddd, J=13.2, 3.0, 3.0 Hz), 4.45 (1H, brs), 3.34–3.26 (1H, m), 2.97 (3H, s), 2.75 (3H, s), 2.68 (3H, s), 2.52–2.46 (2H, m), 2.38 (3H, s).

MS (FAB, m/z): 605 (M+1)$^+$.

REFERENCE EXAMPLE 9

Compounds j and k 10.0 g (16.6 mmol) of Compound i was dissolved in 1 L of dichloromethane followed by adding 18 mL (17 mmol) of titanium tetrachloride at 0° C., then 150 mL (150 mmol) of 1.0 mol/L dichloromethyl methyl ether in dichloromethane was dropwise added thereto over 2 hours, and the mixture was stirred at 0° C. for 3 hours and then at room temperature for 4 hours. 1 L of a saturated aqueous solution of sodium bicarbonate was added to the reaction mixture, and the mixture was adjusted to pH 2 with 6 mol/L hydrochloric acid, and then subjected to extraction with chloroform. The organic layer was washed with water and then with a saturated saline solution and dried over anhydrous sodium sulfate followed by distilling the solvent away under reduced pressure. The residue was purified by silica gel column chromatography (eluted with chloroform/ethyl acetate=20/1, then with the same eluting solvent combination in a ratio of 9/1 and further in a ratio 4/1), to give 5.24 g of Compound j (yield 50%) and 1.53 g of Compound k (yield 14%).

Compound j $^1$H-NMR (270 MHz, CDCl$_3$) δ (ppm): 10.17 (1H, s), 9.63 (1H, d, J=1.3 Hz), 8.01 (1H, dd, J=8.6, 1.7 Hz), 7.98 (1H, brd, J=7.9 Hz), 7.73 (1H, d, J=8.3 Hz), 7.52 (1H, ddd, J=8.3, 7.3, 1.0 Hz), 7.42 (1H, dd, J=7.6, 7.3 Hz), 7.26 (1H, d, J=8.9 Hz), 6.78 (1H, dd, J=9.2, 4.6 Hz), 5.26 (1H, d, J=17.8 Hz), 5.14 (1H, d, J=17.8 Hz), 5.06 (1H, ddd, J=13.2, 5.6, 1.3 Hz), 4.03 (1H, brs), 3.00 (3H, brs), 2.77 (3H, s), 2.56 (3H, s), 2.52–2.46 (2H, m), 2.37 (3H, s).

MS (FAB, m/z): 633 (M+1)$^+$.

Compound k $^1$H-NMR (270MHz, CDCl$_3$) δ (ppm): 10.20 (1H, s), 10.20 (1H, s), 9.71 (1H, d, J=1.0 Hz), 8.45 (1H, d, J=1.3 Hz), 8.09 (1H, dd, J=8.6, 1.7 Hz), 8.07 (1H, dd, J=8.9, 1.7 Hz), 7.85 (1H, d, J=8.9 Hz), 7.35 (1H, d, J=8.6 Hz), 6.83 (1H, dd, J=8.9, 5.0 Hz), 5.36 (1H, d, J=17.8 Hz), 5.25 (1H, d, J=17.8 Hz), 5.05 (1H, ddd, J=12.9, 5.3, 1.6 Hz), 4.12 (1H, brs), 3.02 (3H, s), 2.78 (3H, s), 2.57 (3H, s), 2.52–2.46 (2H, m), 2.51 (3H, s).

MS (FAB, m/z): 661 (M+1)$^+$.

REFERENCE EXAMPLE 10

Compound m 478 mg (0.768 mmol) of Compound j was dissolved in 10 mL of dichloromethane followed by adding 4.4 mL (77 mmol) of acetic acid and 850 mg (4.01 mmol) of sodium triacetoxyborohydride, and the mixture was stirred at room temperature for 10 hours. After the solvent was distilled away under reduced pressure, a saturated aqueous solution of sodium bicarbonate was added thereto, and then the mixture was extracted with chloroform. The organic layer was washed with a saturated aqueous solution of sodium bicarbonate and then with a saturated saline solution, and dried over anhydrous sodium sulfate. The solvent was distilled away under reduced pressure. The residue was purified by silica gel column chromatography (eluted with chloroform/methanol=from 100/1 to 50/1) to give 492 mg of Compound m (yield 100%).

$^1$H-NMR (270 MHz, CDCl$_3$) δ (ppm): 9.09 (1H, d, J=1.0 Hz), 7.74 (1H, d, J=8.6 Hz), 7.62 (1H, dd, J=8.3, 1.3 Hz), 7.60 (1H, d, J=7.3 Hz), 7.47 (1H, dd, J=7.3, 7.3 Hz), 7.34 (1H, dd, J=7.3, 7.3 Hz), 6.96 (1H, d, J=8.6 Hz), 5.89 (1H, dd, J=9.2, 3.3 Hz), 5.10–4.80 (2H, m), 4.90 (2H, s), 4.83 (1H, d, J=17.8 Hz), 4.35 (1H, d, J=17.8 Hz), 3.79 (1H, brs), 2.88 (3H, s), 2.84 (3H, s), 2.59 (3H, s), 2.52–2.46 (2H, m), 2.05 (3H, s).

MS (FAB, m/z): 635 (M+1)$^+$.

REFERENCE EXAMPLE 11

Compound n

In a manner similar to that in Reference Example 10, 422 mg of Compound n (yield 84%) was obtained from 502 mg (0.761 mmol) of Compound k, 4.4 mL (77 mmol) of acetic acid and 800 mg (3.77 mmol) of sodium triacetoxyborohydride.

$^1$H-NMR (270MHz, CDCl$_3$) δ (ppm): 9.09 (1H, brs), 7.73 (1H, d, J=7.9 Hz), 7.72 (1H, brs), 7.56 (1H, dd, J=8.3, 1.7 Hz), 7.53 (1H, dd, J=7.9, 1.3 Hz), 7.02 (1H, d, J=8.3 Hz), 6.16 (1H, dd, J=9.2, 4.0 Hz), 5.00–4.60 (9H, m), 3.87 (1H, brs), 2.90 (3H, s), 2.70 (3H, s), 2.58 (3H, s), 2.52–2.46 (2H, m), 2.17 (3H, s).

MS (FAB, m/z): 665 (M+1)$^+$.

REFERENCE EXAMPLE 12

Compound p 113 mg (0.192 mmol) of Compound g was dissolved in a mixed solvent of 4 mL of chloroform and 1 mL of methanol followed by adding 23.8 mg (0.629 mmol) of sodium borohydride at 0° C., and the mixture was stirred at 0° C. for 1 hour. 1 mol/mL hydrochloric acid and a saturated aqueous solution of sodium bicarbonate were added thereto in this order, and then the mixture was extracted with tetrahydrofuran. The organic layer was washed with a saturated saline solution and dried over anhydrous sodium sulfate. The solvent was distilled away under reduced pressure. The residue was purified by preparative thin-layer M chromatography (developed with chloroform/methanol/28% aqueous ammonia=100/10/1) to give 51.0 mg of Compound p (yield 54%).

$^1$H-NMR (270 MHz, DMSO-d$_6$) δ (ppm): 9.19 (1H, d, J=1.0 Hz), 8.50 (1H, brs), 7.97 (1H, d, J=8.6 Hz), 7.94 (1H, d, J=7.3 Hz), 7.54 (1H, d, J=8.6 Hz), 7.44 (1H, dd, J=8.3, 1.7 Hz), 7.40 (1H, ddd, J=7.3, 7.3, 1.3 Hz), 7.27 (1H, dd, J=7.6, 7.3 Hz), 6.69 (1H, brs), 5.16 (1H, t, J=5.6 Hz), 4.93 (2H, s), 4.66 (2H, d, J=5.6 Hz), 4.08 (1H, d, J=3.3 Hz), 3.41 (3H, s), 3.34–3.26 (1H, m), 2.52–2.46 (2H, m), 2.30 (3H, s), 1.46 (3H, s).

MS (FAB, m/z): 497 (M+1)$^+$.

REFERENCE EXAMPLE 13

Compound q

In a manner similar to that in Reference Example 12, 88.7 mg of Compound q (yield 99%) was obtained from 105 mg (0.170 mmol) of Compound h and 21.4 mg (0.565 mmol) of sodium borohydride.

$^1$H-NMR (270 MHz, DMSO-d$_6$) δ (ppm): 9.18 (1H, d, J=1.0 Hz), 8.49 (1H, brs), 7.92 (1H, d, J=8.9 Hz), 7.86 (1H, d, J=1.0 Hz), 7.54 (1H, d, J=8.6 Hz), 7.43 (1H, dd, J=8.6, 1.7 Hz), 7.36 (1H, dd, J=8.6, 1.3 Hz), 6.69 (1H, dd, J=3.3, 3.3 Hz), 5.19 (1H, t, J=5.9 Hz), 5.16 (1H, t, J=5.6 Hz), 4.91 (2H, s), 4.67 (2H, d, J=5.3 Hz), 4.65 (2H, d, J=5.3 Hz), 4.06 (1H, d, J=3.3 Hz), 3.42 (3H, s), 3.34–3.26 (1H, m), 2.52–2.46 (2H, m), 2.29 (3H, s), 1.45 (3H, s).

MS (FAB, m/z): 527 (M+1)$^+$.

REFERENCE EXAMPLE 14

Compound r 104 mg (0.176 mmol) of Compound g was dissolved in 10 mL dichloromethane followed by adding 152 mg (0.881 mmol) of p-chloroperbenzoic acid and 119 mg (1.41 mmol) of sodium bicarbonate, and the mixture was stirred at room temperature for 2 hours. A saturated aqueous solution of sodium thiosulfate was added to the reaction mixture, and then the mixture was extracted with chloroform. The organic layer was washed with a saturated saline solution and dried over anhydrous sodium sulfate, and the solvent was distilled away under reduced pressure. 10 mL (68 mmol) of a 6.8 mol/L methanolic solution of ammonia was added to the residue and the mixture was stirred for 24 hours. The solvent was distilled away under reduced pressure, and the residue was purified by preparative thin-layer chromatography (developed with chloroform/methanol=9/1) to give 36.4 mg of Compound r (yield 43%).

$^1$H-NMR (270 MHz, DMSO-d$_6$) δ (ppm): 10.08 (1H, s), 9.80 (1H, d, J=1.3 Hz), 8.66 (1H, brs), 8.10–7.90 (3H, m), 7.80 (1H, d, J=8.6 Hz), 7.44 (1H, dd, J=7.9, 7.6 Hz), 7.29 (1H, dd, J=7.6, 7.3 Hz), 6.81 (1H, brs), 4.98 (2H, s), 4.10 (1H, d, J=3.0 Hz), 3.41 (3H, s), 3.34–3.26 (1H, m), 2.60–2.50 (2H, m), 2.31 (3H, s), 1.41 (3H, brs).

MS (FAB, m/z): 495 (M+1)$^+$.

REFERENCE EXAMPLE 15

Compound s

In a manner similar to that in Reference Example 14, 48.4 mg of Compound s (yield 63%) was obtained from 95.8 mg (0.155 mmol) of Compound h, 134 mg (0.776 mmol) of p-chloroperbenzoic acid, J=107 mg (1.27 mmol) of sodium bicarbonate and 10 mL (68 mmol) of a 6.8 mol/L methanolic solution of ammonia.

$^1$H-NMR (270 MHz, DMSO-d$_6$) δ (ppm): 10.14 (1H, s), 10.09 (1H, s), 9.82 (1H, d, J=1.0 Hz), 8.78 (1H, brs), 8.55 (1H, brs), 8.16 (1H, d, J=8.9 Hz), 8.02 (1H, dd, J=8.6, 1.3 Hz), 7.94 (1H, dd, J=8.9, 1.3 Hz), 7.83 (1H, d, J=8.6 Hz), 6.83 (1H, brs), 5.07 (2H, s), 4.13 (1H, d, J=3.3 Hz), 3.40 (3H, s), 3.34–3.26 (1H, m), 2.64–2.42 (2H, m), 2.34 (3H, s), 1.31 (3H, s).

MS (FAB, m/z): 523 (M+1)$^+$.

REFERENCE EXAMPLE 16

Compound t 1.00 g (1.58 mmol) of Compound j was dissolved in 200 mL of 2-methyl-2-propanol and 100 mL of chloroform followed by adding 10 mL (94 mmol) of 2-methyl-2-butene and 15 mL (17 mmol) of a 1.1 mol/L aqueous solution of sodium chlorite, and the mixture was stirred at room temperature for 6 hours. Water was added to the reaction mixture, and the mixture was extracted with chloroform. The organic layer was washed with a saturated aqueous solution of sodium thiosulfate, water, 0.1 mol/L hydrochloric acid and a saturated saline solution, and dried over anhydrous sodium sulfate followed by distilling the solvent away under reduced pressure, to give 1.16 g of Compound t (quant.)

$^1$H-NMR (270 MHz, DMSO-d$_6$) δ (ppm): 12.65 (1H, m), 9.85 (1H, d, J=1.3 Hz), 8.10 (1H, dd, J=8.9, 1.7 Hz), 8.07 (1H, d, J=7.9 Hz), 8.03 (1H, d, J=8.6 Hz), 7.71 (1H, d, J=8.6 Hz), 7.53 (1H, ddd, J=8.3, 7.3, 1.0 Hz), 7.41 (1H, dd, J=7.6, 7.3 Hz), 7.10 (1H, dd, J=8.6, 6.6 Hz), 5.40 (1H, d, J=17.8 Hz), 5.33 (1H, d, J=17.8 Hz), 4.96–4.84 (1H, m), 4.46 (1H, brs), 2.96 (3H, brs), 2.73 (3H, s), 2.68 (3H, s), 2.52–2.46 (2H, m), 2.37 (3H, s).

MS (FAB, m/z): 649 (M+1)$^+$.

REFERENCE EXAMPLE 17

Compound u

In a manner similar to that in Reference Example 16, 145 mg of Compound u (yield 28%) was obtained from 501 mg (0.760 mmol) of Compound k, 5.0 mL (47 mmol) of 2-methyl-2-butene, and 7.5 mL (8.3 mmol) of a 1.1 mol/L aqueous solution of sodium chlorite.

MS (FAB, m/z): 693 $(M+1)^+$.

REFERENCE EXAMPLE 18

Compound v 347 mg (0.588 mmol) of Compound g was dissolved in a mixed solvent of 50 mL of 2-methyl-2-propanol and 25 mL of chloroform followed by adding 3.1 mL (29 mmol) of 2-methyl-2-butene and 5.2 mL (5.7 mmol) of a 1.1 mol/L aqueous solution of sodium chlorite, and the mixture was stirred at room temperature for 7 hours. Water was added to the reaction mixture, and the mixture was adjusted to pH 2 with 6 mol/L hydrochloric acid, and subjected to extraction with chloroform. The organic layer was washed with a saturated saline solution and dried over anhydrous sodium sulfate, and the solvent was distilled away under reduced pressure. The residue was purified by silica gel column chromatography (eluted with chloroform/methanol/water=80/10/1) and then treated with a 6 mol/L aqueous solution of sodium hydroxide in a manner similar to that in step 2 of Example 3, to give 70.5 mg of Compound v (yield 24%).

$^1$H-NMR (270 MHz, DMSO-$d_6$) δ (ppm): 9.92 (1H, d, J=1.7 Hz), 8.56 (1H, brs), 8.05 (1H, dd, J=8.6, 1.7 Hz), 7.99 (1H, d, J=7.6 Hz), 7.96 (1H, d, J=5.9 Hz), 7.66 (1H, d, J=8.6 Hz), 7.42 (1H, dd, J=7.6, 7.3 Hz), 7.28 (1H, dd, J=7.6, 7.3 Hz), 6.75 (1H, brs), 4.95 (2H, s), 4.08 (1H, d, J=3.3 Hz), 3.44 (3H, s), 3.34–3.26 (1H, m), 2.60–2.40 (2H, m), 2.30 (3H, s), 1.40 (3H, s).

MS (FAB, m/z): 511 $(M+1)^+$.

REFERENCE EXAMPLE 19

Compound w

In a manner similar to that in Reference Example 18, 90.3 mg of Compound w (yield 33%) was obtained from 308 mg (0.499 mmol) of Compound h, 2.7 mL (25 mmol) of 2-methyl-2-butene, 4.4 mL (4.8 mmol) of a 1.1 mol/L aqueous solution of sodium chlorite and a 6 mol/L aqueous solution of sodium hydroxide.

$^1$H-NMR (270 MHz, DMSO-$d_6$) δ (ppm): 9.96 (1H, d, J=1.7 Hz), 8.67 (1H, brs), 8.55 (1H, brs), 8.20–8.00 (3H, m), 7.68 (1H, d, J=8.9 Hz), 6.87 (1H, brs), 5.04 (2H, s), 4.27 (1H, brs), 3.34–3.26 (4H, m), 2.52–2.46 (2H, m), 2.40 (3H, s), 1.60 (3H, m).

MS (FAB, m/z): 555 $(M+1)^+$.

REFERENCE EXAMPLE 20

Compound y 500 mg (0.889 mmol) of Compound a was dissolved in 25 mL of methanol followed by adding 158 mg (0.889 mmol) of N-bromosuccinimide, and the mixture was stirred at room temperature for 1 hour. Water was added to the reaction mixture, then the mixture was extracted with chloroform, the organic layer was washed with a saturated saline solution and dried over anhydrous sodium sulfate, and the solvent was distilled away under reduced pressure. The residue was purified by silica gel column chromatography (eluted with hexane/ethyl acetate=from 2/1 to 1/2) to give 510 mg of Compound y (90%).

$^1$H-NMR (270 MHz, CDCl$_3$) δ (ppm): 9.59 (1H, d, J=2.0 Hz), 7.92 (1H, d, J=7.6 Hz), 7.74 (1H, d, J=8.6 Hz), 7.55 (1H, dd, J=8.6, 2.0 Hz), 7.49 (1H, dd, J=8.3, 7.6 Hz), 7.37 (1H, dd, J=7.6, 7.3 Hz), 7.10 (1H, d, J=8.9 Hz), 6.73 (1H, dd, J=8.6, 5.0 Hz), 6.47 (1H, brs), 5.05 (1H, ddd, J=10.6, 6.3, 2.0 Hz), 4.99 (2H, s), 4.07 (1H, brs), 3.02 (3H, s), 2.67 (2H, m), 2.51 (3H, s), 2.48 (3H, s).

MS (FAB, m/z): 643, 641 $(M+1)^+$.

REFERENCE EXAMPLE 21

Compound z

In a manner similar to that in Example 19, 50.0 mg (0.078 mmol) of Compound y was treated with a 7 mol/L methanolic solution of ammonia, to give 35 mg of Compound z (82%).

$^1$H-NMR (270 MHz, CDCl$_3$) δ (ppm): 9.45 (1H, d, J=1.3 Hz), 8.59 (1H, brs), 7.99 (1H, d, J=7.9 Hz), 7.96 (1H, d, J=6.3 Hz), 7.62 (1H, d, J=8.6 Hz), 7.58 (1H, dd, J=8.6, 2.0 Hz), 7.43 (1H, dd, J=8.6, 6.9 Hz), 7.29 (1H, dd, J=7.6, 7.3 Hz), 6.71 (1H, m), 4.96 (2H, s), 4.07 (1H, d, J=3.3 Hz), 3.36 (3H, s), 3.28 (1H, m), 2.51 (2H, m), 2.30 (3H, s), 1.41 (3H, s).

MS (FAB, m/z): 547, 545 $(M+1)^+$.

REFERENCE EXAMPLE 22

Compound aa

In a manner similar to that in Reference Example 20, 108 mg of Compound aa (84%) was obtained from 100 mg (0.178 mmol) of Compound a and 63.4 mg (0.356 mmol) of N-bromosuccinimide.

$^1$H-NMR (270 MHz, CDCl$_3$) δ (ppm): 9.45 (1H, d, J=2.0 Hz), 8.36 (1H, brs), 7.90 (1H, s), 7.57 (1H, d, J=8.9 Hz), 7.52 (1H, dd, J=9.1, 1.5 Hz), 7.29 (1H, dd, J=8.7, 1.8 Hz), 6.83 (1H, d, J=8.6 Hz), 6.61 (1H, dd, J=9.2, 4.0 Hz), 5.00 (1H, d, J=15.8 Hz), 5.00 (1H, m), 4.91 (1H, d, J=17.2 Hz), 3.85 (1H, brs), 2.91 (3H, s), 2.63 (1H, m), 2.39 (1H, ddd, J=14.8, 12.9, 4.0 Hz), 2.16 (3H, s).

MS (FAB, m/z): 723, 721, 719 $(M+1)^+$.

REFERENCE EXAMPLE 23

Compound ab

In a manner similar to that in Example 19, 28.1 mg (0.039 p mmol) of Compound aa was treated with a 7 mol/L methanolic solution of ammonia, to give 17.1 mg of Compound ab (70%).

$^1$H-NMR (270 MHz, DMSO-$d_6$) δ (ppm): 9.46 (1H, d, J=1.7 Hz), 8.64 (1H, s), 8.08 (1H, d, J=2.0 Hz), 7.95 (1H, d, J=8.9 Hz), 7.64 (1H, d, J=8.9 Hz), 7.59 (1H, dd, J=8.9, 2.0 Hz), 7.53 (1H, dd, J=8.9, 2.0 Hz), 6.73 (1H, m), 4.98 (2H, s), 4.07 (1H, d, J=3.6 Hz), 3.38 (3H, s), 3.26 (1H, m), 2.51 (2H, m), 2.28 (3H, s), 1,35 (3H, s).

MS (FAB, m/z): 627, 625, 623 $(M+1)^+$.

REFERENCE EXAMPLE 24

Compound ac

In a manner similar to that in Reference Example 22, 4.89 g Compound ac (80%) was obtained from 5.00 g (8.89 mmol) of Compound a and 3.00 g (13.3 mmol) of N-iodosuccinimide.

¹H-NMR (270 MHz, CDCl₃) δ (ppm): 9.71 (1H, d, J=1.7 Hz), 7.81 (1H, d, J=7.6 Hz), 7.70 (1H, d, J=8.6 Hz), 7.56 (1H, dd, J=8.4, 1.8 Hz), 7.45 (1H, dd, J=7.3, 7.3 Hz), 7.38 (1H, brs), 7.34 (1H, dd, J=7.9, 7.3 Hz), 6.83 (1H, d, J=8.6 Hz), 6.58 (1H, dd, J=8.9, 4.3 Hz), 4.97 (1H, m), 4.90 (1H, d, J=17.2 Hz), 4.80 (1H, d, J=16.8 Hz), 3.93 (1H, brs), 2.93 (3H, s), 2.62 (1H, m), 2.52 (3H, s), 2.47 (1H, ddd, J=14.9, 12.7, 4.5 Hz), 2.26 (3H, s).

MS (FAB, m/z): 689 (M+1)⁺.

REFERENCE EXAMPLE 25

Compound ad 1.00 g (1.78 mmol) of Compound a was dissolved in a mixed solvent of 9 mL of methanol and 24 mL of chloroform followed by adding 1.34 g (3.92 mmol) of mercury nitrate [Hg(NO₃)₂] and 994 mg (3.92 mmol) of iodine, and the mixture was stirred at room temperature for 1 hour. A 0.1 mol/L aqueous solution of sodium thiosulfate was added to the reaction mixture, and then the mixture was extracted with chloroform. The organic layer was washed with a saturated saline solution, and dried over anhydrous sodium sulfate, and the solvent was distilled away under reduced pressure. The residue was purified by silica gel column chromatography (eluted with hexane/ethyl acetate =from 1/1 to 1/2) to give 965 mg of Compound ad (67%) and 60.8 mg of Compound 26 (4%).

¹H-NMR (270 MHz, CDCl₃) δ (ppm): 9.70 (1H, d, J=1.3 Hz), 8.10 (1H, d, J=1.7 Hz), 7.71 (1H, dd, J=8.9, 1.7 Hz), 7.62 (1H, dd, J=8.6, 1.7 Hz), 7.49 (1H, d, J=8.9 Hz), 6.95 (1H, brs), 6.87 (1H, d, J=8.6 Hz), 6.64 (1H, dd, J=9.1, 4.5 Hz), 5.00 (1H, m), 4.89 (2H, s), 3.95 (1H, brs), 2.96 (3H, s), 2.65 (1H, m), 2.51 (3H, s), 2.47 (1H, m), 2.33 (3H, s).

MS (FAB, m/z): 815 (M+1)⁺.

REFERENCE EXAMPLE 26

Compound ae

In a manner similar to that in Example 19, 52.4 mg (0.0643 mmol) of Compound ad was treated with a 7 mol/L methanolic solution of ammonia, to give 35.7 mg of Compound ae (77%).

¹H-NMR (270 MHz, DMSO-d₆) δ (ppm): 9.64 (1H, d, J=1.7 Hz), 8.62 (1H, brs), 8.22 (1H, d, J=1.7 Hz), 7.82 (1H, d, J=9.2 Hz), 7.72 (1H, dd, J=8.6, 1.7 Hz), 7.67 (1H, dd, J=8.9, 1.7 Hz), 7.50 (1H, d, J=8.6 Hz), 6.70 (1H, m), 4.97 (2H, s), 4.05 (1H, d, J=3.3 Hz), 3.37 (3H, s), 3.28 (1H, m), 2.49 (2H, m), 2.26 (3H, s), 1.34 (3H, s).

MS (FAB, m/z): 719 (M+1)⁺.

PREPARATION EXAMPLE 1

(Tablets)

Tablets having the following composition were prepared in a usual manner.

| Compound 166 | 5 mg |
|---|---|
| Lactose | 60 mg |
| Potato starch | 30 mg |
| Polyvinyl alcohol | 2 mg |
| Magnesium stearate | 1 mg |

Tar pigment trace

PREPARATION EXAMPLE 2

(Granules)

Granules having the following composition were prepared in a usual manner.

| Compound 108 | 5 mg |
|---|---|
| Lactose | 280 mg |

PREPARATION EXAMPLE 3

(Syrup)

A syrup having the following composition was prepared in a usual manner.

| Compound 16 | 1 mg |
|---|---|
| Refined white sugar | 40 g |
| Ethyl p-hydroxybenzoate | 40 mg |
| Propyl p-hydroxybenzoate | 10 mg |
| Strawberry flavor | 0.1 cc |

Water is added to these ingredients to adjust the total volume to 100 cc.

Industrial Applicability

According to the present invention, there are provided novel staurosporin derivatives effective for the treatment of tumors or pharmaceutically acceptable salts thereof.

What is claimed is:

1. A compound of formula (IA):

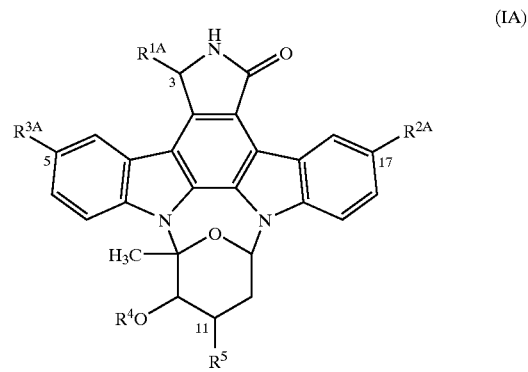

(IA)

wherein

R¹ᴬ represents hydroxy or lower alkoxy;

R²ᴬ represents hydrogen, hydroxy, halogen, formyl, nitro, amino, COR⁶ᴬ¹ (wherein R⁶ᴬ¹ represents substituted or unsubstituted lower alkyl, hydroxy, or substituted or unsubstituted lower alkoxy), OR¹⁴ᴬ¹ (wherein R¹⁴ᴬ¹ represents substituted or unsubstituted lower alkyl), substituted or unsubstituted lower alkyl, substituted or unsubstituted lower alkenyl, substituted or unsubstituted lower alkadienyl, substituted or unsubstituted lower alkynyl, substituted or unsubstituted aryl, a substituted or unsubstituted heterocyclic group, COR⁶ᴬ³ (wherein R⁶ᴬ³ has the same meaning as defined for R⁶ᴬ²), NR¹¹ᴬ²R¹²ᴬ² (wherein R¹¹ᴬ² and R¹²ᴬ² have the same meaning as defined for R¹¹ᴬ¹ and R¹²ᴬ¹, respectively), or OR¹⁴ᴬ³ (wherein R¹⁴ᴬ³ has the same meaning as defined for R¹⁴ᴬ²);

when $R^{2A}$ represents hydrogen, hydroxymethyl, hydroxy, halogen, formyl, nitro, amino, $COR^{6A1}$ (wherein $R^{6A1}$ represents substituted or unsubstituted lower alkyl, hydroxy, or substituted or unsubstituted lower alkoxy), or $OR^{14A1}$ (wherein $R^{14A1}$ represents substituted or unsubstituted lower alkyl), then $R^{3A}$ represents substituted or unsubstituted lower alkyl (other than hydroxymethyl), substituted or unsubstituted lower alkenyl, substituted or unsubstituted lower alkadienyl, substituted or unsubstituted lower alkynyl, substituted or unsubstituted aryl, a substituted or unsubstituted heterocyclic group, $COR^{6A2}$ {wherein $R^{6A2}$ represents substituted or unsubstituted aryl, a substituted or unsubstituted heterocyclic group, $NR^{7A1}R^{8A1}$ (wherein $R^{7A1}$ and $R^{8A1}$ independently represent hydrogen, substituted or unsubstituted lower alkyl, substituted or unsubstituted lower alkenyl, cycloalkyl having 3 to 6 carbon atoms, substituted or unsubstituted aryl, or a substituted or unsubstituted heterocyclic group, or are combined with their adjacent N to form a substituted or unsubstituted heterocyclic group that may contain an oxygen atom, a sulfur atom, or another nitrogen atom), $OR^{9A1}$ (wherein $R^{9A1}$ represents substituted or unsubstituted lower alkenyl, cycloalkyl having 3 to 6 carbon atoms, or substituted or unsubstituted aryl), or $SR^{10A1}$ (wherein $R^{10A1}$ represents substituted or unsubstituted lower alkyl, or substituted or unsubstituted aryl)}, $NR^{11A1}R^{12A1}$ {wherein $R^{11A1}$ and $R^{12A1}$ independently represent hydrogen, substituted or unsubstituted lower alkyl, substituted or unsubstituted lower alkenyl, cycloalkyl having 3 to 6 carbon atoms, $COR^{13A}$ [wherein $R^{13A}$ represents substituted or unsubstituted lower alkyl, substituted or unsubstituted lower alkenyl, lower alkoxycarbonyl, substituted or unsubstituted aryl, a substituted or unsubstituted heterocyclic group, $OR^{9A}$ (wherein $R^{9A}$ represents hydrogen, substituted or unsubstituted lower alkyl, substituted or unsubstituted lower alkenyl, cycloalkyl having 3 to 6 carbon atoms, or substituted or unsubstituted aryl), $NR^{7A}R^{8A}$ (wherein $R^{7A}$ and $R^{8A}$ have the same meaning as defined for $R^{7A1}$ and $R^{8A1}$, respectively)], $CSR^{13A1}$, $SO_2R^{13B}$ (wherein $R^{13B}$ has the same meaning as defined for $R^{13A}$), or a group derived from an amino acid (wherein a hydroxyl group in a carboxyl group is excluded from the amino acid and a functional group in the amino acid may be protected with a protective group), with the proviso that $R^{11A1}$ and $R^{12A1}$ are not simultaneously hydrogen}, or $OR^{14A2}$ {wherein $R^{14A2}$ represents substituted or unsubstituted lower alkenyl, cycloalkyl having 3 to 6 carbon atoms, substituted or unsubstituted lower alkanoyl, substituted or unsubstituted aroyl, or $CONR^{7B1}R^{8B1}$ (wherein $R^{7B1}$ and $R^{8B1}$ have the same meanings as defined for $R^{7A1}$ and $R^{8A1}$, respectively)};

when $R^{2A}$ represents lower alkyl, substituted lower alkyl (other than hydroxymethyl), substituted or unsubstituted lower alkenyl, substituted or unsubstituted lower alkadienyl, substituted or unsubstituted lower alkynyl, substituted or unsubstituted aryl, a substituted or unsubstituted heterocyclic group, $COR^{6A3}$ (wherein $R^{6A3}$ has the same meaning as defined for $R^{6A2}$), $NR^{11A2}R^{12A2}$ (wherein $R^{11A2}$ and $R^{12A2}$ have the same meanings as defined for $R^{11A1}$ and $R^{12A1}$, respectively), or $OR^{14A3}$, then $R^{3A}$ represents substituted or unsubstituted lower alkyl, substituted or unsubstituted lower alkenyl, substituted or unsubstituted lower alkadienyl, substituted or unsubstituted lower alkynyl, substituted or unsubstituted aryl, a substituted or unsubstituted heterocyclic group, halogen, nitro, formyl, $COR^{6A4}$ [wherein $R^{6A4}$ represents substituted or unsubstituted lower alkyl, substituted or unsubstituted aryl, a substituted or unsubstituted heterocyclic group, $NR^{7A2}R^{8A2}$ {wherein $R^{7A2}$ and $R^{8A2}$ have the same meanings as defined for $R^{7A1}$ and $R^{8A1}$, respectively}, $OR^{9A2}$ (wherein $R^{9A2}$ has the same meaning as defined for $R^{9A}$), or $SR^{10A2}$ (wherein $R^{10A2}$ has the same meaning as defined for $R^{10A1}$)], $NR^{11A3}R^{12A3}$ (wherein $R^{11A3}$ and $R^{12A3}$ have the same meaning as defined for $R^{11A1}$ and $R^{12A1}$, respectively), or $OR^{14A4}$ (wherein $R^{14A4}$ represents hydrogen, substituted or unsubstituted lower alkyl, substituted or unsubstituted lower alkenyl, cycloalkyl having 3 to 6 carbon atoms, substituted or unsubstituted lower alkanoyl, substituted or unsubstituted aroyl, or $CONR^{7A1}R^{8A1}$);

$R^4$ represents hydrogen, or substituted or unsubstituted lower alkyl; and $R^5$ represents $NR^{11A}R^{12A}$; (wherein $R^{11A}$ and $R^{12A}$ have the same meaning as defined for $R^{11}$ and $R^{12}$, respectively;

wherein the substituents in the substituted lower alkyl and substituted lower alkoxy are independently selected from the group consisting of halogen, carboxy, lower alkoxycarbonyl, lower alkanoyl, substituted or unsubstituted aryl, a substituted or unsubstituted heterocyclic group, $CONR^{15}R^{16}$ (wherein $R^{15}$ and $R^{16}$ independently represent hydrogen, hydroxy, aralkyl, lower alkyl, lower alkenyl, substituted or unsubstituted aryl, a substituted or unsubstituted heterocyclic group, or are combined with their adjacent N to form a heterocyclic group), $NR^{17}R^{18}$ {wherein $R^{17}$ and $R^{18}$ independently represent hydrogen, lower alkyl, lower alkenyl, lower alkanoyl, aroyl, substituted or unsubstituted aryl, a substituted or unsubstituted heterocyclic group, substituted lower alkyl [the substituted lower alkyl is replaced by at least one of hydroxy, lower alkoxy, $O(CH_2CH_2O)_nR^{19}$ (wherein n is an integer of 1 to 15, and $R^{19}$ is lower alkyl), oxo, carboxy, lower alkoxycarbonyl, substituted or unsubstituted aryl, a substituted or unsubstituted heterocyclic group, $CONR^{15A}R^{16A}$ (wherein $R^{15A}$ and $R^{16A}$ have the same meaning as defined for $R^{15}$ and $R^{16}$, respectively), amino, lower alkylamino, and di(lower alkyl)amino], cycloalkyl having 3 to 6 carbon atoms, or aralkyloxycarbonyl, are combined with their adjacent N to form a substituted or unsubstituted heterocyclic group}, $N^+R^{20}R^{21}R^{22}X^-$ [wherein $R^{20}$ and $R^{21}$ independently represent lower alkyl, or are combined with their adjacent N to form a heterocyclic group, $R^{22}$ is lower alkyl, and X is an atom of chlorine, bromine or iodine], $OR^{23}$ {wherein $R^{23}$ represents hydrogen, lower alkyl, lower alkanoyl, lower alkyl [which is substituted with at least one of hydroxy, lower alkoxy, $O(CH_2CH_2O)_{nA}R^{19A}$ (wherein nA is an integer of 1 to 15, and $R^{19A}$ is lower alkyl), oxo, carboxy, lower alkoxycarbonyl, substituted or unsubstituted aryl, a substituted or unsubstituted heterocyclic group, $CONR^{15B}R^{16B}$ (wherein $R^{15B}$ and $R^{16B}$ have the same meaning as defined for $R^{15}$ and $R^{16}$, respectively), amino, lower alkylamino, and di(lower alkyl)amino], substituted or unsubstituted aryl, and a substituted or unsubstituted heterocyclic group}, $SR^{23A}$ (wherein $R^{23A}$ has the same meaning as defined for $R^{23}$) and $SO_2R^{23B}$ (wherein $R^{23B}$ is lower alkyl);

the substituents for lower alkenyl, lower alkadienyl and lower alkynyl include oxo in addition to the substituents permitted for lower alkyl;

the substituents for lower alkanoyl are independently selected from the group consisting of halogen and $NR^{17A}R^{18A}$ (wherein $R^{17A}$ and $R^{18A}$ have the same meaning as defined for $R^{17}$ and $R^{18}$, respectively);

the substituents for aryl and aroyl are independently selected from the group consisting of halogen, lower alkyl (optionally substituted with halogen, oxo, carboxy, lower alkoxycarbonyl, amino, lower alkylamino, di(lower alkyl) amino, hydroxy or lower alkoxy), nitro, hydroxy, lower alkoxy, amino, lower alkylamino, di(lower alkyl)amino, lower alkanoyl and cyano; and the substituents for the heterocyclic group and the heterocyclic group formed using the adjacent N include oxo in addition to the substituents permitted for aryl and aroyl; and wherein the heterocyclic group is selected from the group consisting of pyrrolidinyl, imidazolidinyl, piperidinyl, morpholinyl, thiomorpholinyl, piperidino, morpholino, piperadinyl, furyl, thienyl, pyrrolyl, imidazolyl, triazolyl, oxazolyl, thiazolyl, pyridyl, pyrimidinyl, indolyl, quinolyl, isoquinolyl and quinazolinyl; and the heterocyclic group formed together using the adjacent N is selected from the group consisting of pyrrolidinyl, morpholino, thiomorpholino, N-methylpiperadinyl, pyrazolidinyl, piperidino, piperadinyl, homopiperadinyl, indolyl and isoindolyl;

or a pharmaceutically acceptable salt thereof.

2. A compound of formula (IB):

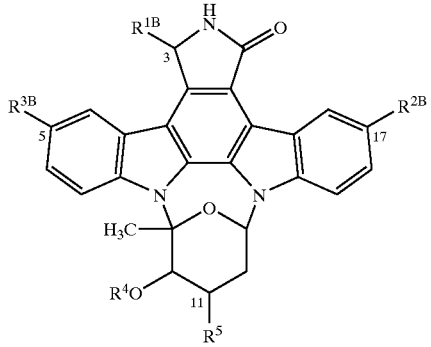

(IB)

wherein $R^{1B}$ represents hydroxy or lower alkoxy;

$R^{2B}$ and $R^{3B}$ independently represent substituted or unsubstituted lower alkyl, substituted or unsubstituted lower alkenyl, substituted or unsubstituted lower alkadienyl, substituted or unsubstituted lower alkynyl, substituted or unsubstituted aryl, a substituted or unsubstituted heterocyclic group, nitro, formyl, $COR^6$ <wherein $R^6$ represents substituted lower alkyl, substituted or unsubstituted aryl, a substituted or unsubstituted heterocyclic group, $NR^7R^8$ {wherein $R^7$ and $R^8$ independently represent hydrogen, substituted or unsubstituted lower alkyl, substituted or unsubstituted lower alkenyl, cycloalkyl having 3 to 6 carbon atoms, substituted or unsubstituted aryl, or a substituted or unsubstituted heterocyclic group, or are combined with their adjacent N to form a substituted or unsubstituted heterocyclic group (which may contain an oxygen atom, a sulfur atom, or another nitrogen atom)}, $OR^9$ (wherein $R^9$ represents hydrogen, substituted or unsubstituted lower alkyl, substituted or unsubstituted lower alkenyl, cycloalkyl having 3 to 6 carbon atoms, or substituted or unsubstituted aryl), or $SR^{10}$ (wherein $R^{10}$ represents substituted or unsubstituted lower alkyl, or substituted or unsubstituted aryl) >, $NR^{11}R^{12}$ <wherein $R^{11}$ and $R^{12}$ independently represent hydrogen, substituted or unsubstituted lower alkyl, substituted or unsubstituted lower alkenyl, cycloalkyl having 3 to 6 carbon atoms, $COR^{13}$ {wherein $R^{13}$ represents substituted or unsubstituted lower alkyl, substituted or unsubstituted lower alkenyl, lower alkoxycarbonyl, substituted or unsubstituted aryl, a substituted or unsubstituted heterocyclic group, $OR^{9A}$ (wherein $R^{9A}$ has the same meaning as defined for $R^9$), $NR^{7A}R^{8A}$ (wherein $R^{7A}$ and $R^{8A}$ have the same meanings as defined for $R^7$ and $R^8$, respectively)}, $CSR^{13A}$ (wherein $R^{13A}$ has the same meaning as defined for $R^{13}$), $SO_2R^{13B}$ (wherein $R^{13B}$ has the same meaning as defined for $R^{13}$), or a group derived from an amino acid (wherein a hydroxyl group in a carboxyl group is excluded from the amino acid and a functional group in the amino acid may be protected with a protective group) >, or $OR^{14}$ {wherein $R^{14}$ represents substituted lower alkyl, substituted or unsubstituted lower alkenyl, cycloalkyl having 3 to 6 carbon atoms, substituted or unsubstituted lower alkanoyl, substituted or unsubstituted aroyl, or $CONR^{7B}R^{8B}$ (wherein $R^{7B}$ and $R^{8B}$ have the same meaning as defined for $R^7$ and $R^8$, respectively)};

$R^4$ represents hydrogen, or substituted or unsubstituted lower alkyl; and $R^1$ represents $NR^{11A}R^{12A}$ (wherein $R^{11A}$ and $R^{12A}$ have the same meaning as defined for $R^{11}$ and $R^{12}$, respectively);

wherein the substituents in the lower alkyl and lower alkoxy are independently selected from the group consisting of halogen, carboxy, lower alkoxycarbonyl, lower alkanoyl, substituted or unsubstituted aryl, a substituted or unsubstituted heterocyclic group, $CONR^{15}R^{16}$ [wherein $R^{15}$ and $R^{16}$ independently represent hydrogen, hydroxy, aralkyl, lower alkyl, lower alkenyl, substituted or unsubstituted aryl, a substituted or unsubstituted heterocyclic group, or are combined with their adjacent N to form a heterocyclic group], $NR^{17}NR^{18}$ (wherein $R^{17}$ and $R^{18}$ independently represent hydrogen, lower alkyl, lower alkenyl, lower alkanoyl, aroyl, substituted or unsubstituted aryl, a substituted or unsubstituted heterocyclic group, substituted lower alkyl [which is substituted with at least one of hydroxy, lower alkoxy, $O(CH_2CH_2O)_nR^{19}$ (wherein n is an integer of 1 to 15, and $R^{19}$ is lower alkyl), oxo, carboxy, lower alkoxycarbonyl, substituted or unsubstituted aryl, a substituted or unsubstituted heterocyclic group, $CONR^{15A}R^{16A}$ (wherein $R^{15A}$ and $R^{16A}$ have the same meaning as defined for $R^{15}$ and $R^{16}$, respectively), amino, lower alkylamino, and di(lower alkyl)amino], cycloalkyl having 3 to 6 carbon atoms, or aralkyloxycarbonyl, or are combined with their adjacent N to form a substituted or unsubstituted heterocyclic group}, $N^+R^{20}R^{21}R^{22}X^-$ [wherein $R^{20}$ and $R^{21}$ independently represent lower alkyl, or are combined with their adjacent N to form a heterocyclic group, $R^{22}$ is lower alkyl, and X is an atom of chlorine, bromine or iodine], $OR^{23}$ {wherein $R^{23}$ represents hydrogen, lower alkyl, lower alkanoyl, substituted lower alkyl [which is substituted with at least one of hydroxy, lower alkoxy, O(CH$_2$CH$_2$O)$_{nA}$R$^{19A}$ (wherein nA is an integer of 1 to 15, and R$^{19A}$ is lower alkyl), oxo, carboxy, lower alkoxycarbonyl, substituted or unsubstituted aryl, a substituted or unsubstituted heterocyclic group, CONR$^{15B}$R$^{16B}$ (wherein R$^{15B}$ and R$^{16B}$ have the same meaning as defined for R$^{15}$ and R$^{16}$, respectively), amino, lower alkylamino, and di(lower alkyl)amino), substituted or unsubstituted aryl, and a substituted or unsubstituted heterocyclic group, SR$^{23A}$ (wherein R$^{23A}$ has the same meaning as defined for R$^{23}$) and SO$_2$R$^{23B}$ (wherein R$^{23B}$ is lower alkyl);

the substituents for the lower alkenyl, lower alkadienyl and lower alkynyl include oxo in addition to the substituents in the lower alkyl;

the substituents for the lower alkanoyl are independently selected from the group consisting of halogen and NR$^{17A}$R$^{18A}$ (wherein R$^{17A}$ and R$^{18A}$ have the same meaning as defined for R$^{17}$ and R$^{18}$, respectively);

the substituents for the aryl and aroyl are independently selected from the group consisting of halogen, lower alkyl (optionally substituted with halogen, oxo, carboxy, lower alkoxycarbonyl, amino, lower alkylamino, di(lower alkyl) amino, hydroxy or lower alkoxy), nitro, hydroxy, lower alkoxy, amino, lower alkylamino, di(lower alkyl)amino, lower alkanoyl and cyano; and the substituents for the heterocyclic group and the heterocyclic group formed to using the adjacent N include oxo in addition to the substituents permitted for aryl and aroyl; and wherein the heterocyclic group is selected from the group consisting of pyrrolidinyl, imidazolidinyl, piperidinyl, morpholinyl, thiomorpholinyl, piperidino, niorpholino, piperadinyl, furyl, thienyl, pyrrolyl, imidazolyl, triazolyl, oxazolyl, thiazolyl, pyridyl, pyrimidinyl, indolyl, quinolyl, isoquinolyl and quinazolinyl; and the heterocyclic group formed using the adjacent N is selected from the group consisting of pyrrolidinyl, morpholino, thiomorpholino, N-methylpiperadinyl, pyrazolidinyl, piperidino, piperadinyl, homopiperadinyl, indolyl and isoindolyl;

or a pharmaceutically acceptable salt thereof.

3. The compound according to claim 2, wherein

R$^{2A}$ represents amino, halogen, formyl, or hydroxy, and R$^{3A}$ represents substituted or unsubstituted lower alkenyl, substituted or unsubstituted lower alkynyl, substituted or unsubstituted lower alkyl (other than hydroxymethyl), or NHCOR$^{13A1}$ [wherein R$^{13A1}$ represents substituted or unsubstituted lower alkyl, substituted or unsubstituted lower alkenyl, lower alkoxycarbonyl, substituted or unsubstituted aryl, a substituted or unsubstituted heterocyclic group, OR$^{9A}$, or NR$^{7A}$R$^{8A}$; or R$^{2A}$ represents substituted or unsubstituted lower alkenyl, substituted or unsubstituted lower alkynyl, substituted or unsubstituted lower alkyl (other than hydroxymethyl), or NHCOR$^{13A2}$ (wherein R$^{13A2}$ has the same meaning as defined for R$^{13A1}$), and R$^{3A}$ represents substituted or unsubstituted lower alkenyl, substituted or unsubstituted lower alkynyl, amino, substituted or unsubstituted lower alkyl, or NHCOR$^{13A3}$ (wherein R$^{13A3}$ has the same meaning as defined for R$^{13A1}$), or a pharmaceutically acceptable salt thereof.

4. The compound according to claim 2, wherein R$^{2B}$ and R$^{3B}$ independently represent substituted or unsubstituted lower alkenyl, substituted or unsubstituted lower alkynyl, amino, halogen, formyl, hydroxy, substituted or unsubstituted lower alkyl, or NHCOR$^{13}$.

5. The compound according to claim 1 or 3, wherein R$^{1A}$ is hydroxy, or a pharmaceutically acceptable salt of the compound.

6. The compound according to claim 2 or 4, wherein R$^{1B}$ is hydroxy or a pharmaceutically acceptable salt of the compound.

7. A pharmaceutical composition comprising at least compound according to any one of claims 1 to 4, and a pharmaceutically acceptable carrier.

8. A pharmaceutical composition comprising at least one pharmaceutically acceptable salt according to any one of claim, 1 to 4, and a pharmaceutically acceptable carrier.

9. A method for treating a pulmonary tumor, comprising the step of administering, to a patient in need thereof, a therapeutically effective amount of the compound or pharmaceutically acceptable salt according to any one of claims 1 to 4.

10. A method for enhancing the activity of an antitumor agent for solid tumors, comprising the step of administering a therapeutically effective amount of the compound or the pharmaceutically acceptable salt according to any one of claims 1 to 4, together with said antitumor agent, to a patient in need thereof.

11. A method for treating a pulmonary tumor, comprising the step of administering, to a patient in need thereof, a therapeutically effective amount of the compound or pharmaceutically acceptable salt according to claim 5.

12. A method for treating a pulmonary tumor, comprising the step of administering, to a patient in need thereof, a therapeutically effective amount of the compound or pharmaceutically acceptable salt according to claim 6.

13. A method for enhancing the activity of an antitumor agent for solid tumors, comprising the step of administering a therapeutically effective amount of the compound or the pharmaceutically acceptable salt thereof according to claim 5, together with said antitumor agent, to a patient in need thereof.

14. A method for enhancing the activity of an antitumor agent for solid tumors, comprising the steps of administering a therapeutically effective amount of the compound or the pharmaceutically acceptable salt thereof according to claim 6, together with said antitumor agent, to a patient in need thereof.

* * * * *

UNITED STATES PATENT AND TRADEMARK OFFICE
CERTIFICATE OF CORRECTION

PATENT NO.   : 6,806,266 B1
DATED        : October 19, 2004
INVENTOR(S)  : Fumihiko Kanai et al.

It is certified that error appears in the above-identified patent and that said Letters Patent is hereby corrected as shown below:

Title page,
Item [56], References Cited, FOREIGN PATENT DOCUMENTS,
"JP      03072485       3/1991
JP       03220194       9/1991
JP       04364186       12/1992" should be deleted and
"JP      05140168       6/1993" should read -- JP       5-140168       6/1993 --;
OTHER PUBLICATIONS,
"Cantrell et al." reference, "Letters (1999)." should read -- Letters (1999)). -- and after "Tsubotani et al." reference, "3565-74." should read -- 3565-74)." --.

Column 1,
Line 49, "unexamined" should read -- Unexamined --; and
Line 58, "Japanese. Published." should read -- Japanese Published --.

Column 2,
Line 35, "the is" should read -- this is --; and
Line 52, "usefulness." should read -- usefulness --.

Column 3,
Line 65, "above)" should read -- above), --.

Column 5,
Line 40, "alkyl" should read -- alkyl, --.

Column 6,
Line 37, "$R^{12A1}$" should read -- $R^{13A1}$ --;
Line 40, "a" should be deleted;
Line 48, "$NHCOR^{13A}$" should read -- $NHCOR^{13A3}$ --;
Line 49, "$R^{13A}$" should read -- $R^{13A3}$ --; and
Line 63, "Wherein" should read -- wherein --.

Column 10,
Line 65, "defined" should read -- defined for --.

UNITED STATES PATENT AND TRADEMARK OFFICE
CERTIFICATE OF CORRECTION

PATENT NO. : 6,806,266 B1
DATED : October 19, 2004
INVENTOR(S) : Fumihiko Kanai et al.

It is certified that error appears in the above-identified patent and that said Letters Patent is hereby corrected as shown below:

Column 27,
Table 1 (cont.)

" 145  169  Br 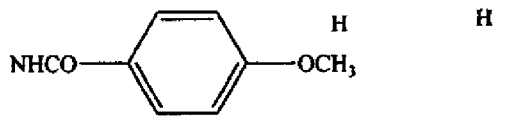  H  H 146  170  CH═CHCO₂CH₃ 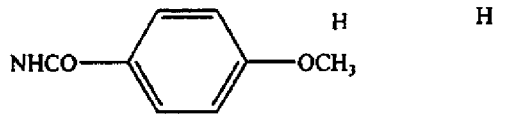  H  H 147  171  NH₂ 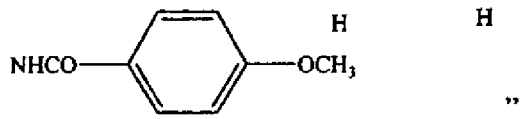  H  H
"

should read

-- 145  169  Br 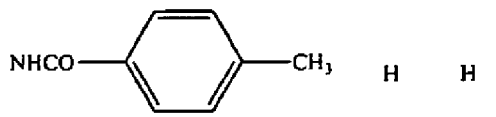  H  H 146  170  CH═CHCO₂CH₃ 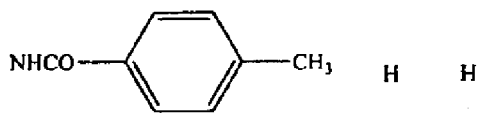  H  H 147  171  NH₂ 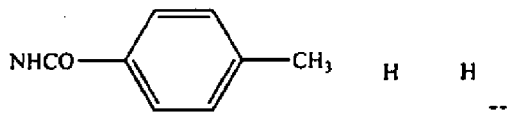  H  H
--

Column 33,
Line 49, "Accumlation" should read -- Accumulation --.

Column 34,
Line 17, "propidiumiodide" should read -- propidium iodide --;
Table 4, "C II cycl distributi n %" should read -- Cell cycle distribution (%) --;
Line 58, "(50 mmol/L)" should read -- (50 nmol/L) --; and
Line 63, "200 mmol/L)" should read -- 200 nmol/L) --.

UNITED STATES PATENT AND TRADEMARK OFFICE
CERTIFICATE OF CORRECTION

PATENT NO.     : 6,806,266 B1
DATED          : October 19, 2004
INVENTOR(S)    : Fumihiko Kanai et al.

It is certified that error appears in the above-identified patent and that said Letters Patent is hereby corrected as shown below:

Column 37,
Line 41, "a:" should read -- a --; and
Line 46, "there action" should read -- the reaction --.

Column 42,
Line 48, "compound 21" should read -- Compound 21 --;
Line 52, "was." should read -- was --.

Column 46,
Line 25, "4, 92" should read -- 4.92 --.

Column 47,
Line 65, "compound 39" should read -- Compound 39 --; and
Line 67, "(81%)" should read -- (81%). --.

Column 48,
Line 15, "(7.2%" should read -- (7.2%) --.

Column 50,
Line 23, "24,5.1" should read -- 24, 5.1 --; and
Line 56, "(0.3$^9$5" should read -- (0.395 --.

Column 51,
Line 23, "(0.1.45" should read -- (0.145 --; and
Line 24, "w" should be deleted.

Column 53,
Line 61, "(1R," should read -- (1H, --.

Column 55,
Line 29, "7:31" should read -- 7.31 --.

Column 56,
Line 50, "6,73" should read -- 6.73 --.

Column 57,
Line 5, "(31, s)," should read -- 3H, s), --.

Column 58,
Line 40, "2.5" should read -- 2.51 --.

UNITED STATES PATENT AND TRADEMARK OFFICE
CERTIFICATE OF CORRECTION

PATENT NO.    : 6,806,266 B1
DATED         : October 19, 2004
INVENTOR(S)   : Fumihiko Kanai et al.

It is certified that error appears in the above-identified patent and that said Letters Patent is hereby corrected as shown below:

Column 59,
Line 29, "(0.474%) mol)" should read -- (0.474 mmol) --; and
Line 56, "(3H, 8)," should read -- (3H, s), --.

Column 61,
Line 21, "8.591" should read -- 8.59 --;
Line 36, "mol)" should read -- mmol) --; and
Line 39, "(1H, d)," should read -- (1H, s). --.

Column 62,
Line 1, "Of" should read -- of --; and
Line 44, "(1H, 8)," should read -- (1H, s), --.

Column 63,
Line 7, "(50" should read -- (50% --;
Line 11, "7.5" should read -- J = --;
Line 12, "d=7.6," should read -- J=7.6, --;
Line 27, "(1H, d)," should read -- (1H, s), --;
Line 28, "(7H," should read -- (1H, --; and
Line 59, "2.32(3H," should read -- 2.32(3H, s). --.

Column 65,
Line 39, "dichoroethane," should read -- dichloroethane, --.

Column 68,
Line 37, "3.0" should read -- 3.0 mL --.

Column 70,
Line 15, "2.52 (3H., s)," should read -- 2.52 (3H, s), --.

Column 71,
Line 3, "7.3.7" should read -- 7.37 --; and
Line 27, "(2H, 9)," should read -- (2H, s), --.

Column 73,
Line 28, "J=6.3," should read -- J=8.3, --; and
Line 53, "for2" should read -- for 2 --.

Column 74,
Line 39, "(3H; s)," should read -- (3H, s), --.

UNITED STATES PATENT AND TRADEMARK OFFICE
CERTIFICATE OF CORRECTION

PATENT NO. : 6,806,266 B1
DATED : October 19, 2004
INVENTOR(S) : Fumihiko Kanai et al.

It is certified that error appears in the above-identified patent and that said Letters Patent is hereby corrected as shown below:

Column 75,
Line 6, "(73.7 d.e.)" should read -- (73.7% d.e.) --.

Column 76,
Line 20, "mol/mL" should read -- mol/L --;
Line 23, "(27 0 MHz," should read -- 270 MHz, --; and
Line 33, "m g" should read -- mg --; and
Line 38, "1 0" should read -- 10 -- and "an" should read -- and --.

Column 77,
Line 29, "(1H, m)," should read -- (1H, m), 1.08 (3H, t, J=7.1 Hz). --; and
Line 53, "129 + (50%)" should read -- 129 (50%) --.

Column 78,
Line 8, "J=36" should read -- 36 --; and
Line 54, "(3H, 8)," should read -- (3H, s), --.

Column 79,
Line 35, "for2" should read -- for 2 --.

Column 83,
Line 17, "0.08.0 mL" should read -- 0.080 mL --; and
Line 24, "(2H, 9)," should read -- (2H, s), --.

Column 84,
Line 25, "J=6 Hz)," should read -- J=8.6 Hz), --.

Column 85,
Line 26, "608: $(M+1)^+$." should read -- 608 $(M+1)^+$. --; and
Line 50, "(1R," should read -- (1H, --.

Column 86,
Line 55, "(0, 0900 mmol)" should read -- (0.0900 mmol) --.

Column 89,
Line 29, "benzoylchloride," should read -- benzoyl chloride, --.

Column 90,
Line 42, "(30 4)." should read -- (30 %). --; and
Line 43, "(2701 MHz," should read -- (270 MHz, --.

UNITED STATES PATENT AND TRADEMARK OFFICE
CERTIFICATE OF CORRECTION

PATENT NO.    : 6,806,266 B1
DATED         : October 19, 2004
INVENTOR(S)   : Fumihiko Kanai et al.

It is certified that error appears in the above-identified patent and that said Letters Patent is hereby corrected as shown below:

Column 94,
Line 13, "brd," should read -- t, --.

Column 96,
Line 41, "sodiumbicarbonate," should read -- sodium bicarbonate, --; and
Line 53, "2.58 2.40" should read -- 2.58-2.40 --.

Column 98,
Line 24, "3-(3-dimethylaminopropyl )" should read -- 3-(3-dimethylaminopropyl) --;
Line 42, "0.98 mL," should read -- 0.98 mL --; and
Line 44, "2.0 mL," should read -- 2.0 mL --.

Column 99,
Line 6, "mmol/L" should read -- mol/L --.

Column 106,
Line 16, "N,N-dimethyl formamide" should read -- N,N-dimethylformamide --; and
Line 63, "(10 mmol)" should read -- (110 mmol) --.

Column 109,
Line 31, "M" should be deleted.

Column 110,
Line 29, "J=107 mg" should read -- 107 mg --.

Column 112,
Line 2, "hexanelethyl" should read -- hexane/ethyl --; and
Line 59, "1,35" should read -- 1.35 --.

Column 115,
Line 41, "$CSR^{13A1}$," should read -- $CSR^{13A}$, --.

Column 116,
Line 22, "tively;" should read -- tively); --.

Column 118,
Line 32, "$R^1$ represents" should read -- $R^5$ represents --; and
Line 46, "(wherein $R^{17}$" should read -- {wherein $R^{17}$ --.

UNITED STATES PATENT AND TRADEMARK OFFICE
CERTIFICATE OF CORRECTION

PATENT NO.   : 6,806,266 B1
DATED        : October 19, 2004
INVENTOR(S)  : Fumihiko Kanai et al.

It is certified that error appears in the above-identified patent and that said Letters Patent is hereby corrected as shown below:

Column 119,
Line 7, "alkyl)amino)," should read -- alkyl)amino]. --;
Line 28, "to" should be deleted; and
Line 34, "niorpholino," should read -- morpholino, --.

Column 120,
Line 7, "$R^{13A1}$)," should read -- $R^{13A1}$);-- and
Line 21, "compound" should read -- one compound --; and
Line 25, "claim, 1" should read -- claims 1 --.

Signed and Sealed this

Fifteenth Day of March, 2005

JON W. DUDAS
*Director of the United States Patent and Trademark Office*